US008940730B2

(12) United States Patent
Glenn et al.

(10) Patent No.: US 8,940,730 B2
(45) Date of Patent: Jan. 27, 2015

(54) METHODS AND COMPOSITIONS OF TREATING A *FLAVIVIRIDAE* FAMILY VIRAL INFECTION

(75) Inventors: Jeffrey S. Glenn, Palo Alto, CA (US); Wenjin Yang, Foster City, CA (US); Ingrid C. Choong, Los Altos, CA (US)

(73) Assignee: The Board of Trustees of the Leland Stanford Junior University, Palo Alto, CA (US)

( * ) Notice: Subject to any disclaimer, the term of this patent is extended or adjusted under 35 U.S.C. 154(b) by 157 days.

(21) Appl. No.: 13/376,486

(22) PCT Filed: Mar. 16, 2010

(86) PCT No.: PCT/US2010/027405
§ 371 (c)(1),
(2), (4) Date: Mar. 5, 2012

(87) PCT Pub. No.: WO2010/107742
PCT Pub. Date: Sep. 23, 2010

(65) Prior Publication Data
US 2012/0148534 A1    Jun. 14, 2012

Related U.S. Application Data

(63) Continuation-in-part of application No. 12/383,071, filed on Mar. 18, 2009, and a continuation-in-part of application No. 12/383,030, filed on Mar. 18, 2009, each which is a continuation-in-part of application No. PCT/US2008/076806, filed on Sep. 18, 2008.

(60) Provisional application No. 61/092,537, filed on Aug. 28, 2008, provisional application No. 60/973,309, filed on Sep. 18, 2007, provisional application No. 61/088,759, filed on Aug. 14, 2008, provisional application No. 61/299,886, filed on Jan. 29, 2010.

(51) Int. Cl.
| C07D 231/56 | (2006.01) |
| C07D 401/06 | (2006.01) |
| C07D 401/12 | (2006.01) |
| C07D 401/14 | (2006.01) |
| C07D 403/12 | (2006.01) |
| C07D 405/14 | (2006.01) |
| C07D 413/14 | (2006.01) |
| C07D 491/08 | (2006.01) |
| C07K 14/005 | (2006.01) |
| A61K 31/416 | (2006.01) |
| A61K 31/5377 | (2006.01) |
| A61K 45/06 | (2006.01) |
| A61K 38/21 | (2006.01) |
| A61K 31/55 | (2006.01) |
| A61K 31/454 | (2006.01) |
| A61K 31/7056 | (2006.01) |
| A61K 31/4439 | (2006.01) |
| A61K 31/506 | (2006.01) |
| C12N 7/00 | (2006.01) |

(52) U.S. Cl.
CPC ............. *C07K 14/005* (2013.01); *A61K 31/416* (2013.01); *A61K 31/5377* (2013.01); *C07D 401/14* (2013.01); *C07D 403/12* (2013.01); *A61K 45/06* (2013.01); *C07D 231/56* (2013.01); *C12N 2770/24211* (2013.01); *A61K 38/212* (2013.01); *C07D 401/12* (2013.01); *A61K 31/55* (2013.01); *C07D 401/06* (2013.01); *A61K 31/454* (2013.01); *A61K 31/7056* (2013.01); *C07D 405/14* (2013.01); *A61K 31/4439* (2013.01); *A61K 31/506* (2013.01); *C07D 491/08* (2013.01); *C12N 2770/24222* (2013.01); *C07D 413/14* (2013.01); *C12N 7/00* (2013.01)
USPC .................. 514/217.09; 514/234.5; 514/275; 514/322; 514/338; 514/407; 540/603; 544/124; 544/331; 546/199; 546/275.7; 548/361.5

(58) Field of Classification Search
None
See application file for complete search history.

(56) References Cited

U.S. PATENT DOCUMENTS

| 2,684,327 A |   | 7/1954 | Passal et al. |
| 2,689,853 A |   | 9/1954 | Schenck et al. |
| 3,265,691 A |   | 8/1966 | Helmer Richter et al. |
| 3,423,413 A |   | 1/1969 | Priewe et al. |
| 3,428,634 A | * | 2/1969 | Palazzo ........................ 544/140 |
| 4,011,322 A |   | 3/1977 | Rahtz et al. |
| 4,269,835 A |   | 5/1981 | Whittle |
| 5,552,426 A |   | 9/1996 | Lunn et al. |
| 6,211,177 B1 |   | 4/2001 | Sperl et al. |

(Continued)

FOREIGN PATENT DOCUMENTS

| DE | 102007028521 A1 | 12/2008 |
| EP |     1400241 A1 |  3/2004 |

(Continued)

OTHER PUBLICATIONS

The International Search Report and Written Opinion dated Dec. 24, 2010.
The International Preliminary Report on Patentability dated Sep. 29, 2011.
Selwood, et al., "Synthesis and Biological Evaluation of Novel Pyrazoles and Indazoles as Activators of the Nitric Oxide Receptor, Soluable Guanylate Cyclase," Journal of Medicinal Chemistry, 2001, vol. 44, pp. 78-93.

(Continued)

*Primary Examiner* — Kamal Saeed
(74) *Attorney, Agent, or Firm* — Thomas|Horstemeyer, LLP

(57) ABSTRACT

Briefly described, embodiments of this disclosure include compounds, pharmaceutical compositions, methods of treating a host infected with a virus from the Flaviviridae family of viruses, methods of inhibiting HCV replication in a host, methods of inhibiting the binding of NS4B polypeptide to the 3'UTR of HCV negative strand RNA in a host, methods of treating liver fibrosis in a host, and the like.

59 Claims, No Drawings

(56) References Cited

U.S. PATENT DOCUMENTS

| | | | |
|---|---|---|---|
| 6,369,235 | B1 | 4/2002 | Michejda et al. |
| 6,476,062 | B2 | 11/2002 | Chu |
| 7,495,015 | B2 | 2/2009 | Arora et al. |
| 2002/0128307 | A1 | 9/2002 | Chu |
| 2004/0092575 | A1 | 5/2004 | Peuvot et al. |
| 2004/0097438 | A1 | 5/2004 | Hashimoto et al. |
| 2004/0224876 | A1 | 11/2004 | Jost-Price et al. |
| 2005/0187261 | A1 | 8/2005 | Verner et al. |
| 2005/0192261 | A1 | 9/2005 | Jost-Price et al. |
| 2006/0052602 | A1 | 3/2006 | Kim et al. |
| 2008/0161324 | A1 | 7/2008 | Johansen |
| 2010/0028299 | A1 | 2/2010 | Einav et al. |

FOREIGN PATENT DOCUMENTS

| | | |
|---|---|---|
| KR | 10-1995-0031074 A | 12/1995 |
| WO | 0204425 A2 | 1/2002 |
| WO | 0207761 A1 | 3/2002 |
| WO | 03060475 A2 | 7/2003 |
| WO | 2005012288 A1 | 2/2005 |
| WO | 2005/032329 | 4/2005 |
| WO | 2006010446 A2 | 2/2006 |
| WO | 2006131737 | 12/2006 |
| WO | 2006131737 A2 | 12/2006 |
| WO | 2006135383 A2 | 12/2006 |
| WO | 2007103111 A2 | 9/2007 |
| WO | 2007115077 A2 | 10/2007 |
| WO | 2007117465 A2 | 10/2007 |
| WO | 2007/019932 | 3/2008 |
| WO | 2009039248 A2 | 3/2009 |

OTHER PUBLICATIONS

Patel, et al., "3D QSAR and Molecular Docking Studies of Benzimidazole Derivatives as Hepatitis C Virus NS5B Polymerase Inhibitors," Journal of Chemical Information and Moedling, 2008, vol. 48, pp. 42-55.
The Supplemental European Search Report dated Jul. 2, 2012.
The Supplemental European Search Report dated Aug. 8, 2012.
Einav, et al., Discovery of a Hepatitis C Target and its Pharmacological Inhibitors by Microfluidic Affinity Analysis, Nature Biotechnology, Nature Publishing Group, New York, NY, vol. 26, No. 9, Sep. 1, 2008, pp. 1019-1027.
Caroti, et al., "Synthesis, Antilipidemic and Platelet Antiaggregatory Activity of 2-Aminobenzimidazole Amide Derivatives," Il Farmaco, Elsevier France, Scientifiques Et Medicals, IT, vol. 44, No. 3, Jan. 1, 1989, pp. 227-255.
Tuncbilek, et al., "Synthesis and Antimicrobial Activity of Some New Anilino Benzimidazoles," Archiv Der Pharmazie, Wiley, VH Verlag GmBH & Co. KGAA, Dec. 1, 1997, pp. 372-376.
Manganaro, et al., "Activity of Antiinflammatory Steroidal and Nonsteroidal Compounds in Some Experimental Functions, II, Activity of Certain Nonsteroidal Antiinflammatory Agents as Compared with that of Prednisone in Murine Hepatitis Due to MHV3," Inflammation, Plenum Press, New York, NY, vol. Proc. Int. Symp. No. 1968, Jan. 1, 1968, pp. 67-71.
Anonymous, Registry, Dec. 8, 2008, XP007920913.
Anonymous, Registry, Dec. 18, 1984-Dec. 22, 2009, XP007920912.
Anonymous, Registry, Nov. 8, 2004, XP007920909.
Supplemental European Search Report dated Oct. 13, 2011.
Beaulieu, P.L., et al., "Non-nucleoside Inhibitors of the Hepatitis C Virus NS5B polymerase: Discovery and Preliminary SAR of Benzimidazolde Derivatives," Bioorganic & Medicinal Chemistry Letters, Pergamon, Elsevier Science, GB, vol. 14, No. 1, Jan. 1, 2004, pp. 119-124.
Beaulieu, P.L., et al., "Improved Replicon Cellular Activity of Non-Nucleoside Allosteric Inhibitors of HCV NS5B Polymerase: From Benzimidazole to Indole Scaffolds," Bioorganic & Medicinal Chemistry Letters, Pergamon, Elsevier Science, GB, vol. 16, No. 19, Oct. 1, 2006, pp. 4987-4993.

"Martindale, The Complete Drug Reference", 2000, Pharmaceutical Press, XP000002659125, Clemizole Hydrocholoride, p. 406.
Einav, Shirit, et al., "Discovery of a Hepatitis C Target and its Pharmacological Inhibitors of Microfluidic Affinity Analysis," Nature Biotechnology, Nature Publishing Group, NY, vol. 26, No. 9, Sep. 1, 2008, pp. 1019-1027.
The Office Action dated Sep. 9, 2013 for Chinese Application Serial No. 201080021845.9, 4 pages.
The Office Action dated Sep. 11, 2013 for Chinese Application Serial No. 201080021850.X, 3 pages.
Glenn, JS. et al. In Vitro-Synthesized Hepatitis Delta Virus RNA Initiates Genome Replication in Cultured Cells. Journal of Virology, 1990, vol. 64(6), pp. 3104-3107.
Glenn, JS et al. Identification of a Prenylation Site in Delta Virus Large Antigen. Science, 1992, vol. 256, pp. 1331-1333.
Burd, CG & Dreyfuss G. Conserved Structures and Diversity of Functions of RNA-Binding Proteins. Science, 1994, vol. 265, pp. 615-621.
Wung, CH et al. Identification of the RNA-binding sites of the triple gene block protein 1 of bamboo mosaic potexvirus. J. Gen. Virol. 1999, vol. 80, pp. 1119-1126.
Spangberg, K et al. HuR, a Protein Implicated in Oncogene and Growth Factor mRNA Decay, Binds to the 39 Ends of Hepatitis C Virus RNA of Both Polarities. Virology, 2000, vol. 274, pp. 378-390.
Lindenbach et al. Complete Replication of Hepatitis C Virus in Cell Culture. Science, 2005, vol. 309, pp. 623-626.
Tong X et al. Identification and analysis of fitness of resistance mutations against the HCV protease inhibitor SCH 503034. Antiviral Research, 2006, vol. 70, pp. 28-38.
Blight KJ et al. Efficient Initiation of HCV RNA Replication in Cell Culture. Science, 2000, vol. 290, pp. 1972-1974.
Schilders G. et al. MPP6 is an exosome-associated RNA-binding protein involved in 5.8S rRNA maturation. Nucleic Acids Research, 2005, vol. 33(21), pp. 6795-6804.
International Search Report and Written Opinion dated Aug. 13, 2009.
Testa; "Prodrug research: futile or fertile?", 2004, Biochemical Pharmacology; 68:2097-2106.
International Search Report and Written Opinion dated Dec. 27, 2010.
Beaulieu, C., et al., "Benzimidazoles as New Potent and Selective DP Antagonists for the Treatment of Allergic Rhinitis," Bioorganic & Medicinal Chemistry Letters, 2004, vol. 14, pp. 3195-3199.
Einav, S., et al., "Discovery of a Hepatitis C Target and its Pharmacological Inhibitors by Microfluidic Affiinity Analysis," Nature Biotechnology, Sep. 2008, vol. 26, No. 9, pp. 1019-1027.
Einav, S., et al., "The Hepatitis C Virus (HCV) NS4B RNA Binding Inhibitor Clemizole is Highly Synergistic with HCV Protease Inhibitors," Anti-HCV Drug Synergy with Clemizole, JID 2010:202 (Jul. 1) pp. 65-74.
Cho, et al., "Identification of a Class of HCV Inhibitors Directed Against the Nonstructural Protein NS4B," www.scienceTranslationalMedicine.org, Jan. 20, 2010, vol. 2, Issue 15, pp. 1-8.
Cho, et al., Supplementary Materials for "Identification of a Class of HCV Inhibitors Directed Against the Nonstructural Protein NS4B," www.scienceTranslationalMedicine.org, Jan. 20, 2010, vol. 2, Issue 15, pp. 1-23.
International Search Report and Written Opinion dated Apr. 1, 2009.
Blight, K.J. "Allelic Variation in the Hepatitis C Virus NS4B Protein Dramatically Influences RNA Replication," J. Virology, Jun. 2007, vol. 81, No. 11, pp. 5724-5736.
Einav, S. et al., "A Nucleotide Binding Motif in Hepatitis C Virus (HCV) NS4B Mediates HCV RNA Replication, "J. Virology, Oct. 2004, vol. 78, No. 20, pp. 11288-11295.
Puerstinger, G., et al., "Antiviral 2,5-disubstituted Imidazo[4,5-c]pyridines: From Anti-Pestivirus to Anti-Hepatitis C Virus Activity," Bioorganic * Medicinal Chemistry Letters, Jan. 2007, vol. 17, No. 2, pp. 390-393.

(56) References Cited

OTHER PUBLICATIONS

Hirashima, S., et al. "Benzimidazole Derivatives Bearing Substituted Biphenyls as Hepatitis C Virus NS5B RNA-Dependent RNA Polymerase Inhibitors: Structure-Activity Relationship Studies and Identification of a Potent and Highly Selective Inhibitor JTK-109," J. Medicinal Chemistry, Jun. 2006, vol. 49, No. 15, pp. 4721-4736.
Korba, B.E., et al. "Nitazoxanide, Tizoaxanide and Other Thiazolides are Potent Inhibitors of Hepatitis B Virus and Hepatitis C Virus Replication," Antiviral Research, Sep. 4, 2007, vol. 77, No. 1, pp. 56-63.
Blight, et al.; Efficient Initiation of HCV RNA Replication in Cell Culture; Science; vol. 290; Dec. 8, 2009, 1972-1974.
Takhampunya, et al.; Inhibition of Dengue Virus Replication by Mycophenolic Acid and Ribavirin; Journal of General Virology; vol. 87; 2006; 1947-1952.
Hwang, et al.; Inhibition of Hepatitis C Virus Replication by Arsenic Trioxide; Antimicrobial Agents and Chemotheraphy; vol. 48, No. 8; Aug. 2004; pp. 2876-2882.
Lohmann, et al.; Replication of Subgenomic Hepatitis C Virus RNAs in a Hepatoma Cell Line; Science; vol. 285; Jul. 2, 1999; pp. 110-113.
Maerkl, et al.; A Systems Approach to Measuring the Binding Energy Landscapes of Transcription Factors; Science; vol. 315; Jan. 12, 2007; pp. 233-237.
Patani et al. Bioisosterism: A Rational Approach in Drug Design. Chem. Rev. 1996. vol. 96, pp. 3147-3176.
Supplementary European Search Report dated Sep. 19, 2011.
Iacobellis et al. "External validation of biochemical indices for noninvasive evaluation of liver fibrosis in HCV chronic Hepatitis". American Journal of Gastroenterology, 2005, vol. 100, pp. 868-873.
Voronina et al. "Synthesis and pharmaceutical properties of amidine analogs of pyracetatam". Khimiko-Farmatsevticheskii Zhurnal, 1990, vol. 24, 11:26-29. Caplus Abstract, AN 1991:101601.
Echeverri, A.C. & Dasgupta, A. Amino Terminal Regions of Poliovirus 2C Protein Mediate Membrane Binding. Virology, 1995. vol. 208, pp. 540-553.
Rodriguez, P.L. & Carrasco L. Poliovirus Protein 2C Contains Two Regions Involved in RNA Binding Activity. J. Biol. Chem. 1995, vol. 270 (17), pp. 10105-10112.
Hadd, A.D. et al. Microchip Device for Performing Enzyme Assays. Anal. Chem. 1997, vol. 69, pp. 3407-3412.
El-Hage, N. & Luo, G. Replication of Hepatitis C Virus RNA Occurs in a Membrane-Bound Replication Complex Containing Nonstructural Viral Proteins and RNA. Journal of General Virology, 2003, vol. 84, pp. 2761-2769.
Park-Lee et al. Characterization of the Interaction between Neuronal RNA-binding Protein HuD and AU-rich RNA. Journal of Biological Chemistry, 2003, vol. 278(41) pp. 39801-39808.
Einav, S. et al. A Nucleotide Binding Motif in Hepatitis C Virus (HCV) NS4B Mediates HCV RNA Replication. Journal of Virology, 2004, vol. 78(20) pp. 11288-11295.
Lundin, M et al. Topology of the Membrane-Associated Hepatitis C Virus Protein NS4B. Journal of Virology, 2003, vol. 77(9), pp. 5428-5438.
Gosert, R. et al. Identification of the Hepatitis C Virus RNA Replication Complex in Huh-7 Cells Harboring Subgenomic Replicons. Journal of Virology, 2003, vol. 77(9), pp. 5487-5492.
Tscherne, D.M. Time- and Temperature-Dependent Activation of Hepatitis C Virus for Low-pH-Triggered Entry. Journal of Virology, 2006, vol. 80(4), pp. 1734-1741.
Elazar, M. et al. An N-Terminal Amphipathic Helix in Hepatitis C Virus (HCV) NS4B Mediates Membrane Association, Correct Localization of Replication Complex Proteins, and HCV RNA Replication. Journal of Virology, 2004, vol. 78(20), pp. 11393-11400.
Dimitrova M. et al. Protein-Protein Interactions between Hepatitis C Virus Nonstructural Proteins. Journal of Virology, 2003, vol. 77(9), pp. 5401-5414.
Glenn J.S. et al. In Vitro-Synthesized Hepatitis Delta Virus RNA Initiates Genome Replication in Cultured Cells. Journal of Virology, 1990, vol. 64(6), pp. 3104-3107.
Huang L. et al. Hepatitis C Virus Nonstructural Protein 5A (NS5A) Is an RNA-binding Protein. Journal of Biological Chemistry, 2005, vol. 280(43) pp. 36414-36428.
Elazar, M. et al. Amphipathic Helix-Dependent Localization of NS5A Mediates Hepatitis C Virus RNA Replication. Journal of Virology, 2003, vol. 77(70), pp. 6055-6061.
Egger D. et al. Expression of Hepatitis C Virus Proteins Induces Distinct Membrane Alterations Including a Candidate Viral Replication Complex. Journal of Virology, 2002, vol. 76(12), pp. 5974-5984.
Kang L. et al. Microfluidics for drug discovery and development: From target selection to product lifecycle management. Drug Discovery Today, 2008, vol. 13 (1/2), pp. 1-13.
Kusov YY. et al. Membrane association and RNA binding of recombinant hepatitis a virus protein 2C. Arch Virol. 1998, vol. 143, pp. 931-944.
Liang, T.J. et al. Pathogenesis, Natural History, Treatment, and Prevention of Hepatitis C, Ann. Intern. Med., 2000, vol. 132, pp. 296-305.
Park, S. et al. HuD RNA Recognition Motifs Play Distinct Roles in the Formation of a Stable Complex with AU-Rich RNA. Mol. Cell. Biol. 2000, vol. 20(13), pp. 4765-4772.
Lee, N. L. et al. Solvent Compatibility of Poly(dimethylsiloxane)-Based Microfluidic Devices. Anal. Chem., 2003, vol. 75, pp. 6544-6554.
Roosild, T.P. et al. NMR Structure of Mistic, a Membrane-Integrating Protein for Membrane Protein Expression. Science, 2005, vol. 307, p. 1317.
Reed K.E. & Rice C.M. Overview of Hepatitis C Virus Genome Structure, Polyprotein Processing, and Protein Properties. The Hepatitis C Viruses, Current Topics in Microbiology and Immunology, 2000, vol. 242, pp. 55-84.
Overington, J.P. et al. How many drug targets are there? Nat Rev Drug Discov. 2006, vol. 5, pp. 993-996.
Maerkl, SJ. et al. A Systems Approach to Measuring the Binding Energy Landscapes of Transcription Factors. Science, 2007, vol. 315, pp. 233-237.
Toepke, MW, et al. PDMS absorption of small molecules and consequences in microfluidic applications. Lab on a Chip, 2006, vol. 6, pp. 1484-1483.
Whitesides, GM. The origins and the future of microfluidics. Nature 2006, vol. 442, pp. 368-373.
Myer, VE et al. Identification of HuR as a protein implicated in AUUUA-mediated mRNA decay. The EMBO Journal, 1997, vol. 16, pp. 2130-2139.
Gupta AK et al. Antifungal Agents: An overview. Part I. Journal of the American Academy of Dermatology, 1994, vol. 30(5) Part 1, pp. 677-698.

* cited by examiner

METHODS AND COMPOSITIONS OF TREATING A *FLAVIVIRIDAE* FAMILY VIRAL INFECTION

CROSS-REFERENCE TO RELATED APPLICATION

This application claims priority to U.S. Provisional Patent Application entitled, "Methods and Compositions of Treating a Flaviviridae Family Viral Infection," having Ser. No. 61/299,886, filed on Jan. 29, 2010, which is entirely incorporated herein by reference.

In addition, this application is a National Stage Entry of PCT/US10/27405 filed Mar. 16, 2010, which is a Continuation-in-Part of U.S. patent application entitled, "Methods and Compositions of Treating a Flaviviridae Family Viral Infection," having Ser. No. 12/383,030, filed on Mar. 18, 2009, which is a Continuation-in-Part of PCT/US08/76806 filed Sep. 18, 2008, which claims priority to provisional applications 61/092,537 filed Aug. 28, 2008, 61/088,759 filed Aug. 14, 2008, and 60/973,309 filed Sep. 18, 2007, all of which are entirely incorporated herein by reference.

In addition, this application is a National Stage Entry of PCT/US10/27405 filed March 16, 2010, which is a Continuation-in-Part of U.S. patent application entitled, "Methods and Compositions of Treating a Flaviviridae Family Viral Infection," having Ser. No. 12/383,071, filed on Mar. 18, 2009, which is a Continuation-in-Part of PCT/US08/76806, which claims priority to Provisional applications 61/092,537 filed Aug. 28, 2008, 61/088,759 filed Aug. 14, 2008, and 60/973,309 filed Sep. 18, 2007, all of which are entirely incorporated herein by reference.

In addition, this application claims priority to U.S. patent application entitled, "Methods and Compositions of Treating a Flaviviridae Family Viral Infection," having Ser. No. 12/383,030, filed on Mar. 18, 2009, which is entirely incorporated herein by reference.

In addition, this application claims priority to U.S. patent application entitled, "Methods and Compositions of Treating a Flaviviridae Family Viral Infection," having Ser. No. 12/383,071, filed on Mar. 18, 2009, which is entirely incorporated herein by reference.

STATEMENT REGARDING FEDERALLY SPONSORED RESEARCH OR DEVELOPMENT

This invention was made with Government support under contract DK066793 awarded by the National Institutes of Health. The Government has certain rights in this invention.

BACKGROUND

Over 150 million people are infected with Hepatitis C Virus (HCV) worldwide. Unfortunately, the current standard care, consisting of administration of a combination of interferon and ribavirin, is often unable to clear HCV infection in many infected individuals. Moreover, this treatment is associated with significant side effects, precluding its use by many individuals. Thus, current therapies are inadequate for the majority of the patients, and there is a pressing need for new drugs to treat HCV infection (See, *Annals Internal Med.* 132:296-305 (2000)).

The 9.6-kb positive single-stranded RNA HCV genome encodes a 3,000-amino-acid polyprotein that is proteolytically processed into structural proteins, which are components of the mature virus, and nonstructural proteins (NS), which are involved in replicating the viral genome (*Curr Top Microbiol Immunol* 242, 55-84 (2000)). Like other positive strand RNA viruses (B. N. Fields, D. M. Knipe, and P. M. Howley (ed.), *Fields Virology*. (Lippincott-Raven Publications, Philadelphia, Pa., 1996, in "The viruses and their replication")), HCV appears to replicate in association with intracellular membrane structures. In the case of HCV, the structures are referred to as the membranous web (*J Virol* 76, 5974-5984 (2002)), the formation of which is believed to be induced by the NS4B protein. NS4B is also used to assemble the other viral NS proteins within the apparent sites of RNA replication (*J Virol* 78, 11393-11400 (2004)). It is not known how viral RNA, especially the negative strand template used for production of progeny genomes, might be incorporated or maintained at these replication sites.

There is an ongoing need in the art for agents that treat HCV infection.

SUMMARY

Briefly described, embodiments of this disclosure include compounds, compositions, pharmaceutical compositions, methods of treating a host infected with a virus from the Flaviviridae family of viruses, methods of treating HCV replication in a host, methods of inhibiting the binding of NS4B polypeptide to the 3'UTR of HCV negative strand RNA in a host, methods of treating liver fibrosis in a host, and the like.

In one embodiment, the present invention provides a method of treating a subject infected with a virus from the Flaviviridae family. The method typically comprises administering to the subject a compound of the present invention, or a pharmaceutically acceptable salt, an isomer, a tautomer or a prodrug thereof, in an amount that is effective in reducing viral load of said virus in said subject. The virus of the Flaviviridae family can include a flavivirus; a pestivirus; a Hepatitis C virus; a yellow fever virus; a Dengue virus; a Japanese Encephalitis virus; a Murray Valley Encephalitis virus; a St. Louis Encephalitis virus; a West Nile virus; a tick-borne encephalitis virus; a Kunjin virus; a Central European encephalitis virus; a Russian spring-summer encephalitis virus; a Powassan virus; a Kyasanur Forest disease virus; a Omsk hemorrhagic fever virus; and their respective genotypes and subgenotypes.

In another embodiment, the present invention provides a method of inhibiting formation of a complex between NS4B polypeptide and hepatitis C viral (HCV) RNA in a cell. The method comprises administering to the cell a compound of the present invention, or a pharmaceutically acceptable salt, an isomer, a tautomer or a prodrug thereof, in an amount that is effective in reducing binding of NS4B polypeptide to HCV RNA.

In yet another embodiment, the present invention provides a method of treating liver fibrosis in a subject. The method comprises administering to the subject a therapeutically effective amount of a compound of the present invention, or a pharmaceutically acceptable salt, an isomer, a tautomer or a prodrug thereof.

In some aspects, any of the methods of the present invention involves administration of a compound of the present invention (or a composition (e.g., pharmaceutical) including the compound or consisting essentially of the compound) having a structure of Formula II-a, or a pharmaceutically acceptable salt or an isomer thereof:

Formula II-a

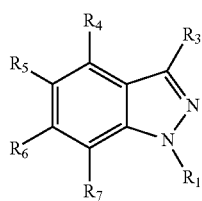

wherein $R_1$ is selected from the group consisting of: —H and

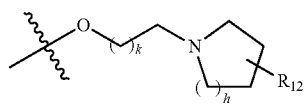

$m = 0, 1, 2$ wherein V is selected from alkyl, cycloalkyl, heterocyclo, aryl, and heteroaryl;

$R_3$ is —H, —OH, —O(CH$_2$)$_n$X, or —(CH$_2$)$_n$X, wherein n is 1, 2, 3, or 4, and X is —NH$_2$, —NH(alkyl), —N(alkyl)$_2$, —OH, —O-alkyl, —O-aryl, —SO$_2$(alkyl), —SO$_2$NH$_2$, —SO$_2$NH(alkyl), NHSO$_2$(alkyl), heteroaryl, N-attached heterocyclo, or C-attached heterocyclo;

each of $R_4$-$R_7$ is independently selected from the group consisting of: —H, —Br, —Cl, —F, —I, —CH$_3$, —CN, —OH, —OCH$_3$, —NO$_2$, —NH$_2$, —OCH$_2$CH$_2$O-alkyl, —NHCO(alkyl), —NHCO(aryl),

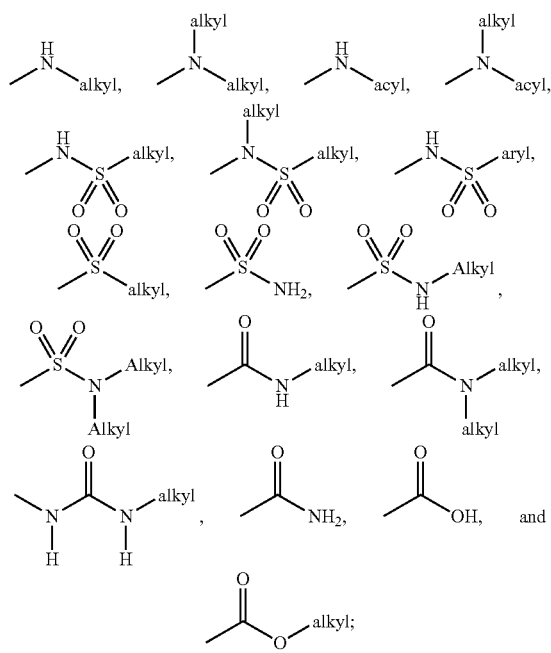

or, optionally, $R_4$ and $R_5$, $R_5$ and $R_6$, or $R_6$ and $R_7$ are joined together with a bond to form a 5, 6, or 7-membered ring; or, optionally, $R_4$ and $R_5$, $R_5$ and $R_6$, or $R_6$ and $R_7$ are joined together to form a 1,2-(methylenedioxy)benzene ring system. In some embodiments, X is selected from the group consisting of: —OCH$_3$, —OCH$_2$CH$_3$, —OCH$_2$CH$_2$OH, —OCH$_2$CH$_2$OCH$_3$,

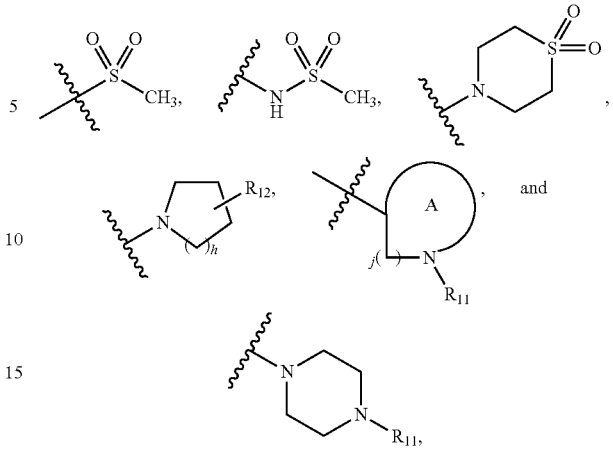

wherein $R_{12}$ is hydrogen, hydroxy, alkoxy, alkyl, oxo, —(CH$_2$)$_n$—OH, —C(O)alkyl, —C(O)aryl, or —SO$_2$alkyl; $R_{11}$ is hydrogen, —C(O)$_2$alkyl, —C(O)alkyl, —C(O)aryl, —C(O)NH$_2$, —C(O)NHalkyl, —C(O)N(alkyl)$_2$, —SO$_2$alkyl, —SO$_2$aryl, —SO$_2$NH$_2$, —SO$_2$NHalkyl, or —SO$_2$N(alkyl)$_2$; ring A is a 5-, 6-, or 7-membered ring, j is 0, 1, or 2; and h is 1, 2, or 3. In other embodiments, $R_3$ is selected from the group consisting of: —O(CH$_2$)$_2$NMe$_2$, —O(CH$_2$)$_2$NEt$_2$, —O(CH$_2$)$_3$NMe$_2$, —O(CH$_2$)$_3$NEt$_2$, and

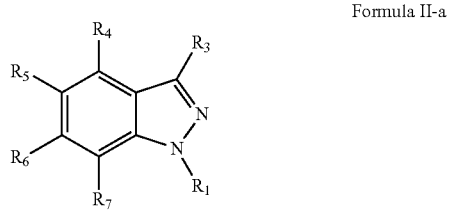

wherein k is 0, 1, or 2, h is 1, 2, or 3, and $R_{12}$ is hydrogen, hydroxy, alkoxy, alkyl, oxo, —(CH$_2$)$_n$—OH, —C(O)alkyl, —C(O)aryl, or —SO$_2$alkyl. Where desired, the indazole compound employed in the subject method can have any of the structures disclosed herein, $R_1$ is —CH$_2$V, wherein V is selected from cycloalkyl, heterocyclo, aryl or heteroaryl.

The treatment methods provided herein may further comprise administering one or more additional therapeutic agents (or a composition (e.g., pharmaceutical) including one or more of these or consisting essentially of the compound and one or more of these) selected from the group consisting of: an HCV NS3 protease inhibitor, an HCV NS5B RNA-dependent RNA polymerase inhibitor, a thiazolide, a sustained release thiazolide, a nucleoside analog, an interferon-alpha, a pegylated interferon, ribavirin, levovirin, viramidine, a TLR7 agonist, a TLR9 agonist, a cyclophilin inhibitor, an alpha-glucosidase inhibitor, an NS5A inhibitor, and an NS3 helicase inhibitor.

The present invention also provides a compound (or a composition (e.g., pharmaceutical) including the compound or consisting essentially of the compound) having a structure of Formula II-a, or a pharmaceutically acceptable salt or an isomer thereof:

Formula II-a wherein $R_1$ is selected from the group consisting of: —H and

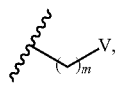

m = 0, 1, 2 wherein V is selected from alkyl, cycloalkyl, heterocyclo, aryl or heteroaryl;

$R_3$ is —H, —OH, —O(CH$_2$)$_n$X, or —(CH$_2$)$_n$X, wherein n is 1, 2, 3, or 4, and X is —NH$_2$, —NH(alkyl), —N(alkyl)$_2$, —OH, —O-alkyl, —O-aryl, —SO$_2$(alkyl), —SO$_2$ NH$_2$, —SO$_2$ NH(alkyl), NHSO$_2$(alkyl), heteroaryl, N-attached heterocyclo, or C-attached heterocyclo;

each of $R_4$-$R_7$ is independently selected from the group consisting of: —H, —Br, —Cl, —F, —I, —CH$_3$, —CN, —OH, —OCH$_3$, —NO$_2$, —NH$_2$, —O-alkyl, —OCH$_2$CH$_2$O-alkyl, —NHCO(alkyl), —NHCO(aryl),

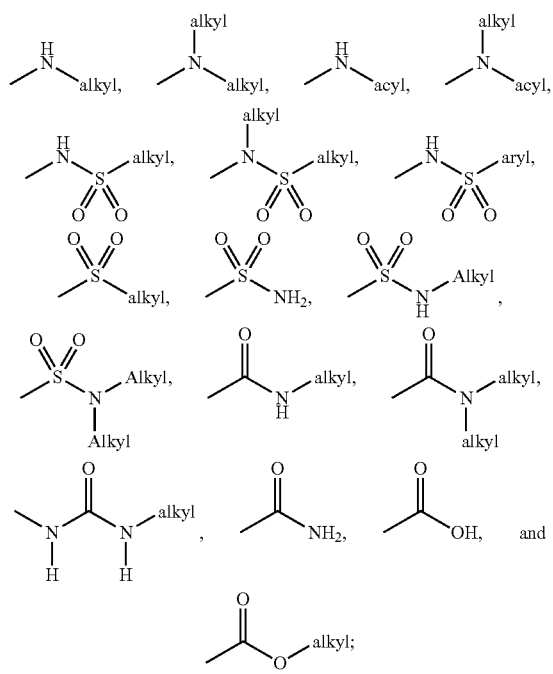

or, optionally, $R_4$ and $R_5$, $R_5$ and $R_6$, or $R_6$ and $R_7$ are joined together with a bond to form a 5, 6, or 7-membered ring; or, optionally, $R_4$ and $R_5$, $R_5$ and $R_6$, or $R_6$ and $R_7$ are joined together to form a 1,2-(methylenedioxy)benzene ring system; provided that the compound of Formula II-a is not

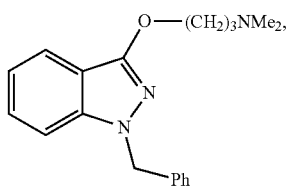

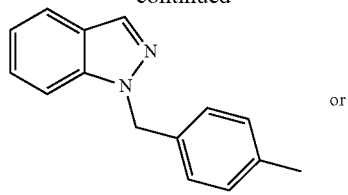

or

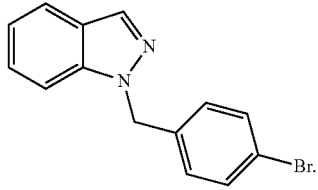

In some embodiments, for the compound of Formula II-a, $R_1$ is

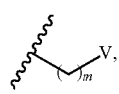

m = 0, 1, 2 and V is aryl. In other embodiments, for the compound of Formula II-a, $R_3$ is —H, —OH, —O(CH$_2$)$_n$X, or —(CH$_2$)$_n$X, wherein n is 1, 2, 3, or 4, and X is —NH$_2$, —NH(alkyl), —N(alkyl)$_2$, —OH, or N-attached heterocyclo. In yet other embodiments, X of Formula II-a is selected from the group consisting of: —OCH$_3$, —OCH$_2$CH$_3$, —OCH$_2$CH$_2$OH, —OCH$_2$CH$_2$OCH$_3$,

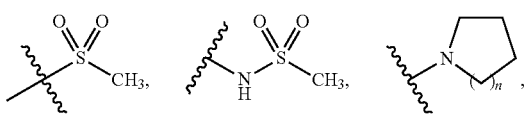

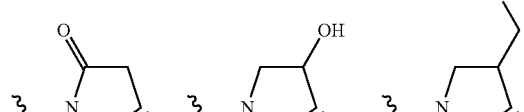

n = 1, 2, or 3    n = 1, 2, or 3    n = 1, 2, or 3

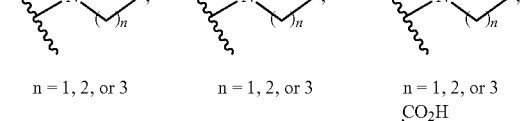

n = 1, 2, or 3    n = 1, 2, or 3

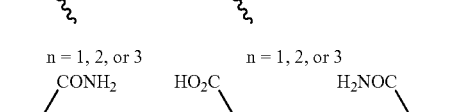

n = 1, 2, or 3    n = 1, 2, or 3    n = 1, 2, or 3

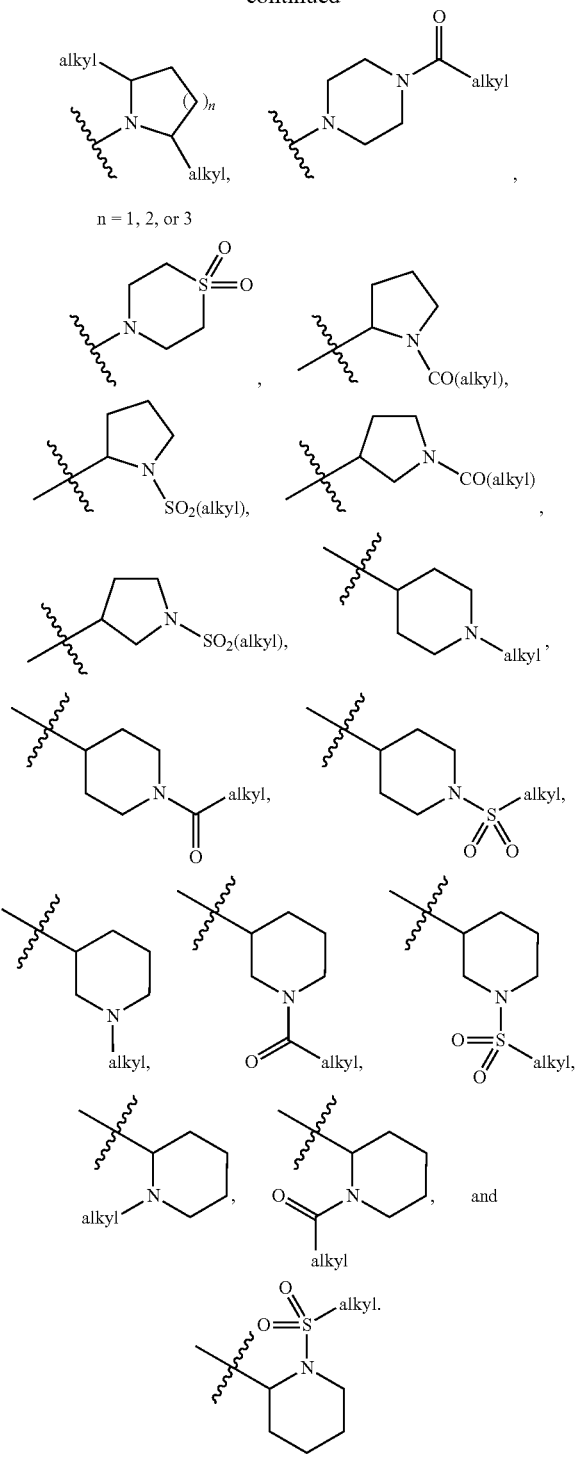

In further embodiments, $R_3$ of a compound of Formula II-a is selected from the group consisting of: —O(CH$_2$)$_2$NMe$_2$, —O(CH$_2$)$_2$NEt$_2$, —O(CH$_2$)$_3$NEt$_2$,

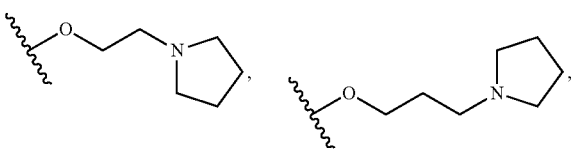

In yet further embodiments, $R_1$ is —CH$_2$V, wherein V is selected from cycloalkyl, heterocyclo, or heteroaryl; and/or $R_4$ and $R_7$ are both hydrogen, and $R_5$ and $R_6$ are both a substituent other than hydrogen.

In one embodiment, the present invention provides a compound (or a composition (e.g., pharmaceutical) including the compound or consisting essentially of the compound) of Formula III Formula III or a pharmaceutically acceptable salt, an isomer, a tautomer or a prodrug thereof wherein
  m is 1 or 2;
  V is an unsubstituted or a monosubstituted phenyl, cyclohexyl, or a 6-membered heterocyclo group where the heterocyclo group contains 1 nitrogen atom;
  $R_3$ is —O-L-X;
  L is an unsubstituted or a monosubstituted $C_1$-$C_5$ alkylene;
  X is an unsubstituted or is a substituted 5, 6, or 7 membered non aromatic heterocyclo containing at least 1 nitrogen atom, —N(R$_{20}$)$_2$, or 4-substituted phenyl;
  $R_5$ is hydrogen, alkyl, halo, a substituted or an unsubstituted 5, 6, 7 membered heterocyclo, or —NR$_2$R$_{22}$;
  each $R_{20}$ is independently a substituted or an unsubstituted $C_1$-$C_3$ alkyl. $R_{21}$ and $R_{22}$ are each independently selected from hydrogen, substituted or unsubstituted $C_1$-$C_3$ alkyl, $C_3$-$C_8$ cycloalkyl, aryl, or heteroaryl group, —COR$_{16}$, or —SO$_2$R$_{16}$, or $R_{21}$ and $R_{22}$ together with the nitrogen atom to which they are attached form a 5-7 membered substituted or unsubstituted heterocyclo group;
  $R_{16}$ is a substituted or an unsubstituted $C_1$-$C_3$ alkyl.
  In another embodiment, m is 1. In another embodiment, m is 2.

In another embodiment, the present invention provides a compound (or a composition (e.g., pharmaceutical) including the compound or consisting essentially of the compound) of Formula III wherein X is a 5, 6, or 7 membered non aromatic heterocyclo that is an unsubstituted or is a substituted with 1-2 —OH, $C_1$-$C_3$ alkoxy, —$CO_2R_{17}$, —$CON(R_{18})_2$, a substituted or an unsubstituted 5 or 6 membered aryl or heteroaryl group, $C_1$-$C_3$ alkyl, or $C_1$-$C_3$ alkyl substituted with —OH, $C_1$-$C_3$ alkoxy, —$CO_2R_{17}$, —$NR_{23}R_{24}$, —$CO_2H$;

$R_{17}$ is a substituted or an unsubstituted $C_1$-$C_6$ alkyl;

each $R_{18}$ is independently selected from hydrogen or substituted or unsubstituted $C_1$-$C_3$ alkyl;

$R_{23}$ and $R_{24}$ are each independently selected from hydrogen, a substituted or an unsubstituted aryl, heteroaryl, $C_1$-$C_3$ alkyl, or $R_{23}$ and $R_{24}$ together with the nitrogen atom they are attached form a substituted or an unsubstituted 5-7 membered non aromatic heterocycle.

In another embodiment, X is 1-pyrrolidinyl that is an unsubstituted or a substituted with 1-2 —OH, $C_1$-$C_3$ alkoxy, a substituted or an unsubstituted 6 membered aryl, $C_1$-$C_3$ alkyl, or $C_1$-$C_3$ alkyl substituted with —OH, $C_1$-$C_3$ alkoxy, or —$NR_{23}R_{24}$. In another embodiment, X is a substituted or an unsubstituted piperidinyl. In another embodiment, X is a 7-membered non aromatic heterocyclo group where the 7-membered non aromatic heterocyclo group contains 1 nitrogen atom.

In another embodiment, the present invention provides a compound of Formula III wherein L is —$(CH_2)_n$— and n is 1, 2, 3, or 4. In another embodiment, L is 3. In another embodiment, L is 2, in another embodiment, L is 1. In another embodiment, L is 4.

In another embodiment, the present invention provides a compound of Formula III wherein V is 4-chlorophenyl or 4-isopropylphenyl. In another embodiment, the present invention provides a compound of Formula III wherein V is 4-chlorophenyl.

In another embodiment, the present invention provides a compound of Formula III wherein $R_5$ is hydrogen, halo, substituted or unsubstituted 5, 6, 7 membered heterocyclo, or —$NR_{21}R_{22}$. In another embodiment, $R_5$ is hydrogen. In another embodiment, $R_5$ is halo. In another embodiment, $R_5$ is a substituted or an unsubstituted 5 membered heterocyclo. In another embodiment, $R_5$ is a substituted or an unsubstituted 6 membered heterocyclo. In another embodiment, $R_5$ is a substituted or an unsubstituted 7 membered non aromatic heterocyclo. In another embodiment, $R_5$ is $NR_{21}R_{22}$. In one embodiment, $R_{21}$ and $R_{22}$ are both a substituted or an unsubstituted $C_1$-$C_3$ alkyl. In another embodiment, $R_{21}$ is a substituted or an unsubstituted $C_1$-$C_3$ alkyl. In another embodiment, $R_{21}$ is hydrogen. In another embodiment, $R_{22}$ is —$COR_{16}$, or —$SO_2R_{16}$. In another embodiment, $R_{22}$ is $C_3$-$C_8$ cycloalkyl. In another embodiment, $R_{22}$ is aryl or heteroaryl.

In another embodiment, the present invention provides a pharmaceutical composition comprising, or consisting essentially of, the compound of Formula III and a pharmaceutically acceptable carrier, excipient, or diluent.

In another embodiment, the present invention provides a method of treating a subject infected with a virus from the Flaviviridae family comprising administering to the subject the compound of Formula III or a pharmaceutical composition comprising, or consisting essentially of the compound of Formula III, in an amount that is effective in reducing viral load of said virus in said subject.

In another aspect of the present invention, a pharmaceutical composition is provided comprising, or consisting essentially of, a compound of the present invention, or a pharmaceutically acceptable salt, isomer, tautomer or prodrug thereof.

In another aspect of the present invention, a pharmaceutical composition is provided, comprising, or consisting essentially of, a compound of the present invention, or a pharmaceutically acceptable salt, isomer, tautomer or prodrug thereof, and further comprising one or more additional anti-HCV therapeutic agents selected from the group consisting of: an HCV NS3 protease inhibitor, an HCV NS5B RNA-dependent RNA polymerase inhibitor, a thiazolide, a sustained release thiazolide, a nucleoside analog, an interferon-alpha, a pegylated interferon, ribavirin, levovirin, viramidine, a TLR7 agonist, a TLR9 agonist, a cyclophilin inhibitor, an alpha-glucosidase inhibitor, an NS5A inhibitor, and an NS3 helicase inhibitor.

In one aspect, the present invention provides a method of treating a subject infected with a virus from the Flaviviridae family. The method comprises administering to the subject a compound (or a composition including the compound or consisting essentially of the compound) of the present invention, or a pharmaceutically acceptable salt, isomer, tautomer or prodrug thereof, in an amount that is effective in reducing viral load of said virus in said subject.

In some embodiments of the treatment methods of the invention, a compound of the present invention that has similar activity to clemizole (a "Clemizole Like Analog", which refers to an analog that has an $EC_{50}$ of less than about 25 micromolar in the genotype 2a infectious clone assay described herein but has an $EC_{50}$ of greater than about 25 micromolar in the genotype 1b replicon assay described herein) is administered to an HCV patient in a daily dose of at least about 200 mg, i.e., about 100 mg BID. Typically, this about 100 mg BID administration schedule, when used with these agents, will be used in treatment regimens in which at least one additional drug is also administered to the patient, i.e., treatment regimens in which a compound of the present invention is co-administered with (i) ribavirin; (ii) interferon; or (iii) ribavirin (e.g., using weight-based dosing or dosing at 15 mg/kg/day) and interferon (e.g., alpha 2a or alpha 2b, and pegylated versions of the same).

Other compound of the present invention provided herein have an $EC_{50}$ of less than about 25 micromolar in both the genotypes 1b replicon assay and the 2a infectious clone assay described herein ("1b Active Analogs"), may also be used at these doses, either in single-agent therapy or in the combination therapies just described. In any of these embodiments and with respect to the compounds of the present invention, the patient can be a previously untreated ("naïve") patient, a patient that has not responded to a prior treatment, such as standard of care ("SOC") therapy, a post-transplant patient, or a patient co-infected with another virus. Combination therapy (e.g., and without limitation, administration of a compound of the present invention in combination with ribavirin and interferon alpha) can be initiated at the beginning of a course of treatment or follow pre-treatment with ribavirin.

In other embodiments of the invention, however, the daily dose of any compound of the present invention for treating HCV infection is higher than about 200 mg; exemplary administration schedules include: 100 mg TID; 200 mg BID; 200 mg TID; 300 mg BID; 300 mg TID; 400 mg BID; 400 mg TID; 500 mg BID; and 500 mg TID. In other embodiments exemplary administration schedules include: about 100 mg TID; about 200 mg BID; about 200 mg TID; about 300 mg BID; about 300 mg TID; about 400 mg BID; about 400 mg TID; about 500 mg BID; and about 500 mg TID. For the more difficult to treat genotype, i.e., genotype 1, more frequent dosing or higher daily doses than that provided by about 100 mg po BID or about 200 mg po BID are preferred if a Clemizole Like Analog is administered as single agent therapy. In all of the various embodiments, however, a compound of the present invention can be administered in combination with another drug, including but not limited to (i) ribavirin (e.g., using fixed or weight-based dosing or dosing at 15 mg/kg/day); (ii) interferon; (iii) ribavirin (e.g., using fixed or weight-based dosing or dosing at 15 mg/kg/day) and interferon (e.g., alpha 2a or alpha 2b, and pegylated versions of the same, and for other interferons as described herein and such as, but not limited to, albuferon). In any of these embodiments, the patient can be a previously untreated ("naïve") patient, a patient that has not responded to a prior treatment, such as standard of care ("SOC") therapy, a post-transplant patient, or a patient co-infected with another virus. Combination therapy (e.g., administration of a compound of the present invention in combination with ribavirin and interferon alpha, or with other direct-acting specific antivirals) can be initiated at the beginning of a course of treatment or follow pre-treatment with ribavirin.

Also provided are methods of treating or prophylactically treating a subject who has been or is likely to be infected with a virus of the Flaviviridae family, comprising administering a compound of the present invention, or their pharmaceutically acceptable salts, isomers, tautomers or prodrugs, in combination with one or more additional therapeutic agent(s), including, without limitation, an HCV NS3 protease inhibitor, an HCV NS5B RNA-dependent RNA polymerase inhibitor, a thiazolide, including but not limited to a sustained release thiazolide, a nucleoside analog, an interferon-alpha, a pegylated interferon, ribavirin, levovirin, viramidine, a TLR7 agonist, a TLR9 agonist, a cyclophilin inhibitor, an alpha-glucosidase inhibitor, an NS5A inhibitor, and an NS3 helicase inhibitor.

DETAILED DESCRIPTION

Before the present invention is described in greater detail, it is to be understood that this invention is not limited to particular embodiments described, and the embodiment of the invention as such may, of course, vary. It is also to be understood that the terminology used herein is for the purpose of describing particular embodiments only, and is not intended to be limiting, because the scope of the present disclosure will be limited only by the appended claims.

Unless defined otherwise, all technical and scientific terms used herein have the same meaning as commonly understood by one of ordinary skill in the art to which this invention belongs.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure. Any recited method can be carried out in the order of events recited or in any other order that is logically possible.

Embodiments of the present disclosure will employ, unless otherwise indicated, techniques of synthetic organic chemistry, biochemistry, biology, molecular biology, recombinant DNA techniques, pharmacology, and the like, which are within the skill of the art. Such techniques are explained fully in the literature.

The examples herein are put forth so as to provide those of ordinary skill in the art with an illustrative disclosure and description of how to perform the methods and use the compounds disclosed and claimed herein. Unless indicated otherwise, parts are parts by weight, temperature is in ° C., and pressure is at or near atmospheric. Standard temperature and pressure are defined as 20° C. and 1 atmosphere.

Before the embodiments of the present disclosure are described in detail, it is to be understood that, unless otherwise indicated, the present disclosure is not limited to particular materials, reagents, reaction materials, manufacturing processes, or the like, as such can vary. It is also to be understood that the terminology used herein is for purposes of describing particular embodiments only, and is not intended to be limiting. It is also contemplated that, where multi-step processes are described in the present disclosure that steps can be executed in different sequence where this is logically possible.

As used in the specification and the appended claims, the singular forms "a," "an," and "the" include plural referents unless the context clearly dictates otherwise. Thus, for example, reference to "a compound" includes a plurality of compounds. In this specification and in the claims that follow, reference will be made to a number of terms that shall be defined to have the following meanings unless a contrary intention is apparent.

A. Definitions

In describing and claiming the disclosed subject matter, the following terminology will be used in accordance with the definitions set forth below.

By "Flaviviridae virus" is meant any virus of the Flaviviridae family, including those viruses that infect humans and non-human animals. The polynucleotide and polypeptides sequences encoding these viruses are well known in the art, and may be found at NCBI's GenBank database, e.g., as Genbank Accession numbers NC_004102, AB031663, D11355, D11168, AJ238800, NC_001809, NC_001437, NC_004355 NC_004119, NC_003996, NC_003690, NC_003687, NC_003675, NC_003676, NC_003218, NC_001563, NC_000943, NC_003679, NC_003678, NC_003677, NC_002657, NC_002032, and NC_001461, the contents of which database entries are incorporated by references herein in their entirety.

As used herein, the terms "treatment", "treating", and "treat" are defined as acting upon a disease, disorder, or condition with an agent to reduce or ameliorate the pharmacologic and/or physiologic effects of the disease, disorder, or condition and/or its symptoms. "Treatment," as used herein, covers any treatment of a disease in a host (e.g., a mammal, typically a human or non-human animal of veterinary interest), and includes: (a) reducing the risk of occurrence of the disease in a subject determined to be predisposed to the disease but not yet diagnosed as infected with the disease (b) impeding the development of the disease, and (c) relieving the disease, i.e., causing regression of the disease and/or relieving one or more disease symptoms. "Treatment" is also meant to encompass delivery of an inhibiting agent to provide a pharmacologic effect, even in the absence of a disease or condition. For example, "treatment" encompasses delivery of a disease or pathogen inhibiting agent that provides for enhanced or desirable effects in the subject (e.g., reduction of pathogen load, reduction of disease symptoms, and the like).

As used herein, the terms "prophylactically treat" and "prophylactically treating" refer completely or partially preventing a disease or symptom thereof and/or may be therapeutic in terms of a partial or complete cure for a disease and/or adverse effect attributable to the disease.

As used herein, the term "host," "subject," "patient," or "organism" includes humans and mammals (e.g., mice, rats, pigs, cats, dogs, and horses). Typical hosts to which compounds of the present disclosure may be administered will be mammals, particularly primates, especially humans. For veterinary applications, a wide variety of subjects will be suitable, e.g., livestock such as cattle, sheep, goats, cows, swine, and the like; poultry such as chickens, ducks, geese, turkeys, and the like; and domesticated animals particularly pets such as dogs and cats. For diagnostic or research applications, a wide variety of mammals will be suitable subjects, including rodents (e.g., mice, rats, hamsters), rabbits, primates, and swine such as inbred pigs and the like. The term "living host" refers to a host noted above or another organism that is alive. The term "living host" refers to the entire host or organism and not just a part excised (e.g., a liver or other organ) from the living host.

The terms "isolated compound" and "purified compound" mean a compound which has been substantially separated from, or enriched relative to, other compounds with which it occurs in nature. Isolated compounds are usually at least about 80%, at least 90% pure, at least 98% pure, or at least about 99% pure, by weight. The present disclosure is meant to include diastereomers as well as their racemic and resolved, enantiomerically pure forms and pharmaceutically acceptable salts thereof.

The term "unit dosage form," as used herein, refers to physically discrete units suitable as unitary dosages for human and/or animal subjects, each unit containing a predetermined quantity of a compound (e.g., an anti-viral compound, as described herein) calculated in an amount sufficient to produce the desired effect in association with a pharmaceutically acceptable diluent, carrier or vehicle. The specifications for unit dosage forms depend on the particular compound employed, the route and frequency of administration, and the effect to be achieved, and the pharmacodynamics associated with each compound in the host.

A "pharmaceutically acceptable excipient", "pharmaceutically acceptable diluent", "pharmaceutically acceptable carrier", and "pharmaceutically acceptable adjuvant" means an excipient, diluent, carrier, and/or adjuvant that are useful in preparing a pharmaceutical composition that are generally safe, non-toxic and neither biologically nor otherwise undesirable, and include an excipient, diluent, carrier, and adjuvant that are acceptable for veterinary use and/or human pharmaceutical use. "A pharmaceutically acceptable excipient, diluent, carrier and/or adjuvant" as used in the specification and claims includes one or more such excipients, diluents, carriers, and adjuvants.

As used herein, a "pharmaceutical composition" and a "pharmaceutical formulation" are meant to encompass a composition suitable for administration to a subject, such as a mammal, especially a human. In general, a "pharmaceutical composition" or "pharmaceutical formulation" is sterile, and preferably free of contaminants that are capable of eliciting an undesirable response within the subject (e.g., the compound(s) in the pharmaceutical composition is pharmaceutical grade). Pharmaceutical compositions can be designed for administration to subjects or patients in need thereof via a number of different routes of administration including oral, intravenous, buccal, rectal, parenteral, intraperitoneal, intradermal, intracheal, intramuscular, subcutaneous, inhalational and the like.

The terms "therapeutically effective amount" and "an effective amount" are used interchangeably herein and refer to that amount of an agent (which may be referred to as a compound, an inhibitory agent, and/or a drug) being administered that is sufficient to effect the intended application including but not limited to disease treatment. For example, an effective amount of an inhibiting agent will relieve to some extent one or more of the symptoms of the disease, i.e., infection, being treated, and/or that amount that will prevent, to some extent, one or more of the symptoms of the disease, i.e., infection, that the host being treated has or is at risk of developing. The therapeutically effective amount may vary depending upon the intended application (in vitro or in vivo), or the subject and disease condition being treated, e.g., the weight and age of the subject, the severity of the disease condition, the manner of administration and the like, which can readily be determined by one of ordinary skill in the art. The term also applies to a dose that will induce a particular response in target cells, e.g. inhibiting viral replication in a target cell, and inhibiting NS4B binding to viral RNA. The specific dose will vary depending on the particular compounds chosen, the dosing regimen to be followed, whether it is administered in combination with other compounds, timing of administration, the tissue to which it is administered, and the physical delivery system in which it is carried.

"Pharmaceutically acceptable salt" refers to those salts (organic or inorganic) that retain the biological effectiveness and optionally other properties of the free bases. Pharmaceutically acceptable salts can be obtained by reaction with inorganic or organic acids such as hydrochloric acid, hydrobromic acid, sulfuric acid, nitric acid, phosphoric acid, methanesulfonic acid, ethanesulfonic acid, p-toluenesulfonic acid, salicylic acid, malic acid, maleic acid, succinic acid, tartaric acid, citric acid, and the like.

In the event that embodiments of the disclosed agents form salts, these salts are within the scope of the present disclosure. Reference to an agent of any of the formulas herein is understood to include reference to salts thereof, unless otherwise indicated. The term "salt(s)", as employed herein, denotes acidic and/or basic salts formed with inorganic and/or organic acids and bases. In addition, when an agent contains both a basic moiety and an acidic moiety, zwitterions ("inner salts") may be formed and are included within the term "salt(s)" as used herein. Pharmaceutically acceptable (e.g., non-toxic, physiologically acceptable) salts are preferred, although other salts are also useful, e.g., in isolation or purification steps which may be employed during preparation. Salts of the compounds of an agent may be formed, for example, by reacting the agent with an amount of acid or base, such as an equivalent amount, in a medium such as one in which the salt precipitates or in an aqueous medium followed by lyophilization.

Embodiments of the agents that contain a basic moiety may form salts with a variety of organic and inorganic acids. Exemplary acid addition salts include acetates (such as those formed with acetic acid or trihaloacetic acid, for example, trifluoroacetic acid), adipates, alginates, ascorbates, aspartates, benzoates, benzenesulfonates, bisulfates, borates, butyrates, citrates, camphorates, camphorsulfonates, cyclopentanepropionates, digluconates, dodecylsulfates, ethanesulfonates, fumarates, glucoheptanoates, glycerophosphates, hemisulfates, heptanoates, hexanoates, hydrochlorides (formed with hydrochloric acid), hydrobromides (formed with hydrogen bromide), hydroiodides, 2-hydroxyethanesulfonates, lactates, malates (salts formed with malic acid), maleates (formed with maleic acid), ethanesulfonates (formed with ethanesulfonic acid), methanesulfonates (formed with methanesulfonic acid), 2-naphthalenesulfonates, nicotinates, nitrates, oxalates, pectinates, persulfates, 3-phenylpropionates, phosphates (formed with phosphoric acid), picrates, pivalates, propionates, salicylates, succinates, sulfates (such as those formed with sulfuric acid), sulfonates (such as those mentioned herein including those formed with p-toluenesulfonic acid), tartrates, thiocyanates, toluenesulfonates such as tosylates, undecanoates, and the like.

Embodiments of the agents that contain an acidic moiety may form salts with a variety of organic and inorganic bases. Exemplary basic salts include ammonium salts, alkali metal salts such as sodium, lithium, and potassium salts, alkaline earth metal salts such as calcium and magnesium salts, salts with organic bases (for example, organic amines) such as benzathines, dicyclohexylamines, hydrabamines (formed with N,N-bis(dehydroabietyl)ethylenediamine), N-methyl-D-glucamines, N-methyl-D-glucamides, t-butyl amines, and salts with amino acids such as arginine, lysine, and the like.

Basic nitrogen-containing groups may be quaternized with agents such as lower alkyl halides (e.g., methyl, ethyl, propyl, and butyl chlorides, bromides and iodides), dialkyl sulfates (e.g., dimethyl, diethyl, dibutyl, and diamyl sulfates), long chain halides (e.g., decyl, lauryl, myristyl and stearyl chlorides, bromides and iodides), aralkyl halides (e.g., benzyl and phenethyl bromides), and others. Solvates of the agents of the disclosure are also contemplated herein.

To the extent that the disclosed active compounds, and salts thereof, may exist in their tautomeric form, all such tautomeric forms are contemplated herein as part of the present disclosure.

All stereoisomers of the agents, such as those that may exist due to asymmetric carbons on the various substituents, including enantiomeric forms (which may exist even in the absence of asymmetric carbons) and diastereomeric forms, are contemplated within the scope of this disclosure. Individual stereoisomers of the compounds of the disclosure may, for example, be substantially free of other isomers, or may be admixed, for example, as racemates or with all other, or other selected, stereoisomers. The stereogenic centers of the compounds of the present disclosure can have the S or R configuration as defined by the IUPAC 1974 Recommendations.

The term "prodrug" refers to an inactive precursor of an agent that is converted into a biologically active form in vivo. Prodrugs are often useful because, in some situations, they may be easier to administer than the parent compound. They may, for instance, be bioavailable by oral administration whereas the parent compound is not. The prodrug may also have improved solubility in pharmaceutical compositions over the parent drug. A prodrug may be converted into the parent drug by various mechanisms, including enzymatic processes and metabolic hydrolysis. Harper, N.J. (1962). Drug Latentiation in Jucker, ed. Progress in Drug Research, 4:221-294; Morozowich et al. (1977). Application of Physical Organic Principles to Prodrug Design in E. B. Roche ed. Design of Biopharmaceutical Properties through Prodrugs and Analogs, APhA; Acad. Pharm. Sci.; E. B. Roche, ed. (1977). Bioreversible Carriers in Drug in Drug Design, Theory and Application, APhA; H. Bundgaard, ed. (1985) Design of Prodrugs, Elsevier; Wang et al. (1999) Prodrug approaches to the improved delivery of peptide drug, Curr. Pharm. Design. 5(4):265-287; Pauletti et al. (1997). Improvement in peptide bioavailability: Peptidomimetics and Prodrug Strategies, Adv. Drug. Delivery Rev. 27:235-256; Mizen et al. (1998). The Use of Esters as Prodrugs for Oral Delivery of β-Lactam antibiotics, Pharm. Biotech. 11:345-365; Gaignault et al. (1996). Designing Prodrugs and Bioprecursors I. Carrier Prodrugs, Pract. Med. Chem. 671-696; M. Asgharnejad (2000). Improving Oral Drug Transport Via Prodrugs, in G. L. Amidon, P. I. Lee and E. M. Topp, Eds., Transport Processes in Pharmaceutical Systems, Marcell Dekker, p. 185-218; Balant et al. (1990) Prodrugs for the improvement of drug absorption via different routes of administration, Eur. J. Drug Metab. Pharmacokinet, 15(2): 143-53; Balimane and Sinko (1999). Involvement of multiple transporters in the oral absorption of nucleoside analogues, Adv. Drug Delivery Rev., 39(1-3):183-209; Browne (1997). Fosphenyloin (Cerebyx), Clin. Neuropharmacol. 20(1): 1-12; Bundgaard (1979). Bioreversible derivatization of drugs—principle and applicability to improve the therapeutic effects of drugs, Arch. Pharm. Chemi. 86(1): 1-39; H. Bundgaard, ed. (1985) Design of Prodrugs, New York: Elsevier; Fleisher et al. (1996). Improved oral drug delivery: solubility limitations overcome by the use of prodrugs, Adv. Drug Delivery Rev. 19(2): 115-130; Fleisher et al. (1985). Design of prodrugs for improved gastrointestinal absorption by intestinal enzyme targeting, Methods Enzymol. 112: 360-81; Farquhar D, et al. (1983). Biologically Reversible Phosphate-Protective Groups, J. Pharm. Sci., 72(3): 324-325; Han, H. K. et al. (2000). Targeted prodrug design to optimize drug delivery, AAPS PharmSci., 2(1): E6; Sadzuka Y. (2000). Effective prodrug liposome and conversion to active metabolite, Curr. Drug Metab, 1(1):31-48; D. M. Lambert (2000) Rationale and applications of lipids as prodrug carriers, Eur. J. Pharm. Sci., 11 Suppl 2:S15-27; Wang, W. et al. (1999) Prodrug approaches to the improved delivery of peptide drugs. Curr. Pharm. Des., 5(4):265-87.

The term "administration" refers to introducing an agent of the present disclosure into a host. One preferred route of administration of the agents is oral administration. Another preferred route is intravenous administration. However, any route of administration, such as topical, subcutaneous, peritoneal, intraarterial, inhalation, vaginal, rectal, nasal, introduction into the cerebrospinal fluid, or instillation into body compartments can be used.

The term "aliphatic group" refers to a saturated or unsaturated linear or branched hydrocarbon group and encompasses alkyl, alkenyl, and alkynyl groups, for example.

The term "alk" or "alkyl" refers to straight or branched chain hydrocarbon groups having 1 to 12 carbon atoms, preferably 1 to 8 carbon atoms, such as methyl, ethyl, n-propyl, i-propyl, n-butyl, i-butyl, t-butyl, pentyl, hexyl, heptyl, n-octyl, dodecyl, octadecyl, amyl, 2-ethylhexyl, and the like. An alkyl group is optionally substituted, unless stated otherwise, with one or more groups, selected from aryl (optionally substituted), heterocyclo (optionally substituted), carbocyclo (optionally substituted), halo, hydroxy, protected hydroxy, alkoxy (e.g., $C_1$ to $C_7$) (optionally substituted), acyl (e.g., $C_1$ to $C_7$), aryloxy (e.g., $C_1$ to $C_7$) (optionally substituted), alkylester (optionally substituted), arylester (optionally substituted), alkanoyl (optionally substituted), aroyl (optionally substituted), carboxy, protected carboxy, cyano, nitro, amino, substituted amino, (monosubstituted)amino, (disubstituted) amino, protected amino, amido, lactam, urea, urethane, sulfonyl, and the like.

The term "alkenyl" refers to straight or branched chain hydrocarbon groups having 2 to 12 carbon atoms, preferably 2 to 4 carbon atoms, and at least one double carbon to carbon bond (either cis or trans), such as ethenyl. An alkenyl group is optionally substituted, unless stated otherwise, with one or more groups, selected from aryl (including substituted aryl), heterocyclo (including substituted heterocyclo), carbocyclo (including substituted carbocyclo), halo, hydroxy, alkoxy (optionally substituted), aryloxy (optionally substituted), alkylester (optionally substituted), arylester (optionally substituted), alkanoyl (optionally substituted), aroyl (optionally substituted), cyano, nitro, amino, substituted amino, amido, lactam, urea, urethane, sulfonyl, and the like.

The term "alkylene" refers to divalent saturated aliphatic hydrocarbon groups having from 1 to 12 carbon atoms and, in some embodiments, from 1 to 6 carbon atoms. The alkylene groups include branched and straight chain hydrocarbon groups. For example, "$C_1$-$C_6$ alkylene" is meant to include methylene, ethylene, propylene, butylene, 2-methypropylene, pentylene, hexylene, and the like. "Substituted alkylene" refers to an alkylene group having from 1 to 5 and, in some embodiments, 1 to 3 or 1 to 2 substituents selected from aryl (optionally substituted), heteroaryl, heterocyclo (optionally substituted), carbocyclo (optionally substituted), halo, hydroxy, protected hydroxy, alkoxy (e.g., $C_1$ to $C_7$) (optionally substituted), acyl (e.g., $C_1$ to $C_7$), aryloxy (e.g., $C_1$ to $C_7$) (optionally substituted), alkylester (optionally substituted), arylester (optionally substituted), alkanoyl (optionally substituted), aroyl (optionally substituted), carboxy, protected carboxy, cyano, nitro, amino, substituted amino, (monosubstituted)amino, (disubstituted)amino, protected amino, amido, lactam, urea, urethane, sulfonyl, and the like, and includes alkylene groups where geminal hydrogens are substituted with =O moiety.

The term "alkynyl" refers to straight or branched chain hydrocarbon groups having 2 to 12 carbon atoms, preferably 2 to 4 carbon atoms, and at least one triple carbon to carbon bond, such as ethynyl. An alkynyl group is optionally substituted, unless stated otherwise, with one or more groups, selected from aryl (including substituted aryl), heterocyclo (including substituted heterocyclo), carbocyclo (including substituted carbocyclo), halo, hydroxy, alkoxy (optionally substituted), aryloxy (optionally substituted), alkylester (optionally substituted), arylester (optionally substituted), alkanoyl (optionally substituted), aroyl (optionally substituted), cyano, nitro, amino, substituted amino, amido, lactam, urea, urethane, sulfonyl, and the like.

The term "alkoxy" refers to an alkyl group linked to oxygen thus: R—O—. In this function, R represents the alkyl group. An example is the methoxy group $CH_3O$—.

"Organic groups" may be functionalized or otherwise comprise additional functionalities associated with the organic group, such as carboxyl, amino, hydroxyl, and the like, which may be protected or unprotected. For example, the phrase "alkyl group" is intended to include not only pure open chain saturated hydrocarbon alkyl substituents, such as methyl, ethyl, propyl, t-butyl, and the like, but also alkyl substituents bearing further substituents known in the art, such as hydroxy, alkoxy, alkylsulfonyl, halogen atoms, cyano, nitro, amino, carboxyl, and the like. Thus, "alkyl group" includes ethers, esters, haloalkyls, nitroalkyls, carboxyalkyls, hydroxyalkyls, sulfoalkyls, and the like. "Cyano" refers to a —CN substituent.

The terms "halo" and "halogen" refer to the fluoro, chloro, bromo or iodo groups. There can be one or more halogen groups, which can be the same or different. In an embodiment, each halogen can be substituted by one of the other halogens.

The term "haloalkyl" refers to an alkyl group as defined above that is substituted by one or more halogen atoms. The halogen atoms may be the same or different. The term "dihaloalkyl" refers to an alkyl group as described above that is substituted by two halo groups, which may be the same or different. The term "trihaloalkyl" refers to an alkyl group as describe above that is substituted by three halo groups, which may be the same or different. The term "perhaloalkyl" refers to a haloalkyl group as defined above wherein each hydrogen atom in the alkyl group has been replaced by a halogen atom. The term "perfluoroalkyl" refers to a haloalkyl group as defined above wherein each hydrogen atom in the alkyl group has been replaced by a fluoro group.

The term "cycloalkyl" refers to a mono-, bi-, or tricyclic saturated ring that is fully saturated or partially unsaturated. Examples of such a group includes cyclopropyl, cyclobutyl, cyclopentyl, cyclohexyl, cycloheptyl, adamantyl, cyclooctyl, cis- or trans decalin, bicyclo[2.2.1]hept-2-ene, cyclohex-1-enyl, cyclopent-1-enyl, 1,4-cyclooctadienyl, and the like. A cycloalkyl group is optionally substituted, unless stated otherwise, with one or more groups, selected from aryl (including substituted aryl), heterocyclo (including substituted heterocyclo), carbocyclo (including substituted carbocyclo), halo, hydroxy, protected hydroxy, alkoxy (e.g., $C_1$ to $C_7$) (optionally substituted), acyl (e.g., $C_1$ to $C_7$), aryloxy (e.g., $C_1$ to $C_7$) (optionally substituted), alkylester (optionally substituted), arylester (optionally substituted), alkanoyl (optionally substituted), aroyl (optionally substituted), carboxy, protected carboxy, cyano, nitro, amino, substituted amino, (monosubstituted)amino, (disubstituted)amino, protected amino, amido, lactam, urea, urethane, sulfonyl, and the like. The term "(cycloalkyl)alkyl" refers to the above-defined cycloalkyl group substituted by an above defined alkyl group. Examples of such a group include (cyclohexyl)methyl, 3-(cyclopropyl)-n-propyl, 5-(cyclopentyl)hexyl, 6-(adamantyl) hexyl, and the like. A (cycloalkyl)alkyl group is optionally substituted, unless stated otherwise, with one or more groups, selected from alkyl (including substituted alkyl), aryl (including substituted aryl), heterocyclo (including substituted heterocyclo), carbocyclo (including substituted carbocyclo), halo, hydroxy, protected hydroxy, alkoxy (e.g., $C_1$ to $C_7$) (optionally substituted), acyl (e.g., $C_1$ to $C_7$), aryloxy (e.g., $C_1$ to $C_7$) (optionally substituted), alkylester (optionally substituted), arylester (optionally substituted), alkanoyl (optionally substituted), aroyl (optionally substituted), carboxy, protected carboxy, cyano, nitro, amino, substituted amino, (monosubstituted)amino, (disubstituted)amino, protected amino, amido, lactam, urea, urethane, sulfonyl, and the like.

The term "substituted phenyl" refers to a phenyl group substituted with one or more moieties, and in some instances one, two, or three moieties, chosen from the groups consisting of halogen, hydroxy, protected hydroxy, cyano, nitro, trifluoromethyl, $C_1$ to $C_7$ alkyl, $C_1$ to $C_7$ alkoxy, $C_1$ to $C_7$ acyl, $C_1$ to $C_7$ acyloxy, carboxy, oxycarboxy, protected carboxy, carboxymethyl, protected carboxymethyl, hydroxymethyl, protected hydroxymethyl, amino, protected amino, (monosubstituted)amino, protected (monosubstituted)amino, (disubstituted)amino, carboxamide, protected carboxamide, N—($C_1$ to $C_6$ alkyl)carboxamide, protected N—($C_1$ to $C_6$ alkyl)carboxamide, N,N-di($C_1$ to $C_6$ alkyl)carboxamide, trifluoromethyl, N—(($C_1$ to $C_6$ alkyl)sulfonyl)amino, N-(phenylsulfonyl)amino or phenyl, substituted or unsubstituted, such that, for example, a biphenyl or naphthyl group results.

Examples of the term "substituted phenyl" include a mono- or di(halo)phenyl group such as 2, 3 or 4-chlorophenyl, 2,6-dichlorophenyl, 2,5-dichlorophenyl, 3,4-dichlorophenyl, 2, 3 or 4-bromophenyl, 3,4-dibromophenyl, 3-chloro-4-fluorophenyl, 2, 3 or 4-fluorophenyl and the like; a mono or di(hydroxy)phenyl group such as 2, 3, or 4-hydroxyphenyl, 2,4-dihydroxyphenyl, the protected-hydroxy derivatives thereof and the like; a nitrophenyl group such as 2, 3, or 4-nitrophenyl; a cyanophenyl group, for example, 2, 3 or 4-cyanophenyl; a mono- or di(alkyl)phenyl group such as 2, 3, or 4-methylphenyl, 2,4-dimethylphenyl, 2, 3 or 4-(isopropyl)phenyl, 2, 3, or 4-ethylphenyl, 2, 3 or 4-(n-propyl)

phenyl and the like; a mono or di(alkoxy)phenyl group, for example, 2,6-dimethoxyphenyl, 2, 3 or 4-(isopropoxy)phenyl, 2, 3 or 4-(t-butoxy)phenyl, 3-ethoxy-4-methoxyphenyl and the like; 2, 3 or 4-trifluoromethylphenyl; a mono- or dicarboxyphenyl or (protected carboxy)phenyl group such as 2, 3 or 4-carboxyphenyl or 2,4-di(protected carboxy)phenyl; a mono- or di(hydroxymethyl)phenyl or (protected hydroxymethyl)phenyl such as 2, 3 or 4-(protected hydroxymethyl)phenyl or 3,4-di(hydroxymethyl)phenyl; a mono- or di(aminomethyl)phenyl or (protected aminomethyl)phenyl such as 2, 3 or 4-(aminomethyl)phenyl or 2,4-(protected aminomethyl)phenyl; or a mono- or di(N-(methylsulfonylamino))phenyl such as 2, 3 or 4-(N-(methylsulfonylamino))phenyl. Also, the term "substituted phenyl" represents disubstituted phenyl groups wherein the substituents are different, for example, 3-methyl-4-hydroxyphenyl, 3-chloro-4-hydroxyphenyl, 2-methoxy-4-bromophenyl, 4-ethyl-2-hydroxyphenyl, 3-hydroxy-4-nitrophenyl, 2-hydroxy-4-chlorophenyl and the like.

The term "(substituted phenyl)alkyl" refers to one of the above substituted phenyl groups attached to one of the above-described alkyl groups. Examples of (substituted phenyl)alkyl include such groups as 2-phenyl-1-chloroethyl, 2-(4'-methoxyphenyl)ethyl, 4-(2',6'-dihydroxy phenyl)n-hexyl, 2-(5'-cyano-3'-methoxyphenyl)n-pentyl, 3-(2',6'-dimethylphenyl)n-propyl, 4-chloro-3-aminobenzyl, 6-(4'-methoxyphenyl)-3-carboxy(n-hexyl), 5-(4'-aminomethylphenyl)-3-(aminomethyl)n-pentyl, 5-phenyl-3-oxo-n-pent-1-yl, (4-hydroxynapth-2-yl)methyl and the like.

The terms "ar" or "aryl" refer to aromatic homocyclic (i.e., hydrocarbon) mono-, bi- or tricyclic ring-containing groups preferably having 6 to 12 members such as phenyl, naphthyl and biphenyl. An aryl group is optionally substituted, unless stated otherwise, with one or more groups, selected from alkyl (optionally substituted alkyl), alkenyl (optionally substituted), aryl (optionally substituted), heterocyclo (optionally substituted), halo, hydroxy, alkoxy (optionally substituted), aryloxy (optionally substituted), alkanoyl (optionally substituted), aroyl, (optionally substituted), alkylester (optionally substituted), arylester (optionally substituted), cyano, nitro, amino, substituted amino, amido, lactam, urea, urethane, sulfonyl, and the like. Optionally, adjacent substituents, together with the atoms to which they are bonded, form a 3- to 7-member ring.

The term "heteroaryl" refers to optionally substituted five-membered or six-membered rings that have 1 to 4 heteroatoms, such as oxygen, sulfur and/or nitrogen atoms, either alone or in conjunction with, additional nitrogen, sulfur or oxygen ring atoms. Furthermore, the above optionally substituted five-membered or six-membered rings can optionally be fused to an aromatic 5-membered or 6-membered ring system. For example, the rings can be optionally fused to an aromatic 5-membered or 6-membered ring system such as a benzene, pyridine or a triazole system.

The following ring systems are nonlimiting examples of the heterocyclic (whether substituted or unsubstituted) radicals denoted by the term "heteroaryl": thienyl, furyl, pyrrolyl, imidazolyl, pyrazolyl, oxazolyl, isoxazolyl, thiazolyl, isothiazolyl, triazolyl, thiadiazolyl, oxadiazolyl, tetrazolyl, thiatriazolyl, oxatriazolyl, pyridyl, pyrimidyl, pyrazinyl, pyridazinyl, oxazinyl, triazinyl, thiadiazinyl tetrazolo, 1,5-[b]pyridazinyl and purinyl, as well as benzo-fused derivatives, for example, benzoxazolyl, benzthiazolyl, benzimidazolyl and indolyl.

A heteroaryl group is optionally substituted, unless stated otherwise, with one or more groups, selected from one to three halo, trihalomethyl, amino, protected amino, amino salts, mono-substituted amino, di-substituted amino, carboxy, protected carboxy, carboxylate salts, hydroxy, protected hydroxy, salts of a hydroxy group, lower alkoxy, lower alkylthio, alkyl (optionally, substituted), cycloalkyl (optionally substituted), (cycloalkyl)alkyl (optionally substituted), phenyl (optionally substituted), phenylalkyl (optionally substituted phenylalkyl). Substituents for the heteroaryl group are as heretofore defined, or in the case of trihalomethyl, can be trifluoromethyl, trichloromethyl, tribromomethyl, or triiodomethyl. As used in conjunction with the above substituents for heteroaryl rings, "lower alkoxy" means a $C_1$ to $C_4$ alkoxy group, similarly, "lower alkylthio" means a $C_1$ to $C_4$ alkylthio group.

The terms "heterocycle", "heterocyclic", "heterocyclic group" or "heterocyclo" refer to fully saturated or partially unsaturated or completely unsaturated, including aromatic ("heteroaryl") or nonaromatic cyclic groups (for example, 3- to 13-member monocyclic, 1-5 to 17-member bicyclic, or 10- to 20-member tricyclic ring systems, preferably containing a total of 3 to 10 ring atoms) which have at least one heteroatom in at least one carbon atom-containing ring. Each ring of the heterocyclic group containing a heteroatom may have 1, 2, 3 or 4 heteroatoms selected from nitrogen atoms, oxygen atoms and/or sulfur atoms, where the nitrogen and sulfur heteroatoms may optionally be oxidized and the nitrogen heteroatoms may optionally be quaternized. The heterocyclic group may be attached at any heteroatom or carbon atom of the ring or ring system. An N-attached heterocyclo is a heterocyclo moiety wherein the heterocyclo moiety is attached to a compound, e.g. a compound of Formula I through a nitrogen that forms part of the heterocyclo ring. Non-limiting examples of N—attached heterocyclo include but are not limited to

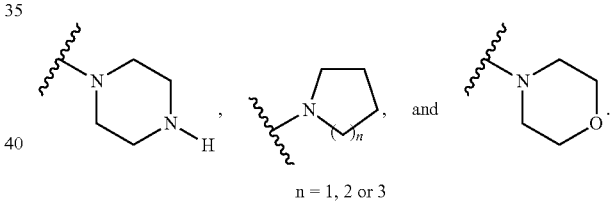

n = 1, 2 or 3

A C-attached heterocyclo is a heterocyclo moiety wherein the heterocyclo moiety is attached to a compound, e.g., a compound of formula II-a, b, or c through a carbon that forms part of the heterocyclo ring. Non-limiting examples include

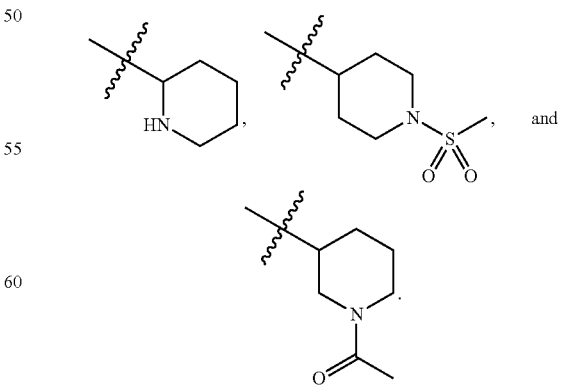

The rings of multi-ring heterocycles may be fused, bridged and/or joined through one or more spiro unions.

Exemplary monocyclic heterocyclic groups include pyrrolidinyl, pyrrolyl, pyrazolyl, oxetanyl, pyrazolinyl, imidazolyl, imidazolinyl, imidazolidinyl, oxazolyl, oxazolidinyl, isoxazolinyl, isoxazolyl, thiazolyl, thiadiazolyl, thiazolidinyl, isothiazolyl, isothiazolidinyl, furyl, tetrahydrofuryl, thienyl, oxadiazolyl, piperidinyl, piperazinyl, 2-oxopiperazinyl, 2-oxopiperidinyl, 2-oxopyrrolodinyl, 2-oxoazepinyl, azepinyl, 4-piperidonyl, pyridyl, pyrazinyl, pyrimidinyl, pyridazinyl, triazinyl, tetrahydropyranyl, tetrazoyl, triazolyl, morpholinyl, thiamorpholinyl, thiamorpholinyl sulfoxide, thiamorpholinyl sulfone, 1,3-dioxolane and tetrahydro-1,1-dioxothienyl, and the like.

Exemplary bicyclic heterocyclic groups include indolyl, benzothiazolyl, benzoxazolyl, benzothienyl, quinuclidinyl, quinolinyl, tetra-hydroisoquinolinyl, isoquinolinyl, benzimidazolyl, benzopyranyl, indolizinyl, benzofuryl, benzofuranly, dihydrobenzofuranyl, chromonyl, coumarinyl, benzodioxolyl, dihydrobenzodioxolyl, benzodioxinyl, cinnolinyl, quinoxalinyl, indazolyl, pyrrolopyridyl, furopyridinyl (such as furo[2,3-c]pyridinyl, furo[3,2-b]pyridinyl, or furo[2,3-b]pyridinyl), dihydroisoindolyl, dihydroquinazolinyl (such as 3,4-dihydro-4-oxo-quinazolinyl), tetrahydroquinolinyl, azabicycloalkyls (such as 6-azabicyclo[3.2.1]octane), azaspiroalkyls (such as 1,4 dioxa-8-azaspiro[4.5]decane), imidazopyridinyl (such as imidazo[1,5-a]pyridin-3-yl), triazolopyridinyl (such as 1,2,4-triazolo[4,3-a]pyridin-3-yl), and hexahydroimidazopyridinyl (such as 1,5,6,7,8,8a-hexahydroimidazo[1,5-a]pyridin-3-yl), and the like.

Exemplary tricyclic heterocyclic groups include carbazolyl, benzidolyl, phenanthrolinyl, acridinyl, phenanthridinyl, xanthenyl and the like.

A heterocyclo group is optionally substituted, unless stated otherwise, with one or more groups, selected from alkyl (including substituted alkyl), alkenyl, oxo, aryl (including substituted aryl), heterocyclo (including substituted heterocyclo), carbocyclo (optionally substituted), halo, hydroxy, alkoxy (optionally substituted), aryloxy (optionally substituted), alkanoyl (optionally substituted), aroyl (optionally substituted), alkylester (optionally substituted), arylester (optionally substituted), cyano, nitro, amido, amino, substituted amino, lactam, urea, urethane, sulfonyl, and the like where optionally one or more pair of substituents together with the atoms to which they are bonded form a 3- to 7-member ring.

The term "alkanoyl" refers to an alkyl group (which may be optionally substituted as described above) linked to a carbonyl group (i.e. —C(O)-alkyl). Similarly, the term "aroyl" refers to an aryl group (which may be optionally substituted as described above) linked to a carbonyl group (i.e., —C(O)-aryl).

The term "(monosubstituted)amino" refers to an amino group with one substituent chosen from the group consisting of phenyl, substituted phenyl, alkyl (including substituted alkyl), $C_1$ to $C_4$ acyl, $C_2$ to $C_7$ alkenyl (including $C_2$ to $C_7$ substituted alkenyl), $C_2$ to $C_7$ alkynyl, $C_7$ to $C_{16}$ alkylaryl (including $C_7$ to $C_{16}$ substituted alkylaryl), and heteroaryl group. The (monosubstituted) amino can additionally have an amino-protecting group as encompassed by the term "protected (monosubstituted)amino." The term "(disubstituted) amino" refers to amino groups with two substituents chosen from the group consisting of phenyl, substituted phenyl, alkyl, substituted alkyl, $C_1$ to $C_7$ acyl, $C_2$ to $C_7$ alkenyl, $C_2$ to $C_7$ alkynyl, $C_7$ to $C_{16}$ alkylaryl, $C_7$ to $C_{16}$ substituted alkylaryl and heteroaryl. The two substituents can be the same or different.

The term "heteroaryl(alkyl)" refers to an alkyl group as defined above, substituted at any position by a heteroaryl group, as above defined.

"Isosteres" are different atoms, molecules, or ions that have different molecular formulae but have similar or identical outer shell electron arrangements and also have similar properties (e.g., pharmacological properties (e.g., pharmacokinetic and pharmacodynamic)).

"Moiety" refers to a specific segment or functional group of a molecule. Chemical moieties are often recognized chemical entities embedded in or appended to a molecule.

"Nitro" refers to the —$NO_2$ radical.

"Oxa" refers to the —O— radical.

"Oxo" refers to the =O radical.

"Sulfonyl" refers to the groups: —$S(O_2)$—H, —$S(O_2)$-(alkyl), —$S(O_2)$-(cycloalkyl), —$S(O_2)$-(amino), —$S(O_2)$-(aryl), —$S(O_2)$-(heteroaryl), and —$S(O_2)$-(heterocycloalkyl).

"Sulfonamidyl" or "sulfonamido" refers to a —$S(O)_2$—NRR radical, where each R is selected independently from the group consisting of hydrogen, alkyl, cycloalkyl, aryl, heteroaryl (bonded through a ring carbon) and heteroalicyclic (bonded through a ring carbon). The R groups in —NRR of the —$S(O)_2$—NRR radical may be taken together with the nitrogen to which it is attached to form a 4-, 5-, 6-, or 7-membered ring (—$S(O_2)$-(heterocycloalkyl). In some embodiments, it is a $C_1$-$C_{10}$ sulfonamido, wherein each R in sulfonamido contains I carbon, 2 carbons, 3 carbons, or 4 carbons total. A sulfonamido group is optionally substituted by one or more of the substituents described herein for alkyl, cycloalkyl, aryl, heteroaryl respectively. A "sulfone" refers to a —$S(O_2)$-(alkyl), —$S(O_2)$-(aryl), —$S(O_2)$-(heteroaryl), or —$S(O_2)$-(heterocycloalkyl) (when the sulfone group is attached to a carbon atom in the heterocycloalkyl). A sulfonamido group is optionally substituted by one or more of the substituents described herein for alkyl, cycloalkyl, aryl, and heteroaryl.

The terms "solvent," "organic solvent," and "inert solvent" each mean a solvent inert under the conditions of the reaction being described. Nonlimiting examples include benzene, toluene, acetonitrile, tetrahydrofuran ("THF"), dimethylformamide ("DMF"), chloroform, methylene chloride (or dichloromethane), diethyl ether, methanol, N-methylpyrrolidone ("NMP"), pyridine and the like.

The term "protecting group" refers to chemical moieties that block some or all reactive moieties of a compound and prevent such moieties from participating in certain chemical reactions until the protective group is removed, for example, those moieties listed and described in T. W. Greene, P. G. M. Wuts, Protective Groups in Organic Synthesis, 3rd ed. John Wiley & Sons (1999). It may be advantageous, where different protecting groups are employed, that each (different) protective group be removable by a different means. Protective groups that are cleaved under totally disparate reaction conditions allow differential removal of such protecting groups. For example, protective groups can be removed by acid, base, and hydrogenolysis. Groups such as trityl, dimethoxytrityl, acetal and tert-butyldimethylsilyl are acid labile and may be used to protect carboxy and hydroxy reactive moieties in the presence of amino groups protected with Cbz groups, which are removable by hydrogenolysis, and Fmoc groups, which are base labile. Carboxylic acid moieties may be blocked with base labile groups such as, without limitation, methyl, or ethyl, and hydroxy reactive moieties may be blocked with base labile groups such as acetyl in the presence of amines blocked with acid labile groups such as tert-butyl carbamate or with carbamates that are both acid and base stable but hydrolytically removable.

In an embodiment, the term "ring" can refer to a chemical moiety having a ring structure comprising 3 to 10 carbon atoms in which one or more carbon atoms may be optionally substituted with a heteroatom, such as N, O, or S. A ring may or may not be aromatic and thus may be completely unsaturated, completely saturated, or partially unsaturated; and a ring may refer to a ring within a fused system or an unfused ring. Unless otherwise stated, this definition of "ring" does not modify other definitions of rings provided herein.

As used herein, the following terms have the meanings ascribed to them unless specified otherwise. In this disclosure, "comprises," "comprising," "containing" and "having" and the like can have the meaning ascribed to them in U.S. patent law and can mean "includes," "including," and the like; "consisting essentially of" or "consists essentially" or the like, when applied to methods and compositions encompassed by the present disclosure refers to compositions like those disclosed herein, but which may contain additional composition components or method steps. Such additional composition components or method steps, etc., however, do not materially affect the basic and novel characteristic(s) of the compositions or methods, compared to those of the corresponding compositions or methods disclosed herein. "Consisting essentially of" or "consists essentially" or the like, when applied to methods and compositions encompassed by the present disclosure have the meaning ascribed in U.S. patent law and the term is open-ended, allowing for the presence of more than that which is recited so long as basic or novel characteristics of that which is recited is not changed by the presence of more than that which is recited, but excludes prior art embodiments.

B.

Aspects and embodiments of the present invention(s) provides methods and compositions for treatment (including prophylactic treatment) of infection by a virus that encodes NS4B. Such virus includes any virus of the Flaviviridae family encompassing e.g., flaviviruses, pestiviruses and hepatitis C viruses. Other NS4B encoding viruses include yellow fever virus (YFV); Dengue virus, including Dengue types 1-4; Japanese Encephalitis virus; Murray Valley Encephalitis virus; St. Louis Encephalitis virus; West Nile virus; tick-borne encephalitis virus; Kunjin virus; Central European encephalitis virus; Russian spring-summer encephalitis virus; Powassan virus; Kyasanur Forest disease virus; Omsk hemorrhagic fever virus; and their respective genotypes as well as subgenotypes. The subject methods and compositions are particularly useful for treating or prophylactically treating HCV, including one or more genotypes 1, 2, 3, 4, 5, 6, and the like, as well as subtypes of an HCV genotype (e.g., 1a, 1b, 2a, 2b, 3a, and the like).

In one embodiment, the method of treating such viral infection comprises administering to a subject infected with a virus from the Flaviviridae family, an effective amount of an isostere of a benzoimidazole core structure, or a pharmaceutically acceptable salt, an isomer, a tautomer or a prodrug thereof. In one embodiment, the isostere is an indazole.

In one aspect, the subject method is effective in reducing viral load in the infected subject by e.g., at least about 5%, 10%, 15%, 20%, 25%, 30%, 35%, 40%, 45%, 50%, 60%, 70%, 80%, 90%, 95% or even higher as compared to the level of viral load present in the subject prior to such treatment. Without being bound by any particular theory, the reduction in viral load can be effected, in whole or in part, by reducing binding of NS4B polypeptide to the viral genome. In the case of HCV, a decrease in viral load upon administering a compound of the present invention can be attributable to, in part, a decrease in binding of NS4B polypeptide to HCV negative strand RNA, e.g., at a site on the 3'UTR.

The subject methods can also utilize one or more other isosteres, including, but not limited to, H1 receptor antagonists that share structural similarity with clemizole and exhibit anti-viral activity. Illustrative H1 receptor antagonists that share structural similarity with clemizole include, but are not limited to, the compounds in the classes known as alcoholamines (e.g., diphenhydramine, carbinoxamine, and clemastine), ethylenediamines (e.g., mepyramine and tripelennamine (clemizole is in this class)), alkylamines (e.g., triprolidine and chlorpheniramine), piperazines (e.g., meclizine and homchlorcyclizine), and phenothiazines (e.g., promethazine).

The subject treatment methods can also employ prodrugs of the compounds provided herein. Exemplary prodrugs can be activated by liver enzymes (e.g., cyclic-1,3-propanyl esters substituted with groups that promote an oxidative cleavage reaction by CYP3A, and the like.). These modifications can render the compounds of the present invention inactive or less active until it reaches the liver (see, Current Opinion in Investigational Drugs 2006 Vol 7 No 2, 109-117; *J. Med. Chem.* 2008, 51, 2328-2345; and Nucleosides, Nucleotides, and Nucleic Acids, 24 (5-7):375-381, (2005) each of which is incorporated herein by reference for the corresponding discussion).

In one embodiment, an exemplary indazole compound has the structure of Formula II-a or Formular II-b:

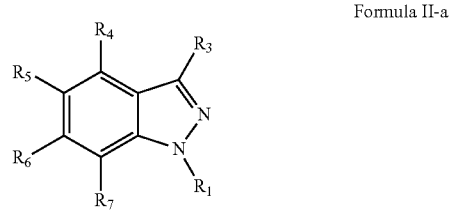

Indazole core

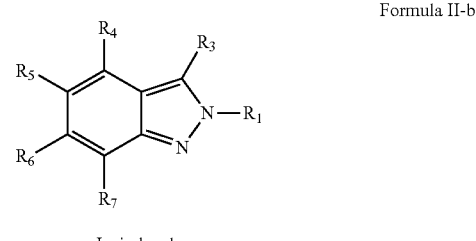

Isoindazole

In one embodiment, for the indazole compounds of Formula II-a or II-b, $R_1$ is —H or

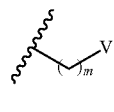

m = 0, 1, 2 wherein V is selected from alkyl, cycloalkyl, heterocyclo, aryl or heteroaryl.

In another embodiment, for the compounds of Formula II-a or II-b, $R_1$ is

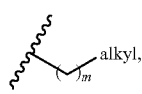

m = 0, 1, 2 wherein the alkyl moiety is an unsubstituted or a substituted. The alkyl moiety forming part (m=1 or 2) or all (m=0) of $R_1$, is branched or unbranched. The alkyl moiety of $R_1$ includes, but is not limited to, methyl, ethyl, n-propyl, iso-propyl, n-butyl, iso-butyl, tert-butyl, n-pentyl, iso-pentyl, n-hexyl, septyl, heptyl, nonyl, and decyl.

In yet another embodiment, $R_1$ is

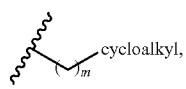

n = 0, 1, 2 wherein the cycloalkyl moiety is unsubstituted or substituted. The cycloalkyl moiety forming part (m=1 or 2) or all (m=0) of $R_1$, includes, but is not limited to, cyclopropyl, cyclobutyl, cyclopentyl and cyclohexyl. Nonlimiting exemplary $R_1$ include the following formulae:

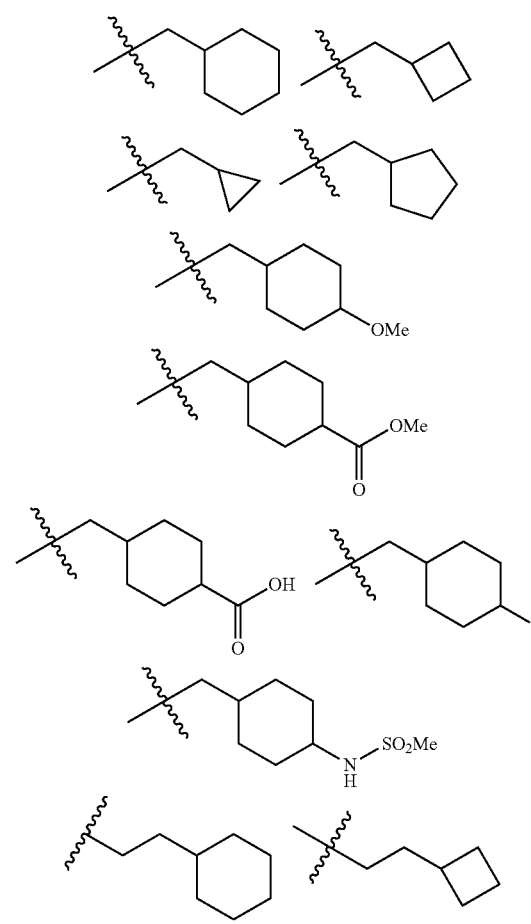

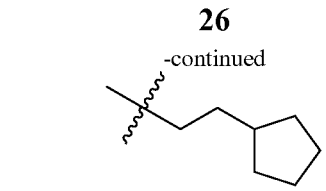

-continued

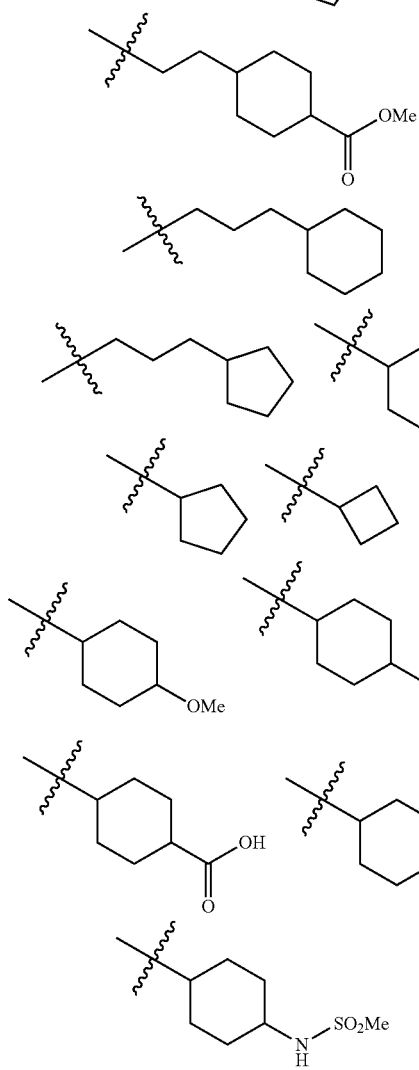

The invention further provides compound of Formula II-a or II-b, wherein $R_1$ is of the formula:

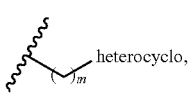

m = 0, 1, 2 and wherein the heterocyclo moiety is unsubstituted or substituted. The heterocyclo moiety forming part (m=1 or 2) or all (m=0) of $R_1$, includes, but is not limited to, azetidinyl, pyrrolidinyl, morpholinyl, piperidinyl, or piperazinyl. An N—attached heterocyclo is a heterocyclo moiety wherein the heterocyclo moiety is attached to the compound of formula II-a or b through a nitrogen that forms part of the heterocyclo ring. Non-limiting N—attached heterocyclo include, but are not limited to,

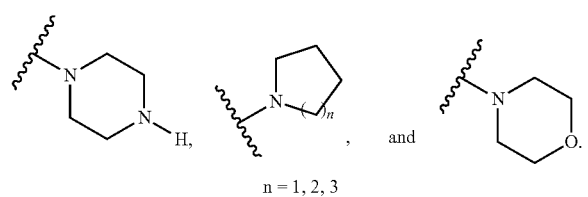

n = 1, 2, 3

In some embodiments, an N— attached heterocyclo is a moiety having the following formula:

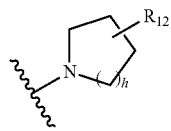

wherein h is 1, 2, or 3, and $R_{12}$ is hydrogen, hydroxy, alkoxy, alkyl, oxo, —$(CH_2)_n$—OH, —C(O)alkyl, —C(O)$_2$alkyl —C(O)aryl, or —SO$_2$alkyl. Examples include, but are not limited to,

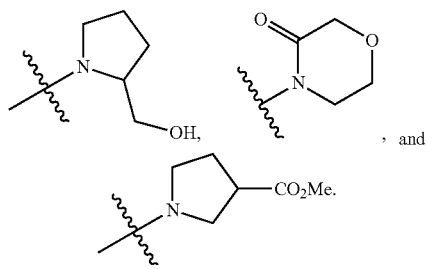

In some embodiments, a C-attached heterocyclo is a heterocyclo moiety wherein the heterocyclo moiety is attached to the compound of formula II-a or b through a carbon that forms part of the heterocyclo ring. Non-limiting examples include

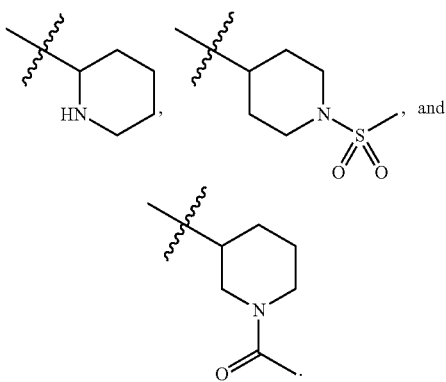

In some embodiments, a C— attached heterocyclo is a moiety of the following formula:

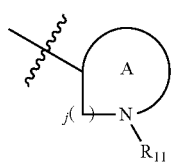

j is 0, 1, or 2 wherein $R_{11}$ is hydrogen, —C(O)alkyl, —C(O)aryl, —C(O)NH$_2$, —C(O)NHalkyl, —C(O)N(alkyl)$_2$, —SO$_2$alkyl, —SO$_2$aryl, —SO$_2$NH$_2$, —SO$_2$NHalkyl, or —SO$_2$N(alkyl)$_2$; ring A is a 5-, 6-, or 7-membered ring, and j is 0, 1, or 2. Examples include, but are not limited to,

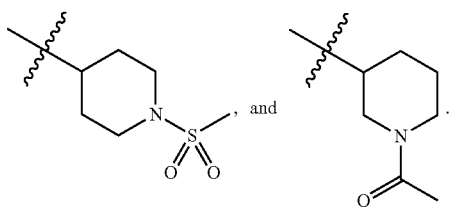

Non-limiting exemplary $R_1$ include the following formulae:

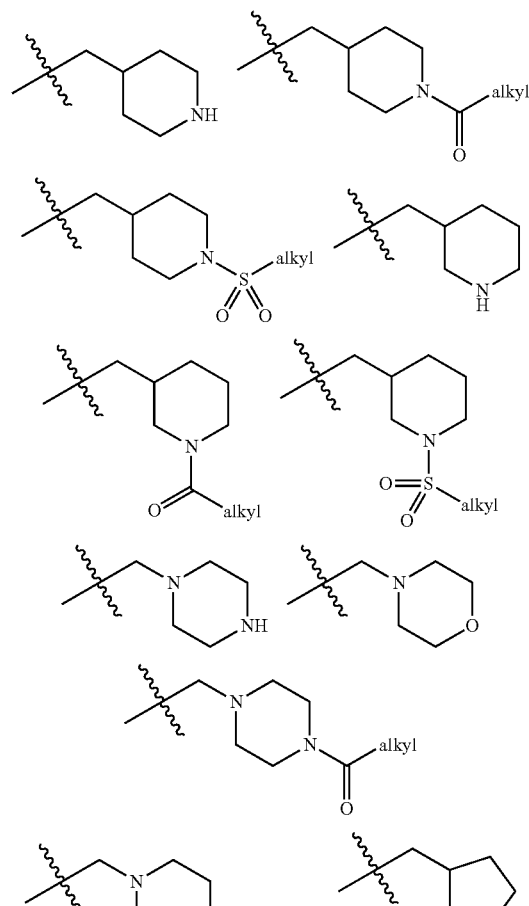

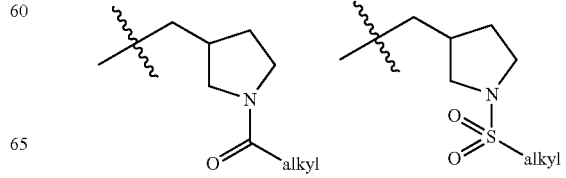

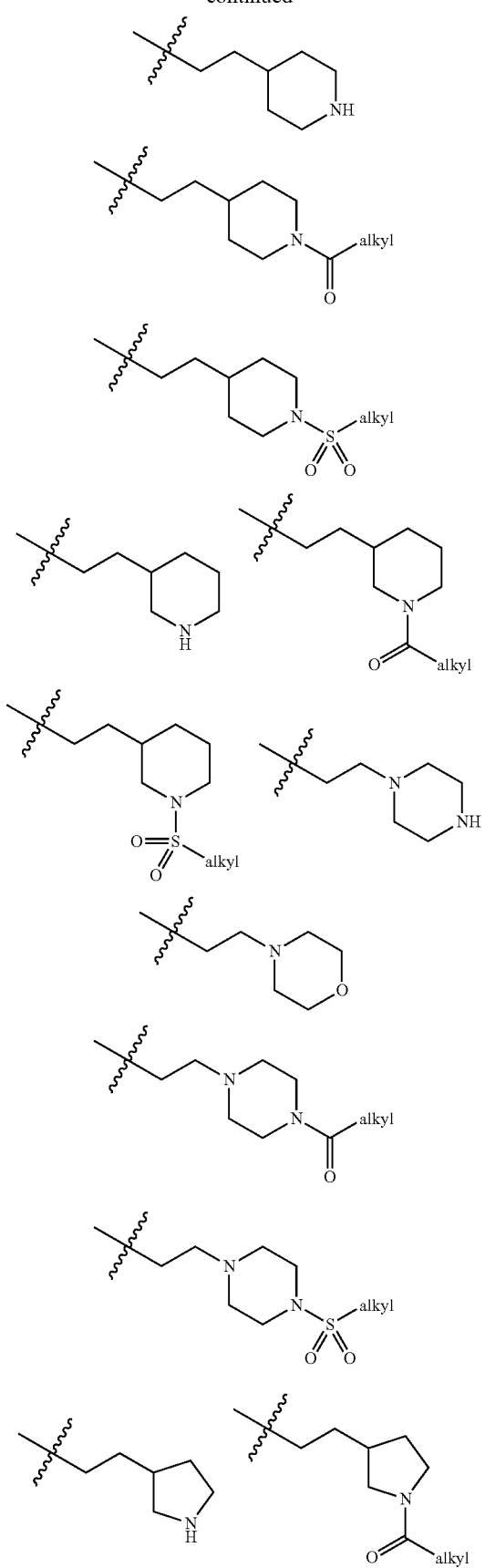
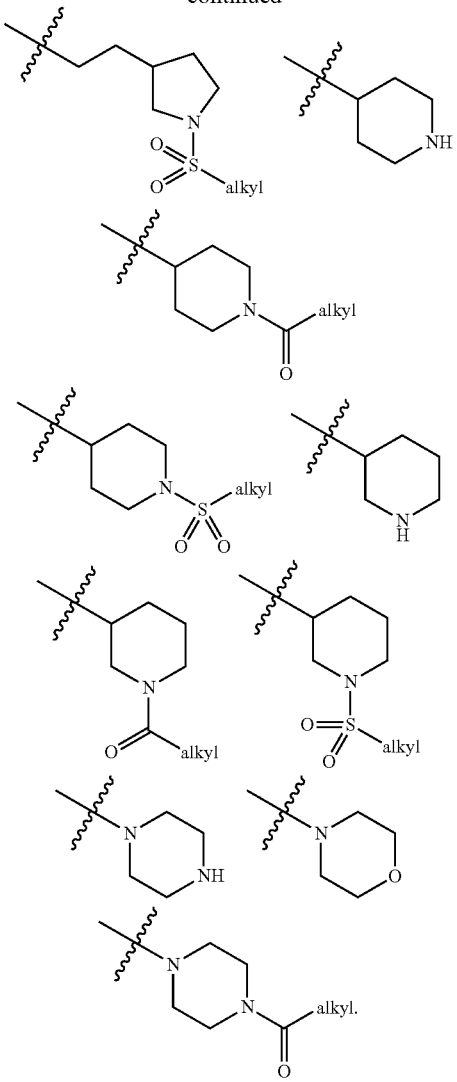

In the above formulae, alkyl includes, but is not limited to, methyl, ethyl, n-propyl, iso-propyl, n-butyl, iso-butyl, tert-butyl, n-pentyl, iso-pentyl, n-hexyl, septyl, heptyl, nonyl, and decyl.

In yet other embodiments, $R_1$ of Formula II-a or II-b is

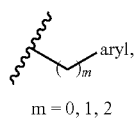

m = 0, 1, 2 wherein the aryl moiety is unsubstituted or substituted. The aryl moiety forming part (m=1 or 2) or all (m=0) of $R_1$, includes, but is not limited to, phenyl, naphthyl, and fluorenyl.

In some embodiments, the aryl is one of the following moieties:

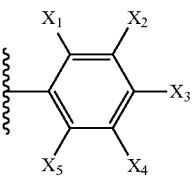

wherein $X_1$-$X_5$ are each independently selected from the group consisting of: —H, -alkyl, —Br, —Cl, —F, —O-alkyl,

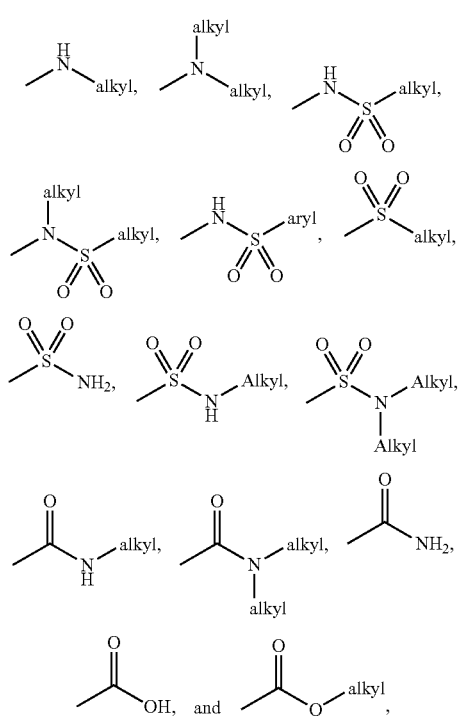
Non-limiting exemplary $R_1$ include the following formulae:
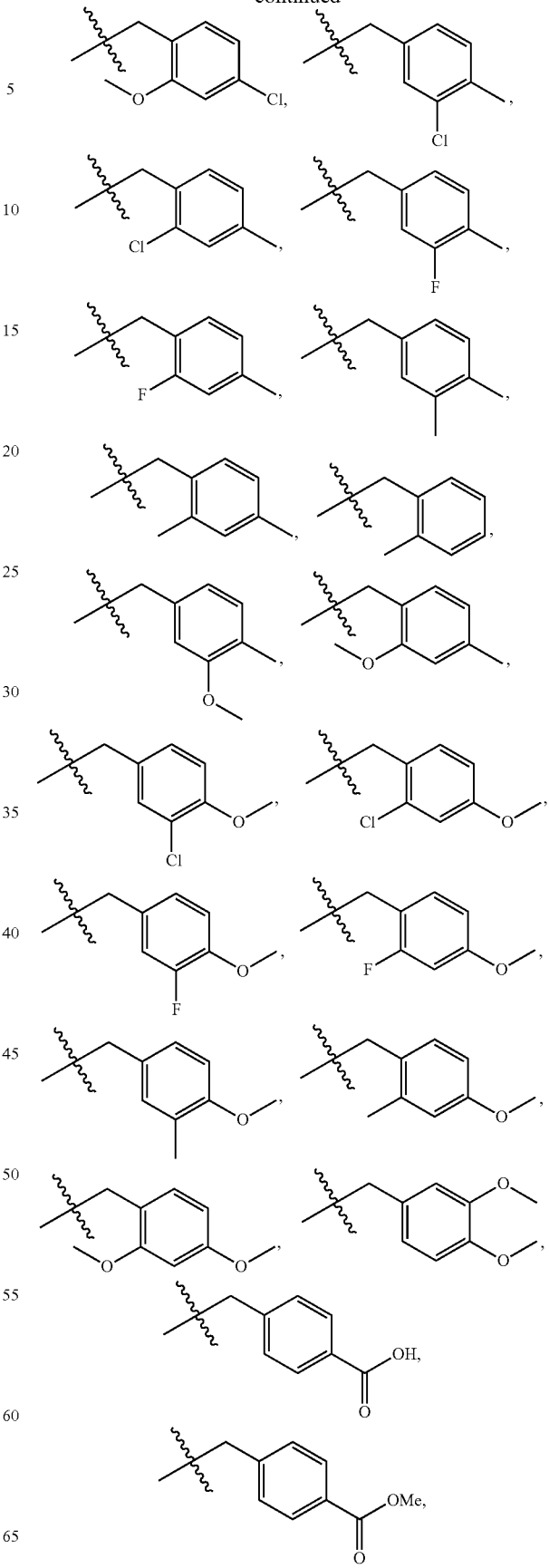

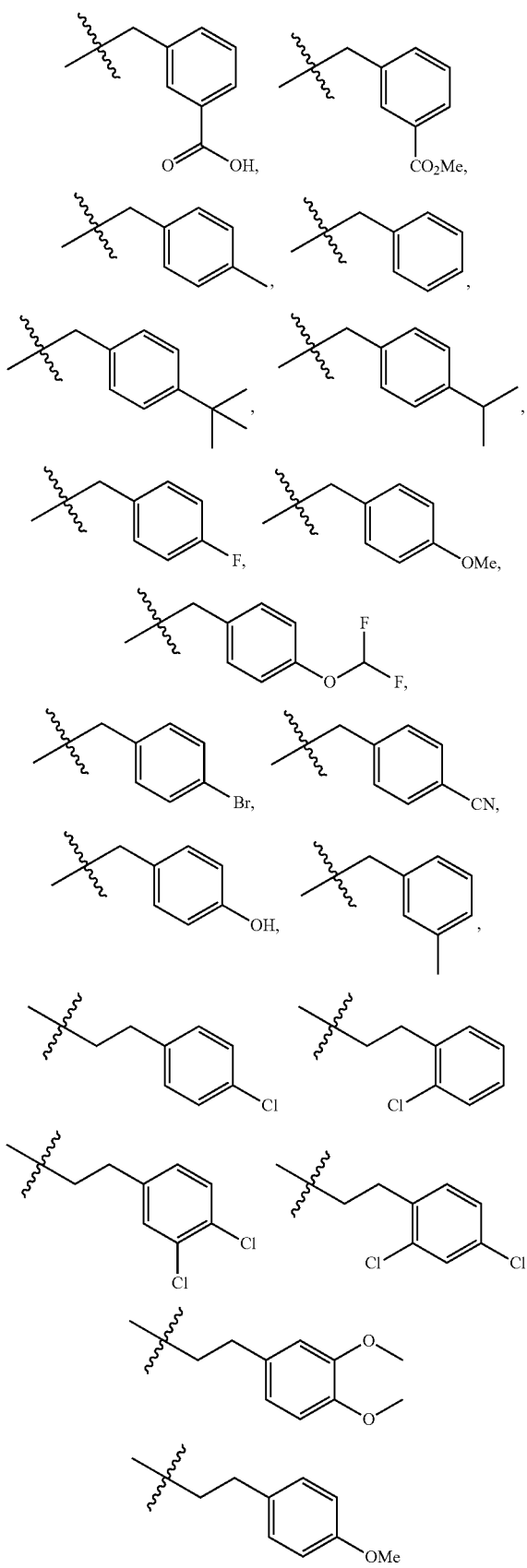

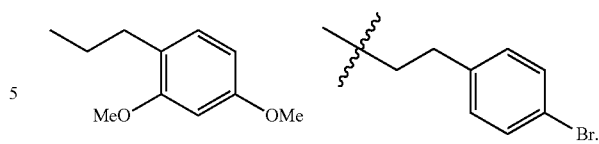

Additionally, R₁ of Formula II-a or II-b can be

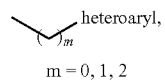

wherein the heteroaryl moiety is unsubstituted or substituted. In some embodiments, the heteroaryl moiety is a monocylic 5 membered heteroaryl. Monocyclic heteroaryl includes, but is not limited to, pyrrolyl, imidazolyl, thiazolyl, and pyrazolyl.

Alternatively, when $R_1$ is

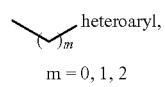

heteroaryl may be a six membered hetereoaryl moiety. The six membered heteroaryl moiety includes, but is not limited to, 2-pyridyl, 3-pyridyl, 4-pyridyl, pyrimidinyl, pyrazinyl, or trianzinyl.

In some embodiments, the $R_1$ heteroaryl is

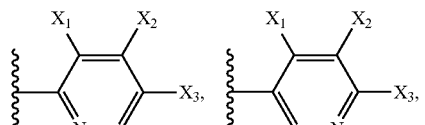

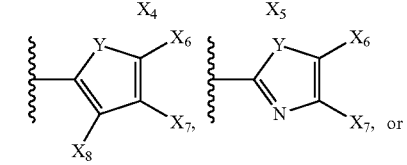

wherein $X_1$-$X_5$ are each independently selected from the group consisting of: —H, -alkyl, —I, —Br, —Cl, —F, —O-alkyl,

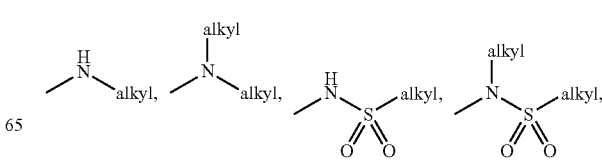

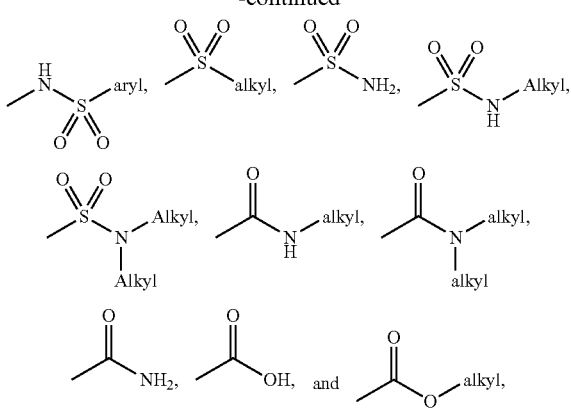

Y is selected from the group consisting of: —O—, —S—, —NH—, —N-alkyl, and —N-acyl; $X_6$ is selected from the group consisting of: —H, —CH$_3$, —I, —Cl, —F, CF$_3$ and —OCH$_3$; and $X_7$ and $X_8$ are independently selected from the group consisting of: H and CH$_3$.

Non-limiting examples of $R_1$ include the following formulae:

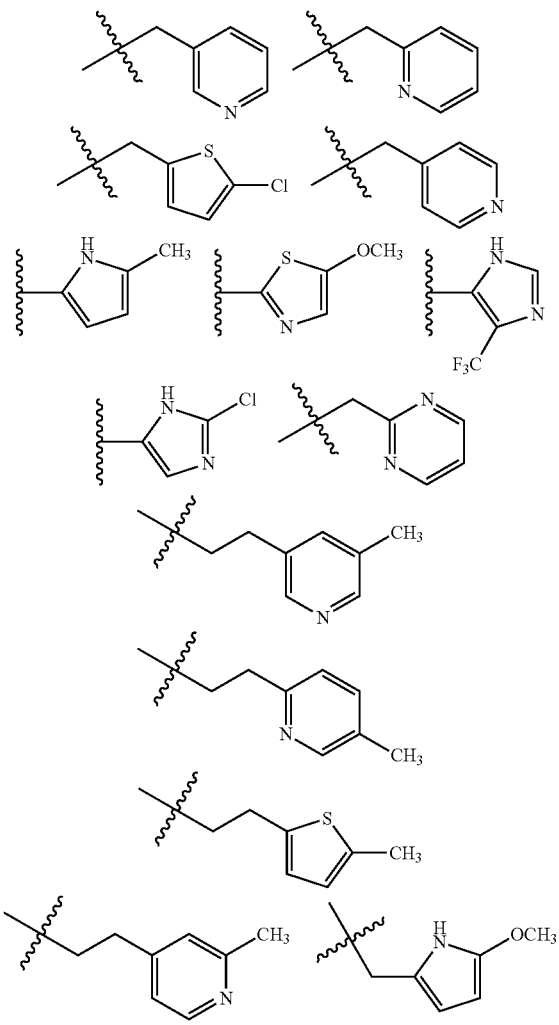
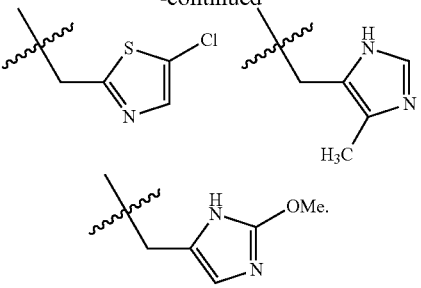

The alkyl, cycloalkyl, heterocyclo, aryl or heteroaryl moiety of $R_1$ may be substituted by one or more substituents selected from the group consisting of alkyl, aryl, heterocyclo, carbocyclo, halo, hydroxy, protected hydroxy, alkoxy, acyl, aryloxy, alkylester, arylester, alkanoyl, aroyl, carboxy, protected carboxy, cyano, nitro, amino, substituted amino, (monosubstituted)amino, (disubstituted)amino, protected amino, amido, lactam, urea, urethane, and sulfonyl.

In various embodiments of the compounds of Formula II-a or II-b, $R_3$ is —H, —OH, —O(CH$_2$)$_n$X, or —(CH$_2$)$_n$X, wherein n is 1, 2, 3, or 4, and X is —NH$_2$, —NH(alkyl), —N(alkyl)$_2$, —OH, —O-alkyl, —O-aryl, —SO$_2$(alkyl), —SO$_2$ NH$_2$, —SO$_2$ NH(alkyl), NHSO$_2$(alkyl), heteroaryl, N-attached heterocyclo, or C-attached heterocyclo. In some embodiments, $R_3$ is —H or —OH. In other embodiments, $R_3$ is —O(CH$_2$)$_n$X, or —(CH$_2$)$_n$X, wherein X is —NH$_2$. Non limiting
examples include: —OCH$_2$CH$_2$ NH$_2$ and —CH$_2$CH$_2$ NH$_2$. In yet other embodiments, $R_3$ is —O(CH$_2$)$_n$X, or —(CH$_2$)$_n$X, wherein X is —NH(alkyl), wherein the alkyl is substituted or unsubstituted. Alkyl includes, but is not limited to, methyl, ethyl, n-propyl, iso-propyl, n-butyl, iso-butyl, tert-butyl, n-pentyl, iso-pentyl, n-hexyl, septyl, heptyl, nonyl, and decyl. Examples of $R_3$—O(CH$_2$)$_n$NH(alkyl), or —(CH$_{2n}$NH (alkyl), include, but are not limited to, —OCH$_2$CH$_2$NHMe, —OCH$_2$CH$_2$CH$_2$NHEt, —CH$_2$CH$_2$NH(iso-propyl), and —CH$_2$CH$_2$CH$_2$NHMe.

The invention also provides compounds of Formula II, II-a, and II-b, wherein $R_3$ is —O(CH$_{2n}$X, or —(CH$_2$)$_n$X, wherein X is —N(alkyl)$_2$), wherein the alkyl is substituted or unsubstituted. Alkyl includes, but is not limited to, methyl, ethyl, n-propyl, iso-propyl, n-butyl, iso-butyl, tert-butyl, n-pentyl, iso-pentyl, n-hexyl, septyl, heptyl, nonyl, and decyl. Examples of $R_3$—O(CH$_2$)$_n$N(alkyl)$_2$, or —(CH$_2$)$_n$N(alkyl)$_2$, include, but are not limited to, —OCH$_2$CH$_2$(Me)$_2$, —OCH$_2$CH$_2$ CH$_2$N(Et)$_2$, —CH$_2$CH$_2$N(iso-propyl)$_2$, and —CH$_2$CH$_2$CH$_2$N(Me)$_2$. Alternatively, $R_3$ is —O(CH$_2$)$_n$X, or —(CH$_2$)$_n$X, wherein X is —OH. Examples include, but are not limited to, —OCH$_2$CH$_2$OH, —OCH$_2$CH$_2$ CH$_2$OH, —CH$_2$CH$_2$OH, and —CH$_2$CH$_2$CH$_2$OH.

In yet other embodiments, $R_3$ is —O(CH$_2$)$_n$X, or —(CH$_2$)$_n$X, wherein X is O-alkyl, wherein the alkyl is unsubstituted or substituted. Alkyl includes, but is not limited to, methyl, ethyl, n-propyl, iso-propyl, n-butyl, iso-butyl, tert-butyl, n-pentyl, iso-pentyl, n-hexyl, septyl, heptyl, nonyl, and decyl. Examples of $R_3$ is —O(CH$_2$)$_n$O-alkyl, or —(CH$_2$)$_n$O-alkyl, include, but are not limited to, —OCH$_2$CH$_2$OMe, —OCH$_2$CH$_2$ CH$_2$OEt, —CH$_2$CH$_2$O(iso-propyl), and —CH$_2$CH$_2$ CH$_2$OEt.

In some other embodiments, $R_3$ is —O(CH$_2$)$_n$X, or —(CH$_2$)$_n$X, wherein X is —O-aryl, wherein the aryl is substituted or unsubstituted. Aryl includes, but is not limited to, phenyl, naphthyl and fluorenyl. Examples of $R_3$ include, but are not limited to, —O(CH$_2$)$_n$O-aryl, or —(CH$_2$)$_n$O-aryl include, but are not limited to, —OCH$_2$CH$_2$O-phenyl, —OCH$_2$CH$_2$CH$_2$O-(3-methoxy-phenyl), —CH$_2$CH$_2$O-(4-methyl phenyl), and —CH$_2$CH$_2$CH$_2$O-phenyl. In other embodiments, R$_3$ is —O(CH$_2$)$_n$X, or —(CH$_2$)$_n$X, wherein X is —SO$_2$(alkyl) and alkyl is unsubstituted or substituted. Alkyl includes, but is not limited to, methyl, ethyl, n-propyl, iso-propyl, n-butyl, iso-butyl, tert-butyl, n-pentyl, iso-pentyl, n-hexyl, septyl, heptyl, nonyl, and decyl. Examples include, but are not limited to, —OCH$_2$CH$_2$SO$_2$Me, —OCH$_2$CH$_2$CH$_2$SO$_2$Et, —CH$_2$CH$_2$SO$_2$(butyl) and —CH$_2$CH$_2$CH$_2$SO$_2$Me. Additionally, R$_3$ is —O(CH$_2$)$_n$X, or —(CH$_2$)$_n$X, wherein X is —SO$_2$NH$_2$ or —SO$_2$NH(alkyl), and alkyl is unsubstituted or substituted. Alkyl includes, but is not limited to, methyl, ethyl, n-propyl, iso-propyl, n-butyl, iso-butyl, tert-butyl, n-pentyl, iso-pentyl, n-hexyl, septyl, heptyl, nonyl, and decyl. Examples include, but are not limited to, —OCH$_2$CH$_2$SO$_2$NH$_2$, —OCH$_2$CH$_2$CH$_2$SO$_2$NHMe, —CH$_2$CH$_2$SO$_2$NH$_2$ and —CH$_2$CH$_2$CH$_2$SO$_2$NHMe.

In other embodiments, R$_3$ is —O(CH$_2$)$_n$X, or —(CH$_2$)$_n$X, wherein X is NHSO$_2$(alkyl), and alkyl is unsubstituted or substituted. Alkyl includes, but is not limited to, methyl, ethyl, n-propyl, iso-propyl, n-butyl, iso-butyl, tert-butyl, n-pentyl, iso-pentyl, n-hexyl, septyl, heptyl, nonyl, and decyl. Examples include, but are not limited to, —OCH$_2$CH$_2$NHSO$_2$Me, —OCH$_2$CH$_2$CH$_2$NHSO$_2$Et, —CH$_2$CH$_2$NHSO$_2$Me and —CH$_2$CH$_2$CH$_2$SO$_2$NHSO$_2$Et.

The invention also provides compounds of Formula II-a and II-b, wherein R$_3$ is —O(CH$_2$)$_n$X, or —(CH$_2$)$_n$X, wherein X is heteroaryl, and the heteroaryl is unsubstituted or substituted. In some embodiments, the heteroaryl moiety is a monocylic 5 membered heteroaryl. Monocyclic heteroaryl includes, but is not limited to, pyrrolyl, imidazolyl, thiazolyl, and pyrazolyl. Additional nonlimiting monocyclic 5 membered heteroaryl moieties include the following formulae:

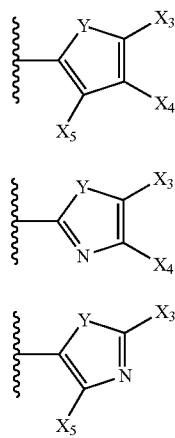

Group E

Group D

Group F

For compounds of Group D, E, and F, Y is selected from the group consisting of: —O, —S, —NH, —N-alkyl, and —N-acyl; X$_3$ is selected from the group consisting of: —H, —CH$_3$, —Cl, —I, —F, CF$_3$ and —OCH$_3$; and X$_4$ and X$_5$ are, when present, independently selected from the group consisting of: H and CH$_3$.

Alternatively, heteroaryl may be a six membered heteroaryl moiety. The six membered heteroaryl moiety includes, but is not limited to, 2-pyridyl, 3-pyridyl, 4-pyridyl, pyrimidinyl, pyrazinyl, or trianzinyl. Non limiting R$_3$—O(CH$_2$)$_n$-heteroaryl or —(CH$_2$)$_n$heteroaryl include —OCH$_2$CH$_2$-pyridinyl, —OCH$_2$CH$_2$ CH$_2$-(4-methyl-pyridin-2-yl), —CH$_2$CH$_2$—(thiazolyl), and —CH$_2$CH$_2$ CH$_2$-pyrazinyl.

In yet other embodiments, R$_3$ is —O(CH$_2$)$_n$X, or —(CH$_2$)$_n$X, wherein X is N-attached heterocyclo, or C-attached heterocyclo, and the heterocyclo is unsubstituted or substituted. The heterocyclo includes, but is not limited to, azetidinyl, pyrrolidinyl, morpholinyl, piperidinyl, or piperazinyl. Non limiting R$_3$—O(CH$_2$)$_n$-heterocyclo (which includes both N-attached or C-attached heterocyclo) or —(CH$_2$)$_n$heterocyclo (which includes both N— attached or C-attached heterocyclo) include —OCH$_2$CH$_2$-morpholinyl, —OCH$_2$CH$_2$CH$_2$-(4N-methyl-piperazinyl), —CH$_2$CH$_2$— (pyrrolidin-2-yl), and —CH$_2$CH$_2$ CH$_2$-(4N-methyl-piperazinyl).

The alkyl, aryl, heteroaryl and heterocyclo moiety forming all or part of X may be substituted by one or more substituents, which is selected from the group consisting of alkyl, aryl, heterocyclo, carbocyclo, halo, hydroxy, protected hydroxy, alkoxy, acyl, aryloxy, alkylester, arylester, alkanoyl, aroyl, carboxy, protected carboxy, cyano, nitro, amino, substituted amino, (monosubstituted)amino, (disubstituted) amino, protected amino, amido, lactam, urea, urethane, and sulfonyl. Additionally, the alkyl and heterocyclo moiety forming all or part of X may be substituted by oxo.

Other R$_3$ moieties useful in the compounds of the invention are listed in Table 2b, 2e, and 2h.

In various embodiments of compounds of Formula II, II-b, or another isostere scaffold as described above, each of R$_4$-R$_7$ is independently selected from the group consisting of: —H, —I, —Cl, —F, —CH$_3$, —OCH$_3$, —OH, —NH$_2$, —NO$_2$,

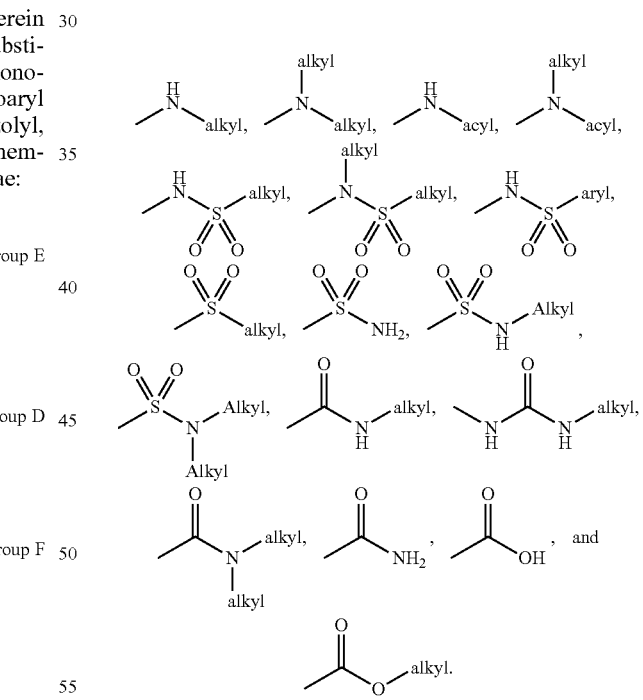

In the moieties forming part of R$_3$-R$_7$, the alkyl and aryl moieties are unsubstituted or substituted. The alkyl moieties that form part of R$_3$-R$_7$ include, but are not limited to, methyl, ethyl, n-propyl, iso-propyl, n-butyl, iso-butyl, tert-butyl, n-pentyl, iso-pentyl, n-hexyl, septyl, heptyl, nonyl, and decyl. The aryl moieties that form part of R$_3$-R$_7$ include, but are not limited to, phenyl, naphthyl and fluorenyl. The alkyl and aryl moieties that form part of R$_3$-R$_7$ may be substituted by one or more substituents, which is selected from the group consisting of alkyl, aryl, heterocyclo, carbocyclo, halo, hydroxy, protected hydroxy, alkoxy, acyl, aryloxy, alkylester, arylester, alkanoyl, aroyl, carboxy, protected carboxy, cyano, nitro, amino, substituted amino, (monosubstituted)amino, (disubstituted)amino, protected amino, amido, lactam, urea, urethane, and sulfonyl.

In one embodiment, at least one of $R_4$-$R_7$ is a hydrogen. In other embodiments, where $R_3$ is present, $R_3$ is hydrogen. In further embodiments, at least two of $R_4$-$R_7$ is a hydrogen. Alternatively, at least two of $R_4$-$R_7$ are hydrogen, and the remaining $R_4$-$R_7$ groups (and $R_3$, if present) are independently selected from the group consisting of: —Cl, —F, —CH$_3$, and —OCH$_3$. In yet other embodiments, $R_5$ and $R_6$ are substituted, and the substituted moiety is, for each substituted position, independently selected from the group consisting of: —Cl, —F, —CH$_3$, and —OCH$_3$, while $R_4$ and $R_7$ (and $R_3$ if present) are hydrogen.

In some other embodiments, $R_4$ and $R_5$, $R_5$ and $R_6$, or $R_6$ and $R_7$ are joined together with a bond to form a ring; or, optionally, $R_4$ and $R_5$, $R_5$ and $R_6$, or $R_6$ and $R_7$ are joined together to form a 1,2-(methylenedioxy)benzene ring system, such as

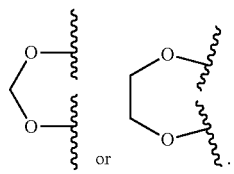

In one embodiment, the ring is composed of a structure selected from the group consisting of:

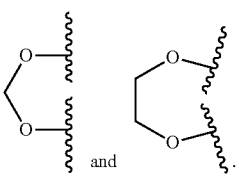 [SMILES: *OCO* ; *OCCO*]

In a further embodiment, $R_5$ and $R_6$ are connected by one of the rings having a structure selected from the group consisting of:

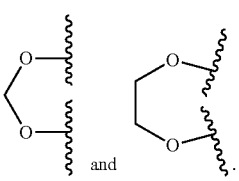 [SMILES: *OCO* ; *OCCO*]

In some embodiments of the invention, the compound of Formula II-a is not

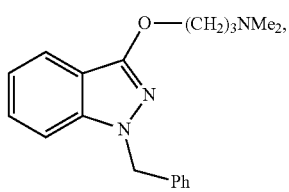

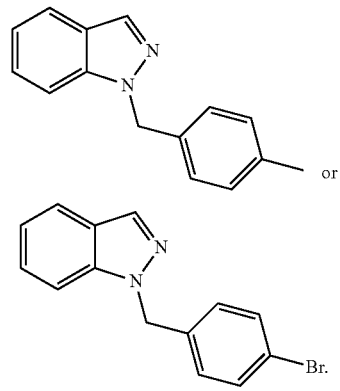

In yet another embodiment, the present invention provides a compound of Formula II-a shown below.

Formula II-a

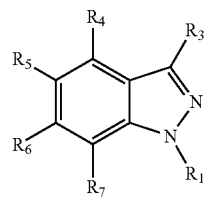

In some embodiments, the compound of Formula II-a is the compound wherein $R_1$ is selected from the group consisting of: —H or

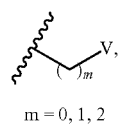

m = 0, 1, 2 and V is selected from alkyl, aryl,

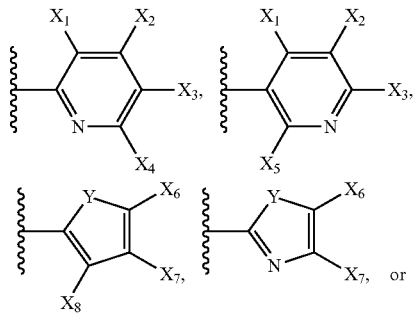

$X_1$-$X_5$ are each independently selected from the group consisting of: —H, -alkyl, —I, —Br, —Cl, —F, —O-alkyl,

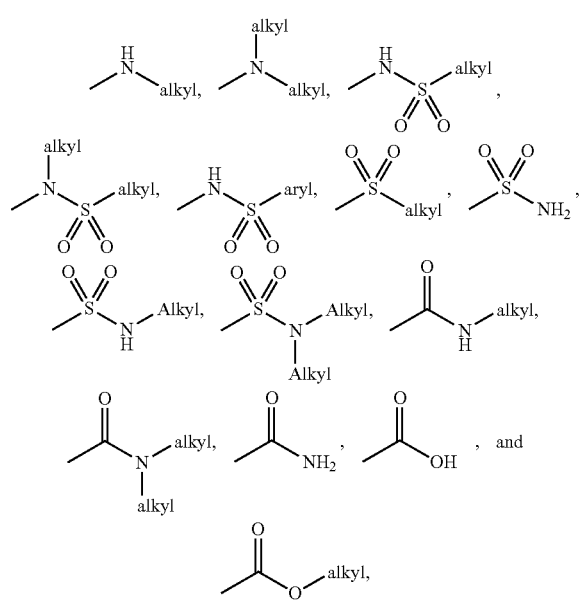

Y is selected from the group consisting of: —O, —S, —NH, —N-alkyl, and —N-acyl; $X_6$ is selected from the group consisting of: —H, —CH$_3$, —I, —Cl, —F, CF$_3$ and —OCH$_3$; and $X_7$ and $X_8$ are independently selected from the group consisting of: H and CH$_3$; each of $R_4$-$R_7$ is independently selected from the group consisting of: —H, —I, —Br, —Cl, —F, —CH$_3$, —CN, —OH, —OCH$_3$, —NO$_2$, —NH$_2$, —OCH$_2$CH$_2$O-alkyl, —NHCO(alkyl), —NHCO(aryl),

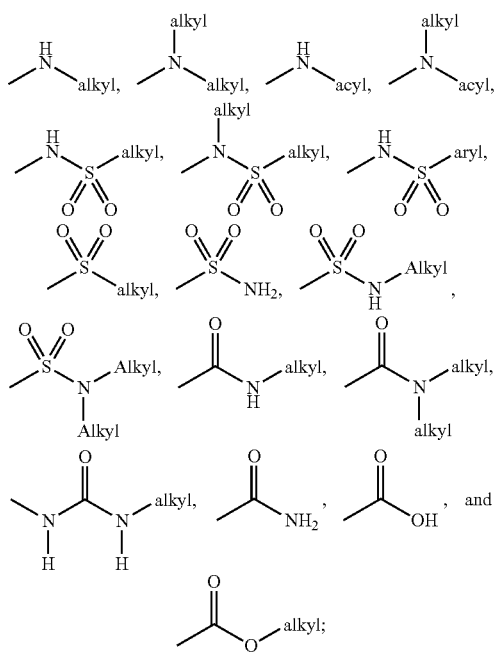

or, optionally, $R_4$ and $R_5$, $R_5$ and $R_6$, or $R_6$ and $R_7$ are joined together with a bond to form a 5, 6, or 7-membered ring; or, optionally, $R_4$ and $R_5$, $R_5$ and $R_6$, or $R_6$ and $R_7$ are joined together to form a 1,2-(methylenedioxy)benzene ring system.

In other embodiments, the compound of Formula II-a is the compound wherein $R_3$ is —O(CH$_2$)$_n$X, or —(CH$_2$)$_n$X, wherein X is selected from the group consisting of: —OCH$_3$, —OCH$_2$CH$_3$, —OCH$_2$CH$_2$OH, —OCH$_2$CH$_2$OCH$_3$,

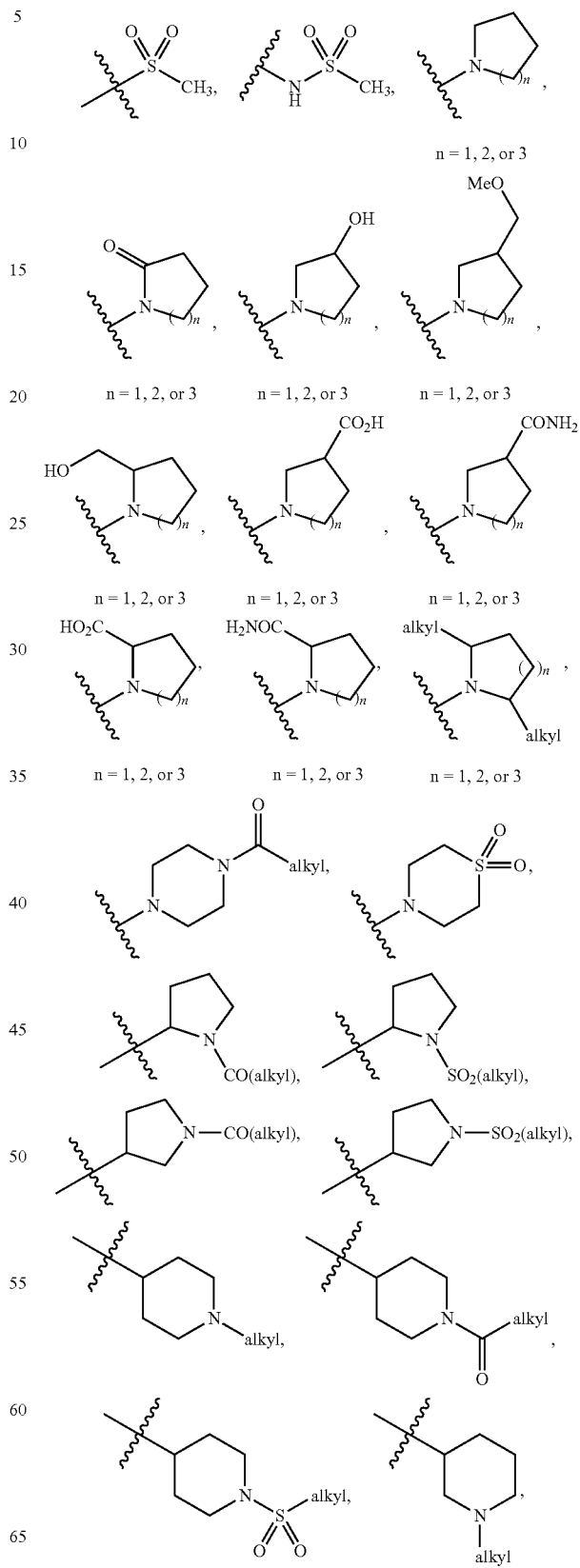

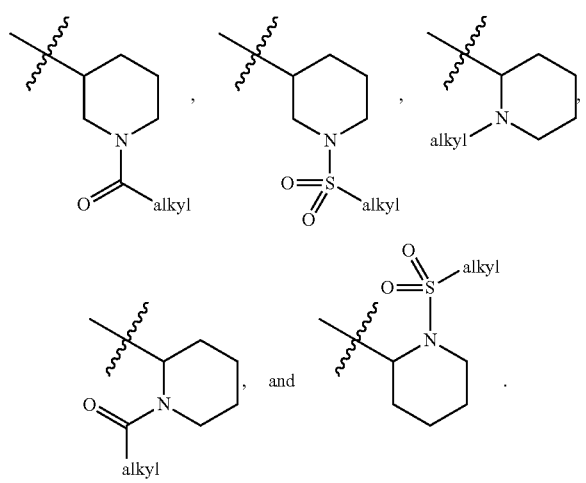
In other embodiments, the compound of Formula II-a is the compound wherein $R_1$ is selected from the group consisting of:
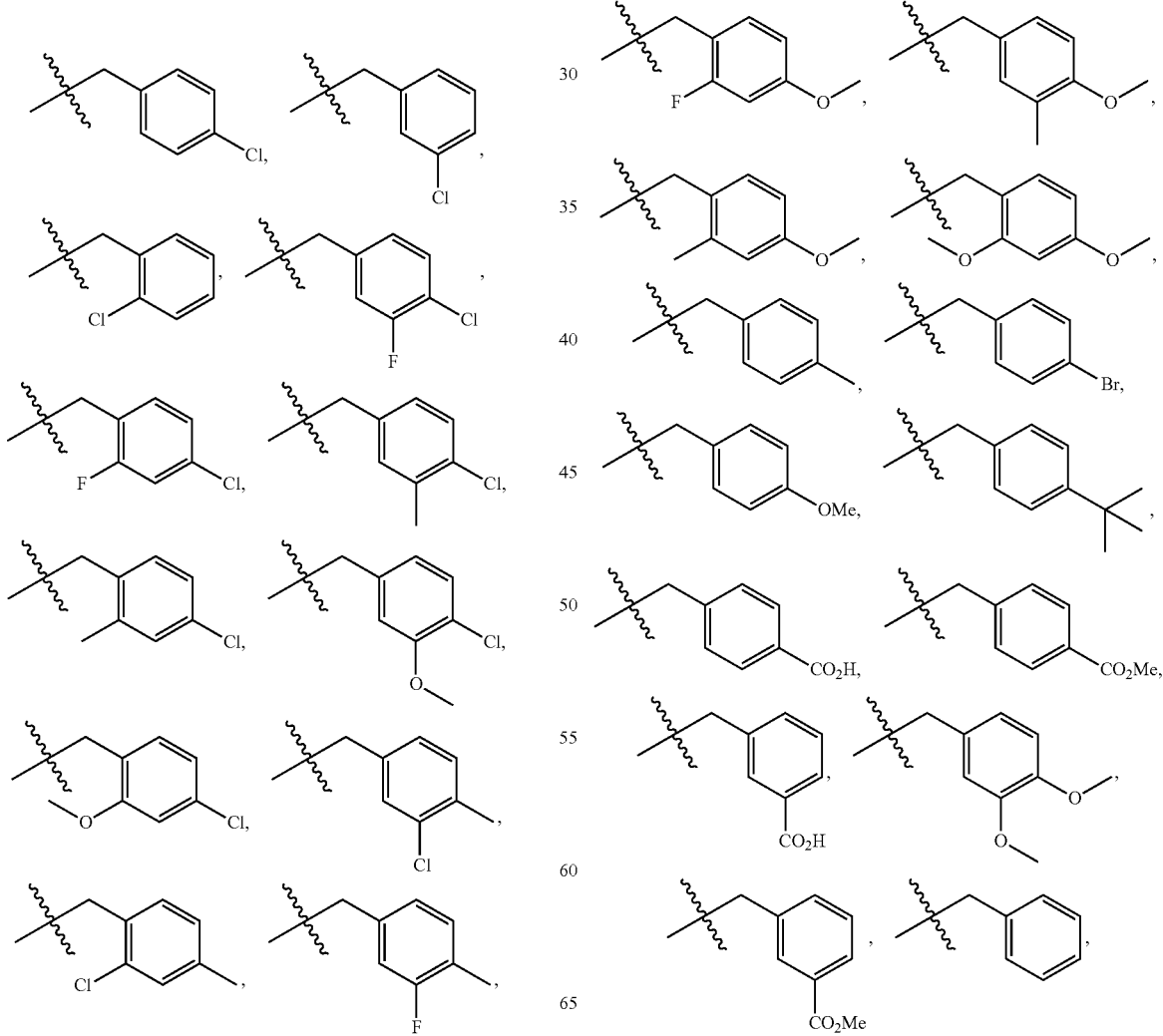
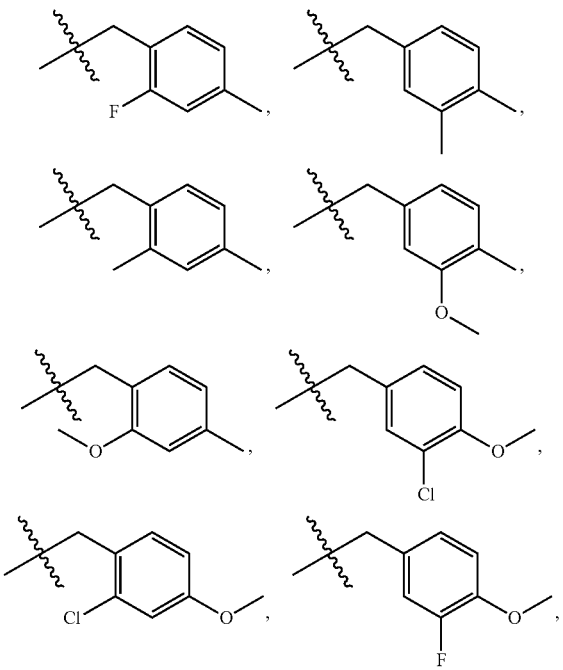

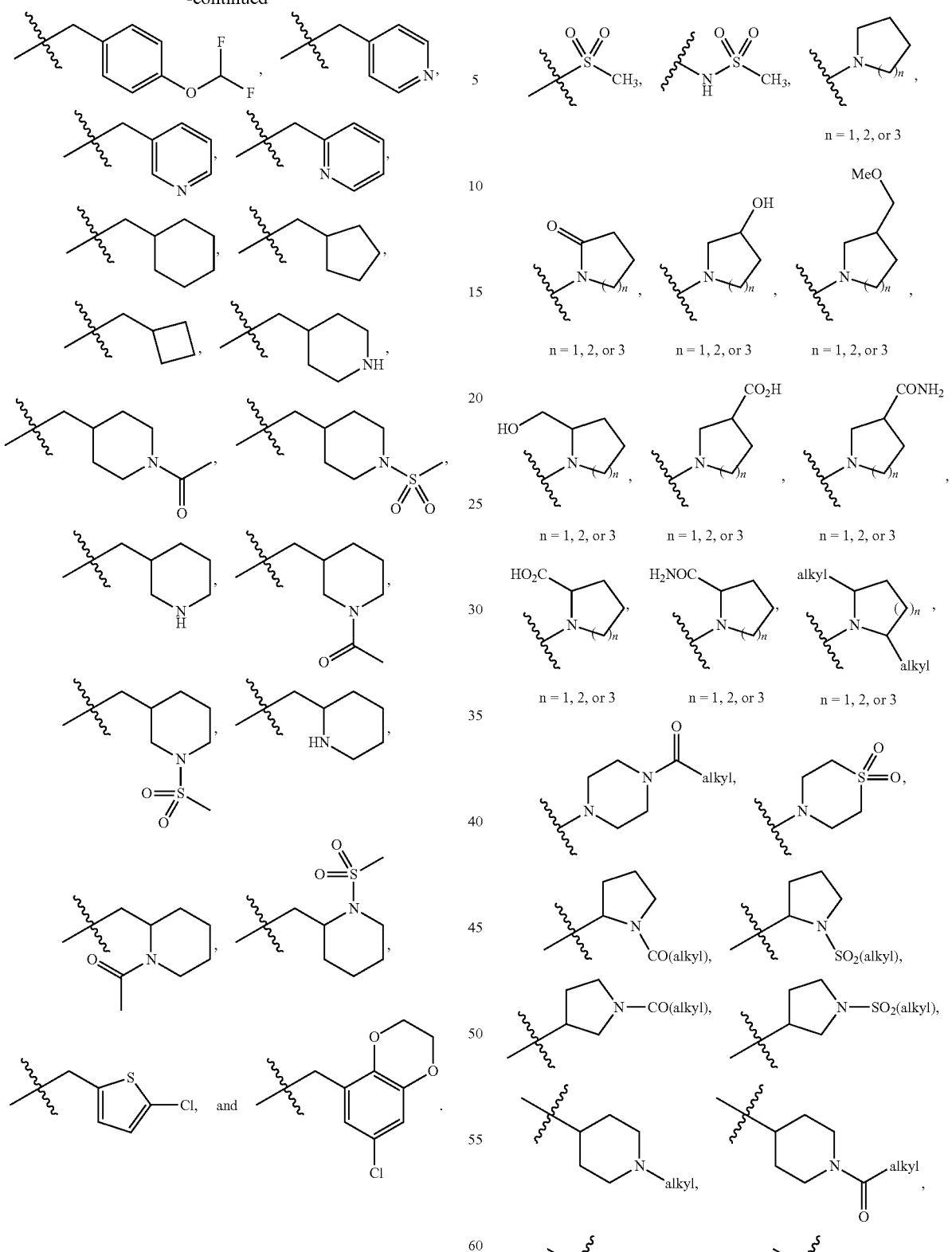
In yet other embodiments, the compound of Formula II-a is the compound, wherein $R_1$ is —$CH_2V$, wherein V is selected from the group consisting of: cycloalkyl, heterocyclo, aryl and heteroaryl; $R_3$ is —$O(CH_2)_nX$, or —$(CH_2)_nX$, wherein X is selected from the group consisting of: —$OCH_3$, —$OCH_2CH_3$, —$OCH_2CH_2OH$, —$OCH_2CH_2OCH_3$,

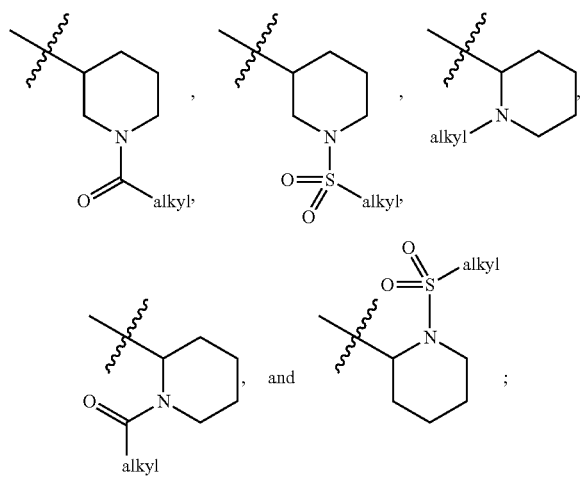
R4 and R7 are both hydrogen, and R5 and R6 are both a substituent other than hydrogen.
In yet other embodiments, the compound of Formula II-a is the compound wherein R1 is selected from the group consisting of:
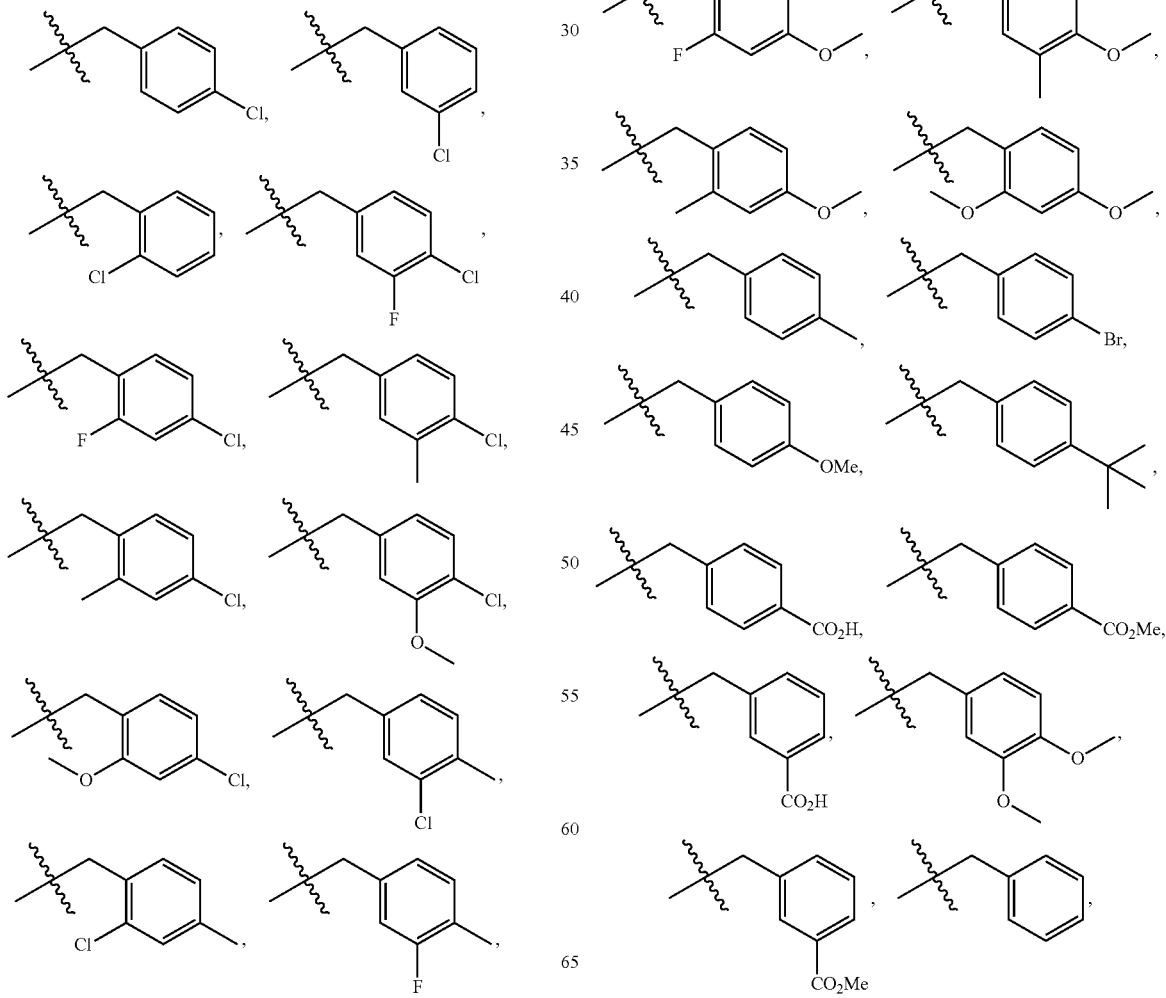
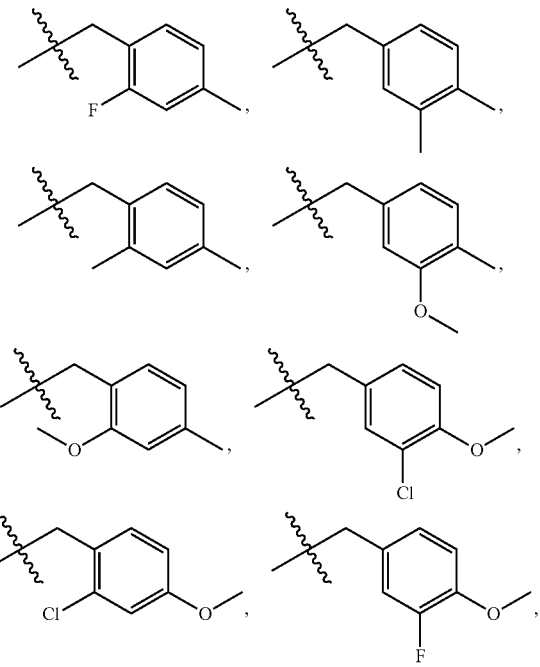

-continued

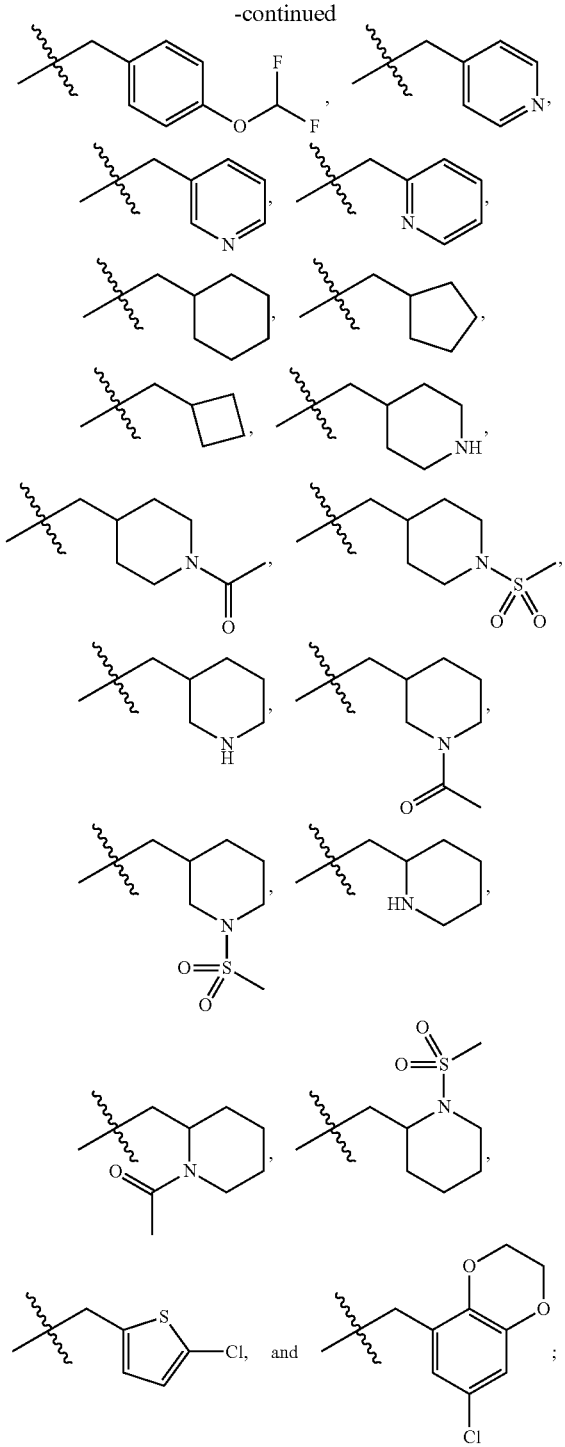

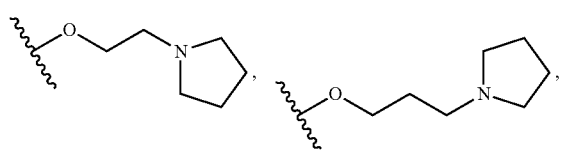

$R_3$ is selected from: —O(CH$_2$)$_2$NMe$_2$, —O(CH$_2$)$_2$NEt$_2$, —O(CH$_2$)$_3$NEt$_2$, -continued

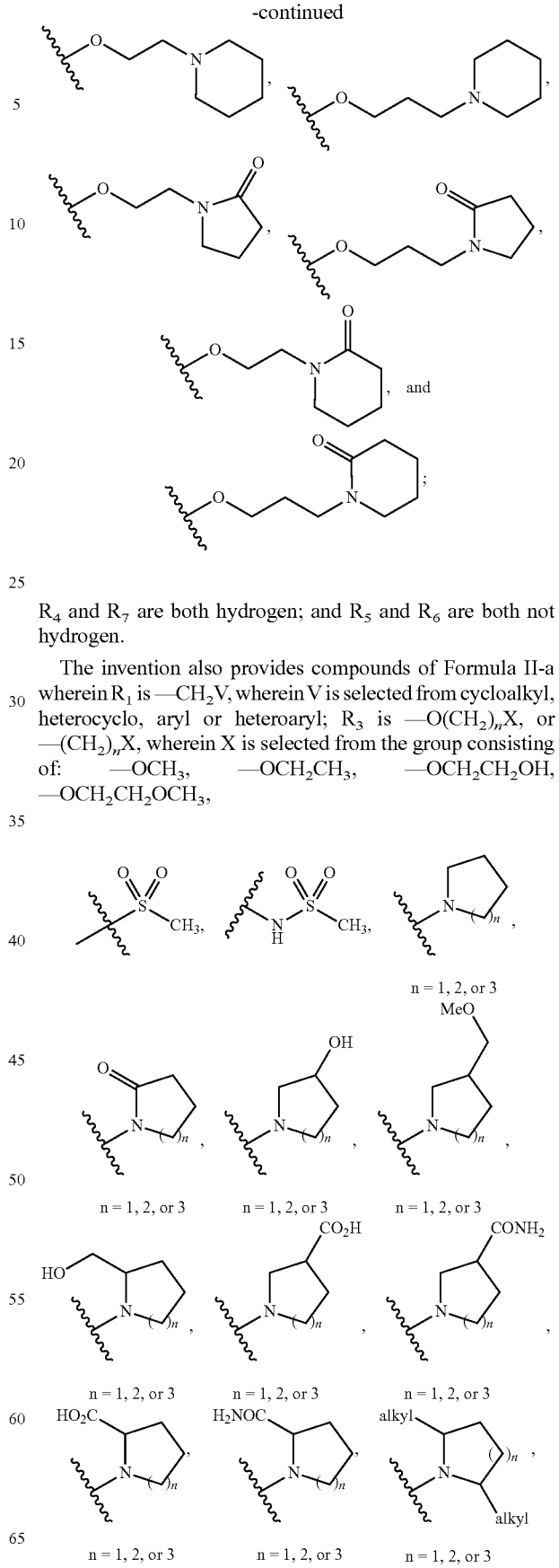

$R_4$ and $R_7$ are both hydrogen; and $R_5$ and $R_6$ are both not hydrogen.

The invention also provides compounds of Formula II-a wherein $R_1$ is —CH$_2$V, wherein V is selected from cycloalkyl, heterocyclo, aryl or heteroaryl; $R_3$ is —O(CH$_2$)$_n$X, or —(CH$_2$)$_n$X, wherein X is selected from the group consisting of: —OCH$_3$, —OCH$_2$CH$_3$, —OCH$_2$CH$_2$OH, —OCH$_2$CH$_2$OCH$_3$,

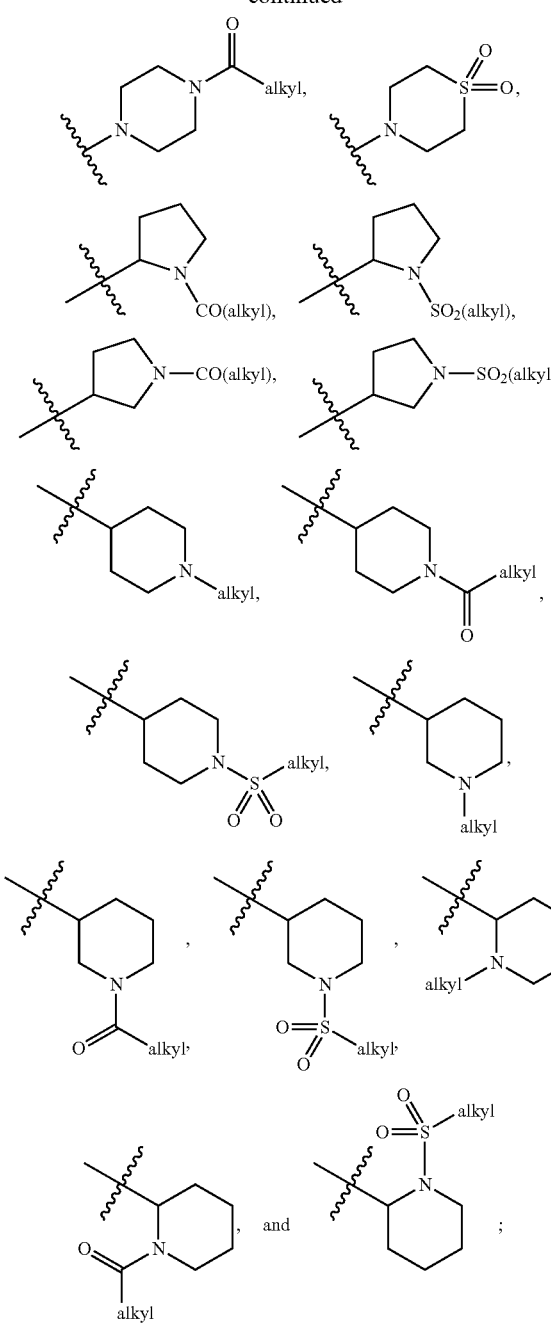
$R_4$ is —NHC(O)aryl, —NHC(O)alkyl, —NHSO$_2$aryl or —NHSO$_2$alkyl; $R_7$ is hydrogen and $R_5$ and $R_6$ are both a substituent other than hydrogen.
The compounds of Formula II-a are also a compound wherein $R_1$ is selected from the group consisting of:
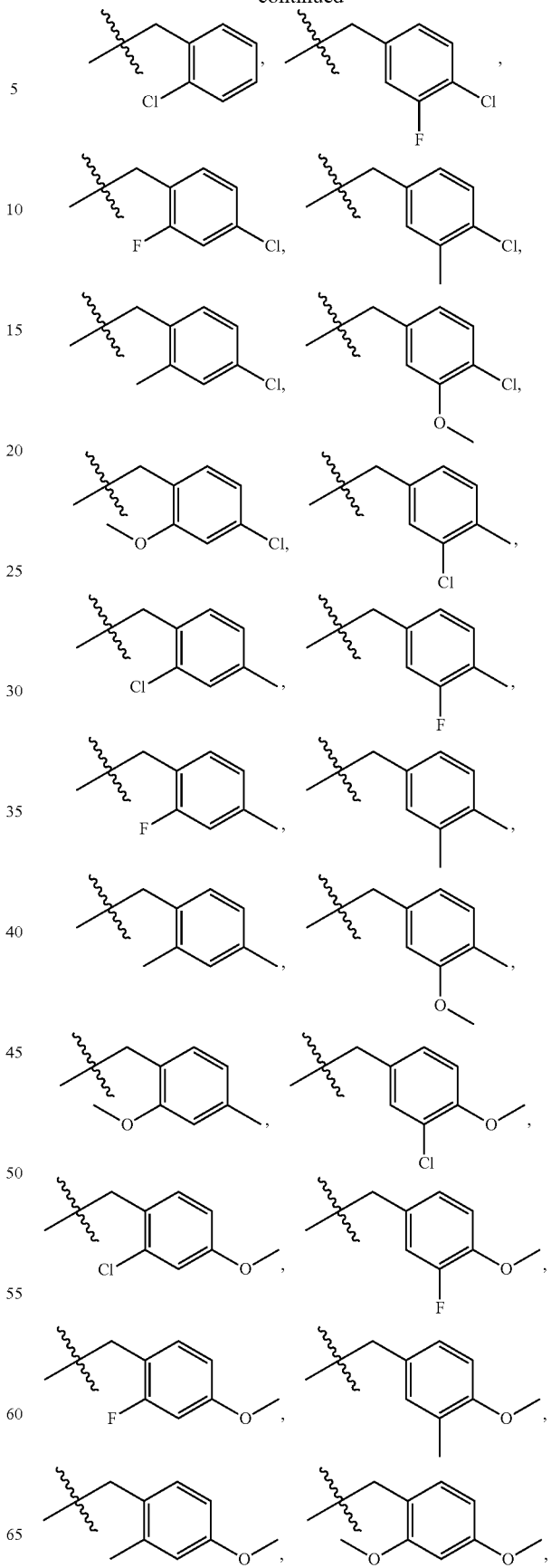

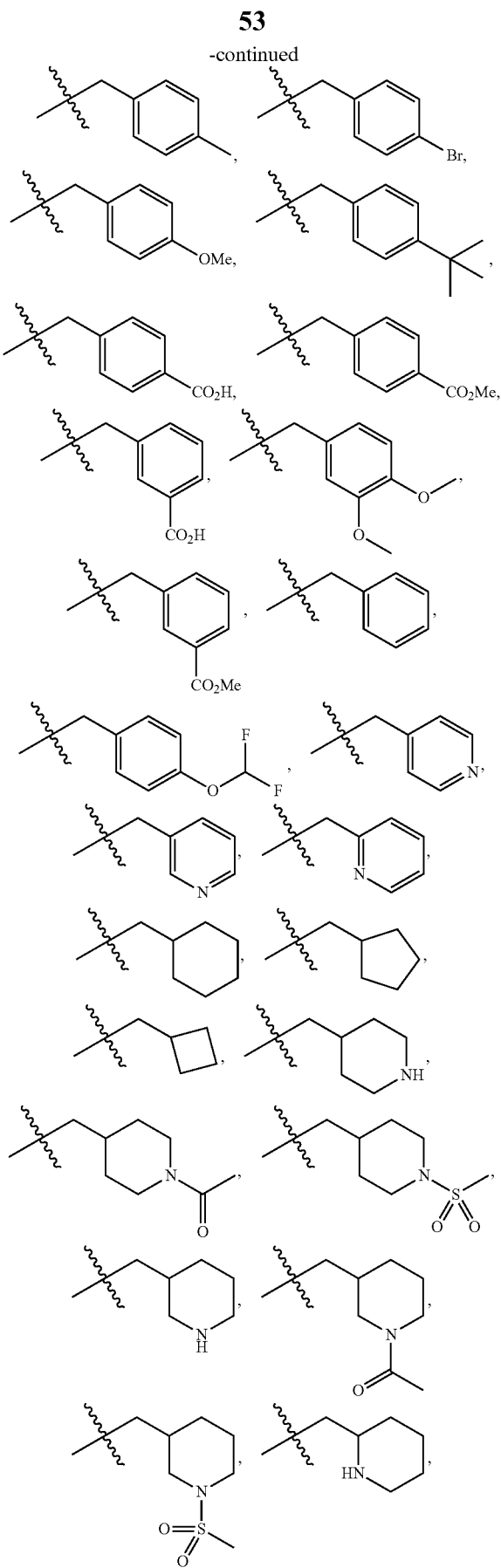

$R_3$ is selected from: —O(CH$_2$)$_2$NMe$_2$, —O(CH$_2$)$_2$NEt$_2$, —O(CH$_2$)$_3$NMe$_2$, —O(CH$_2$)$_3$NEt$_2$, $R_4$ is —NHC(O)aryl, —NHC(O)alkyl, —NHSO$_2$aryl or —NHSO$_2$alkyl; $R_7$ is hydrogen and $R_5$ and $R_6$ are both not hydrogen.

Table 1 shows structures of additional compounds (also referred to as "inhibiting agents", (compounds and inhibiting agents are interchangeable as is appropriate for the particular usage herein)) of the invention and illustrative starting materials to prepare them TABLE 1
| | Structure | Illustrative Starting Material |
|---|---|---|
| 1 | 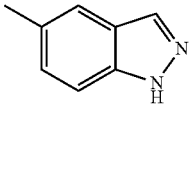 | 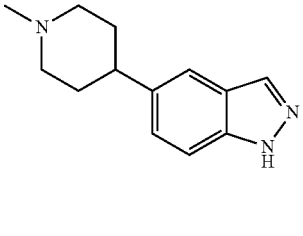 [SMILES: CN1CCC(c2ccc3[nH]ncc3c2)CC1] |
| 2 | 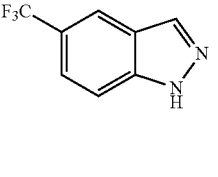 | 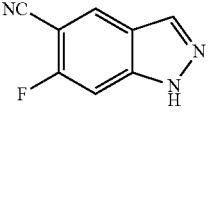 |
| 3 | 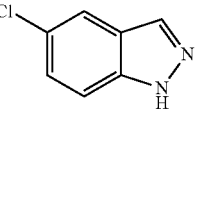 | 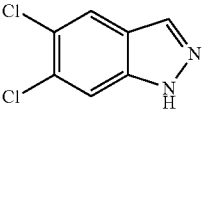 |
| 4 | 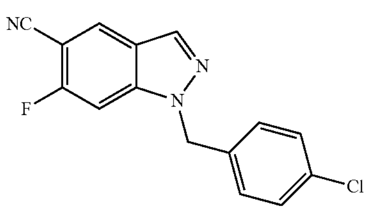 [SMILES: N#Cc1cc2cnn(Cc3ccc(Cl)cc3)c2cc1F] | |
| 5 | 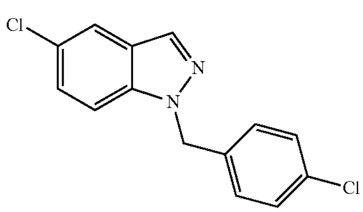 [SMILES: Clc1ccc(Cn2ncc3cc(Cl)ccc32)cc1] | |
| 6 | 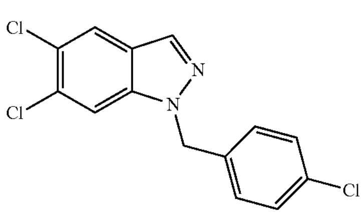 [SMILES: Clc1ccc(Cn2ncc3cc(Cl)c(Cl)cc32)cc1] | |
| 7 | 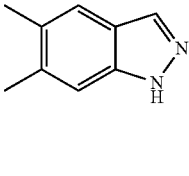 | |

TABLE 1-continued

| Structure | Illustrative Starting Material |
|---|---|
| 8 [6-methyl-1-(4-chlorobenzyl)-1H-indazole structure] | [6-methyl-1H-indazole structure] |
| 9 [5-chloro-6-methyl-1-(4-chlorobenzyl)-1H-indazole structure] | [5-chloro-6-methyl-1H-indazole structure] |
| 10 [5-methoxy-6-methyl-1-(4-chlorobenzyl)-1H-indazole structure] | [5-methoxy-6-methyl-1H-indazole structure] |

Table 2a shows structures of additional inhibiting agents of the invention based on the structure below.

Formula II-a

[Indazole structure with R3 at 3-position, R4 at 4, R5 at 5, R6 at 6, R7 at 7, and R1 on N1]

Some nonlimiting illustrative compounds of the present invention having a structure of Formula II-a include those in which $R_1$ is any $R_1$ moiety described in Table 2a, in combination with any $R_3$ moiety described in Table 2b, and any $R_4$, $R_5$, $R_6$, and $R_7$ as described in Table 2c. A compound of Formula II-a includes any combination of $R_1$, $R_3$, $R_4$, $R_5$, $R_6$, and $R_7$. Additional exemplary compounds of Formula II-a are illustrated in Tables 3, 4 and 5.

TABLE 2a $R_1$ moieties of Formula II-a include, but are not limited to, the following: Illustrative $R_1$ moieties

| | |
|---|---|
| hydrogen | R1-1 |
| methyl | R1-2 |
| ethyl | R1-3 |
| [4-chlorobenzyl] | R1-4 |

TABLE 2a-continued $R_1$ moieties of Formula II-a include, but are not limited to, the following: Illustrative $R_1$ moieties

| | |
|---|---|
| [3-chlorobenzyl] | R1-5 |
| [2-chlorobenzyl] | R1-6 |
| [3,4-dichlorobenzyl] | R1-7 |
| [2,4-dichlorobenzyl] | R1-8 |
| [2-fluoro-4-chlorobenzyl] | R1-9 |

TABLE 2a-continued
R₁ moieties of Formula II-a include, but are not limited to, the following: Illustrative R₁ moieties
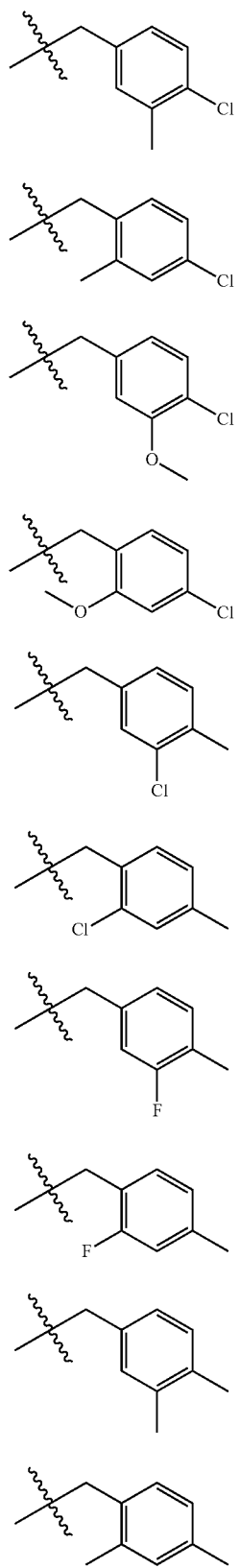
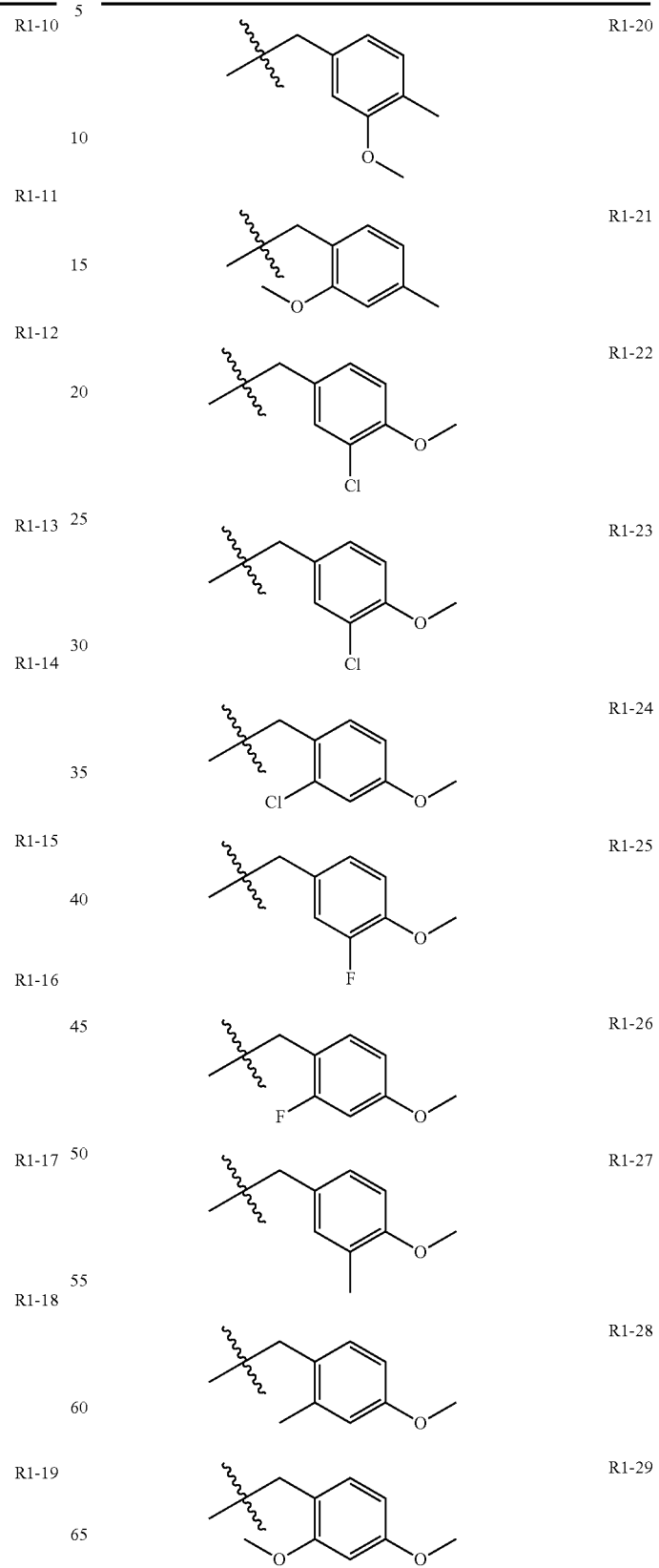

TABLE 2a-continued
R₁ moieties of Formula II-a include, but are not limited to, the following:
Illustrative R₁ moieties
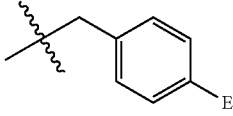 R1-30
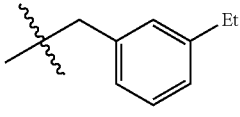 [SMILES: *Cc1cccc(CC)c1] R1-31
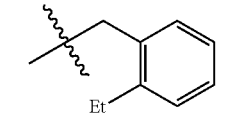 R1-32
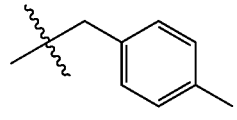 [SMILES: *Cc1ccc(C)cc1] R1-33
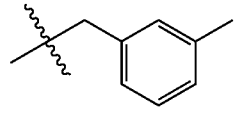 [SMILES: *Cc1cccc(C)c1] R1-34
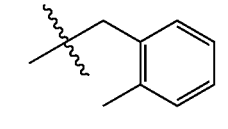 [SMILES: *Cc1ccccc1C] R1-35
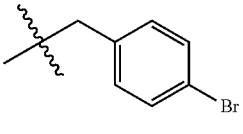 [SMILES: *Cc1ccc(Br)cc1] R1-36
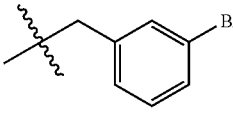 R1-37
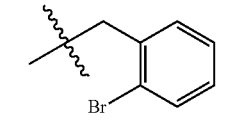 [SMILES: *Cc1ccccc1Br] R1-38
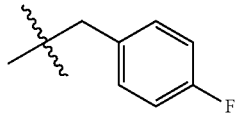 [SMILES: *Cc1ccc(F)cc1] R1-39
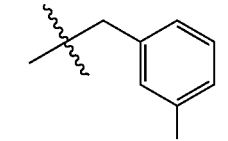 R1-40
TABLE 2a-continued
R₁ moieties of Formula II-a include, but are not limited to, the following:
Illustrative R₁ moieties
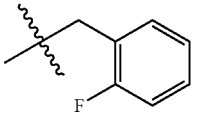 R1-41
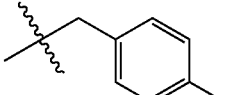 R1-42
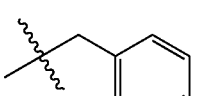 R1-43
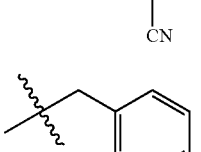 R1-44
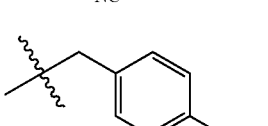 R1-45
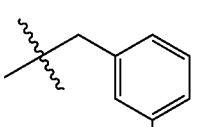 R1-46
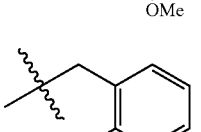 R1-47
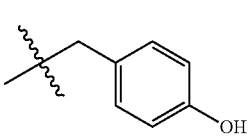 [SMILES: *Cc1ccc(O)cc1] R1-48
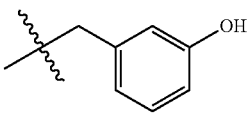 [SMILES: *Cc1cccc(O)c1] R1-49
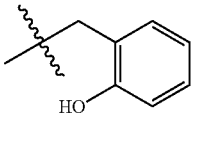 R1-50
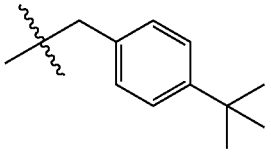 [SMILES: *Cc1ccc(C(C)(C)C)cc1] R1-51

TABLE 2a-continued
R₁ moieties of Formula II-a include, but are not limited to, the following:
Illustrative R₁ moieties
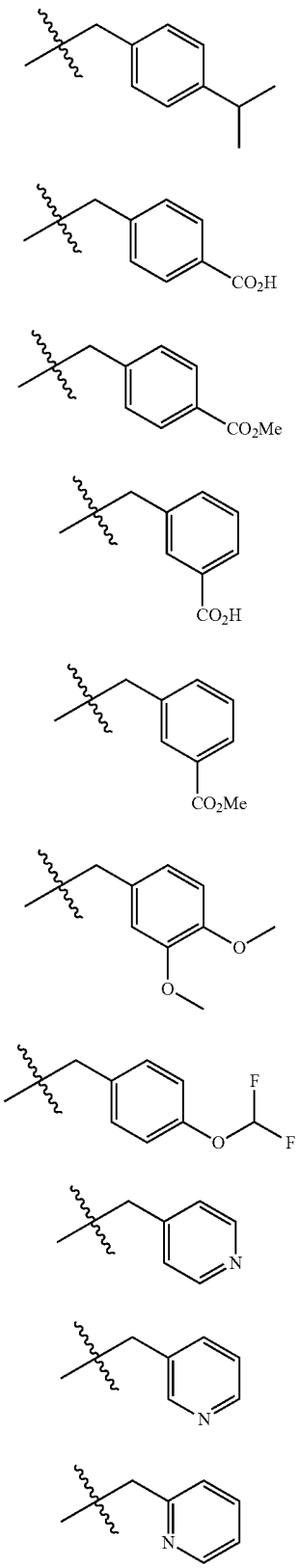
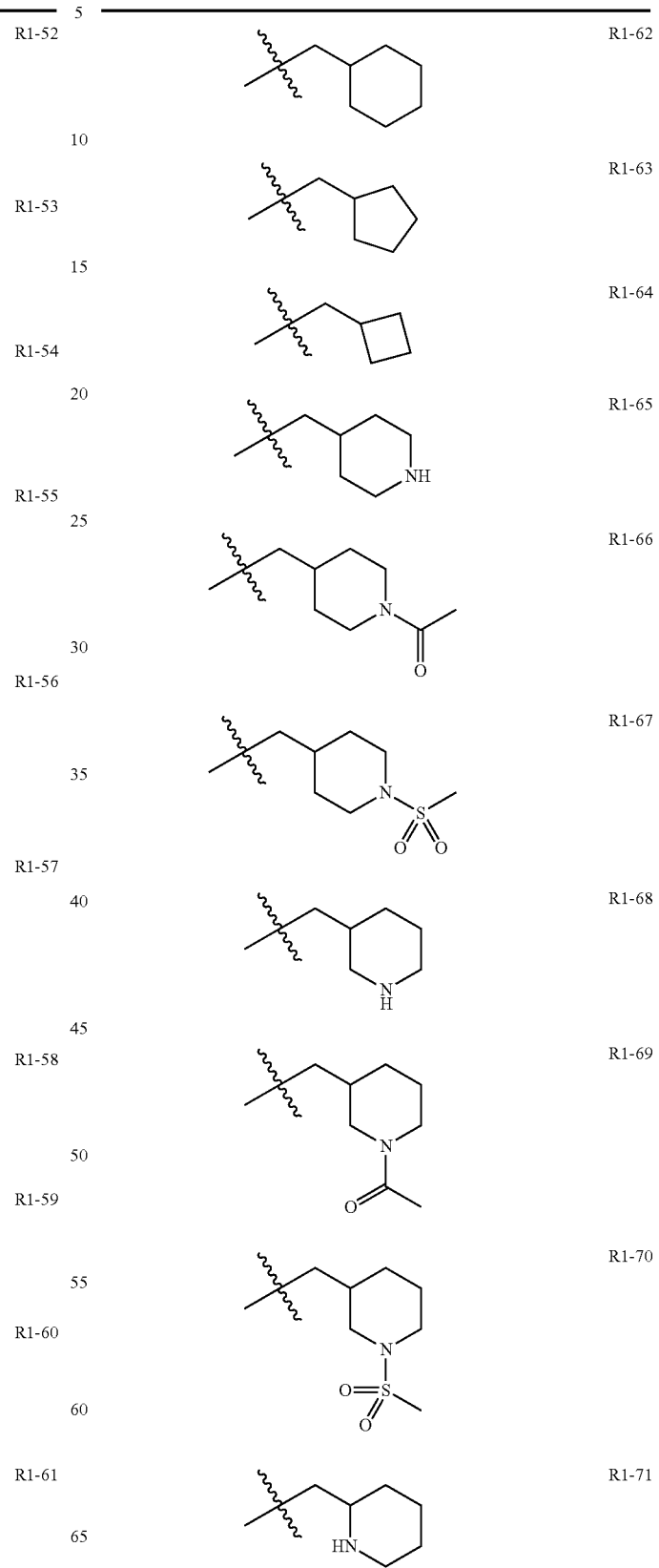

TABLE 2a-continued
R₁ moieties of Formula II-a include, but are not limited to, the following:
Illustrative R₁ moieties
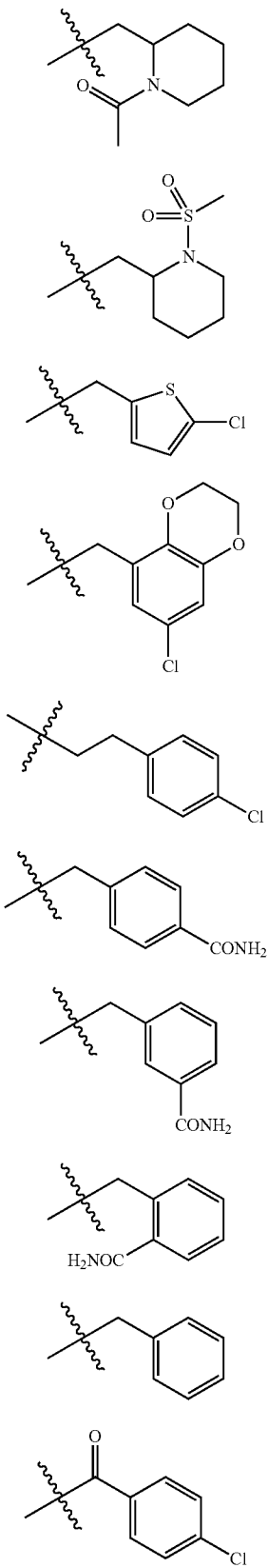
R1-72
R1-73
R1-74
R1-75
R1-76
R1-77
R1-78
R1-79
R1-80
R1-81
R1-82
R1-83
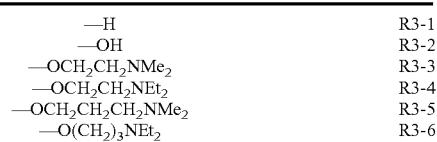
TABLE 2b
R₃ moieties of the compounds of Formula II-a include, but are not limited to, the following:
Exemplary-R₃*
| | |
|---|---|
| —H | R3-1 |
| —OH | R3-2 |
| —OCH₂CH₂NMe₂ | R3-3 |
| —OCH₂CH₂NEt₂ | R3-4 |
| —OCH₂CH₂CH₂NMe₂ | R3-5 |
| —O(CH₂)₃NEt₂ | R3-6 |
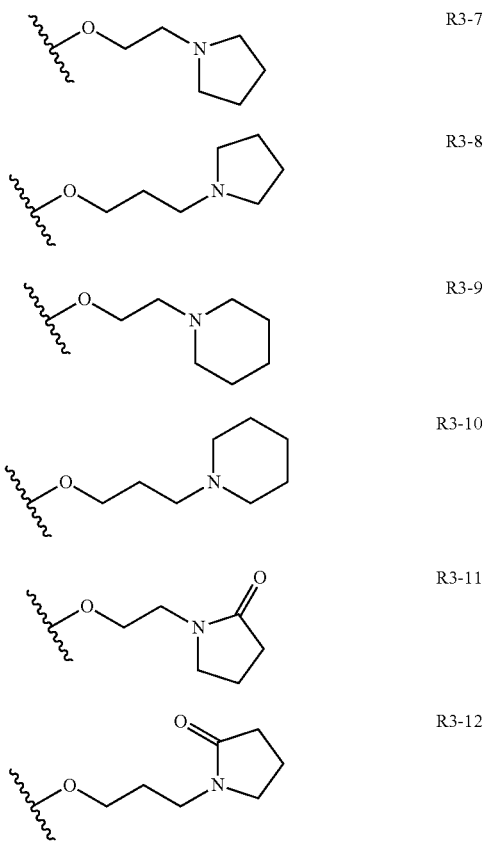
R3-7
R3-8
R3-9
R3-10
R3-11
R3-12

TABLE 2b-continued
R₃ moieties of the compounds of Formula II-a include, but are not limited to, the following:
Exemplary-R₃*
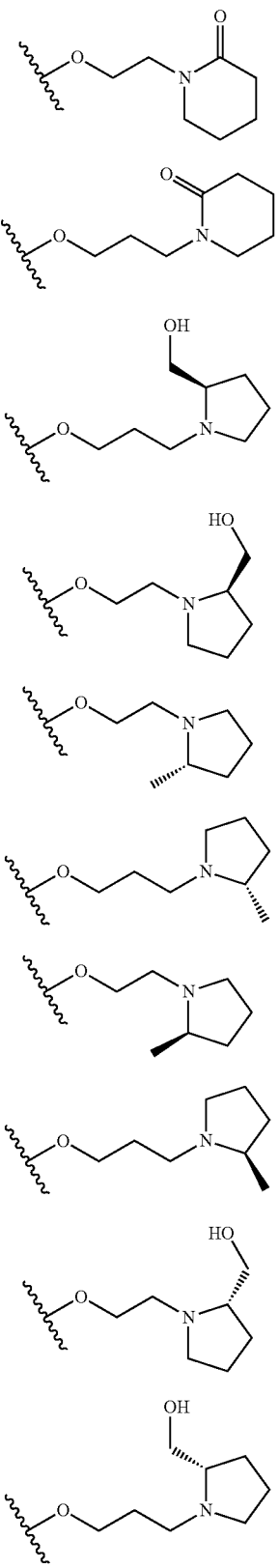
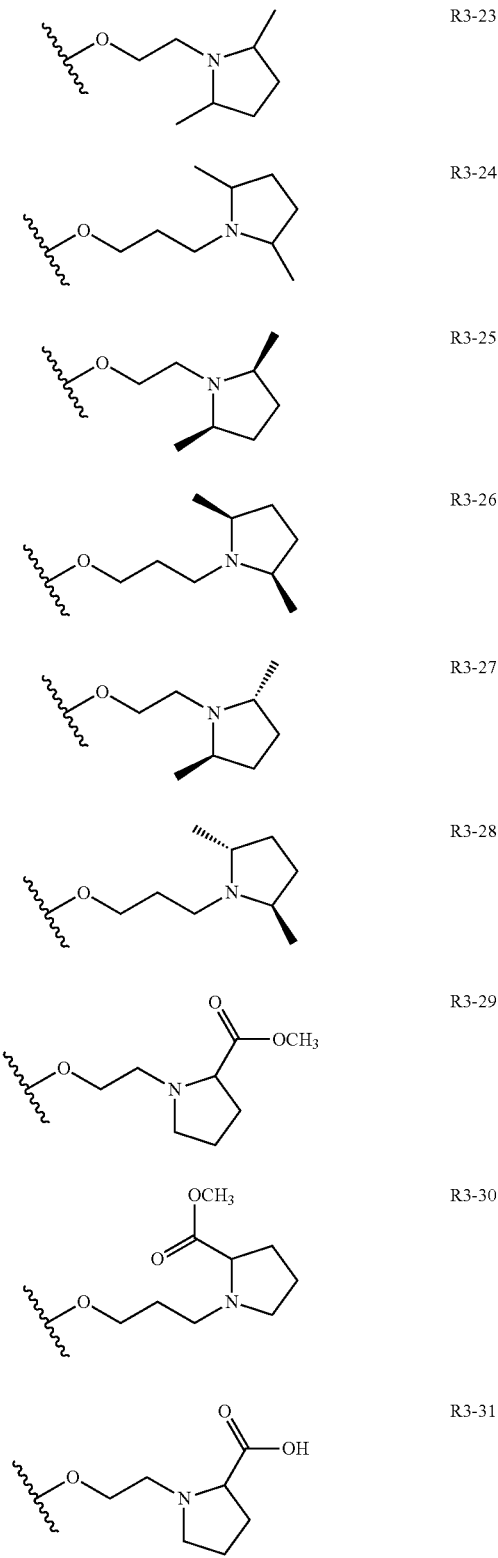

TABLE 2b-continued

R3 moieties of the compounds of Formula II-a include, but are not limited to, the following:
Exemplary-R3

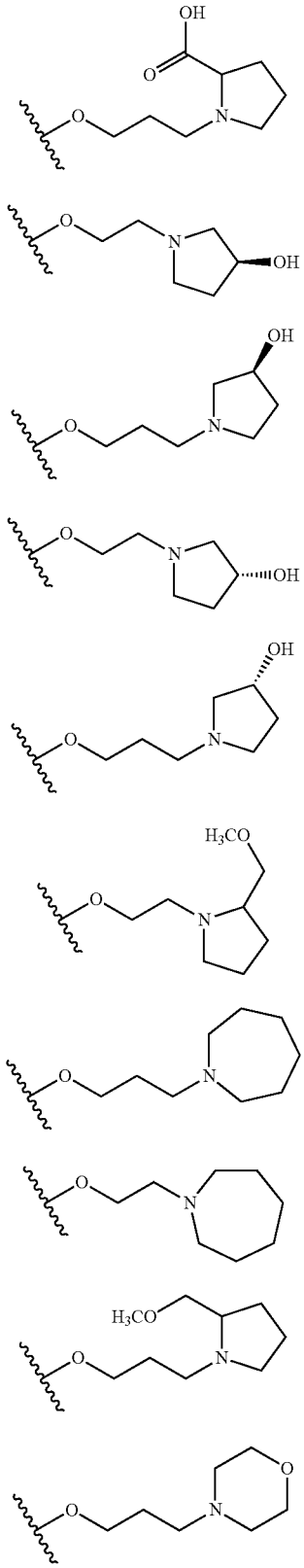

R3-32
R3-33
R3-34
R3-35
R3-36
R3-37
R3-38
R3-39
R3-40
R3-41

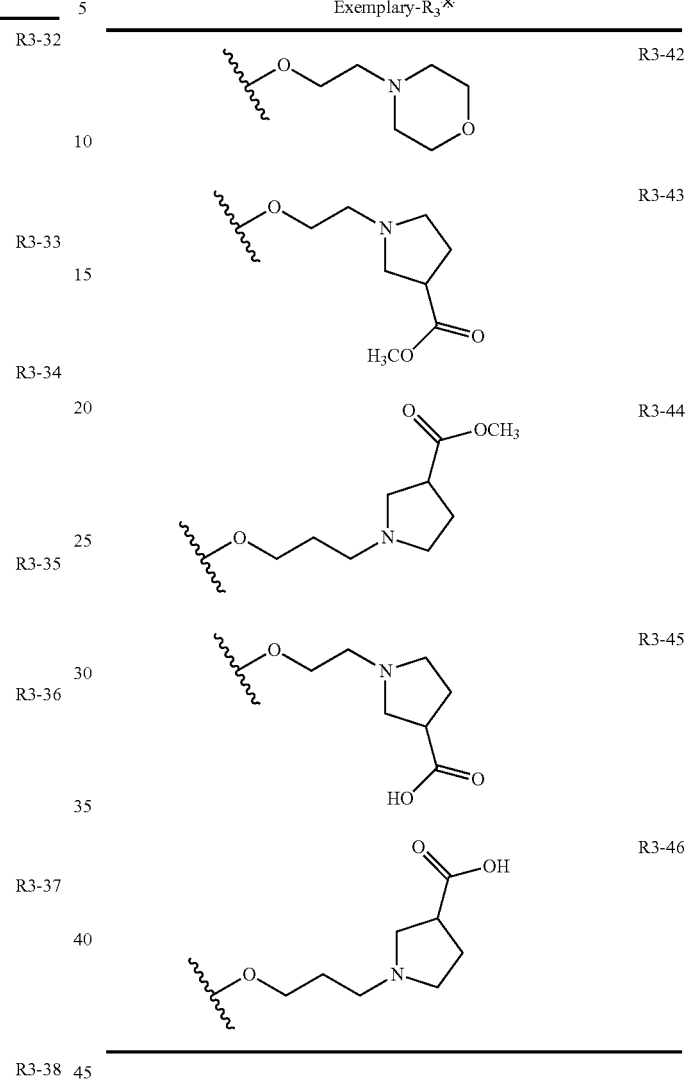

R3-42
R3-43
R3-44
R3-45
R3-46

TABLE 2c

Each of the R4, R5, R6, and R7 moieties of the compounds of Formula II-a include, but are not limited to, the following:
Illustrative R4, R5, R6, and R7 Moieties

| | |
|---|---|
| hydrogen | R4-1 |
| methyl | R4-2 |
| ethyl | R4-3 |
| chloro | R4-4 |
| fluoro | R4-5 |
| bromo | R4-6 |
| hydroxy | R4-7 |
| —OMe | R4-8 |
| —NO$_2$ | R4-9 |
| —NH$_2$ | R4-10 |
| —NHCOCH$_3$ | R4-11 |
| —NHCOCH(CH$_3$)$_2$ | R4-12 |
| —NHCOCF$_3$ | R4-13 |
| —NHCOPh | R4-14 |
| —NHCONHC$_4$H$_9$ | R4-15 |
| —N(Et)$_2$ | R4-16 |
| —NHSO$_2$Me | R4-17 |
| —NHSO$_2$CF$_3$ | R4-18 |

TABLE 2c-continued

Each of the $R_4$, $R_5$, $R_6$, and $R_7$ moieties of the compounds of Formula II-a include, but are not limited to, the following:
Illustrative $R_4$, $R_5$, $R_6$, and $R_7$ Moieties

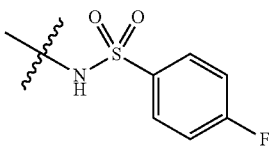 [SMILES: *NS(=O)(=O)c1ccc(F)cc1] R4-19

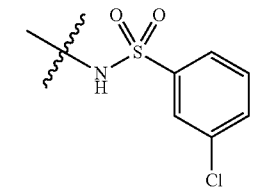 [SMILES: *NS(=O)(=O)c1cccc(Cl)c1] R4-20

| | |
|---|---|
| —SO$_2$Me | R4-21 |
| —CN | R4-22 |
| $R_4$ and $R_5$ are —OCH$_2$O— | R4-23 |
| $R_5$ and $R_6$ are —OCH$_2$O— | R4-24 |
| $R_6$ and $R_7$ are —OCH$_2$O— | R4-25 |
| $R_4$ and $R_5$ are —OCH$_2$CH$_2$O— | R4-26 |
| $R_5$ and $R_6$ are —OCH$_2$CH$_2$O— | R4-27 |
| $R_6$ and $R_7$ are —OCH$_2$CH$_2$O— | R4-28 |
| —CO$_2$H | R4-29 |
| —CF$_3$ | R4-30 |
| —OEt | R4-31 |
| —SO$_2$NH$_2$ | R4-32 |
| —SO$_2$NHMe | R4-33 |
| SO$_2$NMe$_2$ | R4-34 |
| NHC(O)Me | R4-35 |
| —NHC(O)Ph | R4-36 |
| —NMeC(O)Et | R4-37 |
| —NMeC(O)Ph | R4-38 |
| —C(O)NHMe | R4-39 |
| —C(O)NEt$_2$ | R4-40 |
| —C(O)NH$_2$ | R4-41 |
| —NHC(O)NHMe | R4-42 |
| —CO$_2$Me | R4-43 |

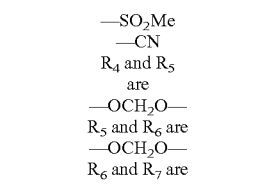 Formula II-b

Some non-limiting illustrative compounds of the present invention having a structure of Formula II-b include those in which $R_1$ is any $R_1$ moiety described in Table 2d, in combination with any $R_3$ moiety described in Table 2e, and any $R_4$, $R_5$, $R_6$, and $R_7$ as described in Table 2f. A compound of Formula II-b includes any combination of $R_1$, $R_3$, $R_4$, $R_5$, $R_6$, and $R_7$. Additional exemplary compounds of Formula II-b are illustrated in Tables 3, 4, and 5.

TABLE 2d $R_1$ moieties of Formula II-b include, but are not limited to, the following:
Illustrative $R_1$ moieties

| | |
|---|---|
| hydrogen | R1-1 |
| methyl | R1-2 |
| ethyl | R1-3 |

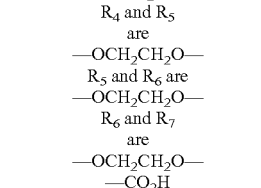 R1-4

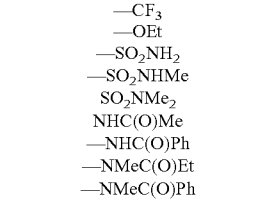 R1-5

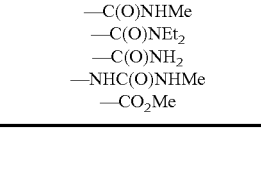 R1-6

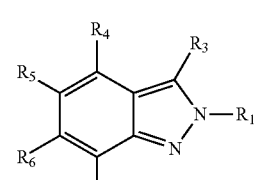 R1-7

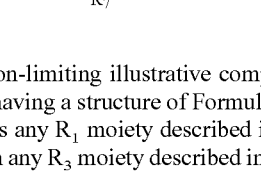 R1-8

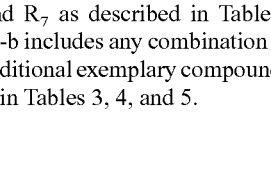 R1-9

 R1-10

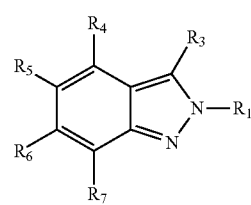 R1-11

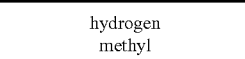 R1-12

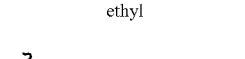 R1-13

TABLE 2d-continued
R₁ moieties of Formula II-b include, but are not limited to, the following:
Illustrative R₁ moieties
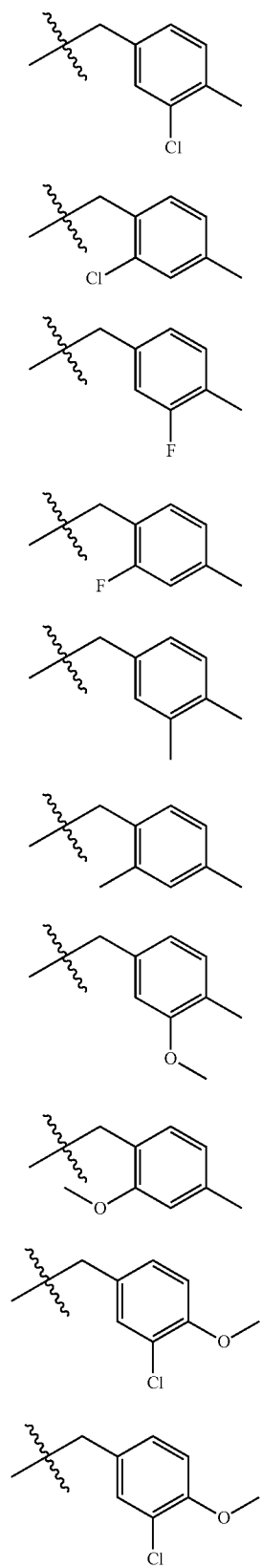
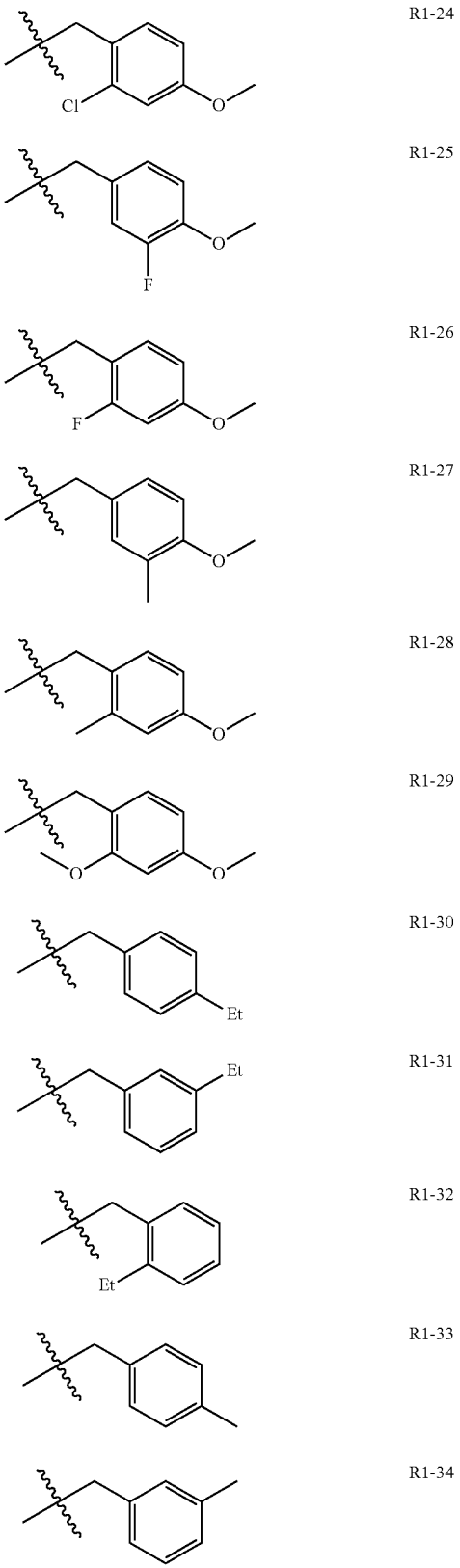

TABLE 2d-continued
R1 moieties of Formula II-b include, but are not limited to, the following:
Illustrative R1 moieties
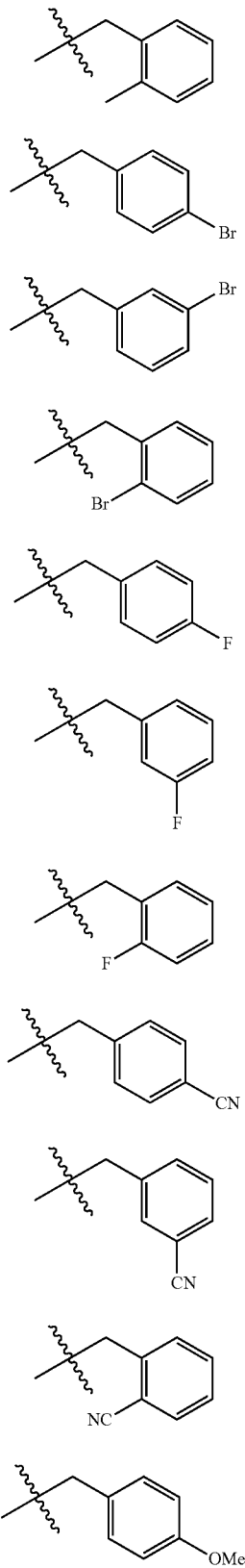
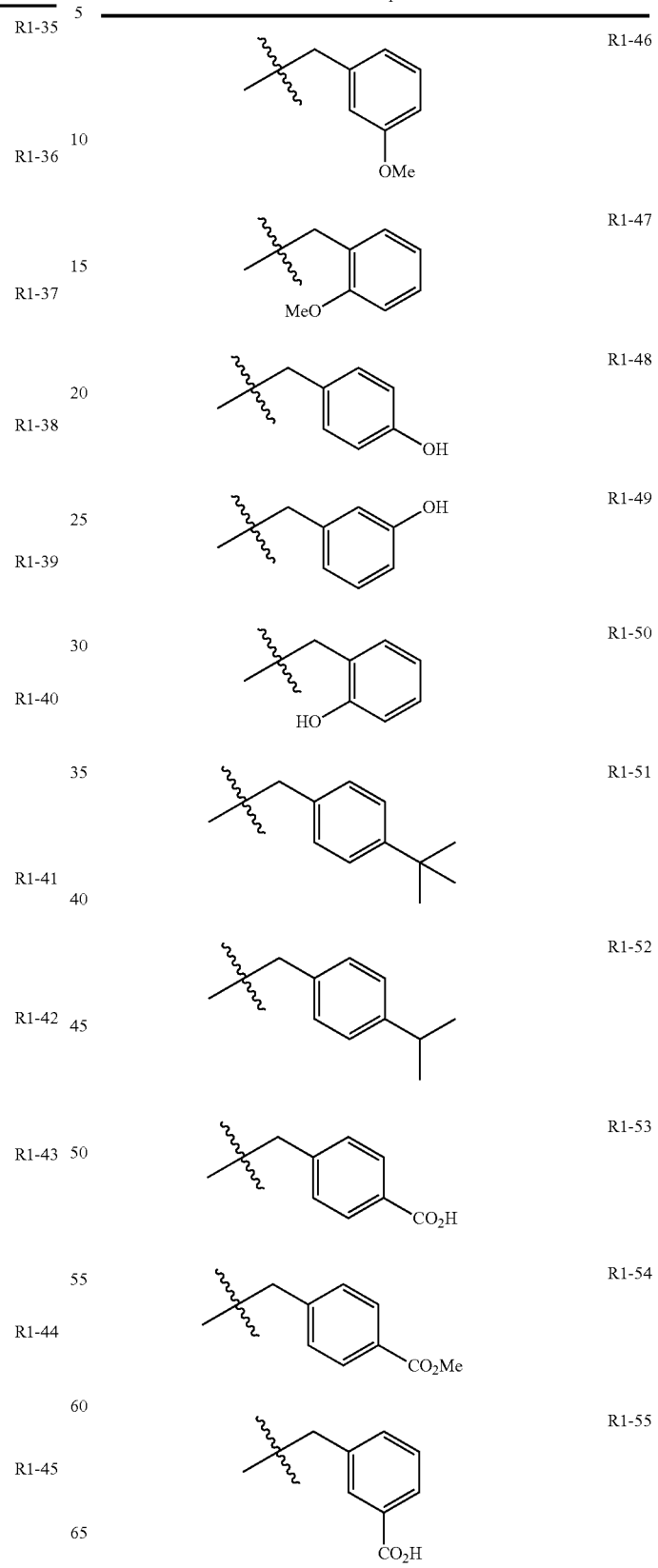

TABLE 2d-continued
R₁ moieties of Formula II-b include, but are not limited to, the following:
Illustrative R₁ moieties
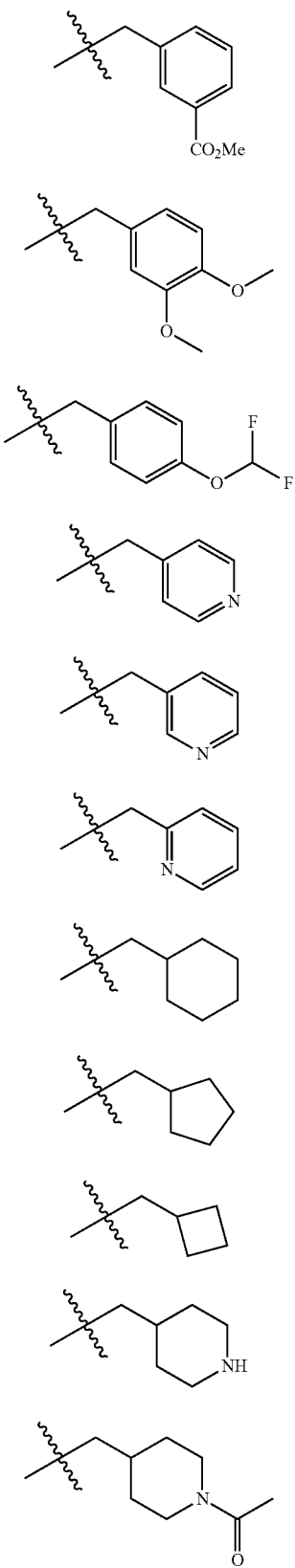
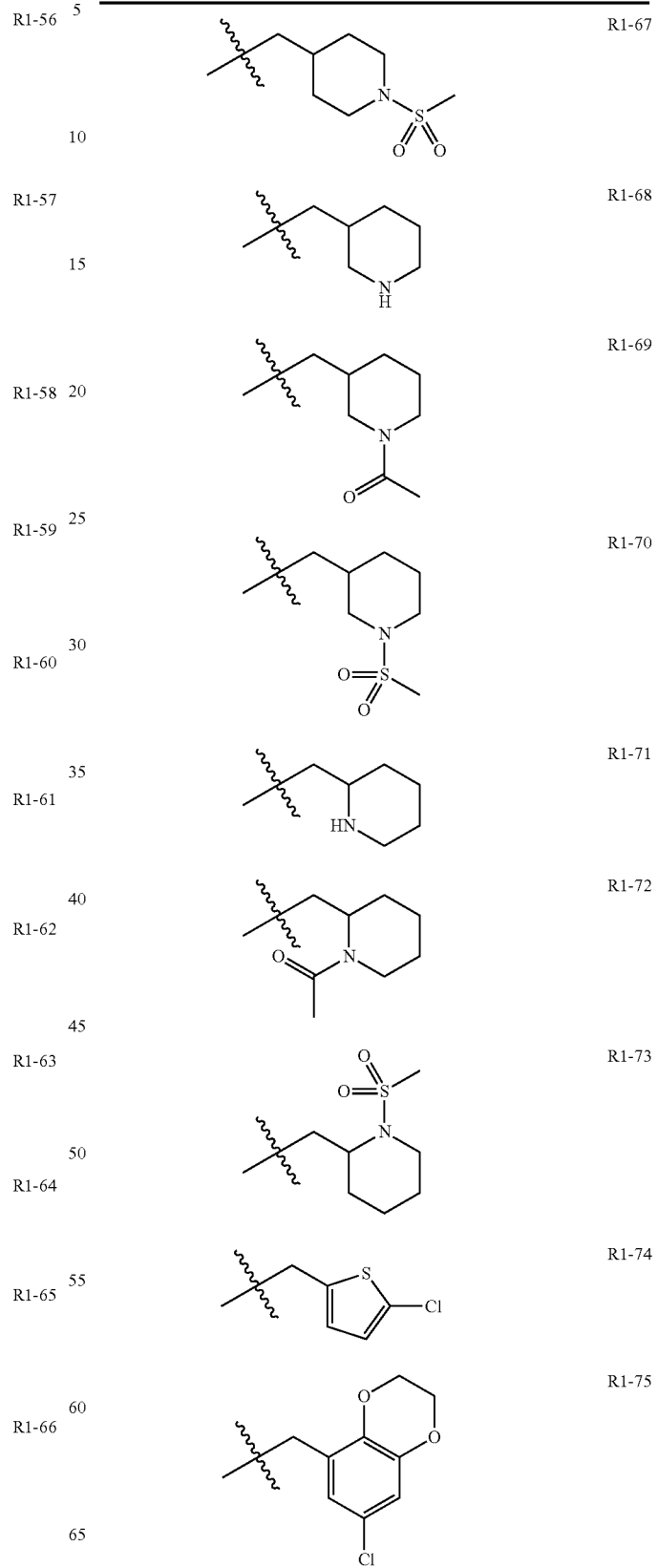

TABLE 2d-continued

R₁ moieties of Formula II-b include, but are not limited to, the following:
Illustrative R₁ moieties

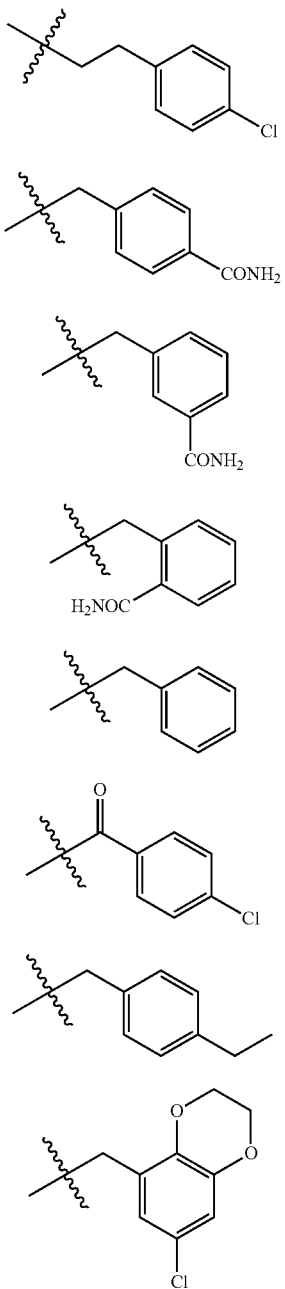

R1-76
R1-77
R1-78
R1-79
R1-80
R1-81
R1-82
R1-83

TABLE 2e

R₃ moieties of the compounds of Formula II-b include, but are not limited to, the following:
Exemplary R₃

| | |
|---|---|
| —H | R3-1 |
| —OH | R3-2 |
| —OCH₂CH₂NMe₂ | R3-3 |
| —OCH₂CH₂NEt₂ | R3-4 |
| —OCH₂CH₂CH₂NMe₂ | R3-5 |
| —O(CH₂)₃NEt₂ | R3-6 |

TABLE 2e-continued

R₃ moieties of the compounds of Formula II-b include, but are not limited to, the following:
Exemplary R₃

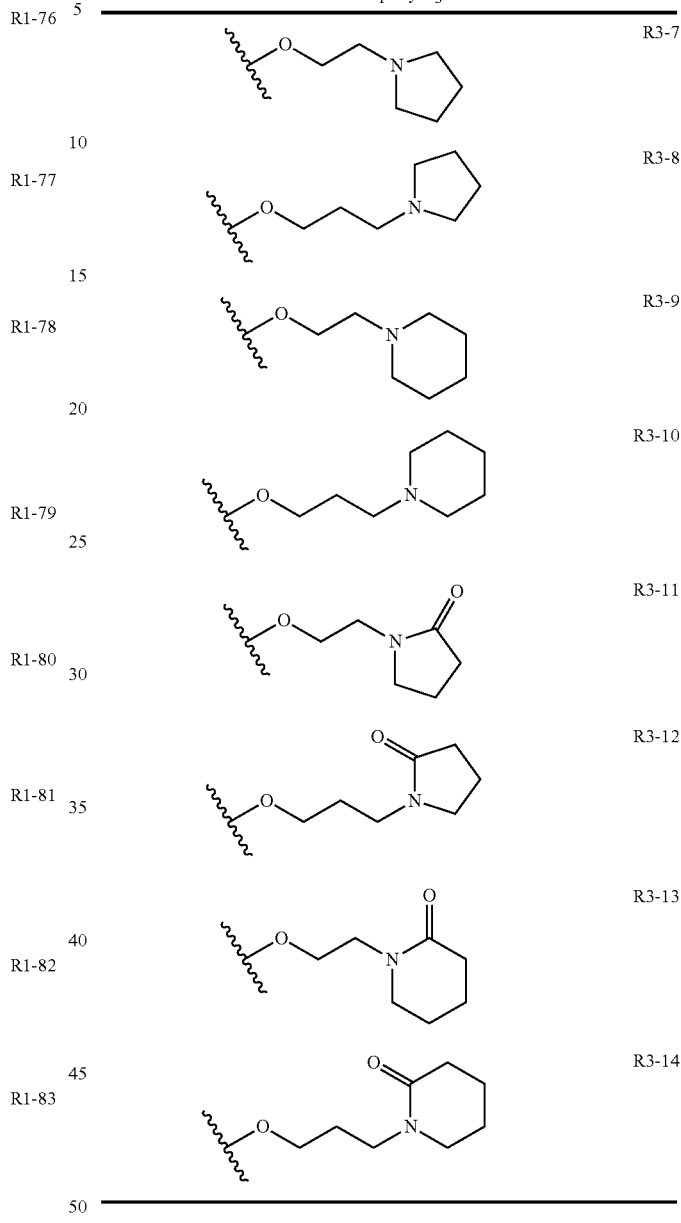

R3-7
R3-8
R3-9
R3-10
R3-11
R3-12
R3-13
R3-14

TABLE 2f

Each of the R₄, R₅, R₆, and R₇ moieties of the compounds of Formula II-b include, but are not limited to, the following:
Illustrative R₄, R₅, R₆, and R₇ Moieties

| | |
|---|---|
| hydrogen | R4-1 |
| methyl | R4-2 |
| ethyl | R4-3 |
| chloro | R4-4 |
| fluoro | R4-5 |
| bromo | R4-6 |
| hydroxy | R4-7 |
| —OMe | R4-8 |
| —NO₂ | R4-9 |
| —NH₂ | R4-10 |
| —NHCOCH₃ | R4-11 |
| —NHCOCH(CH₃)₂ | R4-12 |

TABLE 2f-continued

Each of the $R_4$, $R_5$, $R_6$, and $R_7$ moieties of the compounds of Formula II-b include, but are not limited to, the following:
Illustrative $R_4$, $R_5$, $R_6$, and $R_7$ Moieties

| Moiety | Label |
|---|---|
| —NHCOCF$_3$ | R4-13 |
| —NHCOPh | R4-14 |
| —NHCONHC$_4$H$_9$ | R4-15 |
| —N(Et)$_2$ | R4-16 |
| —NHSO$_2$Me | R4-17 |
| —NHSO$_2$CF$_3$ | R4-18 |
| 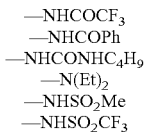 | R4-19 |
| 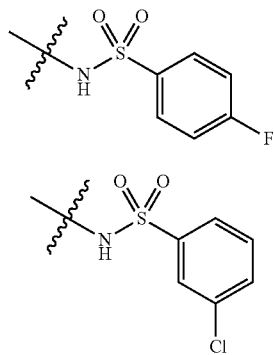 | R4-20 |
| —SO$_2$Me | R4-21 |
| —CN | R4-22 |
| $R_4$ and $R_5$ are —OCH$_2$O— | R4-23 |
| $R_5$ and $R_6$ are —OCH$_2$O— | R4-24 |
| $R_6$ and $R_7$ are —OCH$_2$O— | R4-25 |
| $R_4$ and $R_5$ are —OCH$_2$CH$_2$O— | R4-26 |
| $R_5$ and $R_6$ are —OCH$_2$CH$_2$O— | R4-27 |
| $R_6$ and $R_7$ are —OCH$_2$CH$_2$O— | R4-28 |
| —CO$_2$H | R4-29 |
| —CF$_3$ | R4-30 |
| —OEt | R4-31 |
| —SO$_2$NH$_2$ | R4-32 |
| —SO$_2$NHMe | R4-33 |
| SO$_2$NMe$_2$ | R4-34 |
| NHC(O)Me | R4-35 |
| —NHC(O)Ph | R4-36 |
| —NMeC(O)Et | R4-37 |
| —NMeC(O)Ph | R4-38 |
| —C(O)NHMe | R4-39 |
| —C(O)NEt$_2$ | R4-40 |
| —C(O)NH$_2$ | R4-41 |
| —NHC(O)NHMe | R4-42 |
| —CO$_2$Me | R4-43 |

Embodiments of the present invention include prodrugs of the compounds of Formula II-a or II-b.

In one embodiment, the present invention provides a compound of Formula III

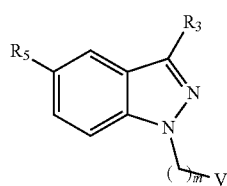

Formula III or a pharmaceutically acceptable salt, an isomer, a tautomer or a prodrug thereof wherein m, V, $R_3$, and $R_5$ are defined as in any aspect of embodiment above. In another embodiment:

m is 1 or 2;

V is an unsubstituted or a monosubstituted phenyl, cyclohexyl, or a 6-membered heterocyclo group where the heterocyclo group contains 1 nitrogen atom;

$R_3$ is —O-L-X;

L is an unsubstituted or a monosubstituted C$_1$-C$_5$ alkylene;

X is an unsubstituted or is a substituted 5, 6, or 7 membered non aromatic heterocyclo containing at least 1 nitrogen atom, —N(R$_{20}$)$_2$, or 4-substituted phenyl;

$R_5$ is hydrogen, alkyl, halo, substituted or unsubstituted 5, 6, 7 membered heterocyclo, or —NR$_{21}$R$_{22}$;

each $R_{20}$ is independently substituted or unsubstituted C$_1$-C$_3$ alkyl.

$R_{21}$ and $R_{22}$ are each independently selected from hydrogen, a substituted or an unsubstituted C$_1$-C$_3$ alkyl, C$_3$-C$_8$ cycloalkyl, aryl, or heteroaryl group, —COR$_{16}$, or —SO$_2$R$_{16}$, or $R_{21}$ and $R_{22}$ together with the nitrogen atom to which they are attached form a 5-7 membered a substituted or an unsubstituted heterocyclo group;

$R_{16}$ is a substituted or an unsubstituted C$_1$-C$_3$ alkyl.

In another embodiment, m is 1. In another embodiment, m is 2.

In another embodiment, the present invention provides a compound of Formula III wherein X is a 5, 6, or 7 membered non aromatic heterocyclo that is an unsubstituted or is sa substituted with 1-2 —OH, C$_1$-C$_3$ alkoxy, —CO$_2$R$_{17}$, —CON(R$_{18}$)$_2$, a substituted or an unsubstituted 5 or 6 membered aryl or heteroaryl group, C$_1$-C$_3$ alkyl, or C$_1$-C$_3$ alkyl substituted with —OH, C$_1$-C$_3$ alkoxy, —CO$_2$R$_{17}$, —NR$_{23}$R$_{24}$, —CO$_2$H;

$R_{17}$ is a substituted or an unsubstituted C$_1$-C$_6$ alkyl;

each $R_{18}$ is independently selected from hydrogen or a substituted or an unsubstituted C$_1$-C$_3$ alkyl;

$R_{23}$ and $R_{24}$ independently are hydrogen, a substituted or an unsubstituted aryl, heteroaryl, C$_1$-C$_3$ alkyl, or $R_{23}$ and $R_{24}$ together with the nitrogen atom they are attached form a substituted or an unsubstituted 5-7 membered non aromatic heterocycle.

In another embodiment, X is 1-pyrrolidinyl that is an unsubstituted or a substituted with 1-2 —OH, C$_1$-C$_3$ alkoxy, a substituted or an unsubstituted 6 membered aryl, C$_1$-C$_3$ alkyl, or C$_1$-C$_3$ alkyl substituted with —OH, C$_1$-C$_3$ alkoxy, or —NR$_{23}$R$_{24}$. In another embodiment, X is a substituted or an unsubstituted piperidinyl. In another embodiment, X is a 7-membered non aromatic heterocyclo group where the 7-membered non aromatic heterocyclo group contains 1 nitrogen atom.

In another embodiment, the present invention provides a compound of Formula III wherein L is —(CH$_2$)$_n$— and n is 1, 2, 3, or 4. In another embodiment, L is 3. In another embodiment, L is 2, in another embodiment, L is 1. In another embodiment, L is 4.

In another embodiment, the present invention provides a compound of Formula III wherein V is 4-chlorophenyl or 4-isopropylphenyl. In another embodiment, the present invention provides a compound of Formula III wherein V is 4-chlorophenyl.

In another embodiment, the present invention provides a compound of Formula III wherein $R_5$ is hydrogen, halo, a substituted or an unsubstituted 5, 6, 7 membered heterocyclo, or —NR$_{21}$R$_{22}$. In another embodiment, $R_5$ is hydrogen. In another embodiment, $R_5$ is halo. In another embodiment, $R_5$ is a substituted or an unsubstituted 5 membered heterocyclo. In another embodiment, $R_5$ is a substituted or an unsubstituted 6 membered heterocyclo. In another embodiment, $R_5$ is a substituted or an unsubstituted 7 membered non aromatic heterocyclo. In another embodiment, $R_5$ is $NR_{21}R_{22}$. In one embodiment, $R_{21}$ and $R_{22}$ are both a substituted or an unsubstituted $C_1$-$C_3$ alkyl. In another embodiment, $R_{21}$ is a substituted or an unsubstituted $C_1$-$C_3$ alkyl. In another embodiment, $R_{21}$ is hydrogen.

In another embodiment, $R_{22}$ is —$COR_{16}$, or —$SO_2R_{16}$. In another embodiment, $R_{22}$ is $C_3$-$C_8$ cycloalkyl. In another embodiment, $R_{22}$ is aryl or heteroaryl.

In one embodiment, the present invention provides the compounds disclosed in Table 6 below. In another embodiment, the present invention provides the compounds disclosed in Table 7 below.

The compounds provided herein as viral inhibiting agents are generally capable of inhibiting viral replication in vitro and/or in vivo. For example a compound of the present invention when contacted with an HCV-infected cell (e.g., an HCV-infected liver cell), reduces the amount of infectious HCV viral particles produced by the HCV-infected cell by at least about 5%, at least about 10%, at least about 15%, at least about 20%, at least about 25%, at least about 30%, at least about 35%, at least about 40%, at least about 45%, at least about 50%, at least about 60%, at least about 70%, at least about 80%, at least about 90%, or at least about 95% or even higher, compared to the number of infectious HCV viral particles produced by the cell not contacted with the inhibiting agent.

A wide variety of methods are available to assess whether a compound can reduce viral load in vitro and/or in vivo. In vitro assay typically determines the number of viral particles present in the culture medium, wherein an in vivo assay typically measures the viral titer present in a bodily fluid of an infected subject. Bodily fluids suitable for viral titer measurement include, but are not limited to, blood, serum, plasma, saliva, semen, spinal fluid, urine, sweat, and cerebral spinal fluid. Commonly employed methods for detecting viral load in vitro or in vivo include quantitative polymerase chain reaction (PCR) and branched DNA (bDNA) test. Numerous quantitative assays for measuring the viral load (titer) of HCV RNA have been developed. Many such assays are available commercially, including a quantitative reverse transcription PCR (RT-PCR) (Amplicor HCV Monitor™, Roche Molecular Systems, New Jersey); and a branched DNA (deoxyribonucleic acid) signal amplification assay (Quantiplex™ HCV RNA Assay (bDNA), Chiron Corp., Emeryville, Calif.). See, e.g., Gretch et al. (1995) *Ann. Intern. Med.* 123:321-329. Also of interest is a nucleic acid test (NAT) sold by Chiron Corporation under the trade name Procleix®, which NAT simultaneously tests for the presence of HIV-1 and HCV. See, e.g., Vargo et al. (2002) *Transfusion* 42:876-885.

The compounds provided herein can also be characterized by their ability to inhibit binding of NS4B polypeptide to the 3'UTR of HCV negative strand RNA by at least about 5%, at least about 10%, at least about 15%, at least about 20%, at least about 25%, at least about 30%, at least about 35%, at least about 40%, at least about 45%, at least about 50%, at least about 60%, at least about 70%, at least about 80%, at least about 90%, or at least about 95% or higher, compared to the binding of NS4B polypeptide to the 3'UTR of HCV negative strand RNA in the absence of the compound.

In some embodiments, the inhibiting agents of the present invention inhibit binding of NS4B polypeptide to the 3'UTR of HCV negative strand RNA with a 50% inhibitory concentration ($IC_{50}$) of about 100 μM to 50 μM, about 50 μM to 25 μM, about 25 μM to 10 μM, about 10 μM to 5 μM, about 5 μM to 1 μM, about 1 μM to 500 nM, about 500 nM to 400 nM, about 400 nM to 300 nM, about 300 nM to 250 nM, about 250 nM to 200 nM, about 200 nM to 150 nM, about 150 nM to 100 nM, about 100 nM to 50 nM, about 50 nM to 30 nM, about 30 nM to 25 nM, about 25 nM to 20 nM, about 20 nM to 15 nM, about 15 nM to 10 nM, about 10 nM to 5 nM, less than about 5 nM, less than about 1 nM, less than about 0.1 nM, or less than about 0.01 nM.

In other embodiments, the inhibiting agents of the present invention lack substantial cross-reactivity with HERG $K^+$ channel. Drug-induced cardiac arrhythmia, such as QT prolongation, is a serious safety concern in the discovery, development and use of new medications. Drug-induced QT interval prolongation is an active field of research and has been reviewed (Pearlstein et al. *J. Med. Chem.* (2003), 46(11): 2017-2022; Fermini et al., *Annual Reports in Medicinal Chemistry* (2004), 39:323; http://www.qtdrugs.org). A common cause of QT prolongation is the inhibition of the cardiac HERG $K^+$ channel by a drug. Drugs from widely different chemical classes and therapeutic utility have been shown to block HERG activity. Many medications known to be HERG channel inhibitors interact with the channel at concentrations similar to the desired therapeutic concentration. One strategy to prevent the occurrence of drug-induced QT interval prolongation is to select drug candidates that show a reduced affinity for the HERG $K^+$ channel. This property can be characterized by an in vitro assay utilizing HEK293 or CHO cells stably transfected with the hERG gene and utilizing a patch-clamp technique to determine Ikr current. Accordingly, some preferred inhibiting agents of the present invention exhibit reduced affinity for or lack substantial cross-reactivity with the HERG $K^+$ channel. In one aspect, an exemplary inhibiting agent of the present invention has a HERG $IC_{50}$ of greater than about 100 nM. In another aspect, the inhibiting agent described herein has a HERG $IC_{50}$ of greater than about 500 nM, 1,000 nM, 5,000 nM, 1 μM, 5 μM, 10 μM, 50 μM, 100 μM or even higher.

Methods of Synthesis

In general, the inhibiting agents provided can be made according to organic synthesis techniques known to those skilled in this art and/or according to the synthesis schemes provided herein. Where desired, synthesis of the subject compound begins with commercially available chemicals and/or from compounds described in the chemical literature. "Commercially available chemicals" may be obtained from standard commercial sources including Acros Organics (Pittsburgh Pa.), Aldrich Chemical (Milwaukee Wis., including Sigma Chemical and Fluka), Apin Chemicals Ltd. (Milton Park UK), Avocado Research (Lancashire U.K.), BDH Inc. (Toronto, Canada), Bionet (Cornwall, U.K.), Chemservice Inc. (West Chester Pa.), Crescent Chemical Co. (Hauppauge N.Y.), Eastman Organic Chemicals, Eastman Kodak Company (Rochester N.Y.), Fisher Scientific Co. (Pittsburgh Pa.), Fisons Chemicals (Leicestershire UK), Frontier Scientific (Logan Utah), ICN Biomedicals, Inc. (Costa Mesa Calif.), Key Organics (Cornwall U.K.), Lancaster Synthesis (Windham N.H.), Maybridge Chemical Co. Ltd. (Cornwall U.K.), Parish Chemical Co. (Orem Utah), Pfaltz & Bauer, Inc. (Waterbury Conn.), Polyorganix (Houston Tex.), Pierce Chemical Co. (Rockford Ill.), Riedel de Haen AG (Hanover, Germany), Spectrum Quality Product, Inc. (New Brunswick, N.J.), TCI America (Portland Oreg.), Trans World Chemicals, Inc. (Rockville Md.), and Wako Chemicals USA, Inc. (Richmond Va.). In addition, Methods known to one of ordinary skill in the art may be identified through various reference books and databases. Suitable reference books and treatises that detail the synthesis of reactants useful in the preparation of the inhibiting agents described herein, or provide references to articles that describe the preparation, include for example, "Synthetic Organic Chemistry", John Wiley & Sons, Inc., New York; S. R. Sandler et al., "Organic Functional Group Preparations," 2nd Ed., Academic Press, New York, 1983; H. O. House, "Modern Synthetic Reactions", 2nd Ed., W. A. Benjamin, Inc. Menlo Park, Calif. 1972; T. L. Gilchrist, "Heterocyclic Chemistry", 2nd Ed., John Wiley & Sons, New York, 1992; J. March, "Advanced Organic Chemistry: Reactions, Mechanisms and Structure", 4th Ed., Wiley-Interscience, New York, 1992. Additional suitable reference books and treatise that detail the synthesis of reactants useful in the preparation of compounds described herein, or provide references to articles that describe the preparation, include for example, Fuhrhop, J. and Penzlin G. "Organic Synthesis: Concepts, Methods, Starting Materials", Second, Revised and Enlarged Edition (1994) John Wiley & Sons ISBN: 3-527-29074-5; Hoffman, R. V. "Organic Chemistry, An Intermediate Text" (1996) Oxford University Press, ISBN 0-19-509618-5; Larock, R. C. "Comprehensive Organic Transformations: A Guide to Functional Group Preparations" 2nd Edition (1999) Wiley-VCH, ISBN: 0-471-19031-4; March, J. "Advanced Organic Chemistry: Reactions, Mechanisms, and Structure" 4th Edition (1992) John Wiley & Sons, ISBN: 0-471-60180-2; Otera, J. (editor) "Modern Carbonyl Chemistry" (2000) Wiley-VCH, ISBN: 3-527-29871-1; Patai, S. "Patai's 1992 Guide to the Chemistry of Functional Groups" (1992) Interscience ISBN: 0-471-93022-9; Solomons, T. W. G. "Organic Chemistry" 7th Edition (2000) John Wiley & Sons, ISBN: 0-471-19095-0; Stowell, J. C., "Intermediate Organic Chemistry" 2nd Edition (1993) Wiley-Interscience, ISBN: 0-471-57456-2; "Industrial Organic Chemicals: Starting Materials and Intermediates: An Ullmann's Encyclopedia" (1999) John Wiley & Sons, ISBN: 3-527-29645-X, in 8 volumes; "Organic Reactions" (1942-2000) John Wiley & Sons, in over 55 volumes; and "Chemistry of Functional Groups" John Wiley & Sons, in 73 volumes. Unless specified to the contrary, the reactions described herein take place at atmospheric pressure, generally within a temperature range from −10° C. to 200° C. Further, except as otherwise specified, reaction times and conditions are intended to be approximate, e.g., taking place at about atmospheric pressure within a temperature range of about −10° C. to about 110° C. over a period of about 1 to about 24 hours; reactions left to run overnight average a period of about 16 hours.

Unless specified to the contrary, the solvents used in the reactions described herein are inert organic solvents. Unless specified to the contrary, for each gram of the limiting reagent, one cc (or mL) of solvent constitutes a volume equivalent.

Isolation and purification of the chemical entities and intermediates described herein can be effected, if desired, by any suitable separation or purification procedure such as, for example, filtration, extraction, crystallization, column chromatography, thin-layer chromatography or thick-layer chromatography, or a combination of these procedures. Specific illustrations of suitable separation and isolation procedures can be had by reference to the examples hereinbelow. However, other equivalent separation or isolation procedures can also be used.

When desired, the (R)- and (S)-isomers of the compounds of the present invention, if present, may be resolved by methods known to those skilled in the art, for example by formation of diastereoisomeric salts or complexes which may be separated, for example, by crystallization; via formation of diastereoisomeric derivatives which may be separated, for example, by crystallization, gas-liquid or liquid chromatography; selective reaction of one enantiomer with an enantiomer-specific reagent, for example enzymatic oxidation or reduction, followed by separation of the modified and unmodified enantiomers; or gas-liquid or liquid chromatography in a chiral environment, for example on a chiral support, such as silica with a bound chiral ligand or in the presence of a chiral solvent. Alternatively, a specific enantiomer may be synthesized by asymmetric synthesis using optically active reagents, substrates, catalysts or solvents, or by converting one enantiomer to the other by asymmetric transformation.

The compounds described herein can be optionally contacted with a pharmaceutically acceptable acid to form the corresponding acid addition salts.

Many of the optionally substituted starting compounds and other reactants are commercially available, e.g., from Aldrich Chemical Company (Milwaukee, Wis.) or can be readily prepared by those skilled in the art using commonly employed synthetic methodology.

The compounds of the invention can be synthesized by an appropriate combination of known synthetic methods in the art and the instant disclosure. The discussion below is offered to illustrate certain of the diverse methods available for use in making the compounds of the invention and is not intended to limit the scope of reactions or reaction sequences that can be used in preparing the compounds of the present invention.

Compounds of the invention can be prepared by the O-alkylation of 1-substituted-benzyl-1H-indazol-3(2H)-one 1.1 with $R_{11}X$ (X=Cl, Br, I, OMs, OTs, and the like), as described in Scheme 1.

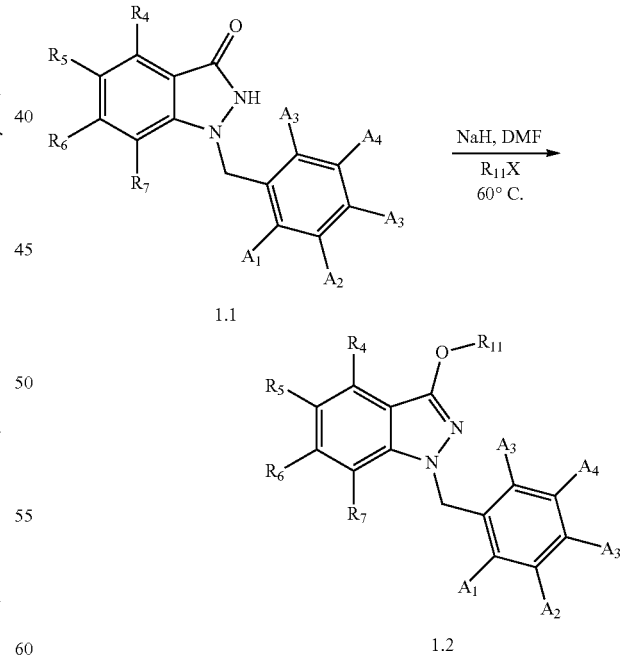

Scheme 1

Scheme 2 illustrates a general method for the synthesis of 1-substituted-benzyl-1H-indazol-3(2H)-ones 2.3 by the N-alkylation of 1H-indazol-3(2H)-one 2.1 with substituted benzyl electrophiles 2.2 (X=Cl, Br, I, OMs, OTs, and the like).

Scheme 2

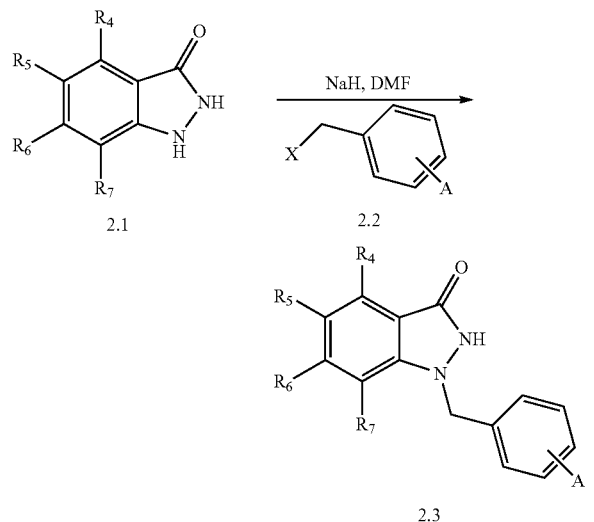

Scheme 3 illustrates the synthesis of compounds of the invention. 3-indazolinone 3.1 can be alkylated in high yields by treatment with NaOH in EtOH, followed by treatment with a substituted benzyl halide to provide 3.2 (Japanese Patent JP49007278). Deprotonation followed by alkylation with a protected bromo-alcohol provides 3.3. Deprotection of the alcohol followed by activation and displacement with primary and secondary amines and/or alkoxides provides 3.4.

Scheme 3

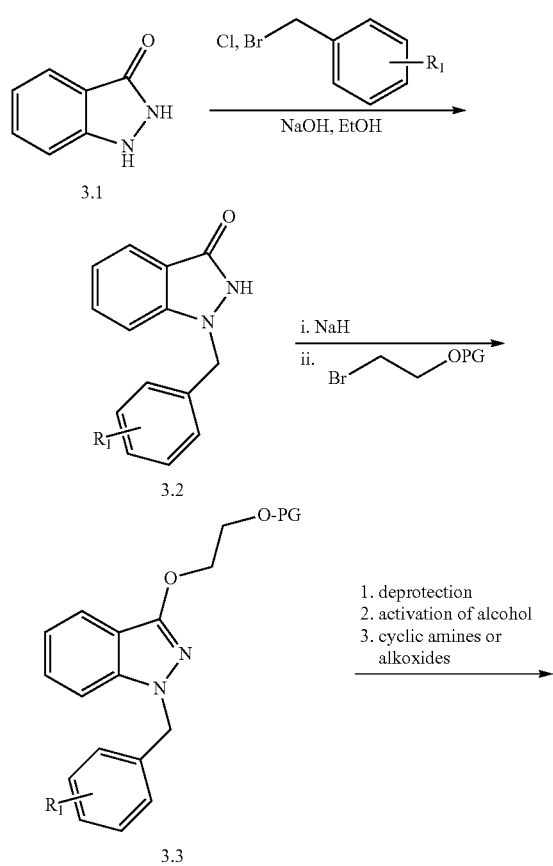

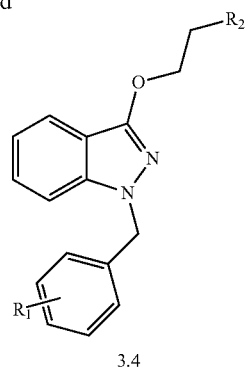

Scheme 4 illustrates a method for the synthesis of compounds of the invention. Treatment of 3-indazilinone 4.1 with $PBu_3$ and diazodipiperidinylamide provides ether 4.2. Deprotonation with NaH followed by alkylation provides compounds of general structure 4.3.

Scheme 4

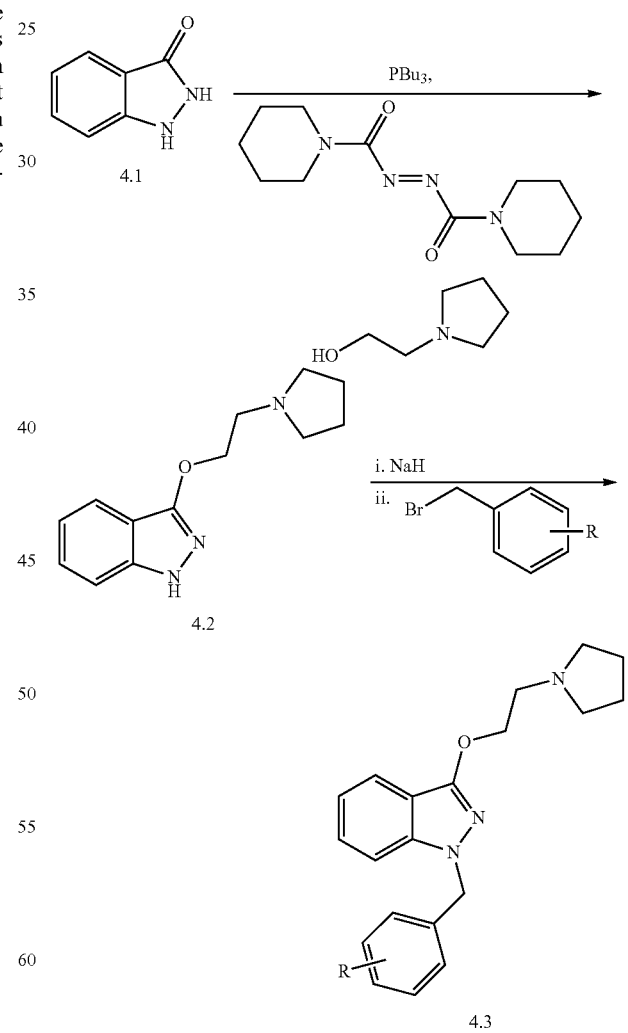

Scheme 5 illustrates the synthesis of 1- or 2-(substituted-benzyl)-indazole 5.2 and 5.3 by the alkylation of indazole 5.1 with benzyl halide (X=Cl, Br, I, OMs, OTs, and the like).

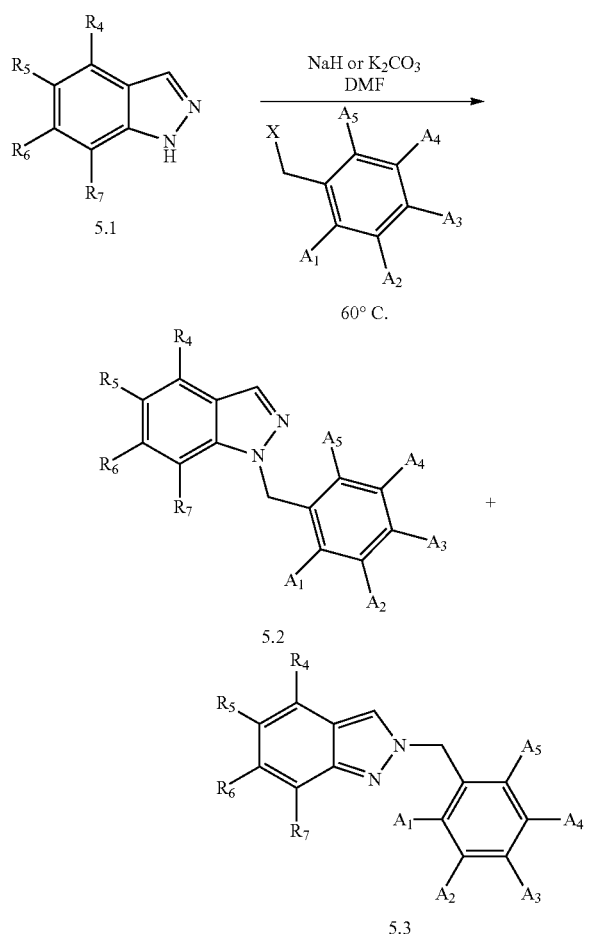

Scheme 5

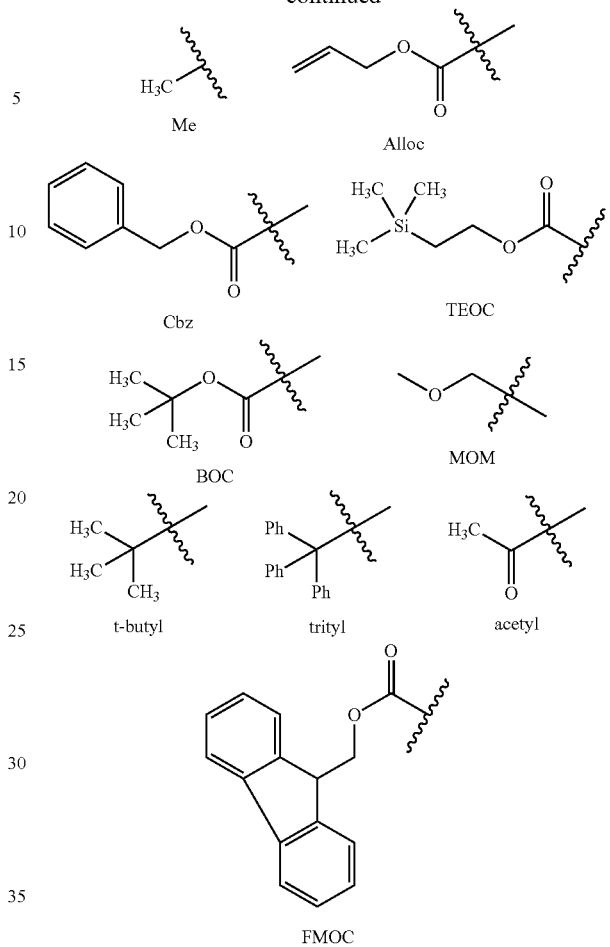

The synthesis of one or more of the inhibiting agents of the present invention may employ protecting groups and blocking groups. Allyl blocking groups are useful in the presence of acid- and base-protecting groups since the former are stable and can be subsequently removed by metal or pi-acid catalysts. For example, an allyl-blocked carboxylic acid can be deprotected with a palladium(0)-catalyzed reaction in the presence of acid labile t-butyl carbamate or base-labile acetate amine protecting groups. Yet another form of protecting group is a resin to which a compound or intermediate may be attached. As long as the residue is attached to the resin, that functional group is blocked and cannot react. Once released from the resin, the functional group is available to react.

Typical blocking/protecting groups are known in the art and include, but are not limited to, the following moieties.

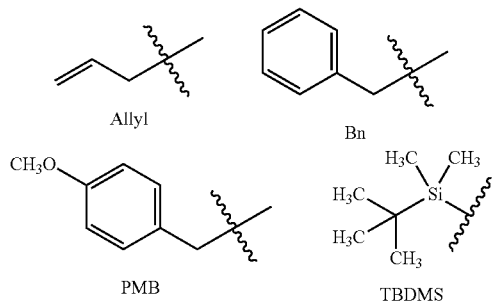

Pharmaceutical Formulations and Routes of Administration

The present invention provides pharmaceutical compositions comprising one or more inhibiting agents disclosed herein with or without pharmaceutically acceptable excipients, diluents, carriers and/or adjuvants. In some embodiment, the pharmaceutical compositions are formulated to be substantially free of excipients. Thus, in one embodiment, the present invention provides a pharmaceutical composition comprising or consisting essentially of the compound of Formula III and a pharmaceutically acceptable carrier, excipient, or diluent.

In other embodiments, inhibiting agents can be formulated with one or more pharmaceutically acceptable auxiliary substances.

In an embodiment, the inhibiting agent can be combined with another anti-viral agent to prepare a composition of the invention, and the composition can include one or more pharmaceutically acceptable excipients, diluents, carriers and/or adjuvants.

A wide variety of pharmaceutically acceptable excipients are known in the art. Pharmaceutically acceptable excipients have been amply described in a variety of publications, including, for example, A. Gennaro (2000) "Remington: The Science and Practice of Pharmacy," 20th edition, Lippincott, Williams, & Wilkins; Pharmaceutical Dosage Forms and Drug Delivery Systems (1999) H. C. Ansel et al., eds., $7^{th}$ ed., Lippincott, Williams, & Wilkins; and Handbook of Pharmaceutical Excipients (2000) A. H. Kibbe et al., eds., $3^{rd}$ ed. Amer. Pharmaceutical Assoc.

The pharmaceutically acceptable excipients, such as vehicles, adjuvants, carriers or diluents, are readily available to the public. Moreover, pharmaceutically acceptable auxiliary substances, such as pH adjusting and buffering agents, tonicity adjusting agents, stabilizers, wetting agents and the like, are readily available to the public.

In an embodiment of the present disclosure, the inhibiting agent is administered to the host using any means capable of resulting in the desired effect (e.g., reduction in viral load, reduction in liver fibrosis, increase in liver function, and the like). Thus, the inhibiting agent can be incorporated into a variety of formulations for therapeutic administration. For example, the inhibiting agent can be formulated into pharmaceutical compositions by combination with appropriate, pharmaceutically acceptable carriers or diluents, and may be formulated into preparations in solid, semi-solid, liquid or gaseous forms, such as tablets, capsules, powders, granules, ointments, solutions, suppositories, injections, inhalants and aerosols.

In pharmaceutical dosage forms, the inhibiting agent may be administered in the form of its pharmaceutically acceptable salts, or a subject active agent may be used alone or in appropriate association, as well as in combination, with other pharmaceutically active compounds. The following methods and excipients are merely exemplary and are in no way limiting.

For oral preparations, the inhibiting agent can be used alone or in combination with appropriate additives to make tablets, powders, granules or capsules, for example, with conventional additives, such as lactose, mannitol, corn starch or potato starch; with binders, such as crystalline cellulose, cellulose derivatives, acacia, corn starch or gelatins; with disintegrators, such as corn starch, potato starch or sodium carboxymethylcellulose; with lubricants, such as talc or magnesium stearate; and if desired, with diluents, buffering agents, moistening agents, preservatives and flavoring agents.

Embodiments of the inhibiting agent can be formulated into preparations for injection by dissolving, suspending or emulsifying them in an aqueous or nonaqueous solvent, such as vegetable or other similar oils, synthetic aliphatic acid glycerides, esters of higher aliphatic acids or propylene glycol; and if desired, with conventional additives such as solubilizers, isotonic agents, suspending agents, emulsifying agents, stabilizers and preservatives.

Embodiments of the inhibiting agent can be utilized in aerosol formulation to be administered via inhalation. Embodiments of the inhibiting agent can be formulated into pressurized acceptable propellants such as dichlorodifluoromethane, propane, nitrogen, and the like.

Furthermore, embodiments of the inhibiting agent can be made into suppositories by mixing with a variety of bases such as emulsifying bases or water-soluble bases. Embodiments of the inhibiting agent can be administered rectally via a suppository. The suppository can include vehicles such as cocoa butter, carbowaxes and polyethylene glycols, which melt at body temperature, yet are solidified at room temperature.

Unit dosage forms for oral or rectal administration, such as syrups, elixirs, and suspensions, may be provided wherein each dosage unit, for example, teaspoonful, tablespoonful, tablet or suppository, contains a predetermined amount of the composition containing one or more inhibiting agents. Similarly, unit dosage forms for injection or intravenous administration may comprise the inhibiting agent in a composition as a solution in sterile water, normal saline or another pharmaceutically acceptable carrier.

Embodiments of the inhibiting agent can be formulated in an injectable composition in accordance with the invention. Typically, injectable compositions are prepared as liquid solutions or suspensions; solid forms suitable for solution in, or suspension in, liquid vehicles prior to injection may also be prepared. The preparation may also be emulsified or the active ingredient (inhibiting agent) encapsulated in liposome vehicles in accordance with the invention.

In an embodiment, the inhibiting agent is formulated for delivery by a continuous delivery system. The term "continuous delivery system" is used interchangeably herein with "controlled delivery system" and encompasses continuous (e.g., controlled) delivery devices (e.g., pumps) in combination with catheters, injection devices, and the like, a wide variety of which are known in the art.

Mechanical or electromechanical infusion pumps can also be suitable for use with the present disclosure. Examples of such devices include those described in, for example, U.S. Pat. Nos. 4,692,147; 4,360,019; 4,487,603; 4,360,019; 4,725,852; 5,820,589; 5,643,207; 6,198,966; and the like. In general, delivery of the inhibiting agent can be accomplished using any of a variety of refillable, pump systems. Pumps provide consistent, controlled release over time. In some embodiments, the inhibiting agent is in a liquid formulation in a drug-impermeable reservoir, and is delivered in a continuous fashion to the individual.

In one embodiment, the drug delivery system is an at least partially implantable device. The implantable device can be implanted at any suitable implantation site using methods and devices well known in the art. An implantation site is a site within the body of a subject at which a drug delivery device is introduced and positioned. Implantation sites include, but are not necessarily limited to, a subdermal, subcutaneous, intramuscular, or other suitable site within a subject's body. Subcutaneous implantation sites are used in some embodiments because of convenience in implantation and removal of the drug delivery device.

Drug release devices suitable for use in the disclosure may be based on any of a variety of modes of operation. For example, the drug release device can be based upon a diffusive system, a convective system, or an erodible system (e.g., an erosion-based system). For example, the drug release device can be an electrochemical pump, osmotic pump, an electroosmotic pump, a vapor pressure pump, or osmotic bursting matrix, e.g., where the drug is incorporated into a polymer and the polymer provides for release of drug formulation concomitant with degradation of a drug-impregnated polymeric material (e.g., a biodegradable, drug-impregnated polymeric material). In other embodiments, the drug release device is based upon an electrodiffusion system, an electrolytic pump, an effervescent pump, a piezoelectric pump, a hydrolytic system, and the like.

Drug release devices based upon a mechanical or electromechanical infusion pump can also be suitable for use with the present disclosure. Examples of such devices include those described in, for example, U.S. Pat. Nos. 4,692,147; 4,360,019; 4,487,603; 4,360,019; 4,725,852, and the like. In general, a subject treatment method can be accomplished using any of a variety of refillable, non-exchangeable pump systems. Pumps and other convective systems are generally preferred due to their generally more consistent, controlled release over time. Osmotic pumps are used in some embodiments due to their combined advantages of more consistent controlled release and relatively small size (see, e.g., PCT published application no. WO 97/27840 and U.S. Pat. Nos. 5,985,305 and 5,728,396). Exemplary osmotically-driven devices suitable for use in the disclosure include, but are not necessarily limited to, those described in U.S. Pat. Nos. 3,760,984; 3,845,770; 3,916,899; 3,923,426; 3,987,790; 3,995,631; 3,916,899; 4,016,880; 4,036,228; 4,111,202; 4,111,203; 4,203,440; 4,203,442; 4,210,139; 4,327,725; 4,627,850; 4,865,845; 5,057,318; 5,059,423; 5,112,614; 5,137,727; 5,234,692; 5,234,693; 5,728,396; and the like.

In some embodiments, the drug delivery device is an implantable device. The drug delivery device can be implanted at any suitable implantation site using methods and devices well known in the art. As noted herein, an implantation site is a site within the body of a subject at which a drug delivery device is introduced and positioned. Implantation sites include, but are not necessarily limited to a subdermal, subcutaneous, intramuscular, or other suitable site within a subject's body.

In some embodiments, an active agent is delivered using an implantable drug delivery system, e.g., a system that is programmable to provide for administration of the agent. Exemplary programmable, implantable systems include implantable infusion pumps. Exemplary implantable infusion pumps, or devices useful in connection with such pumps, are described in, for example, U.S. Pat. Nos. 4,350,155; 5,443,450; 5,814,019; 5,976,109; 6,017,328; 6,171,276; 6,241,704; 6,464,687; 6,475,180; and 6,512,954. A further exemplary device that can be adapted for the present disclosure is the Synchromed infusion pump (Medtronic).

Suitable excipient vehicles for the inhibiting agent are, for example, water, saline, dextrose, glycerol, ethanol, or the like, and combinations thereof. In addition, if desired, the vehicle may contain minor amounts of auxiliary substances such as wetting or emulsifying agents or pH buffering agents. Methods of preparing such dosage forms are known, or will be apparent upon consideration of this disclosure, to those skilled in the art. See, e.g., Remington's Pharmaceutical Sciences, Mack Publishing Company, Easton, Pa., 17th edition, 1985. The composition or formulation to be administered will, in any event, contain a quantity of the inhibiting agent adequate to achieve the desired state in the subject being treated.

Compositions of the present invention include those that comprise a sustained-release or controlled release matrix. In addition, embodiments of the present invention can be used in conjunction with other treatments that use sustained-release formulations. As used herein, a sustained-release matrix is a matrix made of materials, usually polymers, which are degradable by enzymatic or acid-based hydrolysis or by dissolution. Once inserted into the body, the matrix is acted upon by enzymes and body fluids. A sustained-release matrix desirably is chosen from biocompatible materials such as liposomes, polylactides (polylactic acid), polyglycolide (polymer of glycolic acid), polylactide co-glycolide (copolymers of lactic acid and glycolic acid), polyanhydrides, poly(ortho) esters, polypeptides, hyaluronic acid, collagen, chondroitin sulfate, carboxcylic acids, fatty acids, phospholipids, polysaccharides, nucleic acids, polyamino acids, amino acids such as phenylalanine, tyrosine, isoleucine, polynucleotides, polyvinyl propylene, polyvinylpyrrolidone and silicone. Illustrative biodegradable matrices include a polylactide matrix, a polyglycolide matrix, and a polylactide co-glycolide (co-polymers of lactic acid and glycolic acid) matrix. Similarly, the sustained release formulations of embodiments of the invention can help maintain viral-inhibiting concentrations over a longer time interval. In another embodiment, the pharmaceutical composition of the present disclosure (as well as combination compositions) are delivered in a controlled release system. For example, the inhibiting agent may be administered using intravenous infusion, an implantable osmotic pump, a transdermal patch, liposomes, or other modes of administration. In one embodiment, a pump may be used (Sefton (1987). *CRC Crit. Ref. Biomed. Eng.* 14:201; Buchwald et al. (1980). *Surgery* 88:507; Saudek et al. (1989). *N. Engl. J. Med.* 321:574). In another embodiment, polymeric materials are used. In yet another embodiment a controlled release system is placed in proximity of the therapeutic target, i.e., the liver, thus requiring only a fraction of the systemic dose. In yet another embodiment, a controlled release system is placed in proximity of the therapeutic target, thus requiring only a fraction of the systemic. Other controlled release systems are discussed in the review by Langer (1990). *Science* 249:1527-1533.

In another embodiment, the compositions of the present invention (as well as combination compositions separately or together) include those formed by impregnation of an inhibiting agent described herein into absorptive materials, such as sutures, bandages, and gauze, or coated onto the surface of solid phase materials, such as surgical staples, zippers and catheters to deliver the compositions. Other delivery systems of this type will be readily apparent to those skilled in the art in view of the instant disclosure.

The compounds disclosed herein can be formulated in a pharmaceutical composition comprising an effective amount of the inhibiting agent for its intended use. For example, a compound of the present invention can be formulated in a unit dose form between about 10 mg to about 500 mg for treating viral infections, especially infections by a virus of the Flaviviridae family. In some embodiments, a compound of the present invention is formulated in a unit dose form between about 25 mg to about 250 mg, between about 25 mg to about 100 mg, or between about 50 mg to about 100 mg. In particular, a compound of the present invention can be formulated in 25 mg, 50 mg, 75 mg, 100 mg, 125 mg, 150 mg or 200 mg unit dose form. In one embodiment, the unit dose form is a tablet; in another, the unit dose form is a capsule. The tablet can be formulated as immediate release dose form or as sustained release form. In yet another embodiment, the unit dose form is a liquid.

Uses of the Compounds and Pharmaceutical Compositions of the Present Invention

The subject compounds and pharmaceutical compositions thereof are particularly useful for treating infection by a virus of the Flaviviridae family. In one embodiment, the present invention provides a method of treating a subject infected with a virus from the Flaviviridae family comprising administering to the subject the compound of Formula III or a pharmaceutical composition comprising, or consisting essentially of the compound of Formula III, in an amount that is effective in reducing viral load of said virus in said subject.

The treatment methods typically comprise administering to a subject infected with such virus a therapeutically effective amount of an inhibiting agent in one or more doses, alone or in combination with other agents. For subjects already infected with a virus of the Flaviviridae family such as Hepatitis Virus C, the method of the present invention is generally effective in reducing the viral load over a period of a few days, a few weeks or a few months.

The present invention also provides methods of prophylactically treating an infection by a virus of the Flaviviridae family of viruses comprising administering an effective amount of an inhibiting agent described herein to a subject in need thereof. Prophylactic treatment of infection by a virus of the Flaviviridae family (including but not limited to HCV) is particularly important for patients who will be undergoing liver transplantation for HCV-associated end stage liver disease (ESLD). It has been reported that the new graft is nearly certain to be infected with HCV if viremia is present at the time of transplantation. Prophylactic treatment with the compounds of the present invention can be performed to reduce or eliminate HCV viral load prior to liver transplantation, and can help prevent the recurrence of HCV after transplantation. The administration of the compounds of the present invention may also be advantageous for patients who cannot tolerate full doses of standard of care therapy (pegylated interferon and ribavirin). Where desired, for pre-transplant patients with ESLD, or post-transplant patients with HCV recurrence, either an isostere monotherapy, or an isostere of the present invention in combination with regular or reduced doses of pegylated interferon and ribavirin, can be used to treat these patients. Similarly, a compound of the present invention in combination with nitazoxanide (or another thiazolide, or sustained formulations of either of these) can be used to treat these patients, as can indazole plus nitazoxanide (or another thiazolide, or sustained formulations of either of these) plus standard of care medications, at reduced or regular doses, as tolerated. Clemizole, administered via any of the above embodiments, can also be administered as suppressive (e.g., maintenance) or consolidation therapy, such after effective suppression of HCV by regimens containing clemizole or other agents.

The inhibiting agent of the present invention and pharmaceutical composition comprising the same can be administered to a subject in one or more doses. In an embodiment, the inhibiting agent can be administered in an amount of about 10 mg to 1000 mg per dose, e.g., about 10 mg to 20 mg, about 20 mg to 25 mg, about 25 mg to 50 mg, about 50 mg to 75 mg, about 75 mg to 100 mg, about 100 mg to 125 mg, about 125 mg to 150 mg, about 150 mg to 175 mg, about 175 mg to 200 mg, about 200 mg to 225 mg, about 225 mg to 250 mg, about 250 mg to 300 mg, about 300 mg to 350 mg, about 350 mg to 400 mg, about 400 mg to 450 mg, about 450 mg to 500 mg, about 500 mg to 750 mg, or about 750 mg to 1000 mg per dose.

In an embodiment, the amount of the inhibiting agent per dose is determined on a per body weight basis. For example, in an embodiment, the inhibiting agent can be administered in an amount of about 0.5 mg/kg to 100 mg/kg, e.g., about 0.5 mg/kg to 1 mg/kg, about 1 mg/kg to 2 mg/kg, about 2 mg/kg to 3 mg/kg, about 3 mg/kg to 5 mg/kg, about 5 mg/kg to 7 mg/kg, about 7 mg/kg to about 10 mg/kg, about 10 mg/kg to 15 mg/kg, about 15 mg/kg to 20 mg/kg, about 20 mg/kg to 25 mg/kg, about 25 mg/kg to 30 mg/kg, about 30 mg/kg to 40 mg/kg, about 40 mg/kg to 50 mg/kg per dose, about 50 mg/kg to 60 mg/kg, about 60 mg/kg to 70 mg/kg, about 70 mg/kg to 80 mg/kg, about 80 mg/kg to 90 mg/kg, or about 90 mg/kg to 100 mg/kg, or more than about 100 mg/kg.

Those of skill will readily appreciate that dose levels can vary as a function of the specific inhibiting agent administered, the severity of the symptoms and the susceptibility of the subject to side effects. Preferred dosages for a given compound are readily determinable by those of skill in the art by a variety of means.

In an embodiment, multiple doses of the inhibiting agent are administered. The frequency of administration of the inhibiting agent can vary depending on any of a variety of factors, e.g., severity of the symptoms, and the like. For example, in an embodiment, the inhibiting agent is administered once per month, twice per month, three times per month, every other week (qow), once per week (qw), twice per week (biw), three times per week (tiw), four times per week, five times per week, six times per week, every other day (qod), daily (qd), twice a day (qid), or three times a day (tid). As discussed above, in an embodiment, the inhibiting agent is administered continuously.

By way of illustration, efficacious dosing of a compound of the invention can include dosing at about 200 mg po BID, 150 mg po BID, 75 mg po BID, or 50 mg po BID. The total daily dose can also be split among multiple doses, which allows for a lower dose at each administration with less potential for sedation while maintaining sufficient efficacy. Alternatively, a more frequent dosing schedule can be applied for sever cases, for example, TID administration or administration every 4, 6, 8, or 12 hours of a 25 mg, 50 mg, 75 mg, 150 mg or higher dose. Alternatively, a sustained release formulation may be used.

The duration of administration of the inhibiting agent, e.g., the period of time over which the inhibiting agent is administered, can vary, depending on any of a variety of factors, e.g., patient response, and the like. For example, the inhibiting agent can be administered over a period of time of about one day to one week, about two weeks to four weeks, about one month to two months, about two months to four months, about four months to six months, about six months to eight months, about eight months to 1 year, about 1 year to 2 years, or about 2 years to 4 years, or more.

The practice of a method of the present invention typically involves administering an effective amount of an inhibiting agent or a pharmaceutical composition comprising such inhibiting agent. The specific dose will vary depending on the particular compounds chosen, the dosing regimen to be followed, whether it is administered in combination with other compounds, timing of administration, the tissue to which it is administered, and the physical delivery system in which it is carried. In an embodiment, an effective amount of the inhibiting agent is an amount that, when administered in one or more doses to a host (e.g., human) in need thereof, reduces HCV viral load in the individual by at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, or at least about 95% or more, compared to the viral load in the individual not treated with the inhibiting agent.

Viral load can be measured by measuring the titer or level of virus in serum. These methods include, but are not limited to, a quantitative polymerase chain reaction (PCR) and a branched DNA (bDNA) test. Quantitative assays for measuring the viral load (titer) of HCV RNA have been developed. Many such assays are available commercially, including a quantitative reverse transcription PCR (RT-PCR) (Amplicor HCV Monitor™, Roche Molecular Systems, New Jersey); and a branched DNA (deoxyribonucleic acid) signal amplification assay (Quantiplex™ HCV RNA Assay (bDNA), Chiron Corp., Emeryville, Calif.). See, e.g., Gretch et al. (1995) *Ann. Intern. Med.* 123:321-329. Also of interest is a nucleic acid test (NAT) sold by Chiron Corporation under the trade name Procleix®, which NAT simultaneously tests for the presence of HIV-1 and HCV. See, e.g., Vargo et al. (2002) *Transfusion* 42:876-885.

In some embodiments, an effective amount of the inhibiting agent is an amount that, when administered in one or more doses to a host (e.g., human) in need thereof, increases liver function in the individual by at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, or at least about 90%, or more, compared to the liver function in the individual not treated with the inhibiting agent.

In some embodiments, an effective amount of the inhibiting agent is an amount that, when administered in one or more doses to a host (e.g., a human) in need thereof, reduces liver fibrosis in the host by at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, or at least about 90%, or more, compared to the degree of liver fibrosis in the individual not treated with the inhibiting agent.

Liver fibrosis reduction can be determined by analyzing a liver biopsy sample. An analysis of a liver biopsy comprises assessments of two major components: necroinflammation assessed by "grade" as a measure of the severity and ongoing disease activity, and the lesions of fibrosis and parenchymal or vascular remodeling as assessed by "stage" as being reflective of long-term disease progression. See, e.g., Brunt (2000) Hepatol. 31:241-246; and METAVIR (1994) Hepatology 20:15-20. Based on analysis of the liver biopsy, a score is assigned. A number of standardized scoring systems exist which provide a quantitative assessment of the degree and severity of fibrosis. These include the METAVIR, Knodell, Scheuer, Ludwig, and Ishak scoring systems.

The METAVIR scoring system is based on an analysis of various features of a liver biopsy, including fibrosis (portal fibrosis, centrilobular fibrosis, and cirrhosis); necrosis (piecemeal and lobular necrosis, acidophilic retraction, and ballooning degeneration); inflammation (portal tract inflammation, portal lymphoid aggregates, and distribution of portal inflammation); bile duct changes; and the Knodell index (scores of periportal necrosis, lobular necrosis, portal inflammation, fibrosis, and overall disease activity). The definitions of each stage in the METAVIR system are as follows: score: 0, no fibrosis; score: 1, stellate enlargement of portal tract but without septa formation; score: 2, enlargement of portal tract with rare septa formation; score: 3, numerous septa without cirrhosis; and score: 4, cirrhosis.

Knodell's scoring system, also called the Hepatitis Activity Index, classifies specimens based on scores in four categories of histologic features: I. Periportal and/or bridging necrosis; II. Intralobular degeneration and focal necrosis; III. Portal inflammation; and IV. Fibrosis. In the Knodell staging system, scores are as follows: score: 0, no fibrosis; score: 1, mild fibrosis (fibrous portal expansion); score: 2, moderate fibrosis; score: 3, severe fibrosis (bridging fibrosis); and score: 4, cirrhosis. The higher the score, the more severe the liver tissue damage. Knodell (1981) Hepatol. 1:431.

In the Scheuer scoring system scores are as follows: score: 0, no fibrosis; score: 1, enlarged, fibrotic portal tracts; score: 2, periportal or portal-portal septa, but intact architecture; score: 3, fibrosis with architectural distortion, but no obvious cirrhosis; score: 4, probable or definite cirrhosis. Scheuer (1991) J. Hepatol. 13:372.

The Ishak scoring system is described in Ishak (1995) J. Hepatol. 22:696-699. Stage 0, No fibrosis; Stage 1, Fibrous expansion of some portal areas, with or without short fibrous septa; stage 2, Fibrous expansion of most portal areas, with or without short fibrous septa; stage 3, Fibrous expansion of most portal areas with occasional portal to portal (P-P) bridging; stage 4, Fibrous expansion of portal areas with marked bridging (P-P) as well as portal-central (P-C); stage 5, Marked bridging (P-P and/or P-C) with occasional nodules (incomplete cirrhosis); stage 6, Cirrhosis, probable or definite.

The benefit of a therapy provided by the invention can also be measured and assessed by using the Child-Pugh scoring system which comprises a multicomponent point system based upon abnormalities in serum bilirubin level, serum albumin level, prothrombin time, the presence and severity of ascites, and the presence and severity of encephalopathy. Based upon the presence and severity of abnormality of these parameters, patients may be placed in one of three categories of increasing severity of clinical disease: A, B, or C.

The subject inhibiting agents and pharmaceutical compositions containing the agents can be used in combination of one or more other therapeutic agents for treating viral infection and other diseases. For example, the inhibiting agents and pharmaceutical formulations provided herein can be employed in combination with other anti-viral agents to treat viral infection. In an embodiment, in accordance with the methods of the present invention, an inhibiting agent that is used to treat a host infected by a Flaviviridae family viral infection is used in combination with one or more other anti-HCV agents to treat HCV infection. In another embodiment, in accordance with the methods of the present invention, an inhibiting agent that prevents the binding of NS4B to the 3'-UTR of HCV RNA (also referred to herein as an "HCV NS4B antagonist") can be used in combination with one or more other anti-HCV agents to treat HCV infection.

In addition, the inhibiting agents and pharmaceutical compositions containing the agents can be used in combination with another agent (e.g. an anti-viral agent) to prophylactically treat an infection with a virus from the Flaviviridae family of viruses including but not limited to HCV. Embodiments of the method involve administering to an individual in need thereof one or more inhibiting agents that inhibit binding of an NS4B polypeptide to the 3'UTR of HCV negative strand RNA.

Current medical practice to treat HCV infection typically employs either interferon-alpha monotherapy or combination therapy with ribavirin (such as Rebetol or Copegus) and either an interferon-alpha (such as interferon alpha 2b) or pegylated interferon (such as Pegasys, marketed by Roche, or PEG-Intron, marketed by Schering Plough). In accordance with the methods of the present disclosure, an inhibiting compound can be used in combination with these standard therapies to treat HCV infection.

A number of HCV protease inhibitors are in development for the treatment of HCV infection, and in accordance with the methods of the present disclosure, co-administration of an inhibiting agent that prevents the binding of NS4B to the 3'-UTR of HCV RNA and an HCV protease inhibitor can be efficacious in the treatment of HCV. In one embodiment, an interferon alpha and/or a nucleoside analog such as ribavirin is/are also employed in this combination therapy. Suitable HCV protease inhibitors include, but are not limited to, telaprevir (VX-950, Vertex), BILN 2061 and BI12202 (Boehringer Ingelheim), boceprevir (SCH 503034, Schering Plough), ITMN191 (Roche/InterMune/Array BioPharma), MK-7009 (Merck), TMC435350 (Tibotec/Medivir), ACH-1095 and ACH-806 (Achillion/Gilead), and other inhibitors of NS3/NS4A protease, including, but not limited to, compounds in development by Presidio.

A number of HCV RNA polymerase (NS5B) inhibitors are in development for the treatment of HCV infection, and in accordance with the methods of the present disclosure, co-administration of an inhibiting agent that prevents the binding of NS4B to the 3'-UTR of HCV RNA and an HCV RNA polymerase inhibitor can be efficacious in the treatment of HCV. In one embodiment, an interferon alpha and/or a nucleoside analog such as ribavirin and/or an HCV protease inhibitor is/are also employed in this combination therapy. Suitable HCV RNA polymerase inhibitors include, but are not limited to, valopicitabine (NM283, Idenix/Novartis), HCV-796 (Wyeth/ViroPharma), R1626 (Roche), R7128 (Roche/Pharmasset), GS-9190 (Gilead), MK-0608 (Merck), PSI-6130 (Pharmasset), and PFE-868,554 (PFE).

A number of toll-like receptor (TLR) agonists are in development for the treatment of HCV infection, and in accordance with the methods of the present disclosure, co-administration of an NS4B antagonist that prevents the binding of NS4B to the 3'-UTR of HCV RNA and a TLR agonist can be efficacious in the treatment of HCV. In one embodiment, an interferon alpha and/or a nucleoside analog such as ribavirin and/or an HCV protease inhibitor and/or an HCV RNA polymerase inhibitor is/are also employed in this combination therapy. Suitable TLR agonists include, but are not limited to, TLR7 agonists (i.e., ANA245 and ANA975 (Anadys/Novartis)) and TLR9 agonists (i.e., Actilon (Coley) and IMO-2125 (Idera)).

A number of thiazolide derivatives are in development for the treatment of HCV infection, and in accordance with the methods of the present disclosure, co-administration of an NS4B antagonist that prevents the binding of NS4B to the 3'-UTR of HCV RNA and a thiazolide, including, but not limited to, Nitazoxanide (Alinia, or other sustained release formulations of nitazoxanide or other thiazolides, Romark Laboratories) can be efficacious in the treatment of HCV. In an embodiment, an interferon alpha and/or a nucleoside analog such as ribavirin and/or an HCV protease inhibitor and/or an HCV RNA polymerase inhibitor and/or a TLR agonist is/are also employed in this combination therapy.

In another embodiment of the methods of the present disclosure, co-administration of an inhibiting agent that prevents the binding of NS4B to the 3'-UTR of HCV RNA and a cyclophilin inhibitor (i.e., NIM-811 (Novartis) and DEBIO-025 (Debiopharm)) and/or an alpha-glucosidase inhibitor (i.e., Celgosivir (Migenix)) and/or one or more agents from one or more of the other classes of HCV therapeutic agents discussed herein is used to treat HCV infection. Moreover, there are several targets within NS4B, and compounds that interact with these other targets can, in accordance with the methods of the present disclosure, be used in combination with an NS4B antagonist that prevents the binding of NS4B to the 3'-UTR of HCV RNA and, optionally, one or more of the other classes of inhibiting agents mentioned herein, to treat HCV infection. Such additional NS4B targets include: the N-terminal amphipathic helix (see PCT publication WO 2002/089731, incorporated herein by reference), the NS4B GTPase (see PCT publication WO 2005/032329, incorporated herein by reference), the second amphipathic helix, the PIP2 binding activity of the first amphipathic helix in NS4B (see U.S. provisional patent application Ser. No. 60/057,188, incorporated herein by reference).

Other agents that can be used in combination with inhibiting agents of the present disclosure that prevent the binding of NS4B to the 3'-UTR of HCV RNA include (i) agents targeting NS5A, including, but not limited to, A-831 (Arrow Therapeutics), AZD2836 (Astra Zeneca), and agents in development by XTL/Presidio or BMS (see PCT publications WO 2006/133326 and WO 2008/021928, incorporated herein by reference); (ii) agents targeting TBC1D20 and/or NS5A's interaction with TBC1D20 (see PCT publication WO 2007/018692 and U.S. patent application Ser. No. 11/844,993, incorporated herein by reference), (iii) agents targeting NS4B's GTPase activity (see PCT publication WO 2005/032329 and US patent application publication 2006/0199174, incorporated herein by reference); (iv) agents inhibiting membrane association mediated by the HCV amphipathic helices, such as those found in NS5A, NS4B, and NS5B (see PCT publication WO 2002/089731, supra), (v) agents targeting PIP2 or BAAPP domains in HCV proteins, such as those found in NS4B and NS5A (see U.S. provisional patent application 60/057,188, supra); (vi) agents targeting HCV entry, assembly, or release, including antibodies to co-receptors; (vii) agents targeting HCV NS3 helicase; (viii) siRNAs, shRNAs, antisense RNAs, or other RNA-based molecules targeting sequences in HCV; (ix) agents targeting microRNA122 or other microRNAs modulating HCV replication; (x) agents targeting PD-1, PD-L1, or PD-L2 interactions or pathway (see U.S. patent application publications 20080118511, 20070065427, 20070122378, incorporated herein by reference); (xi) agents targeting HCV amphipathic helix function, such as AH2 inhibitors, (xii) prenylation inhibitors (e.g., U.S. Pat. Nos. 5,503,973, 5,876,920, 6,159,939, 6,627,610, 7,342,016, 5,874,442, 7,101,897, and 6,232,338, each of which are incorporated herein by reference).

In another embodiment of the present disclosure, an inhibiting agent that prevents the binding of NS4B to the 3'-UTR of HCV RNA is used in combination with one or more drugs capable of treating an HIV infection to treat a patient that is co-infected with HIV and HCV. In another embodiment of the present disclosure, an inhibiting agent that prevents the binding of NS4B to the 3'-UTR of HCV RNA is used in combination with one or more drugs capable of treating an HBV infection to treat a patient that is co-infected with HBV and HCV. In an embodiment, an inhibiting agent that prevents the binding of NS4B to the 3'-UTR of HCV RNA is used in combination with a PD-L1 inhibitor to treat a viral infection.

As mentioned above, embodiments of the present include the administration of an inhibiting agent identified herein (or by using an embodiment of the screen of the invention) in conjunction with at least one additional therapeutic agent to treat a viral infection. Suitable additional therapeutic agents include, but are not limited to, ribavirin; a nucleoside analog (e.g., levovirin, viramidine, and the like.); an NS3 inhibitor; an NS5 inhibitor; an interferon; and a side effect management agent.

In an embodiment, the at least one additional suitable therapeutic agent includes ribavirin. Ribavirin, 1-β-D-ribofuranosyl-1H-1,2,4-triazole-3-carboxamide, available from ICN Pharmaceuticals, Inc., Costa Mesa, Calif., is described in the Merck Index, compound No. 8199, Eleventh Edition. Its manufacture and formulation is described in U.S. Pat. No. 4,211,771. The disclosure also contemplates use of derivatives of ribavirin (see, e.g., U.S. Pat. No. 6,277,830).

In an embodiment, the at least one additional suitable therapeutic agent includes levovirin. Levovirin is the L-enantiomer of ribavirin, and exhibits the property of enhancing a Th1 immune response over a Th2 immune response. Levovirin is manufactured by ICN Pharmaceuticals.

In an embodiment, the at least one additional suitable therapeutic agent includes viramidine. Viramidine is a 3-carboxamidine derivative of ribavirin, and acts as a prodrug of ribavirin. It is efficiently converted to ribavirin by adenosine deaminases.

Nucleoside analogs that are suitable for use in a combination therapy include, but are not limited to, ribavirin, levovirin, viramidine, isatoribine, an L-ribofuranosyl nucleoside as disclosed in U.S. Pat. No. 5,559,101 and encompassed by Formula I of U.S. Pat. No. 5,559,101 (e.g., 1-β-L-ribofuranosyluracil, 1-β-L-ribofuranosyl-5-fluorouracil, 1-β-L-ribofuranosylcytosine, 9-β-L-ribofuranosyladenine, 9-β-L-ribofuranosylhypoxanthine, 9-β-L-ribofuranosylguanine, 9-β-L-ribofuranosyl-6-thioguanine, 2-amino-α-L-ribofuranl[1',2':4,5]oxazoline, $O^2,O^2$-anhydro-1-α-L-ribofuranosyluracil, 1-α-L-ribofuranosyluracil, 1-(2,3,5-tri-O-benzoyl-α-ribofuranosyl)-4-thiouracil, 1-α-L-ribofuranosylcytosine, 1-α-L-ribofuranosyl-4-thiouracil, 1-α-L-ribofuranosyl-5-fluorouracil, 2-amino-β-L-arabinofurano[1',':4,5]oxazoline, $O^2,O^2$-anhydro-β-L-arabinofuranosyluracil, 2'-deoxy-3-L-uridine, 3'5'-Di-O-benzoyl-2' deoxy-4-thio β-L-uridine, 2'-deoxy-K-cytidine, 2'-deoxy-β-L-4-thiouridine, 2'-deoxy-β-L-thymidine, 2'-deoxy-β-L-5-fluorouridine, 2',3'-dideoxy-β-L-uridine, 2'-deoxy-β-L-5-fluorouridine, and 2'-deoxy-13-L-inosine); a compound as disclosed in U.S. Pat. No. 6,423,695 and encompassed by Formula I of U.S. Pat. No. 6,423,695; a compound as disclosed in U.S. Patent Publication No. 2002/0058635, and encompassed by Formula 1 of U.S. Patent Publication No. 2002/0058635; a nucleoside analog as disclosed in WO 01/90121 A2 (Idenix); a nucleoside analog as disclosed in WO 02/069903 A2 (Biocryst Pharmaceuticals Inc.); a nucleoside analog as disclosed in WO 02/057287 A2 or WO 02/057425 A2 (both Merck/Isis); and the like.

In an embodiment, the at least one additional suitable therapeutic agent can include HCV NS3 inhibitors. Suitable HCV non-structural protein-3 (NS3) inhibitors include, but are not limited to, a tri-peptide as disclosed in U.S. Pat. Nos. 6,642,204, 6,534,523, 6,420,380, 6,410,531, 6,329,417, 6,329,379, and 6,323,180 (Boehringer-Ingelheim); a compound as disclosed in U.S. Pat. No. 6,143,715 (Boehringer-Ingelheim); a macrocyclic compound as disclosed in U.S. Pat. No. 6,608,027 (Boehringer-Ingelheim); an NS3 inhibitor as disclosed in U.S. Pat. Nos. 6,617,309, 6,608,067, and 6,265,380 (Vertex Pharmaceuticals); an azapeptide compound as disclosed in U.S. Pat. No. 6,624,290 (Schering); a compound as disclosed in U.S. Pat. No. 5,990,276 (Schering); a compound as disclosed in Pause et al. (2003) *J. Biol. Chem.* 278:20374-20380; NS3 inhibitor BILN 2061 (Boehringer-Ingelheim; Lamarre et al. (2002) *Hepatology* 36:301 A; and Lamarre et al. (Oct. 26, 2003) Nature doi:10.1038/nature02099); NS3 inhibitor VX-950 (Vertex Pharmaceuticals; Kwong et al. (Oct. 24-28, 2003) 54th Ann. Meeting AASLD); NS3 inhibitor SCH6 (Abib et al. (Oct. 24-28, 2003) Abstract 137. Program and Abstracts of the 54th Annual Meeting of the American Association for the Study of Liver Diseases (AASLD). Oct. 24-28, 2003. Boston, Mass.); any of the NS3 protease inhibitors disclosed in WO 99/07733, WO 99/07734, WO 00/09558, WO 00/09543, WO 00/59929 or WO 02/060926 (e.g., compounds 2, 3, 5, 6, 8, 10, 11, 18, 19, 29, 30, 31, 32, 33, 37, 38, 55, 59, 71, 91, 103, 104, 105, 112, 113, 114, 115, 116, 120, 122, 123, 124, 125, 126 and 127 disclosed in the table of pages 224-226 in WO 02/060926); an NS3 protease inhibitor as disclosed in any one of U.S. Patent Publication Nos. 2003019067, 20030187018, and 20030186895; and the like.

In an embodiment, the NS3 inhibitor used in a combination therapy of the invention is a member of the class of specific NS3 inhibitors, e.g., NS3 inhibitors that inhibit NS3 serine protease activity and that do not show significant inhibitory activity against other serine proteases such as human leukocyte elastase, porcine pancreatic elastase, or bovine pancreatic chymotrypsin, or cysteine proteases such as human liver cathepsin B. In an embodiment, the at least one additional suitable therapeutic agent includes NS5B inhibitors. Suitable HCV non-structural protein-5 (NS5; RNA-dependent RNA polymerase) inhibitors include, but are not limited to, a compound as disclosed in U.S. Pat. No. 6,479,508 (Boehringer-Ingelheim); a compound as disclosed in any of International Patent Application Nos. PCT/CA02/01127, PCT/CA02/01128, and PCT/CA02/01129, all filed on Jul. 18, 2002 by Boehringer Ingelheim; a compound as disclosed in U.S. Pat. No. 6,440,985 (ViroPharma); a compound as disclosed in WO 01/47883, e.g., JTK-003 (Japan Tobacco); a dinucleotide analog as disclosed in Zhong et al. (2003) *Antimicrob. Agents Chemother.* 47:2674-2681; a benzothiadiazine compound as disclosed in Dhanak et al. (2002) *J. Biol. Chem.* 277(41): 38322-7; an NS5B inhibitor as disclosed in WO 02/100846 A1 or WO 02/100851 A2 (both Shire); an NS5B inhibitor as disclosed in WO 01/85172 A1 or WO 02/098424 A1 (both Glaxo SmithKline); an NS5B inhibitor as disclosed in WO 00/06529 or WO 02/06246 A1 (both Merck); an NS5B inhibitor as disclosed in WO 03/000254 (Japan Tobacco); an NS5B inhibitor as disclosed in EP 1 256,628 A2 (Agouron); JTK-002 (Japan Tobacco); JTK-109 (Japan Tobacco); and the like.

In an embodiment, the NS5 inhibitor used in the combination therapies of the invention is a member of the class of specific NS5 inhibitors, e.g., NS5 inhibitors that inhibit NS5 RNA-dependent RNA polymerase and that lack significant inhibitory effects toward other RNA dependent RNA polymerases and toward DNA dependent RNA polymerases.

In an embodiment, the at least one additional therapeutic agent is an interferon, e.g., interferon-alpha (IFN-α). Any known IFN-α can be used in the treatment methods of the invention. The term "interferon-alpha" as used herein refers to a family of related polypeptides that inhibit viral replication and cellular proliferation and modulate immune response. The term "IFN-α" includes naturally occurring IFN-α; synthetic IFN-α; derivatized IFN-α (e.g., PEGylated IFN-α, glycosylated IFN-α, and the like); and analogs of naturally occurring or synthetic IFN-α; essentially any IFN-α that has antiviral properties, as described for naturally occurring IFN-α.

Suitable alpha interferons include, but are not limited to, naturally-occurring IFN-α (including, but not limited to, naturally occurring IFN-α2a, IFN-α2b); recombinant interferon alpha-2b such as Intron-A interferon available from Schering Corporation, Kenilworth, N.J.; recombinant interferon alpha-2a such as Roferon interferon available from Hoffmann-La Roche, Nutley, N.J.; recombinant interferon alpha-2C such as Berofor alpha 2 interferon available from Boehringer Ingelheim Pharmaceutical, Inc., Ridgefield, Conn.; interferon alpha-n1, a purified blend of natural alpha interferons such as Sumiferon available from Sumitomo, Japan or as Wellferon interferon alpha-n1 (INS) available from the Glaxo-Wellcome Ltd., London, Great Britain; and interferon alpha-n3 a mixture of natural alpha interferons made by Interferon Sciences and available from the Purdue Frederick Co., Norwalk, Conn., under the Alferon tradename.

The term "IFN-α" also encompasses consensus IFN-α. Consensus IFN-α (also referred to as "CIFN" and "IFN-con" and "consensus interferon") encompasses, but is not limited to, the amino acid sequences designated IFN-con$_1$, IFN-con$_2$ and IFN-con$_3$ which are disclosed in U.S. Pat. Nos. 4,695,623 and 4,897,471; and consensus interferon as defined by determination of a consensus sequence of naturally occurring interferon alphas (e.g., Infergen®, InterMune, Inc., Brisbane, Calif.). IFN-con$_1$ is the consensus interferon agent in the Infergen® alfacon-1 product. The Infergen® consensus interferon product is referred to herein by its brand name (Infergen®) or by its generic name (interferon alfacon-1). DNA sequences encoding IFN-con may be synthesized as described in the aforementioned patents or other standard methods. In an embodiment, the at least one additional therapeutic agent is CIFN.

In an embodiment, fusion polypeptides comprising an IFN-α and a heterologous polypeptide can also be used in the combination therapies of the invention. Suitable IFN-α fusion polypeptides include, but are not limited to, Albuferon-alpha™ (a fusion product of human albumin and IFN-α; Human Genome Sciences; see, e.g., Osborn et al. (2002) *J. Pharmacol. Exp. Therap.* 303:540-548). Also suitable for use in the present disclosure are gene-shuffled forms of IFN-α. See, e.g., Masci et al. (2003) *Curr. Oncol. Rep.* 5:108-113. Other suitable interferons include, Multiferon (Viragen), Medusa Interferon (Flamel Technology), Locteron (Octopus), and Omega Interferon (Intarcia/Boehringer Ingelheim).

The term "IFN-α" also encompasses derivatives of IFN-α that are derivatized (e.g., are chemically modified relative to the naturally occurring peptide) to alter certain properties such as serum half-life. As such, the term "IFN-α" includes glycosylated IFN-α; IFN-α derivatized with polyethylene glycol ("PEGylated IFN-α"); and the like. PEGylated IFN-α, and methods for making same, is discussed in, e.g., U.S. Pat. Nos. 5,382,657; 5,981,709; and 5,951,974. PEGylated IFN-α encompasses conjugates of PEG and any of the above-described IFN-α molecules, including, but not limited to, PEG conjugated to interferon alpha-2a (Roferon, Hoffman La-Roche, Nutley, N.J.), interferon alpha 2b (Intron, Schering-Plough, Madison, N.J.), interferon alpha-2c (Berofor Alpha, Boehringer Ingelheim, Ingelheim, Germany); and consensus interferon as defined by determination of a consensus sequence of naturally occurring interferon alphas (Infergen®, InterMune, Inc., Brisbane, Calif.).

In an embodiment, the IFN-α polypeptides can be modified with one or more polyethylene glycol moieties, i.e., PEGylated. The PEG molecule of a PEGylated IFN-α polypeptide is conjugated to one or more amino acid side chains of the IFN-α polypeptide. In an embodiment, the PEGylated IFN-α contains a PEG moiety on only one amino acid. In another embodiment, the PEGylated IFN-α contains a PEG moiety on two or more amino acids, e.g., the IFN-α contains a PEG moiety attached to two, three, four, five, six, seven, eight, nine, or ten different amino acid residues. IFN-α may be coupled directly to PEG (i.e., without a linking group) through an amino group, a sulfhydryl group, a hydroxyl group, or a carboxyl group.

To determine the optimum combination of an inhibiting agent, such as indazole, with other anti-HCV agents, HCV replication assays and/or animal studies can be performed in the presence of various combinations of the various anti-HCV agents. Increased inhibition of replication in the presence of an additional agent (above that observed with monotherapy) is evidence for the potential benefit of the combination therapy.

In an embodiment, side effect management agents can be used in the treatment methods of the invention, and these include agents that are effective in pain management; agents that ameliorate gastrointestinal discomfort; analgesics, anti-inflammatories, antipsychotics, antineurotics, anxiolytics, and hematopoietic agents. In addition, embodiments of the invention contemplate the use of any compound for palliative care of patients suffering from pain or any other side effect in the course of treatment with a subject therapy. Exemplary palliative agents include acetaminophen, ibuprofen, other NSAIDs, H2 blockers, and antacids.

The inhibiting agents and pharmaceutical compositions provided herein can be used to treat a variety of patients or hosts infected with a virus of the Flavirivirus family. The subject treatment methods may particularly benefit "treatment failure patients". Such patients include, but are not limited to, those who have failed to respond to previous therapy for HCV (referred to as "non-responders") or who initially responded to previous therapy, but in whom the therapeutic response was not maintained (referred to as "relapsers"). The previous therapy generally can include treatment with any anti-viral agent other than an inhibiting agent of the present disclosure.

Other patients that may benefit from the subject treatments are individuals who have been clinically diagnosed as infected with HCV. Such individuals include naïve individuals (e.g., individuals not previously treated for HCV). Individuals who are infected with HCV can be identified by detecting HCV RNA in their blood, and/or having an anti-HCV antibody in their serum.

In some embodiments, hosts suitable for treatments of the present invention have an HCV titer of at least about $10^5$, at least about $5 \times 10^5$, or at least about $10^6$, genome copies of HCV per milliliter of serum. The patient may be infected with any HCV genotype (genotype 1, including 1a and 1b, 2, 3, 4, 6, and the like. and subtypes (e.g., 2a, 2b, 3a, and the like.)), particularly a difficult to treat genotype such as HCV genotype 1 and particular HCV subtypes and quasispecies.

Also suitable for treatment are HCV-positive hosts (as described above) who exhibit severe fibrosis or early cirrhosis (non-decompensated, Child's-Pugh class A or less), or more advanced cirrhosis (decompensated, Child's-Pugh class B or C) due to chronic HCV infection and who are viremic despite prior anti-viral treatment, or who have a contraindication to therapy with a known anti-viral agent.

In an embodiment, HCV-positive hosts with stage 3 or 4 liver fibrosis according to the METAVIR scoring system are suitable for treatment with the methods of the present disclosure. In another embodiment, hosts suitable for treatment with embodiments of the present disclosure are patients with decompensated cirrhosis with clinical manifestations, including patients with far-advanced liver cirrhosis, including those awaiting liver transplantation. In still another embodiment, hosts suitable for treatment with embodiments of the present disclosure include patients with milder degrees of fibrosis including those with early fibrosis (stages 1 and 2 in the METAVIR, Ludwig, and Scheuer scoring systems; or stages 1, 2, or 3 in the Ishak scoring system).

In an embodiment of the present disclosure, to help optimally select patients most likely to benefit from therapy, as well as to monitor efficacy of therapy—especially in the face of potential drug resistant mutant viruses—the use of appropriate diagnostic tests provided by the present invention can be of great benefit. For example, assessing the sensitivity of the specific virus found in a given patient to the contemplated therapy can help identify the best match between candidate patient and the corresponding appropriate therapy. In the case of compounds of the present invention identified herein, this can be done by isolating the NS4B sequence from a given patient's HCV isolate and determining the efficacy of the drug's inhibition of RNA binding by the patient's NS4B isoform. This is especially important, because there currently is no efficient way of studying the drug sensitivity of a given patient's virus, because patient-derived inoculums cannot be readily cultured. The value of using such diagnostic assays to guide therapy has been extensively validated in HIV.

Combination therapy with a compound of the present invention in accordance with embodiments of the present invention includes, for example and without limitation, (1) treatment with indazole plus nitazoxanide, (2) treatment with indazole followed by nitazoxanide, (3) treatment with indazole plus nitazoxanide and a NS3 protease inhibitor, (4) treatment with indazole plus nitazoxanide plus a NS3 protease inhibitor plus a NS5B polymerase inhibitor, (5) treatment with indazole plus a NS3 protease inhibitor plus a NS5B polymerase inhibitor, (6) treatment with indazole plus nitazoxanide plus a NS3 protease inhibitor plus a NS4B second amphipathic helix inhibitor, (7) treatment with indazole plus nitazoxanide plus a NS4B second amphipathic helix inhibitor, (8) treatment with indazole plus a NS3 protease inhibitor plus a NS4B second amphipathic helix inhibitor, (9) treatment with indazole plus ribavirin, (10) treatment with indazole followed by nitazoxanide plus ribavirin; (11) indazole plus clemizole hydrochloride; and (12) any other combinations of one or more agents listed above (1)-(11). In some embodiments, the one or more additional therapeutica agents are administered prior to, concurrent with, or subsequent to the treatment with indazole, indazole analogs or isosterers of the present invention.

Nitazoxanide administration in accordance with the combination therapies of the invention can be, for illustration and without limitation, 500 mg po BID. Other doses, other thiazolides, or other formulations of nitazoxanide or another thiazolide, such as sustained release formulations, can also be used in the combination therapies of the invention. The inhibiting agents and pharmaceutical compositions thereof can be administered to a subject using any available method and route suitable for drug delivery, including in vivo and ex vivo methods, as well as systemic and localized routes of administration. Routes of administration include intranasal, intramuscular, intratracheal, subcutaneous, intradermal, topical application, intravenous, rectal, nasal, oral, and other enteral and parenteral routes of administration. Routes of administration may be combined, if desired, or adjusted depending upon the agent and/or the desired effect. An active agent can be administered in a single dose or in multiple doses.

Embodiments of the inhibiting agent can be administered to a host using available conventional methods and routes suitable for delivery of conventional drugs, including systemic or localized routes. In general, routes of administration contemplated by the disclosure include, but are not limited to, enteral, parenteral, or inhalational routes.

Parenteral routes of administration other than inhalation administration include, but are not limited to, topical, transdermal, subcutaneous, intramuscular, intraorbital, intracapsular, intraspinal, intrasternal, and intravenous routes, i.e., any route of administration other than through the alimentary canal. Parenteral administration can be conducted to effect systemic or local delivery of the inhibiting agent. Where systemic delivery is desired, administration typically involves invasive or systemically absorbed topical or mucosal administration of pharmaceutical preparations.

The inhibiting agent can also be delivered to the subject by enteral administration. Enteral routes of administration include, but are not limited to, oral and rectal (e.g., using a suppository) delivery.

Methods of administration of the inhibiting agent through the skin or mucosa include, but are not limited to, topical application of a suitable pharmaceutical preparation, transdermal transmission, injection and epidermal administration. For transdermal transmission, absorption promoters or iontophoresis are suitable methods. Iontophoretic transmission may be accomplished using commercially available "patches" that deliver their product continuously via electric pulses through unbroken skin for periods of several days or more. In some embodiments, indazole is administered by oral, intravenous, transdermal, sublingual, intramuscular, or rectal route.

In a seperate but related embodiment, the present invention further provides an in vitro cell-free method of identifying agents (inhibiting agents) that modulate RNA binding to an RNA-binding protein. A test agent that inhibits binding of NS4B polypeptide to the 3'UTR of HCV negative strand RNA can be further tested for its ability to inhibit HCV replication in a cell-based assay. For example, a test agent of interest can be contacted with a mammalian cell that harbors all or part of an HCV genome; and the effect of the test agent on HCV replication is determined. Suitable cells include mammalian liver cells that are permissive for HCV replication, e.g., an immortalized human hepatocyte cell line that is permissive for HCV. For example, a suitable mammalian cell is Huh7 hepatocyte or a subclone of Huh7 hepatocyte, e.g., Huh-7.5. Suitable cell lines are described in, e.g., Blight et al. (2002) *J. Virol.* 76:13001; and Zhang et al. (2004) *J. Virol.* 78:1448. In an embodiment, the HCV genome in the cell comprises a reporter, e.g., a nucleotide sequence encoding luciferase, a fluorescent protein, or other protein that provides a detectable signal; and determining the effect, if any, of the test agent on HCV replication is achieved by detection of a signal from the reporter.

In an embodiment, the test agents are organic moieties. In this embodiment, as is generally described in WO 94/24314, which is incorporated herein by reference, test agents are synthesized from a series of substrates that can be chemically modified. "Chemically modified" herein includes traditional chemical reactions as well as enzymatic reactions. These substrates generally include, but are not limited to, alkyl groups (including alkanes, alkenes, alkynes and heteroalkyl), aryl groups (including arenes and heteroaryl), alcohols, ethers, amines, aldehydes, ketones, acids, esters, amides, cyclic compounds, heterocyclic compounds (including purines, pyrimidines, benzodiazepines, beta-lactams, tetracylines, cephalosporins, and carbohydrates), steroids (including estrogens, androgens, cortisone, ecodysone, and the like), alkaloids (including ergots, vinca, curare, pyrollizdine, and mitomycines), organometallic compounds, hetero-atom bearing compounds, amino acids, and nucleosides. Chemical (including enzymatic) reactions may be done on the moieties to form new substrates or candidate agents which can then be tested using the present methods.

EXAMPLES

The following examples are put forth so as to provide those of ordinary skill in the art with a complete disclosure and description of how to make and use the present disclosure, and are not intended to limit the scope of what the inventors regard as their disclosure nor are they intended to represent that the experiments below are all or the only experiments performed. Efforts have been made to ensure accuracy with respect to numbers used (e.g., amounts, temperature, and the like.) but some experimental errors and deviations should be accounted for. Unless indicated otherwise, parts are parts by weight, molecular weight is weight average molecular weight, temperature is in degrees Celsius, and pressure is at or near atmospheric. Standard abbreviations may be used, e.g., bp, base pair(s); kb, kilobase(s); pl, picoliter(s); s or sec, second(s); min, minute(s); h or hr, hour(s); aa, amino acid(s); kb, kilobase(s); bp, base pair(s); nt, nucleotide(s); i.m., intramuscular(ly); i.p., intraperitoneal(ly); s.c., subcutaneous(ly); and the like.

Example 1

Chemical Synthesis

Synthetic Method 1

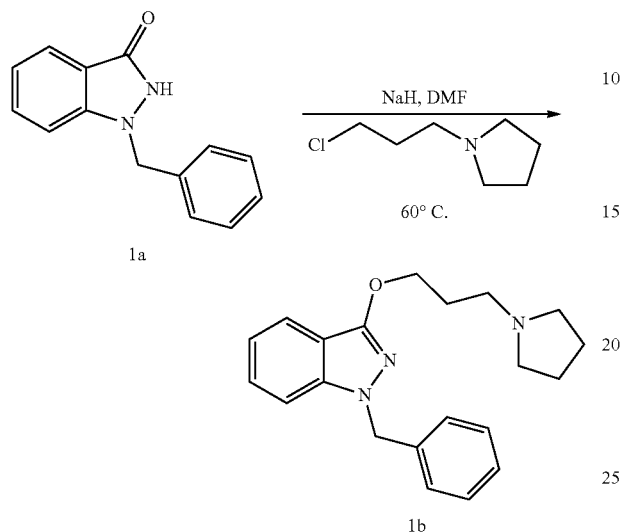

1-Benzyl-1H-indazol-3(2H)-one 1a (44 mg; 0.2 mmol) was dissolved in DMF (1 mL). NaH (12 mg, 0.3 mmol, 60% in mineral oil) was added, the resulting mixture was stirred at room temperature for 10 min. Followed by the addition of 1-(3-chloropropyl)pyrrolidine, the reaction mixture was heated at 60° C. for 2 h and monitored by LC-MS. The crude reaction mixture was purified by prep-HPLC to afford the desired product 1b (48.1 mg, 0.143 mmol, 72%). 1b was converted to the hydrochloride salt by treatment with HCl-ether-methanol.

The compounds is listed below can be prepared following Synthetic Method 1.

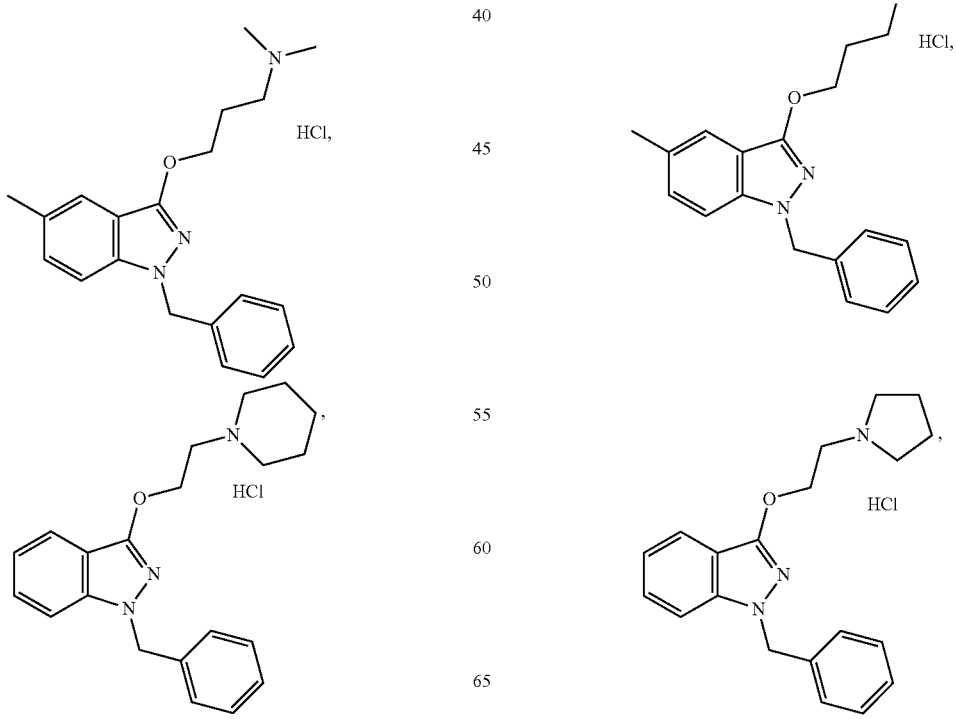

-continued
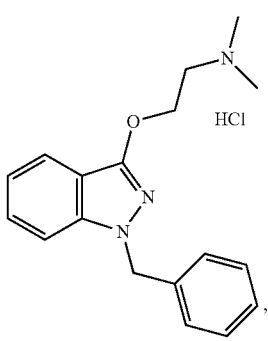
,
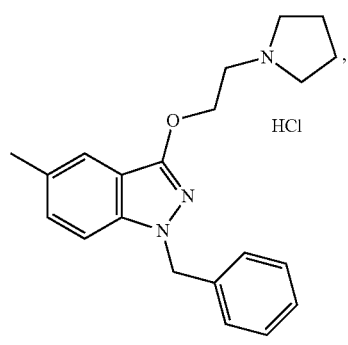
,
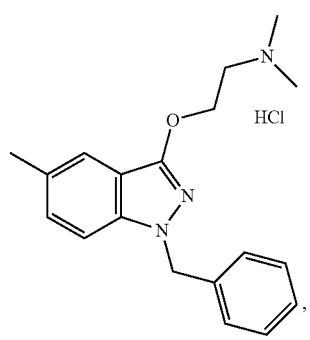
,
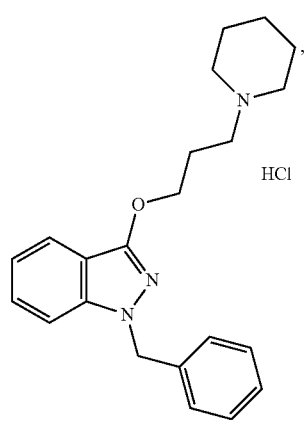
,
-continued
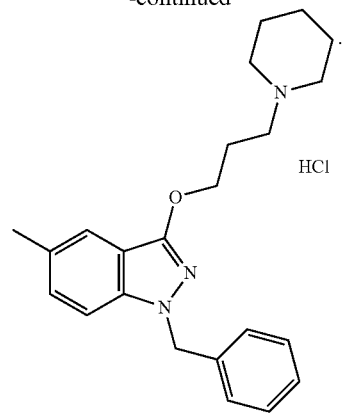
.
Synthetic Method 2
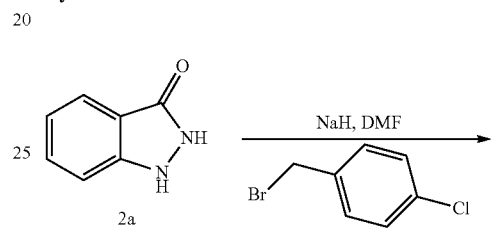
+
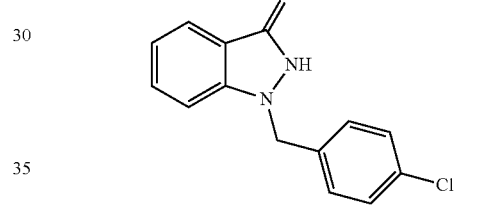
+
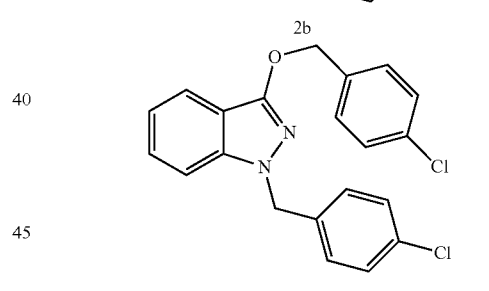
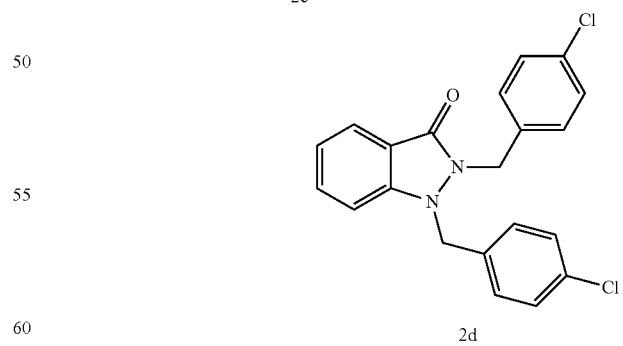
1H-indazol-3(2H)-one 2a (268.3 mg; 2.0 mmol) was dissolved in DMF (5 mL). NaH (120 mg, 3.0 mmol, 60% in mineral oil) was added and the resulting mixture was stirred at room temperature for 10 min. This followed by the addition of 1-(bromomethyl)-4-chlorobenzene and the reaction mixture was stirred at room temperature for additional 2h. The reaction was monitored by LC-MS. The crude reaction mixture was purified by prep-HPLC to afford the desired product 2b (290.1 mg, 1.12 mmol, 56%) as major product along with side products 2c and 2d.
The compounds is listed below can be prepared following Synthetic Method 2.
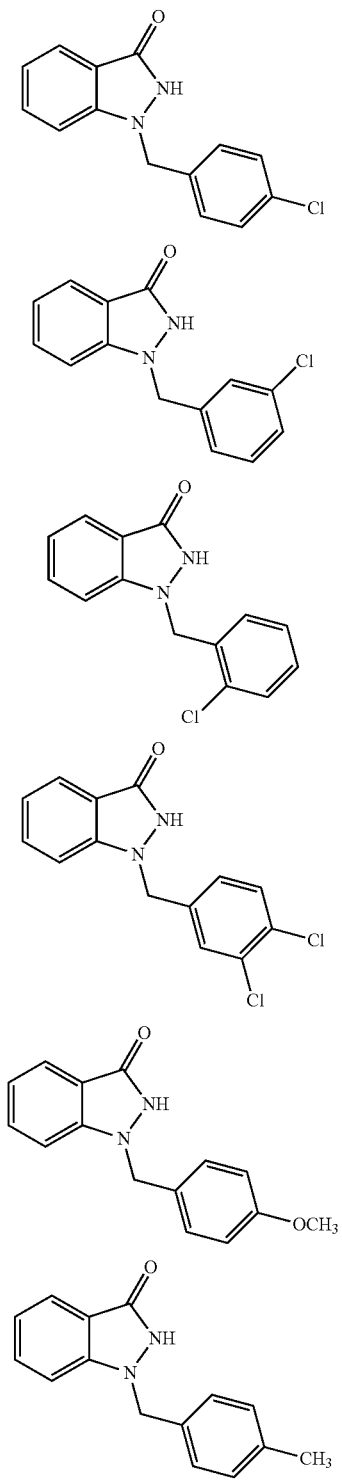
-continued
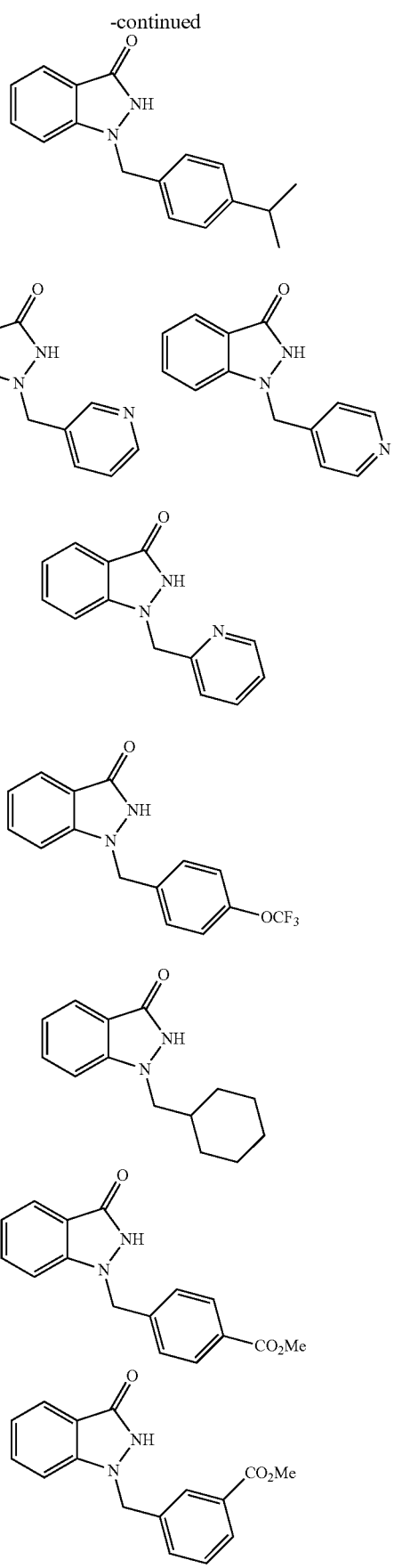

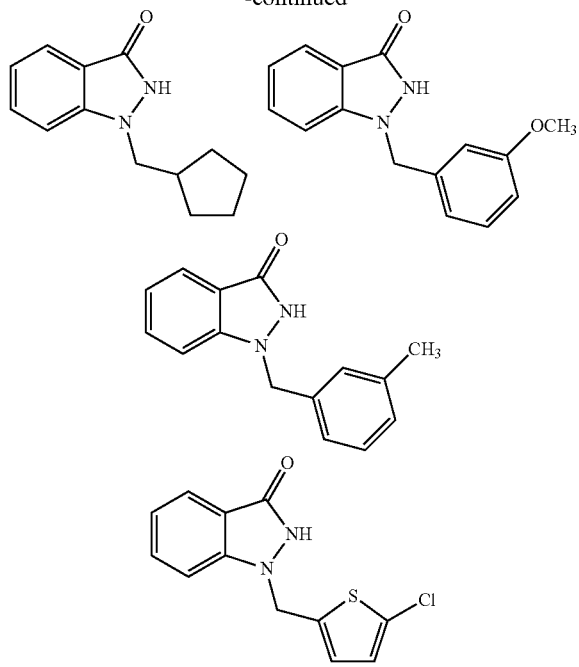

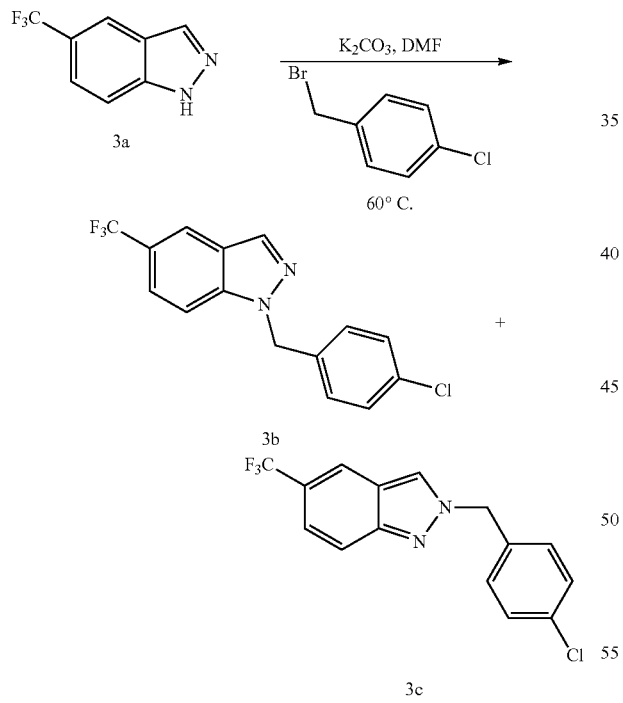

Synthetic Method 3

Indazole compounds can be synthesized according to methods disclosed in the literature, e.g., Lukin et al. *J. Org. Chem.* 2006, 71, 8166-8172 and Souers et al. *J. Med. Chem.* 2005, 48, 1318-1321. A mixture of 5-(trifluoromethyl)-1H-indazole 3a (0.46 g, 2.5 mmol), K$_2$CO$_3$ (1.04 g, 7.5 mmol) in DMF (8 mL) was stirred at room temperature for 30 min. To the mixture was added p-chlorobenzyl bromide (0.77 g, 3.75 mmol). The resulting mixture was heated at 60° C. for 6 h. After cooling, the mixture was poured into water (30 mL). The precipitate was filtered and washed with water and dried. The crude product was purified by chromatography (hexane/dichloromethane, 1:1 to 1:3) to give 1-(4-chlorobenzyl)-5-(trifluoromethyl)-1H-indazole 3b (120 mg, 15%) and 2-(4-chlorobenzyl)-5-(trifluoromethyl)-2H-indazole 3c (60 mg, 7.7%).

1-(4-Chlorobenzyl)-5-(trifluoromethyl)-1H-indazole: $^1$H NMR (300 MHz, CDCl$_3$) δ 8.15 (s, 1H), 8.08 (d, 1H), 7.56 (dd, 1H), 7.41 (d, 1H), 7.28 (d, 2H), 7.12 (d, 2H), 5.60 (s, 2H). MS calcd for (C$_{15}$H$_{10}$ClF$_3$N$_2$+H)$^+$: 310.9. MS found: (M+H)$^+$=310.7 2-(4-Chlorobenzyl)-5-(trifluoromethyl)-2H-indazole: $^1$H NMR (300 MHz, CDCl$_3$) δ 8.04 (s 1H), 7.99 (s, 1H), 7.45 (dd, 1H), 7.35 (d, 2H), 7.22 (d, 2H), 5.60 (s, 2H). MS calcd for (C$_{15}$H$_{10}$ClF$_3$N$_2$+H)$^+$: 310.9. MS found: (M+H)$^+$=310.7

The compounds listed below can be prepared following Synthetic Method 3.

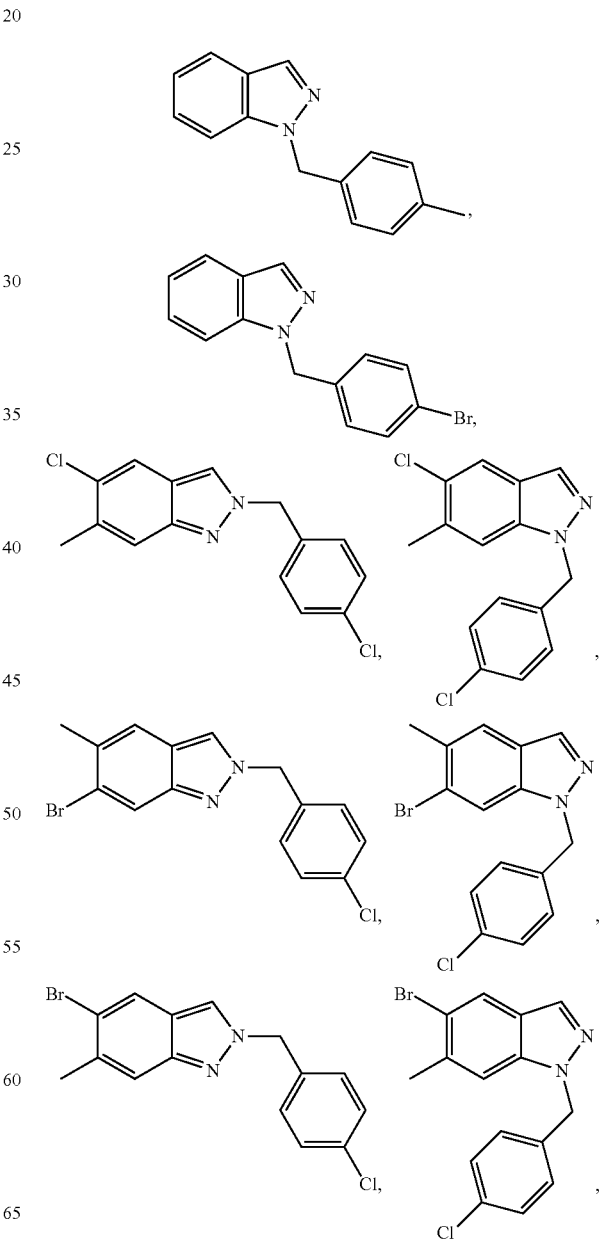

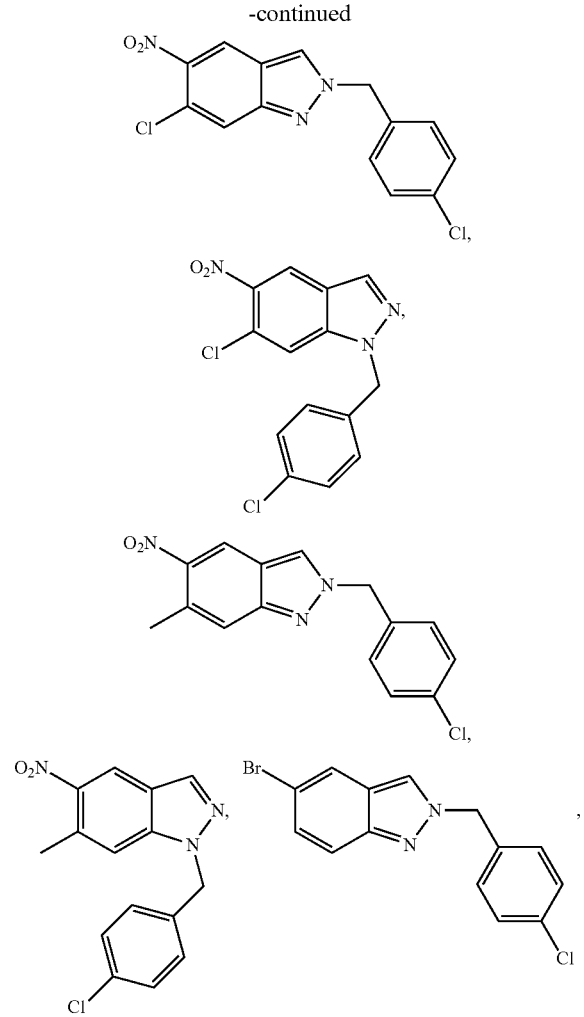

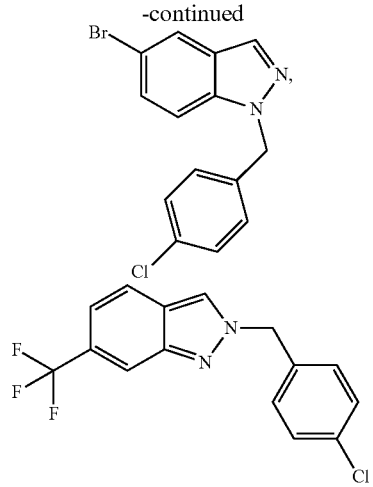

Example 2

Table 3 shown below illustrates the effects of certain indazole isosteres on HCV RNA replication (AV) and cell viability (Viab) using the Luciferase and Alamar Blue assays described herein. Compound activities were measured at two concentrations to determine whether the effects were dose-dependent. Numerical values represent the percent of normal activity (either viral replication or cell viability) remaining after compound treatment; these values have also been binned to provide a rough measure of relative activity.

The amount of residual luciferase activity (indicating HCV replication) in the treated cells relative to the no drug control for each compound was determined at two concentrations of compound, 5 micromolar and 10 micromolar, and recorded in the table. In addition, these percentages were converted to a scoring system as follows: "+">80% residual activity; "++"=55-80% residual activity; "+++"=20-54% residual activity; "++++"<20% residual activity. Thus a compound scored as +++ in the replication assay has greater antiviral activity (AV) than a compound scored as +.

TABLE 3

In-vitro activity of the compounds of the invention in the RNA replication inhibition assay described herein.

| Residual Luciferase activity[1] | <20% ++++ (Compound No.) | 20-54% +++ (Compound No.) | 55-80% ++ (Compound No.) | >80% + (Compound No.) |
|---|---|---|---|---|
| 5 micromolar | | 193, 198, 199, 210, | 187, 191, 192, 196, 208, 204, 212 | 184, 185, 186, 188, 189, 190, 194, 195, 197, 206, 200, 207, 201, 202, 209, 203, 211, 205 |
| 10 micromolar | 191, 193, 198, 199 | 184, 187, 188, 192, 196, 197, 208, 203, 210, 204, 212 | 190, 194, 206, 200, 207, 201, 211, 205, | 185, 186, 189, 195, 202, 209, |

[1]Luciferase reporter activity is stated as a percentage of the luciferase reporter activity in a treated cell population compared to the luciferase activity in an untreated control population of same cell type.

TABLE 4

In-vitro activity of the compounds of the invention in the cell viability assay described herein.

| Cell Viability[2] | 90% or greater (Compound No.) | 75% or greater (Compound No.) | 50% or greater (Compound No.) | <50% (Compound No.) |
|---|---|---|---|---|
| 5 micromolar | 184, 185, 186, 187, 188, 189, 190, 191, | 198, 208, 212 | | |

TABLE 4-continued

In-vitro activity of the compounds of the invention
in the cell viability assay described herein.

| Cell Viability[2] | 90% or greater (Compound No.) | 75% or greater (Compound No.) | 50% or greater (Compound No.) | <50% (Compound No.) |
|---|---|---|---|---|
| 10 micromolar | 192, 193, 194, 195, 196, 197, 199, 206, 200, 207, 201, 202, 209, 203, 210, 204, 211, 205, 184, 185, 186, 189, 190, 191, 192, 194, 195, 196, 197, 200, 207, 201, 202, 209, 203, 211, | 187, 188, 193, 198, 199, 206, 208, 210, 204, 205, 212 | | |

[2]Cell viability is stated as a percentage of viable cells in a treated population of cells in comparison to an untreated population of same cell type.

TABLE 5

Structures of the compounds listed in Tables 3 and 4

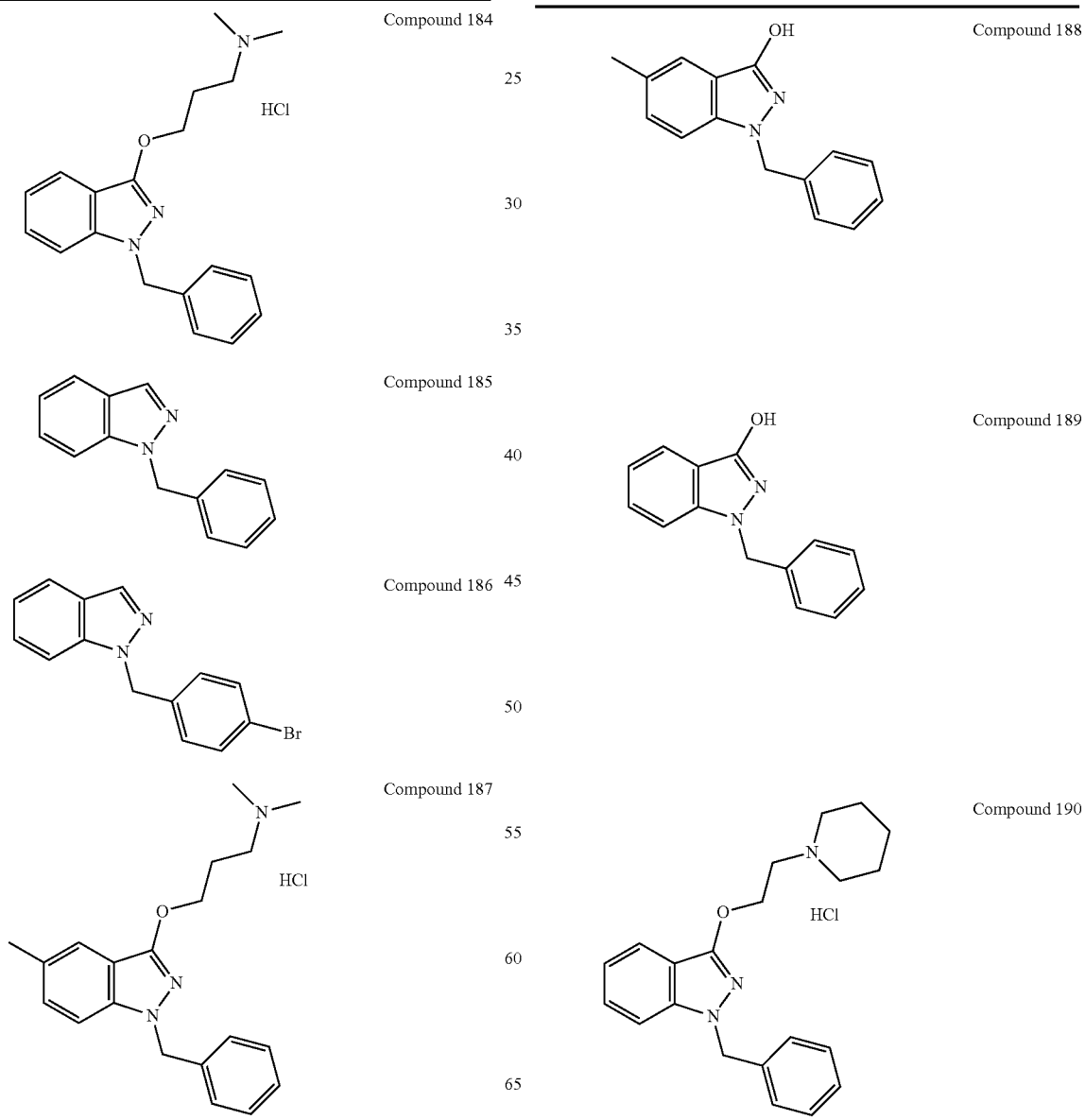

TABLE 5-continued
Structures of the compounds listed in Tables 3 and 4
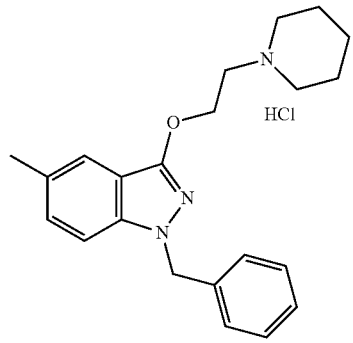 [SMILES: Cc1ccc2c(c1)c(OCCN1CCCCC1)nn2Cc1ccccc1 ; Cl]
Compound 191
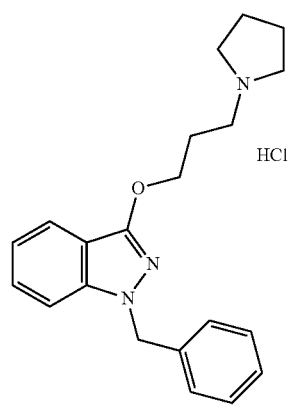 [SMILES: c1ccc(Cn2nc(OCCCN3CCCC3)c3ccccc32)cc1 ; Cl]
Compound 192
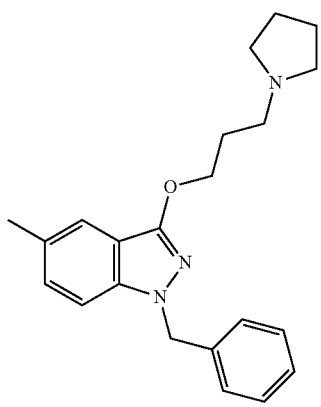 [SMILES: Cc1ccc2c(c1)c(OCCCN1CCCC1)nn2Cc1ccccc1]
Compound 193
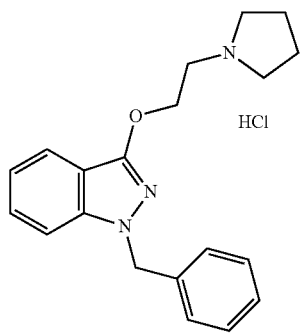 [SMILES: c1ccc(Cn2nc(OCCN3CCCC3)c3ccccc32)cc1 ; Cl]
Compound 194
TABLE 5-continued
Structures of the compounds listed in Tables 3 and 4
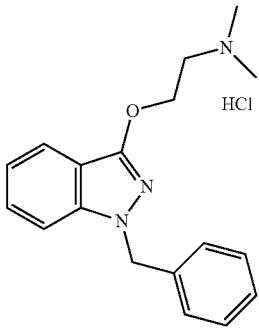 [SMILES: CN(C)CCOc1nn(Cc2ccccc2)c2ccccc12 ; Cl]
Compound 195
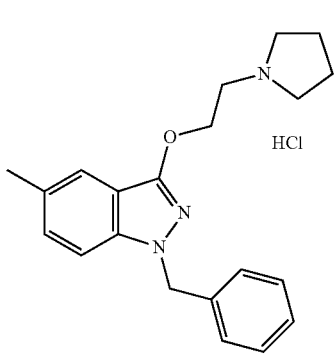 [SMILES: Cc1ccc2c(c1)c(OCCN1CCCC1)nn2Cc1ccccc1 ; Cl]
Compound 196
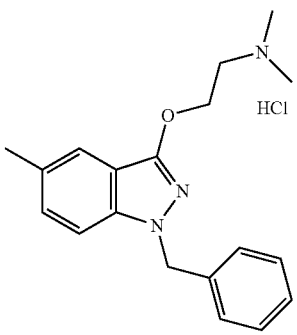
Compound 197
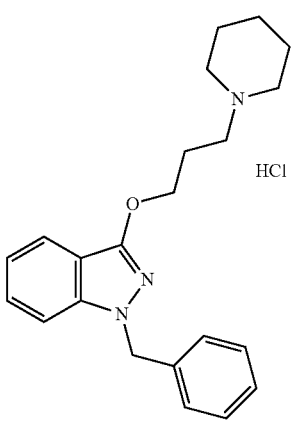 [SMILES: c1ccc(Cn2nc(OCCCN3CCCCC3)c3ccccc32)cc1 ; Cl]
Compound 198

TABLE 5-continued
Structures of the compounds listed in Tables 3 and 4
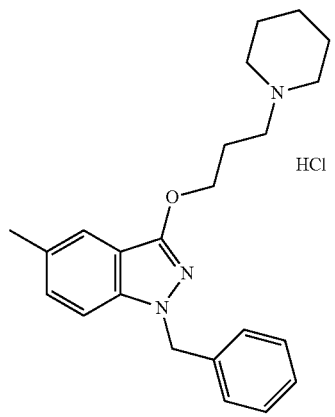 [SMILES: Cc1ccc2c(c1)c(OCCCN1CCCCC1)nn2Cc1ccccc1 ; Cl]
Compound 199
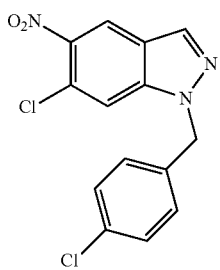 [SMILES: O=[N+]([O-])c1cc2cnn(Cc3ccc(Cl)cc3)c2cc1Cl]
Compound 200
Compound 201
Compound 202
Compound 203
TABLE 5-continued
Structures of the compounds listed in Tables 3 and 4
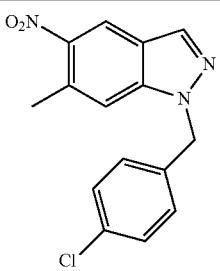 [SMILES: Cc1cc2c(cnn2Cc2ccc(Cl)cc2)cc1[N+](=O)[O-]]
Compound 204
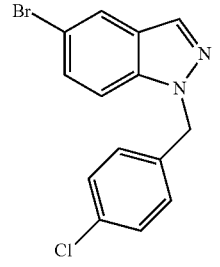
Compound 205
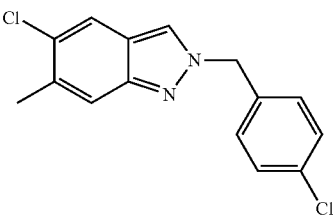 [SMILES: Cc1cc2nn(Cc3ccc(Cl)cc3)cc2cc1Cl]
Compound 206
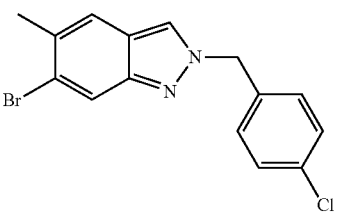 [SMILES: Cc1cc2cn(Cc3ccc(Cl)cc3)nc2cc1Br]
Compound 207
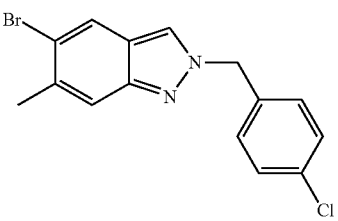 [SMILES: Cc1cc2nn(Cc3ccc(Cl)cc3)cc2cc1Br]
Compound 208
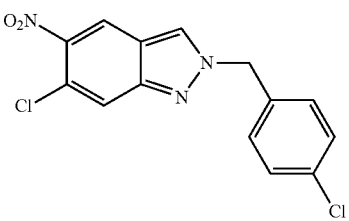 [SMILES: O=[N+]([O-])c1cc2cn(Cc3ccc(Cl)cc3)nc2cc1Cl]
Compound 209

TABLE 5-continued

Structures of the compounds listed in Tables 3 and 4

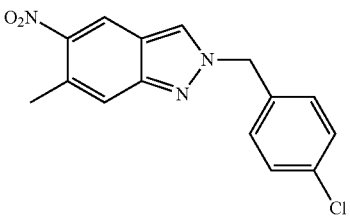 [SMILES: Cc1cc2nn(Cc3ccc(Cl)cc3)cc2cc1[N+](=O)[O-]]
Compound 210

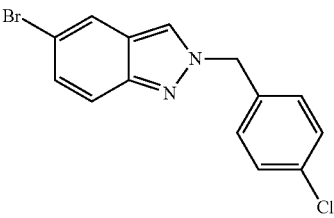 [SMILES: Clc1ccc(Cn2cc3cc(Br)ccc3n2)cc1]
Compound 211

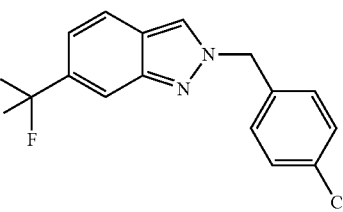
Compound 212

Example 3

Assay

A suitable 1b HCV RNA replicon assay uses the Huh7 cell line, which contains an HCV 1b RNA replicon with a stable luciferase (LUC) reporter. This construct contains modifications that make the cell line more robust and provides stable LUC expression for anti-viral screening. The LUC reporter is used as an indirect measure of HCV replication. The activity of the LUC reporter is directly proportional to HCV RNA levels and positive control anti-viral compounds behave comparably using LUC endpoints.

HCV assays suitable for use in demonstrating the anti-viral activity of the compounds useful in the methods of the invention include the Luciferase Assay for HCV Replicon Reporter Cell Lines and the MTT Assay for HCV Replicon Reporter Cell Lines described in this example. The embodiments of these assays described in this example were developed by Shanghai ChemPartner Co., Ltd., a corporation of China with its principal office located at 720 Cailun Road, Building No. 3, Shanghai 201203, China.

A. Luciferase Assay for HCV Genotype 1b Replicon Reporter Cell Lines

Fresh growth medium is prepared just before use. The container used in the procedure is a 10 cm diameter culture dish. HCV replicon reporter cell lines are used. Prepare complete medium: add FBS and appropriate additives as described in "Culture Media", below. Pre-warm the medium in a 37° C. thermostat water bath. Remove the dish from a 37° C./$CO_2$ incubator. Check the cell name and complete medium and passage number marked on the dish. Aspirate the medium carefully and add 1 ml PBS to rinse the cells. Remove and discard the solution and add 1 ml of 0.25% Trypsin/0.02% EDTA. Rinse the cells with the added Trypsin/EDTA to ensure all the cells have been rinsed. Remove the Trypsin/EDTA with a vacuum pump and incubate at 37° C. for 3-5 minutes. Examine the cell morphology under an inverted microscope to confirm that a single cell suspension is clearly visible. Add 3 ml of complete medium to the dish and suspend the cell by gentle pipetting. Count the cell numbers with a hematometer. Adjust cell density to 100 k/ml by adding appropriate volume of the complete medium. Add 100 μl of cell suspension to each well of a 96-well white plate; the cell density is thus 10 k per well. Mark the plate with cell name, passage number, seeding density, date and the name of the operator. Place the 96-well assay plate in 37° C./5% $CO_2$ incubator for 24 hours.

Compounds are prepared or provided at 25 mM in 100% DMSO. This is the compound stock solution. The dilution procedure should be performed in a cell culture hood. Dispense the stock solution into the second column of a 96-well plate. Prepare 9-step (10 concentrations total), 5-fold serial dilutions by transferring 10 μl of the compound into the next well containing 40 μl of DMSO. Repeat for all compounds. Aspirate 2 μl of the above compound solution from each well and add into 198 μl complete media using a 12-channel pipetter to obtain the 10-fold concentration compound solution with 1% DMSO, mix well.

Remove the 96-well assay plate from the 37° C./5% $CO_2$ incubator, examine the cell morphology under an inverted microscope. In a cell culture hood, add 10 μl of the 10× concentration compounds solution into each well on the 96-well assay plate. All compound's dose responses are done in duplicate. The starting final concentration of the compounds is 25 μM, and DMSO final concentration 0.1%. Mark the plate with compound code(s) and concentrations. Place the 96-well assay plate into $CO_2$ incubator for 48 hours. Add 30 μl of Stead-Glo Luciferase System (Promega) reagent to each well and mix by gentle shaking on a plate shaker for 5 minutes to allow throughout cell lysis. Measure the luminescence with Envision (Perkin Elmer) with an integration time of 2 seconds. Record and analyze the data.

The cell culture media is DMEM complete: DMEM (Life Technologies #41965-039) supplemented with 10% FCS, 2 mM Glutamin (Life Technologies #25030-024), Penicillin (100 IU/ml)/Streptomycin (100 μg/ml) (Life Technologies #15140-114) and 1× nonessential amino acids (Life Technologies #11140-035). G418 ("Geneticin", Life Technologies): concentrations are given as weight per volume of the original substance. Specific activity of a typical batch is ca. 700 μg/mg as stated by the manufacturer. This value does not necessarily reflect the biological activity in a user's system. Therefore each new batch of G418 should be tested individually e.g., in an electroporation experiment using different selection conditions (0.2-1 mg/ml).

B. MTT Assay for HCV Replicon Reporter Cell Lines

The MTT assay (and the MTS assay) is a laboratory test and standard colorimetric assay (an assay which measures changes in color) for measuring the activity of enzymes that reduce MTT or MTS+PMS to formazan, giving a purple color. It can also be used to determine cytotoxicity of potential medicinal agents and other toxic materials, since those agents would result in cell toxicity and therefore metabolic dysfunction and therefore decreased performance in the assay. Yellow MTT (3-(4,5-dimethylthiazol-2-yl)-2,5-diphenyltetrazolium bromide, a tetrazole) is reduced to purple formazan in living cells.http://en.wikipedia.org/wiki/MTT_assay-cite_note-pmid6606682-0#cite_note-pmid6606682-0 A solubilization solution (usually either dimethyl sulfoxide, an acidified ethanol solution, or a solution of the detergent sodium dodecyl sulfate in diluted hydrochloric acid) is added to dissolve the insoluble purple formazan product into a colored solution. The absorbance of this colored solution can be quantified by measuring at a certain wavelength (usually from 500 and 600 nm) by a spectrophotometer. The absorption maximum is dependent on the solvent employed.

Culture medium, culture plates, and additives are prepared as described in part A of this example. Pre-warm the medium in a 37° C. thermostat water bath. Remove the dish from a 37° C./$CO_2$ incubator. Check the cell name and complete medium and passage number marked on the dish. Aspirate the medium carefully and add 1 ml PBS to rinse the cells. Remove and discard the solution and add 1 ml of 0.25% Trypsin/0.02% EDTA. Rinse the cells with the added Trypsin/EDTA to ensure all the cells have been rinsed. Remove the Trypsin/EDTA with a vacuum pump and incubate at 37° C. for 3-5 minutes. Examine the cell morphology under an inverted microscope until single cell suspension is clearly visible. Add 3 ml of complete medium to the dish and suspend the cell by gentle pipetting. Count the cell numbers with a hematometer. Adjust cell density to 100 k/ml by adding appropriate volume of the complete medium. Add 100 µl of cell suspension to each well of a 96-well white plate; the cell density is thus 10 k per well. Mark the plate with cell name, passage number, seeding density, date and the name of the operator. Place the 96-well assay plate in 37° C./5% $CO_2$ incubator for 24 hours.

Compounds are prepared or provided at 25 mM in 100% DMSO. This is the compound stock solution. The dilution procedure should be performed in a cell culture hood. Dispense the stock solution into the second column of a 96-well plate. Prepare 9-step (10 concentrations total), 5-fold serial dilutions by transferring 10 µl of the compound into the next well containing 90 µl of DMSO. Repeat for all compounds. Aspirate 2 µl of the above compound solution from each well and add into 198 ml complete media using a 12-channel pipetter to obtain the 10-fold concentration compound solution with 1% DMSO, mix well. Remove the 96-well assay plate from 37° C./5% $CO_2$ incubator, examine the cell morphology under an inverted microscope. In a cell culture hood, add 10 µl of the 10× concentration compound solution into each well on the 96-well assay plate. All compound's dose responses are done in duplicate. The starting final concentration of the compounds is 25 µM, and DMSO final concentration 0.1%.

Mark the plate with compound code(s) and concentrations. Place the 96-well assay plate into $CO_2$ incubator for 48 hours. Add 10 µl of 5 mg/ml MTT to each well and incubate in the 37° C./$CO_2$ incubator for 4 hours. Add 100 µl of testing solution (10% SDS+5% isobutyl alcohol+10 mmol/L HCl) to each well directly and incubate in the 37° C./5% $CO_2$ incubator overnight. Measure the absorbance at 580/680 nm on SpectraMax Plus 384 (MDC). Record and analyze the results.

C. HCV Genotype 2a Infectious Clone Assay

The assays in parts A and B were used to generate the genotype 1b inhibitory activity and related cell toxicity (viability) data supported herein. This assay has been used to generate the genotype 2a inhibitory activity data supported herein.

Stage 1: RNA transcription

1) Linearize the FL-J6/JFH-5'C19Rluc2AUbi plasmid with XbaI at 37° C. for 2 hrs, and run on 1% agarose gel to check completeness of digestion. 2) Digest the 5' overhangs by treatment with mung bean nuclease at 30° C. for 30 min. 3) For linearization of the Bart79I-luc plasmid (similar to Bart79I plasmid as described in Elazar et al. J. Virol. 2003, 77(10):6055-61 (which is incorporated herein by reference) except that the neomycinphosphotransferase gene has been replaced with the gene encoding firefly luciferase) use ScaI restriction endonuclease, then examine the linearized template DNA on a gel to confirm that cleavage is complete, follow this with proteinase k digestion. 4) Purify templates by digestion with proteinase K for 30 min, phenol-chloroform extraction, ethanol precipitation, and then resuspend at 1 µg/µl. 5) For the transcription reaction, use 1 µg of purified template by using the T7 Megascript kit for FL-J6/JFH-5'C19Rluc2AUbi (Ambion, Austin, Tex.) or the RiboMax™ kit for Bart79I-luc (Promega, Madison, Wis.). Incubate reactions at 37° C. for 4 h. 6) Add DNAse for 15 min. 7) Extract with an equal volume of phenol/chloroform and then with an equal volume of chloroform. Recover aqueous phase and transfer to new tube. 8) Precipitate the RNA by adding 1 volume of isopropanol and mixing well. 9) Chill the mixture for at least 15 min at –20° C. Centrifuge at 4° C. for 15 min at maximum speed to pellet the RNA. 10) Carefully remove the supernatant solution and resuspend the RNA in RNase/DNase-free Water at 1 µg/µl. 11) Run on a gel and check RNA concentration. 12) Make aliquots and store in –80° C.

Stage 2: Electroporating Huh7.5 cells

1) Wash cells once with PBS, trypsinize. 2) Resuspend cells in a total volume of 5 ml per 10 cm plate of complete medium (pull all together) in 50 ml tubes. 3) Pellet cells at 1000×RPM for 5 min at 4° C. Aspirate supernatant and resuspend in 10 ml ice cold RNAse free filtered 1×PBS (BioWhitaker)—pipette up and down ~5 times gently to get rid of cell clumps. 4) Pellet cells again at 1000×RPM as before and again resuspend in 10 ml ice cold PBS (BioWhitaker). 5) Remove a 10 µl aliquot to determine cell concentration. 6) Pellet cells again and resuspend in a final concentration of $1.5 \times 10^7$ cells/ml in ice cold RNAse free-PBS. Need: $6 \times 10^6$ cells in 0.4 ml per each electroporation (ep) and 5 µg of FL-J6/JFH-5'C19Rluc2AUbi RNA or Bart79I-luc RNA. 7) Place 5 µg RNA aliquot in an eppendorf tube (1 tube per ep). 8) Remove 0.4 ml of the cell suspension and add to the RNA. Mix twice by pipeting. 9) Immediately transfer 0.4 ml to a 2 mm gap ep cuvette. 10) Pulse the cells: 820v, 5 pulses, 99 µsec, 220 ms interval, unipolar. 11) Allow cells to rest for 15 min. 12) Transfer cells using the Pasteur pipette in the cuvette package to medium. Make a common stock from all tubes. 13) Plate 10,000 cells/well in 96 well plates. 14) Rotate plate a little for even cell plating. 15) Incubate for 24 hr before treatment.

Stage 3: Treating plates

1) About 24 hr following electroporation prepare medium with the desired concentration of the drug. 2) Aspirate the medium and add 100 µl of fresh medium and drug. Leave untreated wells at the beginning and again at the end. 3) Repeat daily for 2 more days.

Stage 4: Harvesting (day 5 from electroporation)

1) Alamar blue assay—a) Include medium for background subtraction (and also for seeing change in color easily). b) Aspirate medium. c) Make a stock of medium plus 10% Alamar blue. Total volume per well is 100 µl. d) Incubate for 2-2.5 hrs at 37° C. (or until there is a color change). c) Read plates at flex station.

2) *Renilla* Luciferase assay—a) Aspirate medium with Alamar blue. b) Wash with 1×PBS. c) Aspirate completely (aspirate, then tilt and aspirate remainders of buffer again). d) Make sure which lysis buffer is needed: firefly or *renilla*. e) Add 30 µl of 1× lysis buffer (add 1 volume of 5× lysis buffer to 4 volumes of sterile water). f) Shake the plate for 15 min. g) Freeze at –80° C. At this point, one can stop or continue to the next phase.

Stage 5: Reading by Luminometer. a) Thaw the plate. b) Leave plate on ice until ready to read. c) Prepare substrate reagent you need; for the *renilla*: thaw *renilla* buffer, make 1 volume 100× *Renilla* luc substrate plus 100 vol luc assay buffer+2 ml for priming luminometer (e.g., for 4 ml *Renilla* lucsubstrate, add 40 μA assay buffer). For the firefly; thaw 10 ml firefly buffer and add to the luciferase reagent. d) Read plates using a standard luminometer according to the manufacturer's directions.

D. HERG Channel Assay:

Drugs belonging to different classes have been shown to be associated with QT prolongation and in some cases serious ventricular arrhythmias. The most common mechanism for these adverse events is the inhibition of one or more cardiac potassium channels, in particular hERG. This current is important for cardiac myocyte repolarization and is a common target for drugs that prolong the QT interval. Test articles in this study were therefore characterized to determine their ability to inhibit the hERG channel. Ion channel activity was measured using a stably transfected Chinese Hamster Ovary (CHO) cell line expressing the hERG mRNA. The pharmacology of this cloned channel expressed in the CHO cell line is very similar to that observed in native tissue.

Cells: AVIVA's CHO cell line, which stably expresses hERG channels, was used for the study. Cells were cultured in DMEM/F12 containing 10% FBS, 1% penicillin/streptomycin and 500 μg/ml G418. Before testing, cells were harvested using Accumax (Innovative Cell Technologies).

Solutions: For electrophysiological recordings, the following solutions were used. External Solution: 2 mM $CaCl_2$; 2 mM $MgCl_2$; 4 mM KCl; 150 mM NaCl; 10 mM Glucose; 10 mM HEPES; 310-320 mOsm; pH 7.4 (adjusted with 1M NaOH). Internal Solution: 140 mM KCl; 10 mM $MgCl_2$; 6 mM EGTA; 5 mM HEPESNa; mM ATP-Mg; 300-320 mOsm; pH 7.25 (adjusted with 1M KOH).

Electrophysiology: Whole cell recordings were performed using PX 7000A (Axon Instruments) with VIVA's Seal-Chip™ technology. Cells were voltage clamped at a holding potential of −80 mV. The hERG current was then activated by a depolarizing step to −50 mV for 300 ms. This first step at −50 mV was used as a baseline for measuring peak amplitude of the tail current. Next, a voltage step to +20 mV was applied for 5 s to activate the channels. Finally a step back to −50 mV for 5 seconds removed activation and the deactivating tail current was recorded.

Compound Handling and Dilutions: All compounds were prepared from either 10 or 30 mM DMSO stock solutions. Solutions were mixed by sonication for 20 min, followed by vigorous vortexing. Prior to testing, compounds were diluted to test concentrations in glass vials using External Solution. Dilutions were prepared no longer than 20 min prior to use. Equal amounts of DMSO (0.1%) were present in all final dilutions.

Electrophysiology Procedures: After achieving whole cell configuration, cells were monitored for 90 s to assess stability and then washed with External Solution for 66 s. The voltage protocol described above was then applied to the cells every 12 s throughout the procedure. Only stable cells with recording parameters above threshold (see Quality Control section) were allowed to enter the drug addition procedure. External solution containing 0.1% DMSO (vehicle) was applied to the cells to establish a baseline. After allowing the current to stabilize for 3 to 5 min, test articles were applied. Test article solutions were added to cells in 4 separate additions. Cells were kept in test solution until effect of the test article reached steady state, to a maximum of 12 min. Next, 1 μM cisapride (positive control) was added. Finally, washout with External Solution was performed until the recovery current reached a steady state.

Data Analysis: Data analysis was performed using DataXpress (Axon Instruments), Clampfit (Axon Instruments) and Origin (Originlab Corporation) software.

Quality Control: Data included in the report originated from experiments that satisfied all of the following criteria: a) Recording Parameters: membrane resistance (Rm): >200 MΩ; access resistance (Ra): <15MΩ; tail current amplitude: >150 pA; b) Pharmacological Parameters: 1 μM cisapride: >95% inhibition.

Following these procedures, several compounds provided by the present invention are found to lack substantial cross reactivity with hERG channel.

Example 4

This Example presents the results of testing illustrative compounds of the invention in the assays described in Example 1. The compounds are divided into two tables: Table 6 presents "1b Active Analogs"; and Table 7 presents "Clemizole Like Analogs". Each of these categories is discussed below.

Table 6 presents results for compounds that demonstrate significant activity against HCV in the 1b replicon assay. Therefore, Table 6 provides certain non-limiting examples of 1b Active Analogs provided by the present invention. Many of these compounds also show activity in the 2a infectious clone assay; compounds that are active in the 1b replicon assay are typically active in the 2a infectious clone assay as well. In the 1b replicon assay, test compounds were tested at 3-fold serial dilutions from concentrations of 25 μM to 0.001 μM. The results are reported as micromolar activity against inhibition of 50% of replication of the 1b replicon ($EC_{50}$). A high value of >25 μM means that >25 μM of test compound is required to inhibit 50% of replication of the 1b replicon. A low value of 1 μM means that 1 μM of test compound is required to inhibit 50% of replication of the 1b replicon. Thus, lower $EC_{50}$ values correspond to higher potency. To illustrate, see compound EBP899 from Table 6, which shows for this assay an $EC_{50}$ value of 2.2 μM, indicating that this compound is a relatively potent inhibitor against 1b replicon replication. In addition, Table 6 lists only compounds with test results demonstrating cell viability >10 μM, and activity in 1b replicon assay of <10 μM. Compounds were tested for cell toxicity at 3-fold serial dilutions from concentrations of 25 μM to 0.001 μM. The results are reported as micromolar activity. A high value of >25 μM indicates that no toxicity was observed at 25 μM.

In addition, activity against hERG potassium channel was tested on representative compounds. In this assay, the results are reported as micromolar activity against inhibition of hERG channel repolarization activity. A low value of <1 μM means that <1 μM of compound is required to inhibit 50% of hERG channel activity. A high value of >10 μM means that >10 μM of compound is required to inhibit 50% of hERG channel activity. To illustrate, see compound EBP288 in Table 6, which shows for this assay a value of 1 μM, indicating that plasma concentrations of at least 1 μM would likely be required to cause potential QT prolongation in humans. Compounds having a structure similar to that of EBP288 (compounds that contain, in $R_3$, an N-attached heterocycle where substitutions adjacent to the nitrogen are small) should have a similar activity in this assay. To illustrate further, compound EBP640 in Table 6, which shows for this assay a value of 5.3 μM, indicating that a much higher plasma concentration of 5 μM would be required to cause QT prolongation. Compounds having a structure similar to the aforementioned compound (compounds that contain, in $R_3$, a C-attached heterocycle where heteroatom is acylated N) should have a similar activity in this assay. Generally, compounds that show no or only low activity in the hERG assay are preferred.

TABLE 6

| | | | | 2a | | |
|---|---|---|---|---|---|---|
| | | | Cell | (% | 2a cell | |
| | | 1b | Viability | activity @ | viability (@ | hERG |
| | | EC50 | EC50 | 5 | 5 | IC50 |
| Structure | Cmpd # | (μM) | (μM) | μM) | μM) | (μM) |

1b Active Analogs

| Structure | Cmpd # | 1b EC50 (μM) | Cell Viability EC50 (μM) | 2a (% activity @ 5 μM) | 2a cell viability (@ 5 μM) | hERG IC50 (μM) |
|---|---|---|---|---|---|---|
| (structure) | EBP899 | 2.2 | >25 | | | |
| (structure) | EBP397 | 2.8 | >25 | 14 | 100 | |
| (structure) | EBP548 | 3.2 | >25 | | | |
| (structure) | EBP534 | 3.3 | >25 | | | 2.8 |
| (structure) | EBP288 | 3.7 | >25 | 24 | 89 | 1 |

TABLE 6-continued

1b Active Analogs

| Structure | Cmpd # | 1b EC50 (μM) | Cell Viability EC50 (μM) | 2a (% activity @ 5 μM) | 2a cell viability (@ 5 μM) | hERG IC50 (μM) |
|---|---|---|---|---|---|---|
| 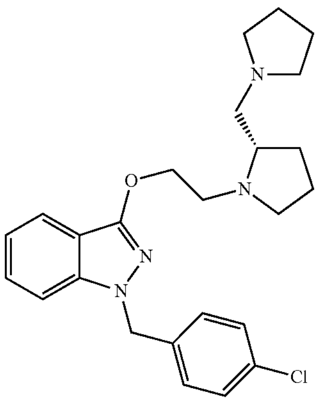 [SMILES: Clc1ccc(Cn2nc(OCCN3CCC[C@H]3CN3CCCC3)c3ccccc32)cc1] | EBP403 | 3.8 | >25 | 50 | 97 | |
| 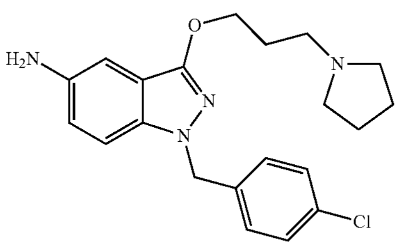 [SMILES: Nc1ccc2c(c1)c(OCCCN1CCCC1)nn2Cc1ccc(Cl)cc1] | EBP531 | 3.9 | >25 | | | |
| 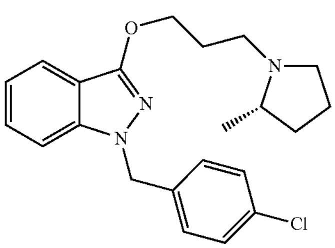 [SMILES: C[C@H]1CCCN1CCCOc1nn(Cc2ccc(Cl)cc2)c2ccccc12] | EBP391 | 4 | >25 | 35 | 100 | 0.23 |
| 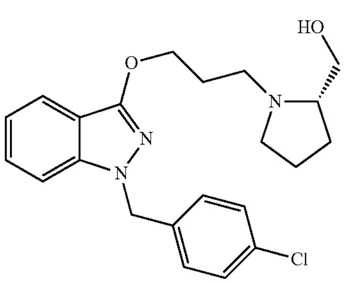 [SMILES: OC[C@@H]1CCCN1CCCOc1nn(Cc2ccc(Cl)cc2)c2ccccc12] | EBP383 | 4.2 | >25 | 35 | 100 | 0.9 |
| 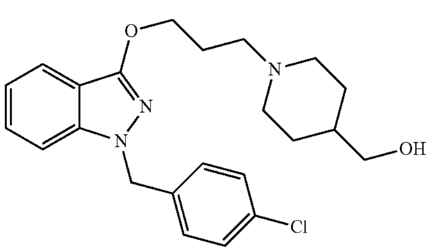 [SMILES: OCC1CCN(CCCOc2nn(Cc3ccc(Cl)cc3)c3ccccc23)CC1] | EBP502 | 4.2 | >25 | | | |

TABLE 6-continued

1b Active Analogs

| Structure | Cmpd # | 1b EC50 (μM) | Cell Viability EC50 (μM) | 2a (% activity @ 5 μM) | 2a cell viability (@ 5 μM) | hERG IC50 (μM) |
| --- | --- | --- | --- | --- | --- | --- |
| 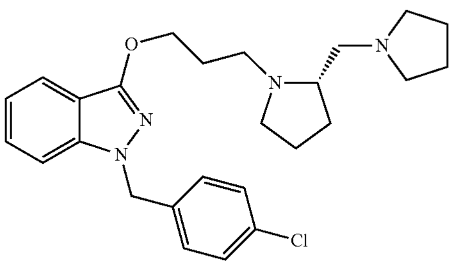 [SMILES: Clc1ccc(Cn2nc(OCCCN3CCC[C@H]3CN3CCCC3)c3ccccc32)cc1] | EBP395 | 4.4 | >25 | 41 | 89 | 2 |
| 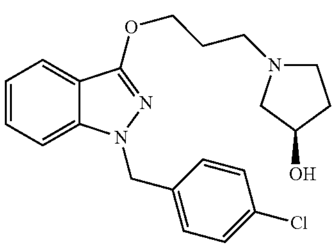 [SMILES: O[C@@H]1CCN(CCCOc2nn(Cc3ccc(Cl)cc3)c3ccccc23)C1] | EBP393 | 4.5 | >25 | 42 | 100 | 0.9 |
| 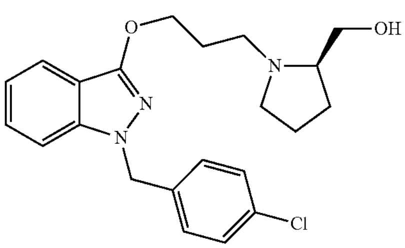 [SMILES: OC[C@H]1CCCN1CCCOc1nn(Cc2ccc(Cl)cc2)c2ccccc12] | EBP516 | 4.7 | >25 | | | 0.81 |
| 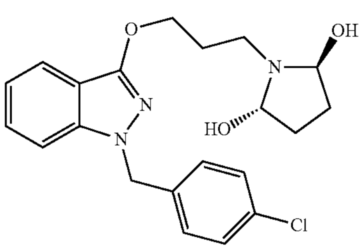 [SMILES: O[C@H]1CC[C@H](O)N1CCCOc1nn(Cc2ccc(Cl)cc2)c2ccccc12] | EBP515 | 4.9 | >25 | | | 2.6 |
| 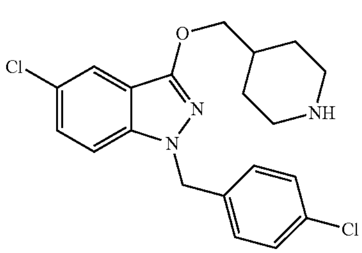 [SMILES: Clc1ccc(Cn2nc(OCC3CCNCC3)c3cc(Cl)ccc32)cc1] | EBP640 | 5 | >25 | | | 5.3 |

TABLE 6-continued

1b Active Analogs

| Structure | Cmpd # | 1b EC50 (μM) | Cell Viability EC50 (μM) | 2a (% activity @ 5 μM) | 2a cell viability (@ 5 μM) | hERG IC50 (μM) |
| --- | --- | --- | --- | --- | --- | --- |
| 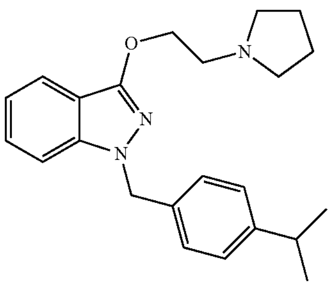 [SMILES: CC(C)c1ccc(Cn2nc(OCCN3CCCC3)c3ccccc32)cc1] | EBP336 | 5.1 | >25 | 38 | 95 | |
| 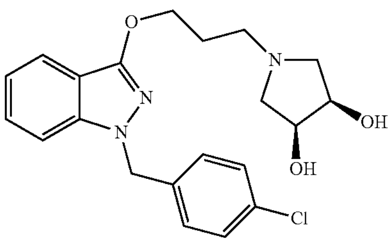 [SMILES: O[C@@H]1CN(CCCOc2nn(Cc3ccc(Cl)cc3)c3ccccc23)C[C@@H]1O] | EBP514 | 5.1 | >25 | | | |
| 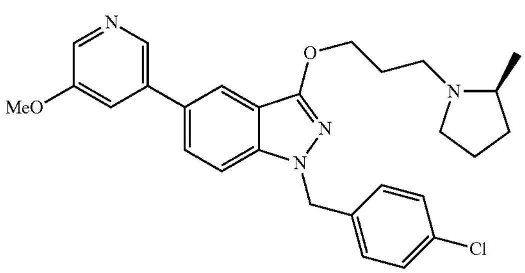 [SMILES: COc1cncc(-c2ccc3c(c2)c(OCCCN2CCC[C@@H]2C)nn3Cc2ccc(Cl)cc2)c1] | EBP898 | 5.3 | >25 | | | |
| 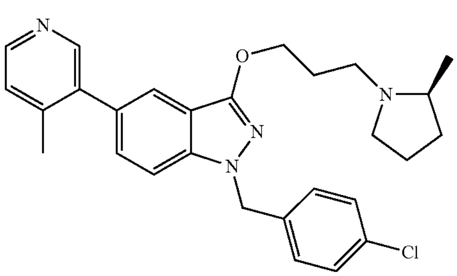 [SMILES: Cc1ccncc1-c1ccc2c(c1)c(OCCCN1CCC[C@@H]1C)nn2Cc1ccc(Cl)cc1] | EBP901 | 5.5 | >25 | | | |
| 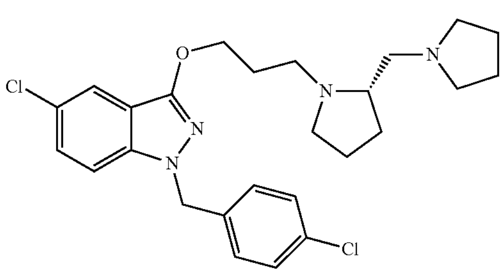 [SMILES: Clc1ccc(Cn2nc(OCCCN3CCC[C@H]3CN3CCCC3)c3cc(Cl)ccc32)cc1] | EBP649 | 5.6 | >25 | | | |

TABLE 6-continued

1b Active Analogs

| Structure | Cmpd # | 1b EC50 (μM) | Cell Viability EC50 (μM) | 2a (% activity @ 5 μM) | 2a cell viability (@ 5 μM) | hERG IC50 (μM) |
|---|---|---|---|---|---|---|
| | EBP900 | 5.6 | >25 | | | |
| | EBP924 | 5.7 | >25 | | | |
| | EBP925 | 5.7 | >25 | | | |
| | EBP522 | 6 | >25 | | | |
| | EBP387 | 6.4 | >25 | 35 | 100 | 3.3 |

TABLE 6-continued

1b Active Analogs

| Structure | Cmpd # | 1b EC50 (μM) | Cell Viability EC50 (μM) | 2a (% activity @ 5 μM) | 2a cell viability (@ 5 μM) | hERG IC50 (μM) |
|---|---|---|---|---|---|---|
| (structure) | EBP864 | 6.4 | >25 | | | |
| (structure) | EBP903 | 6.5 | >25 | | | |
| (structure) | EBP646 | 6.6 | >25 | | | |
| (structure) | EBP503 | 7.2 | >25 | 36 | 86 | |
| (structure) | EBP897 | 7.2 | >25 | | | |

TABLE 6-continued
1b Active Analogs
| Structure | Cmpd # | 1b EC50 (μM) | Cell Viability EC50 (μM) | 2a (% activity @ 5 μM) | 2a cell viability (@ 5 μM) | hERG IC50 (μM) |
|---|---|---|---|---|---|---|
| 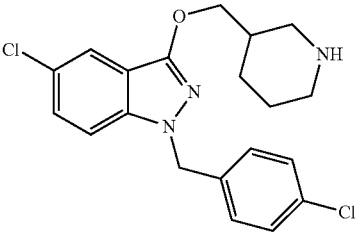 [SMILES: Clc1ccc(Cn2nc(OCC3CCCNC3)c3cc(Cl)ccc32)cc1] | EBP590 | 7.3 | 11 | | | |
| 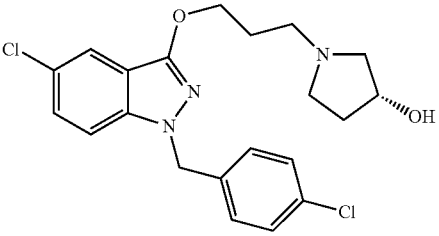 [SMILES: O[C@@H]1CCN(CCCOc2nn(Cc3ccc(Cl)cc3)c3ccc(Cl)cc23)C1] | EBP644 | 7.5 | >25 | | | |
| 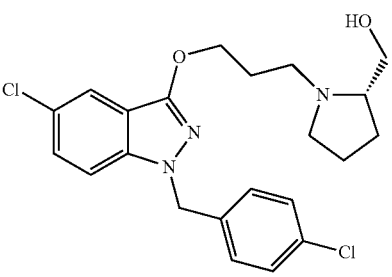 [SMILES: OC[C@@H]1CCCN1CCCOc1nn(Cc2ccc(Cl)cc2)c2ccc(Cl)cc12] | EBP647 | 7.6 | >25 | | | |
| 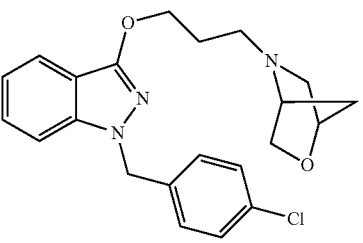 [SMILES: Clc1ccc(Cn2nc(OCCCN3CC4CC3CO4)c3ccccc32)cc1] | EBP528 | 7.9 | 8.4 | | | |
| 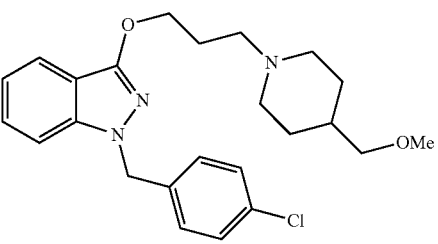 [SMILES: COCC1CCN(CCCOc2nn(Cc3ccc(Cl)cc3)c3ccccc23)CC1] | EBP530 | 7.9 | >25 | | | |

TABLE 6-continued
1b Active Analogs
| Structure | Cmpd # | 1b EC50 (μM) | Cell Viability EC50 (μM) | 2a (% activity @ 5 μM) | 2a cell viability (@ 5 μM) | hERG IC50 (μM) |
|---|---|---|---|---|---|---|
| 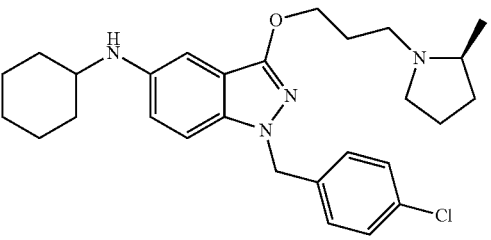 [SMILES: C[C@H]1CCCN1CCCOc1nn(Cc2ccc(Cl)cc2)c2ccc(NC3CCCCC3)cc12] | EBP917 | 8 | >25 | | | |
| 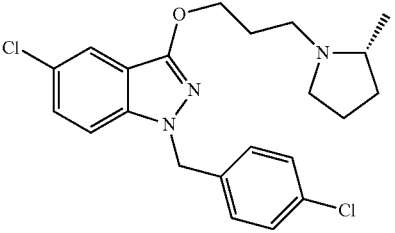 [SMILES: C[C@@H]1CCCN1CCCOc1nn(Cc2ccc(Cl)cc2)c2ccc(Cl)cc12] | EBP645 | 8 | >25 | | | |
| 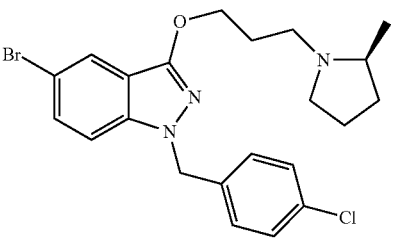 | EBP743 | 8.1 | | | | |
| 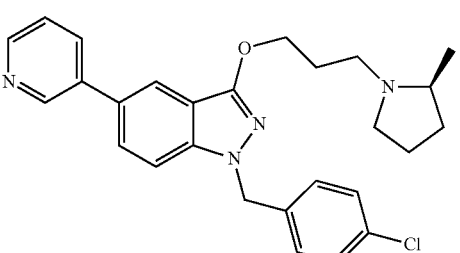 | EBP846 | 8.2 | | | | |
| 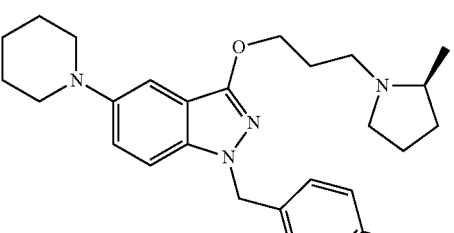 | EBP865 | 8.2 | | | | |

TABLE 6-continued
1b Active Analogs
| Structure | Cmpd # | 1b EC50 (μM) | Cell Viability EC50 (μM) | 2a (% activity @ 5 μM) | 2a cell viability (@ 5 μM) | hERG IC50 (μM) |
|---|---|---|---|---|---|---|
| 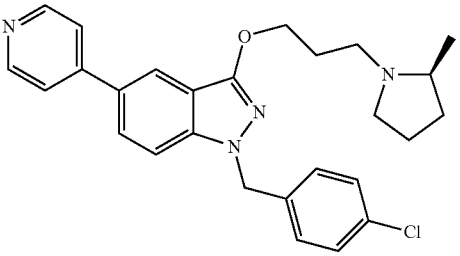 [SMILES: C[C@H]1CCCN1CCCOc1nn(Cc2ccc(Cl)cc2)c2ccc(-c3ccncc3)cc12] | EBP904 | 8.2 | >25 | | | |
| 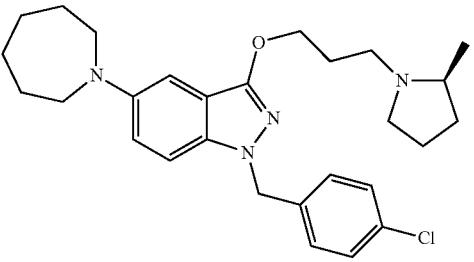 [SMILES: C[C@H]1CCCN1CCCOc1nn(Cc2ccc(Cl)cc2)c2ccc(N3CCCCCC3)cc12] | EBP918 | 8.2 | 11 | | | |
| 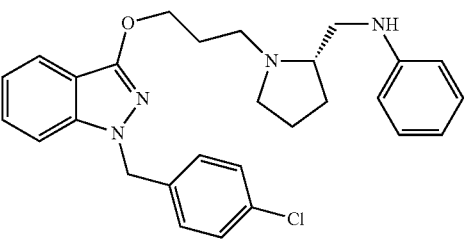 [SMILES: Clc1ccc(Cn2nc(OCCCN3CCC[C@H]3CNc3ccccc3)c3ccccc32)cc1] | EBP524 | 8.3 | >25 | | | 2.6 |
| 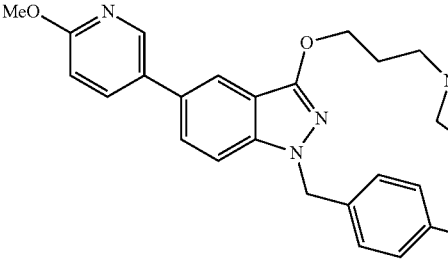 | EBP902 | 8.3 | >25 | | | |
| 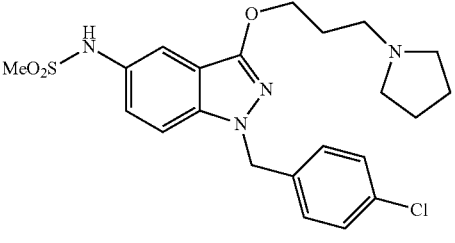 [SMILES: CS(=O)(=O)Nc1ccc2c(c1)c(OCCCN1CCCC1)nn2Cc1ccc(Cl)cc1] | EBP532 | 8.5 | >25 | | | |

TABLE 6-continued

1b Active Analogs

| Structure | Cmpd # | 1b EC50 (µM) | Cell Viability EC50 (µM) | 2a (% activity @ 5 µM) | 2a cell viability (@ 5 µM) | hERG IC50 (µM) |
|---|---|---|---|---|---|---|
| 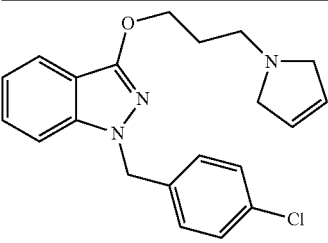 | EBP519 | 18 | >25 | | | |

Table 7 presents results for compounds that demonstrate significant activity against HCV in the 2a infectious clone assay at 5 µM. Table 7 provides certain examples of Clemizole Like Analogs provided by the present invention. In the 2a infectious clone assay, test compounds are tested at two concentrations of 5 µM and 10 µM. Only the results from testing at 5 µM are shown in Table 7. The results are reported as % replication activity of a control sample with no test compound present. A low value of 40% indicates that, at 5 µM of test compound, 40% of replication activity remains, indicative of a compound of high potency. A high value of 90% indicates that, at 5 µM of test compound, 90% of replication activity remains, indicative of a compound of low potency. In addition, Table 7 lists only compounds with test results demonstrating cell viability levels of >85% at 5 µM and >80% at 10 µM, and activity in 2a infectious clone assay of <90%. Compounds were tested for cell toxicity at concentrations of 5 µM and 10 µM. The results are reported as % cell survival. High values of >85% at 5 µM and >80% at 10 µM indicate that at 5 µM, greater than 85% of cells are viable and at 10 µM, greater than 80% of cells are viable.

TABLE 7

Clemizole like Analogs

| Structure | Cmpd # | 2a (% activity @ 5 µM) | 2a cell viability (@ 5 µM) |
|---|---|---|---|
| 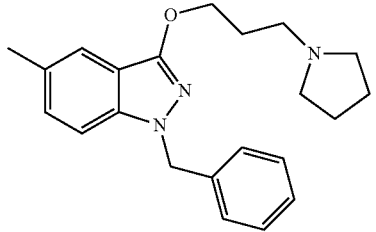 [SMILES: Cc1ccc2c(c1)c(OCCCN1CCCC1)nn2Cc1ccccc1] | EBP178 | 25 | 92 |
| 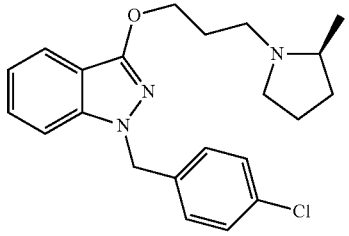 [SMILES: C[C@H]1CCCN1CCCOc1nn(Cc2ccc(Cl)cc2)c2ccccc12] | EBP389 | 44 | 100 |
| 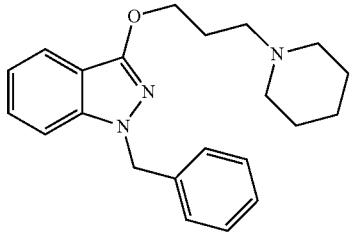 [SMILES: c1ccc(Cn2nc(OCCCN3CCCCC3)c3ccccc32)cc1] | EBP192 | 50 | 88 |

TABLE 7-continued
Clemizole like Analogs
| Structure | Cmpd # | 2a (% activity @ 5 μM) | 2a cell viability (@ 5 μM) |
|---|---|---|---|
| 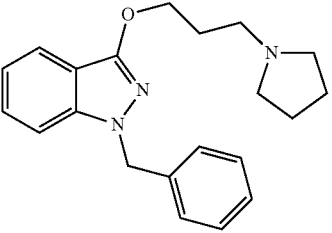 [SMILES: c1ccc(Cn2nc(OCCCN3CCCC3)c3ccccc32)cc1] | EBP177 | 53 | 100 |
| 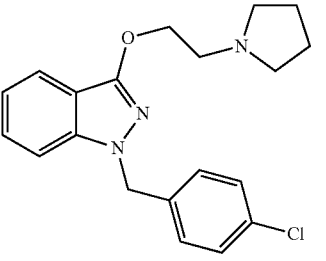 [SMILES: Clc1ccc(Cn2nc(OCCN3CCCC3)c3ccccc32)cc1] | EBP333 | 56 | 97 |
| 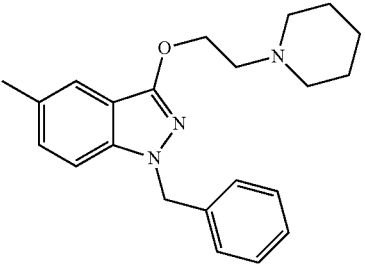 [SMILES: Cc1ccc2c(c1)c(OCCN1CCCCC1)nn2Cc1ccccc1] | EBP176 | 58 | 98 |
| 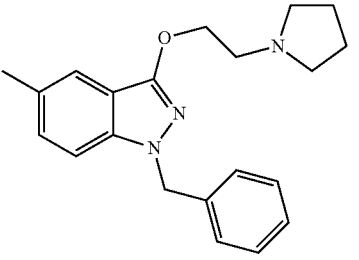 [SMILES: Cc1ccc2c(c1)c(OCCN1CCCC1)nn2Cc1ccccc1] | EBP181 | 58 | 100 |
| 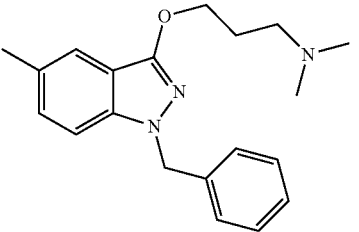 | EBP151 | 62 | 92 |

TABLE 7-continued
| Clemizole like Analogs | | | |
|---|---|---|---|
| Structure | Cmpd # | 2a (% activity @ 5 µM) | 2a cell viability (@ 5 µM) |
| 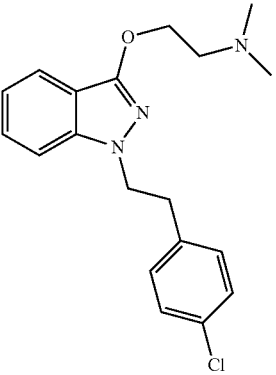 [SMILES: CN(C)CCOc1nn(CCc2ccc(Cl)cc2)c2ccccc12] | EBP332 | 66 | 100 |
| 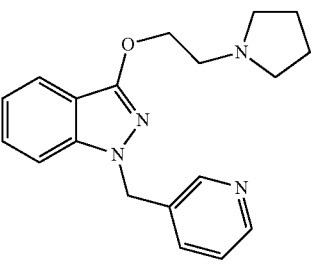 [SMILES: c1cncc(Cn2nc(OCCN3CCCC3)c3ccccc32)c1] | EBP356 | 68 | 95 |
| 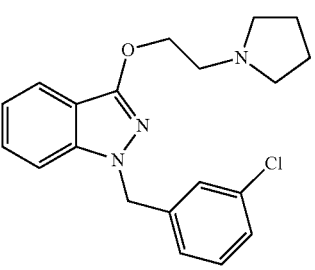 [SMILES: Clc1cccc(Cn2nc(OCCN3CCCC3)c3ccccc32)c1] | EBP334 | 69 | 100 |
| 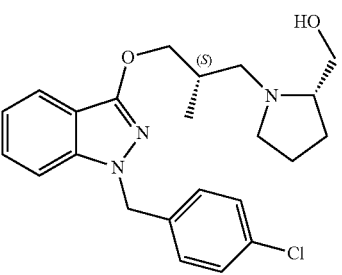 | EBP454 | 69 | 93 |
| 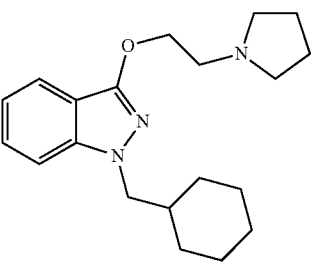 [SMILES: c1ccc2c(c1)c(OCCN1CCCC1)nn2CC1CCCCC1] | EBP339 | 69 | 100 |

TABLE 7-continued
Clemizole like Analogs
| Structure | Cmpd # | 2a (% activity @ 5 μM) | 2a cell viability (@ 5 μM) |
|---|---|---|---|
| 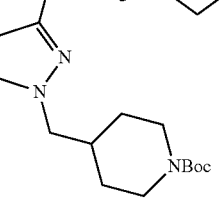 | EBP340 | 62 | 98 |
| 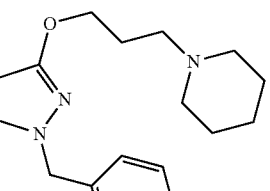 | EBP328 | 71 | 100 |
| 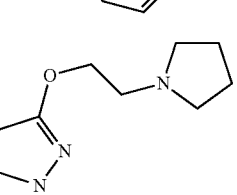 | EBP335 | 73 | 10 |
| 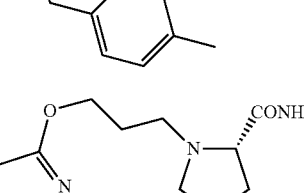 | EBP385 | 75 | 100 |
| 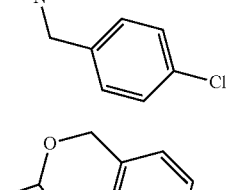 | EBP330 | 75 | 100 |
| 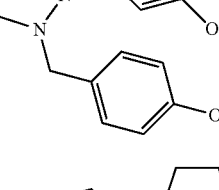 | EBP357 | 77 | 94 |

TABLE 7-continued
| Clemizole like Analogs | | | |
|---|---|---|---|
| Structure | Cmpd # | 2a (% activity @ 5 μM) | 2a cell viability (@ 5 μM) |
| 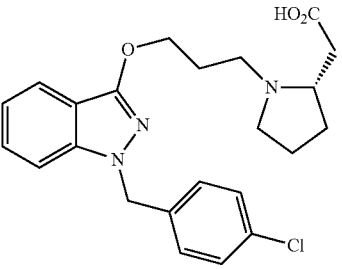 [SMILES: O=C(O)C[C@@H]1CCCN1CCCOc1nn(Cc2ccc(Cl)cc2)c2ccccc12] | EBP508 | 77 | 100 |
| 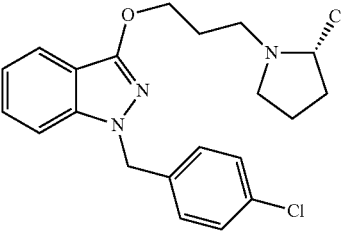 | EBP512 | 78 | 100 |
| 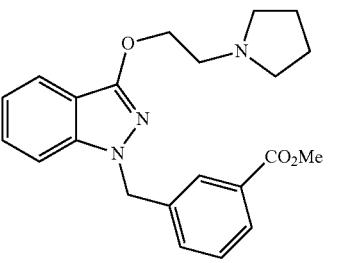 [SMILES: COC(=O)c1cccc(Cn2nc(OCCN3CCCC3)c3ccccc32)c1] | EBP338 | 79 | 100 |
| 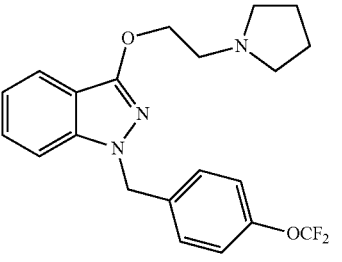 | EBP353 | 79 | 100 |
| 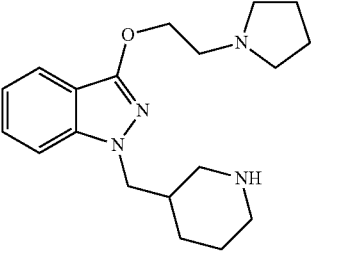 [SMILES: c1ccc2c(c1)c(OCCN1CCCC1)nn2CC1CCCNC1] | EBP360 | 80 | 92 |

TABLE 7-continued
| | Clemizole like Analogs | |
|---|---|---|
| Structure | Cmpd # | 2a (% activity @ 5 μM) | 2a cell viability (@ 5 μM) |
|---|---|---|---|
| 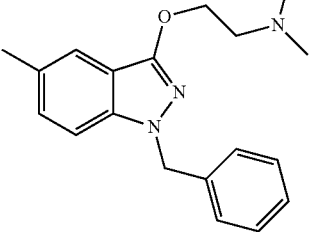 | EBP182 | 82 | 100 |
| 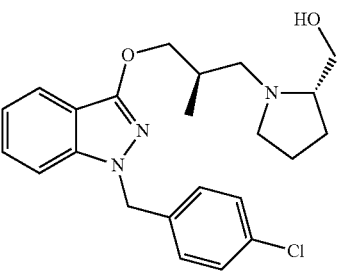 [SMILES: C[C@@H](COc1nn(Cc2ccc(Cl)cc2)c2ccccc12)CN1CCC[C@H]1CO] | EBP449 | 83 | 99 |
| 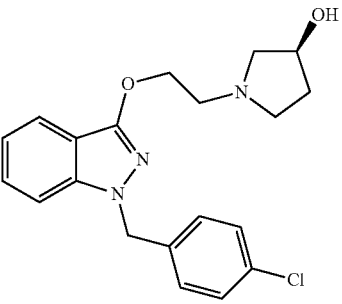 [SMILES: O[C@H]1CCN(CCOc2nn(Cc3ccc(Cl)cc3)c3ccccc23)C1] | EBP400 | 84 | 100 |
| 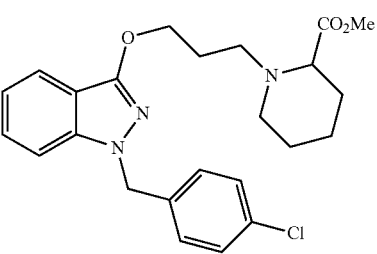 [SMILES: COC(=O)C1CCCCN1CCCOc1nn(Cc2ccc(Cl)cc2)c2ccccc12] | EBP505 | 87 | 94 |
| 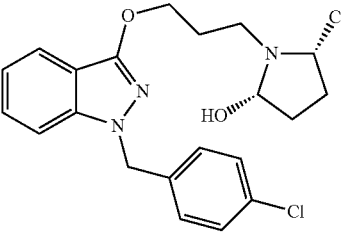 | EBP507 | 87 | 90 |

TABLE 7-continued
Clemizole like Analogs
| Structure | Cmpd # | 2a (% activity @ 5 μM) | 2a cell viability (@ 5 μM) |
|---|---|---|---|
| 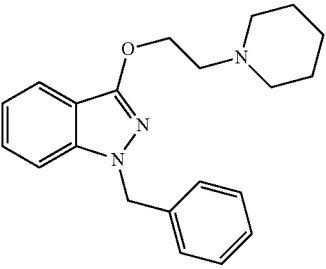 [SMILES: c1ccc(Cn2nc(OCCN3CCCCC3)c3ccccc32)cc1] | EBP175 | 89 | 98 |
| 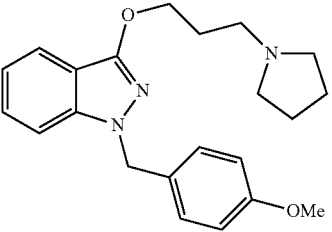 [SMILES: COc1ccc(Cn2nc(OCCCN3CCCC3)c3ccccc32)cc1] | EBP327 | 89 | 98 |
Listed below are compounds that are inactive in the 1b replicon assay. These include compounds where $R_1$ is Me and $R_3$ N-linked 5 or 6 membered non aromatic heterocycle containing 1 nitrogen atom directly attached to a carboxylic acid or carboxyl ester substituent.
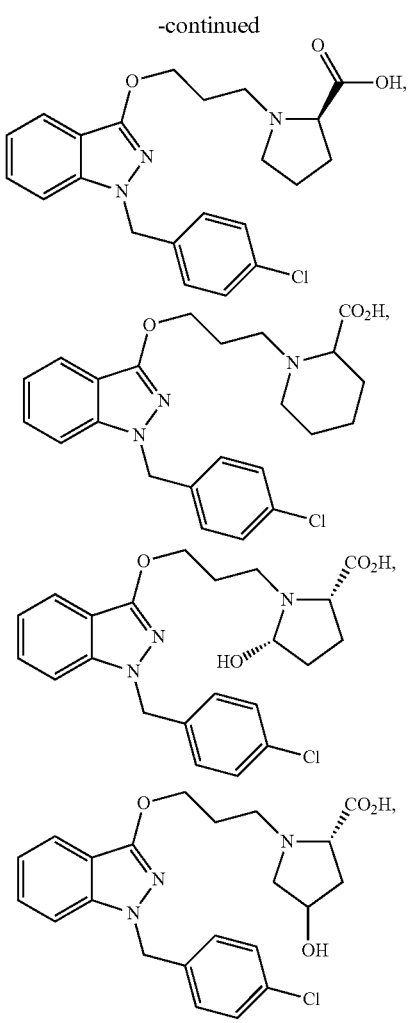

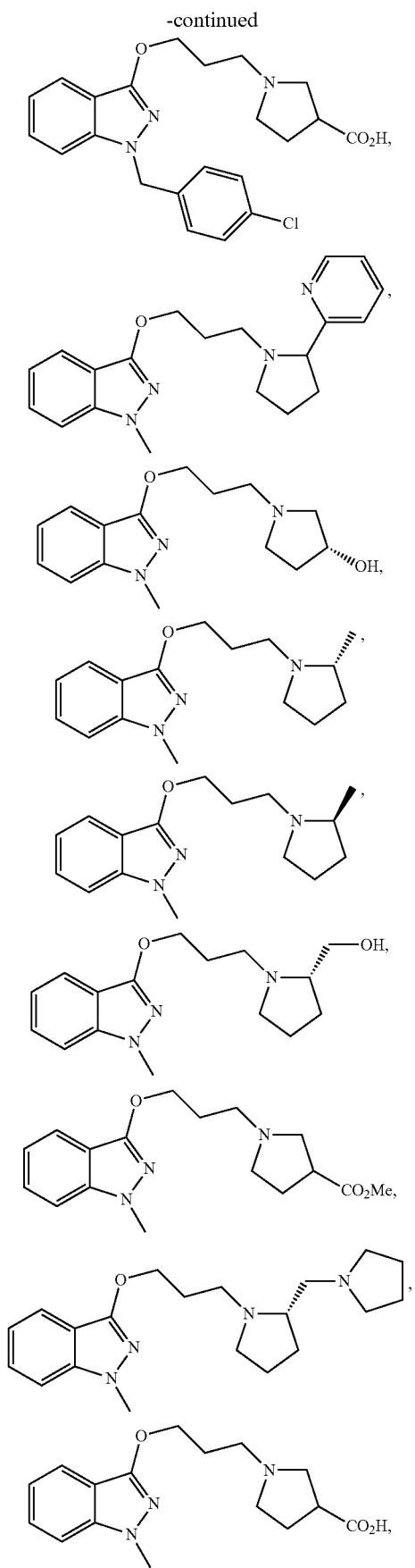
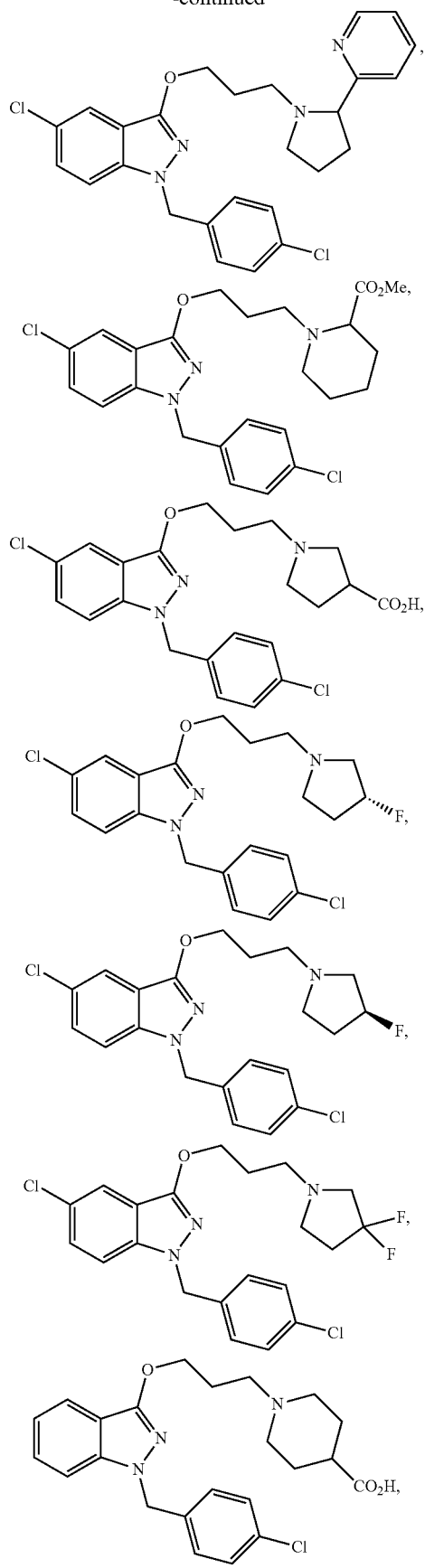

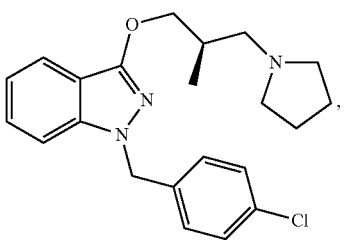

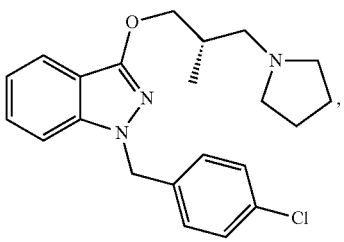

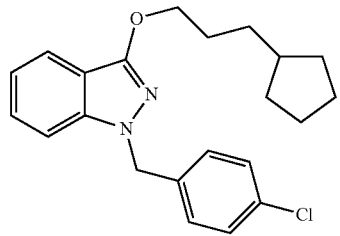

In an embodiment, a compound other than one of those described above can be used to treat HCV. In another embodiment, one or more of the compounds above can be used in other embodiments of the present disclosure to treat HCV.

It should be noted that ratios, concentrations, amounts, and other numerical data may be expressed herein in a range format. It is to be understood that such a range format is used for convenience and brevity, and thus, should be interpreted in a flexible manner to include not only the numerical values explicitly recited as the limits of the range, but also to include all the individual numerical values or sub-ranges encompassed within that range as if each numerical value and sub-range is explicitly recited. To illustrate, a concentration range of "about 0.1% to about 5%" should be interpreted to include not only the explicitly recited concentration of about 0.1 wt % to about 5 wt %, but also include individual concentrations (e.g., 1%, 2%, 3%, and 4%) and the sub-ranges (e.g., 0.5%, 1.1%, 2.2%, 3.3%, and 4.4%) within the indicated range. The term "about" can include ±1%, ±2%, ±3%, ±4%, ±5%, ±6%, ±7%, ±8%, ±9%, or ±10%, or more of the numerical value(s) being modified. In addition, the phrase "about 'x' to 'y'" includes "about 'x' to about 'y'".

It should be emphasized that the above-described embodiments of the present disclosure are merely possible examples of implementations, and are set forth only for a clear understanding of the principles of the disclosure. Many variations and modifications may be made to the above-described embodiments of the disclosure without departing substantially from the spirit and principles of the disclosure. All such modifications and variations are intended to be included herein within the scope of this disclosure.

What is claimed is:

1. A compound having the structure shown in Formula II-a, or a pharmaceutically acceptable salt or a stereoisomer thereof:

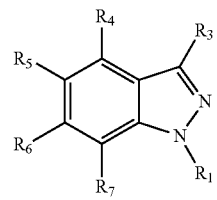

Formula II-a wherein $R_1$ is

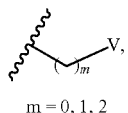

$m = 0, 1, 2$ wherein V is selected from the group consisting of alkyl, cycloalkyl, heterocyclo, aryl, and heteroaryl, and m is 0, 1 or 2;

$R_3$ is —OH, —O(CH$_2$)$_n$X, or —(CH$_2$)$_n$X, wherein n is 1, 2, 3, or 4, and X is selected from the group consisting of: —NH$_2$, —NH(alkyl), —N(alkyl)$_2$, —OH, —O-alkyl, —O-aryl, —SO$_2$(alkyl), —SO$_2$NH$_2$, —SO$_2$NH(alkyl), NHSO$_2$(alkyl),

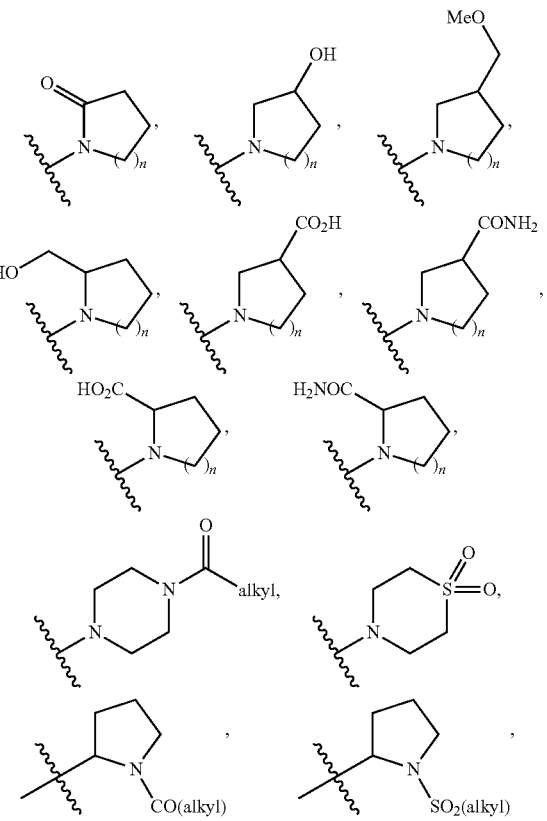

-continued

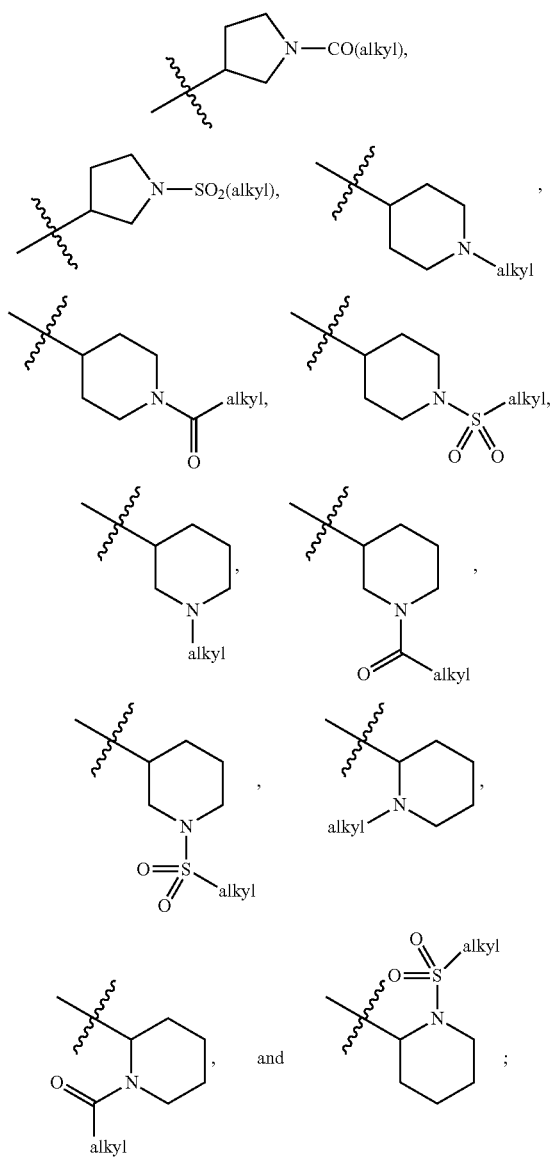

n = 1, 2, or 3 each of $R_4$-$R_7$ are independently selected from the group consisting of: —H, —Br, —Cl, —F, —I, —CH$_3$, —CN, —OH, —OCH$_3$, —NO$_2$, —NH$_2$, —NHCO(alkyl), —NHCO(aryl),

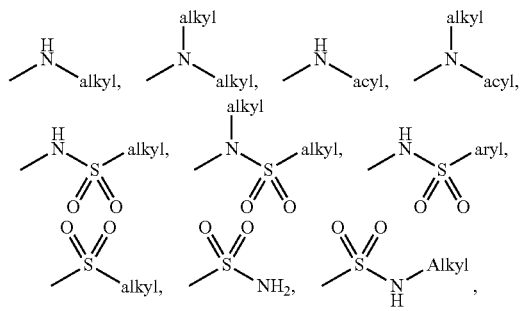

-continued

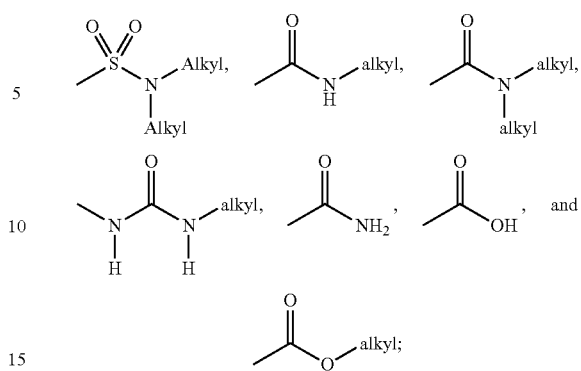

or, optionally, $R_4$ and $R_5$, $R_5$ and $R_6$, or $R_6$ and $R_7$ are joined together with a bond to form a 5, 6, or 7-membered ring; or, optionally, $R_4$ and $R_5$, $R_5$ and $R_6$, or $R_6$ and $R_7$ are joined together to form a 1,2-(methylenedioxy)benzene ring system; provided that the compound of Formula II-a is not

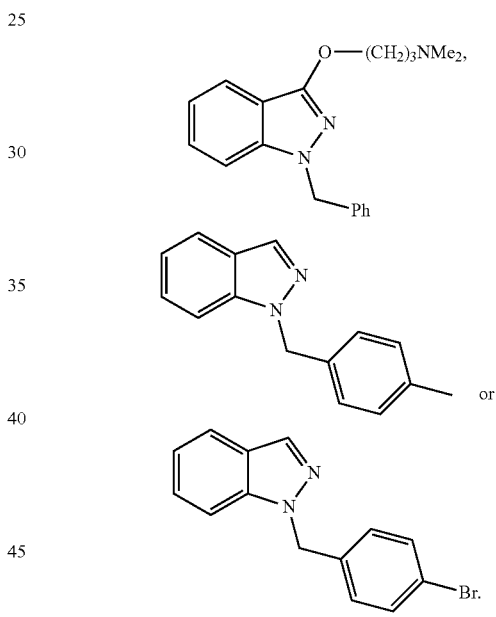

2. The compound of claim 1, wherein $R_1$ is

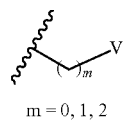

m = 0, 1, 2 and V is aryl.

3. The compound of claim 1, wherein $R_3$ is —OH, —O(CH$_2$)$_n$X, or —(CH$_2$)$_n$X, wherein n is 1, 2, 3, or 4, and X is —NH$_2$, —NH(alkyl), —N(alkyl)$_2$, or —OH.

4. The compound of claim 1, wherein $R_3$ is selected from the group consisting of: —O(CH$_2$)$_2$NMe$_2$, —O(CH$_2$)$_2$NEt$_2$, —O(CH$_2$)$_3$NEt$_2$, 5. The compound of claim 1, wherein $R_1$ is —$CH_2V$, wherein V is selected from cycloalkyl, heterocyclo, or heteroaryl.

6. The compound of claim 1, wherein $R_4$ and $R_7$ are both hydrogen, and $R_5$ and $R_6$ are both a substituent other than hydrogen.

7. A pharmaceutical composition comprising a compound as shown in Formula II-a, or a pharmaceutically acceptable salt, a stereoisomer a tautomer, or a prodrug thereof:

Formula II-a wherein $R_1$ is m = 0, 1, 2, wherein V is selected from the group consisting of: alkyl, cycloalkyl, heterocyclo, aryl, and heteroaryl, and m is 0, 1 or 2;

$R_3$ is —OH, —$O(CH_2)_nX$, or —$(CH_2)_nX$, wherein n is 1, 2, 3, or 4, and X is selected from the group consisting of: —$NH_2$, —NH(alkyl), —N(alkyl)$_2$, —OH, —O-alkyl, —O-aryl, —$SO_2$(alkyl), —$SO_2NH_2$, —$SO_2NH$(alkyl), $NHSO_2$(alkyl)

n = 1, 2, or 3 each of $R_4$-$R_7$ are independently selected from the group consisting of: —H, —Br, —Cl, —F, —I, —CH$_3$, —CN, —OH, —OCH$_3$, —NO$_2$, —NH$_2$, —NHCO(alkyl), —NHCO(aryl),

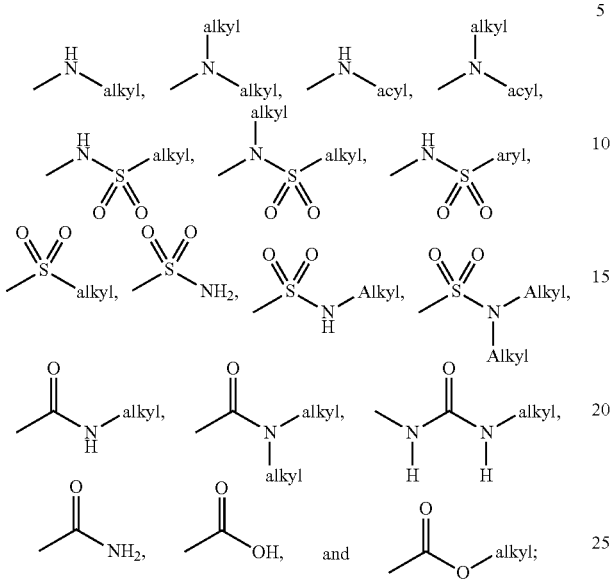

or, optionally, $R_4$ and $R_5$, $R_5$ and $R_6$, or $R_6$ and $R_7$ are joined together with a bond to form a 5, 6, or 7-membered ring; or optionally, $R_4$ and $R_5$, $R_5$ and $R_6$, or $R_6$ and $R_7$ are joined together to form a 1,2-(methylenedioxy) benzene ring system; provided that the compound of Formula II-a is not

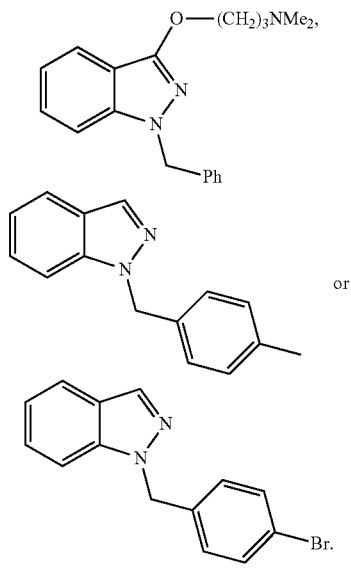

8. A compound having the structure shown in Formula III

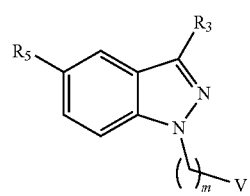

Formula III or a pharmaceutically acceptable salt, a stereoisomer, a tautomer or a prodrug thereof, wherein m is 1 or 2;

V is an unsubstituted or a monosubstituted phenyl, cyclohexyl, or a 6-membered heterocyclo group, where the heterocyclo group contains 1 nitrogen atom;

$R_3$ is —O-L-X;

L is an unsubstituted or a monosubstituted $C_1$-$C_5$ alkylene;

X is selected from the group consisting of: —N(R$_{20}$)$_2$, 4-substituted phenyl;

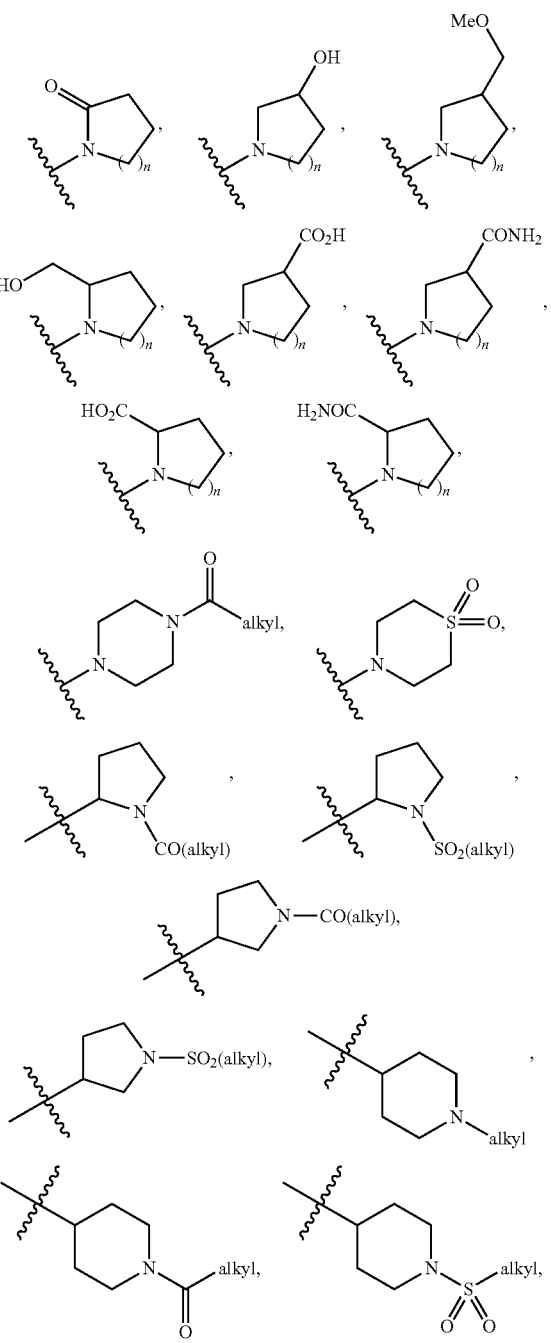

-continued

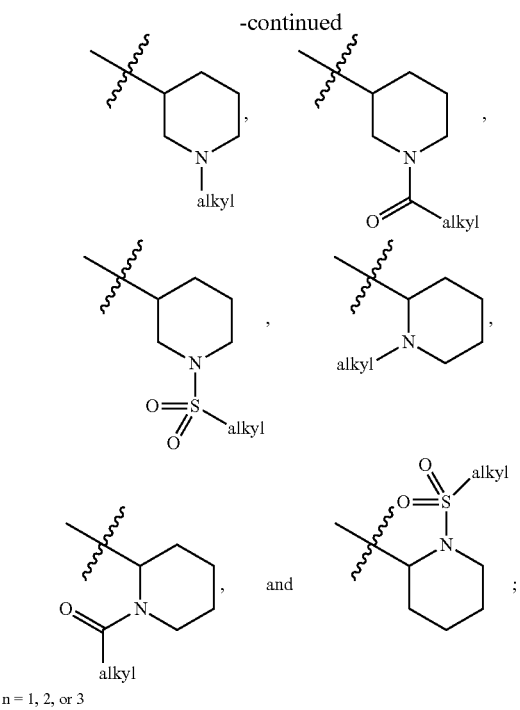

n = 1, 2, or 3

$R_5$ is hydrogen, alkyl, halo, a substituted or an unsubstituted 5, 6, 7 membered heterocyclo, or —$NR_{21}R_{22}$;

each $R_{20}$ is independently selected from a substituted or an unsubstituted $C_1$-$C_3$ alkyl;

$R_{21}$ and $R_{22}$ are each independently selected from hydrogen, a substituted or an unsubstituted $C_1$-$C_3$ alkyl, $C_3$-$C_8$ cycloalkyl, aryl, heteroaryl group, —$COR_{16}$, or —$SO_2R_{16}$, or $R_{21}$ and $R_{22}$ together with the nitrogen atom to which they are attached form a 5-7 membered substituted or unsubstituted heterocyclo group; and $R_{16}$ is substituted or unsubstituted $C_1$-$C_3$ alkyl.

9. The compound of claim 8, wherein m is 1.

10. The compound of claim 8, wherein

X is selected from the group consisting of: a 5, 6, or 7 membered non aromatic heterocyclo that is unsubstituted or is substituted with 1 or 2 —OH, $C_1$-$C_3$ alkoxy, —$CO_2R_{17}$, or —$CON(R_{18})_2$, a substituted or an unsubstituted 5 or 6 membered aryl or heteroaryl group, a $C_1$-$C_3$ alkyl, and a $C_1$-$C_3$ alkyl substituted with —OH, $C_1$-$C_3$ alkoxy, —$CO_2R_{17}$, —$NR_{23}R_{24}$, or —$CO_2H$;

$R_{17}$ is a substituted or an unsubstituted $C_1$-$C_6$ alkyl;

each $R_{18}$ is independently selected from hydrogen or a substituted or an unsubstituted $C_1$-$C_3$ alkyl; and $R_{23}$ and $R_{24}$ are each independently selected from hydrogen, a substituted or an unsubstituted aryl, heteroaryl, or $C_1$-$C_3$ alkyl, or $R_{23}$ and $R_{24}$ together with the nitrogen atom they are attached form a substituted or an unsubstituted 5-7 membered non aromatic heterocycle.

11. The compound of claim 10, wherein X is 1-pyrrolidinyl that is unsubstituted or substituted with 1 or 2 —OH, $C_1$-$C_3$ alkoxy, a substituted or an unsubstituted 6 membered aryl, a $C_1$-$C_3$ alkyl, or a $C_1$-$C_3$ alkyl substituted with —OH, $C_1$-$C_3$ alkoxy, or —$NR_{23}R_{24}$.

12. The compound of claim 10, wherein X is a substituted or an unsubstituted piperidinyl or a 7-membered non aromatic heterocyclo group where the 7-membered non aromatic heterocyclo group contains 1 nitrogen atom.

13. The compound of claim 8, wherein L is —$(CH_2)_n$— and n is 1, 2, 3, or 4.

14. The compound of claim 13, wherein V is 4-chlorophenyl or 4-isopropylphenyl.

15. The compound of claim 13, wherein V is 4-chlorophenyl.

16. The compound of claim 13, wherein $R_5$ is hydrogen, halo, a substituted or an unsubstituted 5, 6, 7 membered heterocyclo, or —$NR_{21}R_{22}$.

17. A pharmaceutical composition comprising the compound as shown in formula III and a pharmaceutically acceptable carrier, excipient, or diluent:

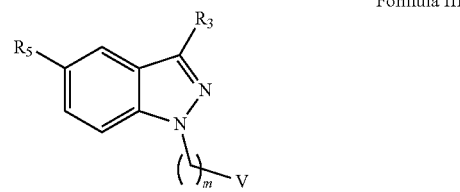

Formula III or a pharmaceutically acceptable salt, a stereoisomer, a tautomer or a prodrug thereof, wherein m is 1 or 2;

V is an unsubstituted or a monosubstituted phenyl, cyclohexyl, or a 6-membered heterocyclo group, where the heterocyclo group contains 1 nitrogen atom;

$R_3$ is —O-L-X;

L is an unsubstituted or a monosubstituted $C_1$-$C_5$ alkylene;

X is selected from the group consisting of: —$N(R_{20})_2$, 4-substituted phenyl,

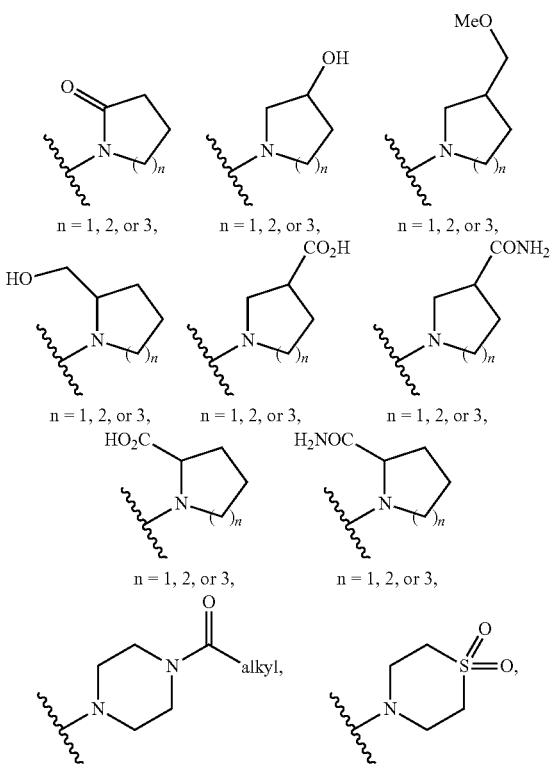

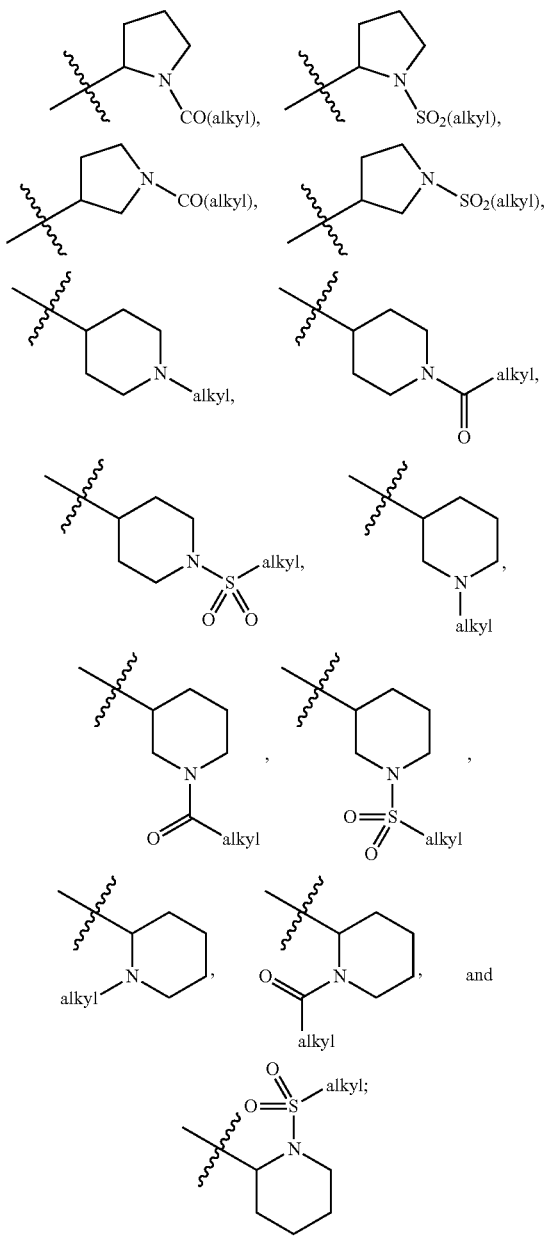

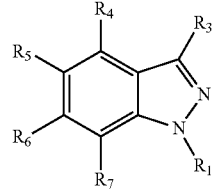

Formula II-a wherein $R_1$ is —H;

$R_3$ is selected from the group consisting of: —OH, —O(CH$_2$)$_n$X, or —(CH$_2$)$_n$X, wherein n is 1, 2, 3, or 4, and X is —NH$_2$, —NH(alkyl), —N(alkyl)$_2$, —OH, —O-alkyl, —O-aryl, —SO$_2$(alkyl), —SO$_2$NH$_2$, —SO$_2$NH(alkyl), NHSO$_2$(alkyl),

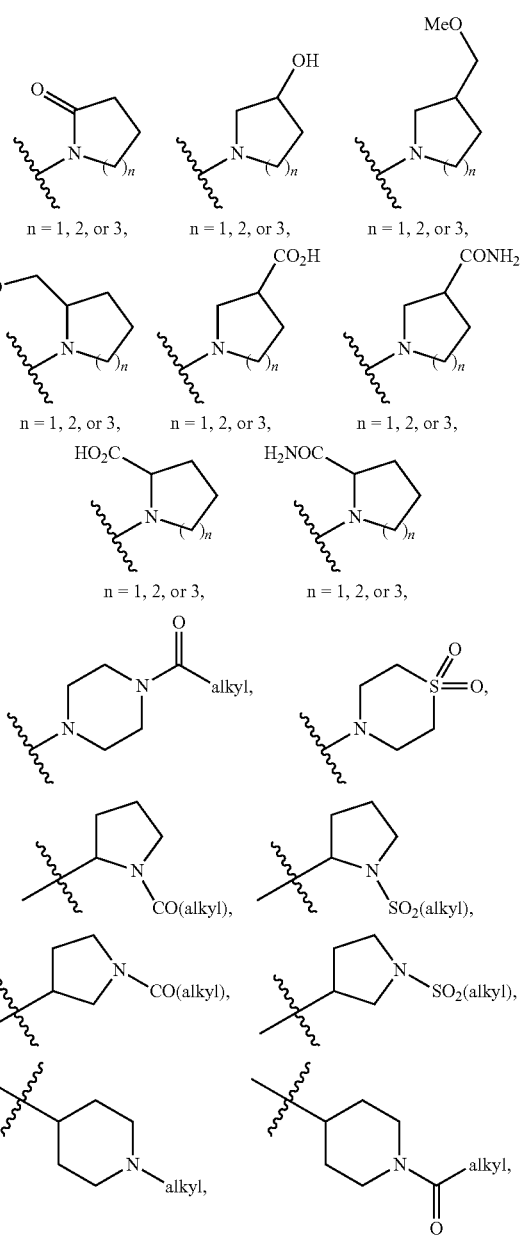

$R_5$ is hydrogen, alkyl, halo, a substituted or an unsubstituted 5, 6, 7 membered heterocyclo, or —NR$_{21}$R$_{22}$;

each $R_{20}$ is independently selected from a substituted or an unsubstituted C$_1$-C$_3$ alkyl;

$R_{21}$ and $R_{22}$ are each independently selected from hydrogen, a substituted or an unsubstituted C$_1$-C$_3$ alkyl, C$_3$-C$_8$ cycloalkyl, aryl, heteroaryl group, —COR$_{16}$, or —SO$_2$R$_{16}$, or $R_{21}$ and $R_{22}$ together with the nitrogen atom to which they are attached form a 5-7 membered substituted or unsubstituted heterocyclo group; and $R_{16}$ is substituted or unsubstituted C$_1$-C$_3$ alkyl.

18. A compound having the structure shown in Formula II-a, or a pharmaceutically acceptable salt or a stereoisomer thereof:

-continued

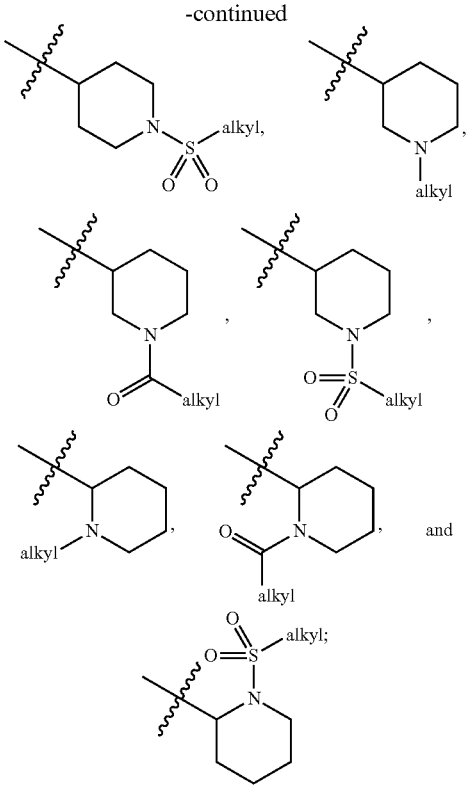

each of $R_4$-$R_7$ are independently selected from the group consisting of: —H, —Br, —Cl, —F, —I, —CH$_3$, —CN, -OH, -OCH$_3$, —NO$_2$, —NH$_2$, —NHCO(alkyl), —NHCO(aryl),

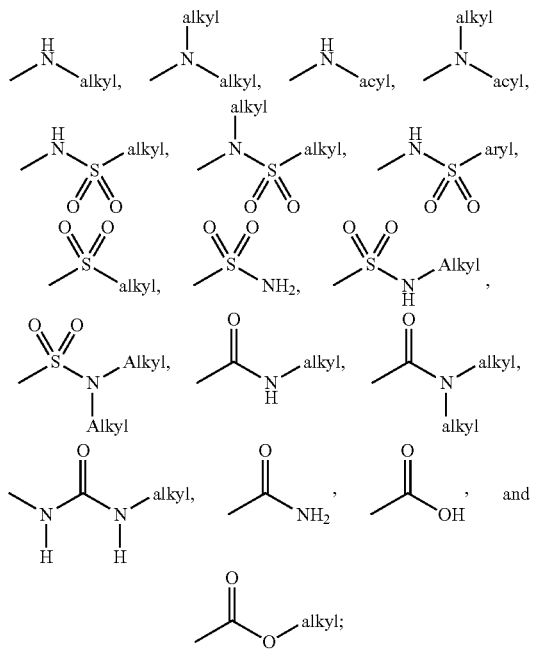

or, optionally, $R_4$ and $R_5$, $R_5$ and $R_6$, or $R_6$ and $R_7$ are joined together with a bond to form a 5, 6, or 7-membered ring; or, optionally, $R_4$ and $R_5$, $R_5$ and $R_6$, or $R_6$ and $R_7$ are joined together to form a 1,2-(methylenedioxy)benzene ring system; provided that the compound of Formula II-a is not

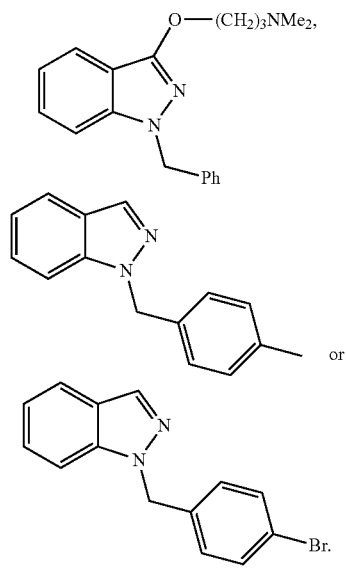

19. A pharmaceutical composition comprising a compound as shown in Formula II-a, or a pharmaceutically acceptable salt, a stereoisomer, a tautomer, or a prodrug thereof:

Formula II-a

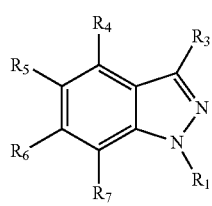

wherein $R_1$ is selected from the group consisting of: —H;

$R_3$ is selected from the group consisting of: —OH, —O(CH$_2$)$_n$X, or —(CH$_2$)$_n$X, wherein n is 1, 2, 3, or 4, and X is —NH$_2$, —NH(alkyl), —N(alkyl)$_2$, —OH, —O-alkyl, —O-aryl, —SO$_2$(alkyl), —SO$_2$NH$_2$, —SO$_2$NH(alkyl), NHSO$_2$(alkyl),

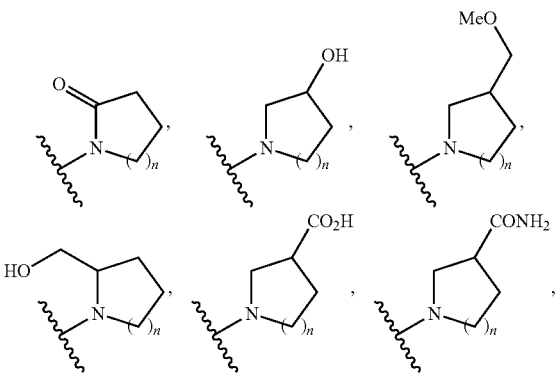

-continued

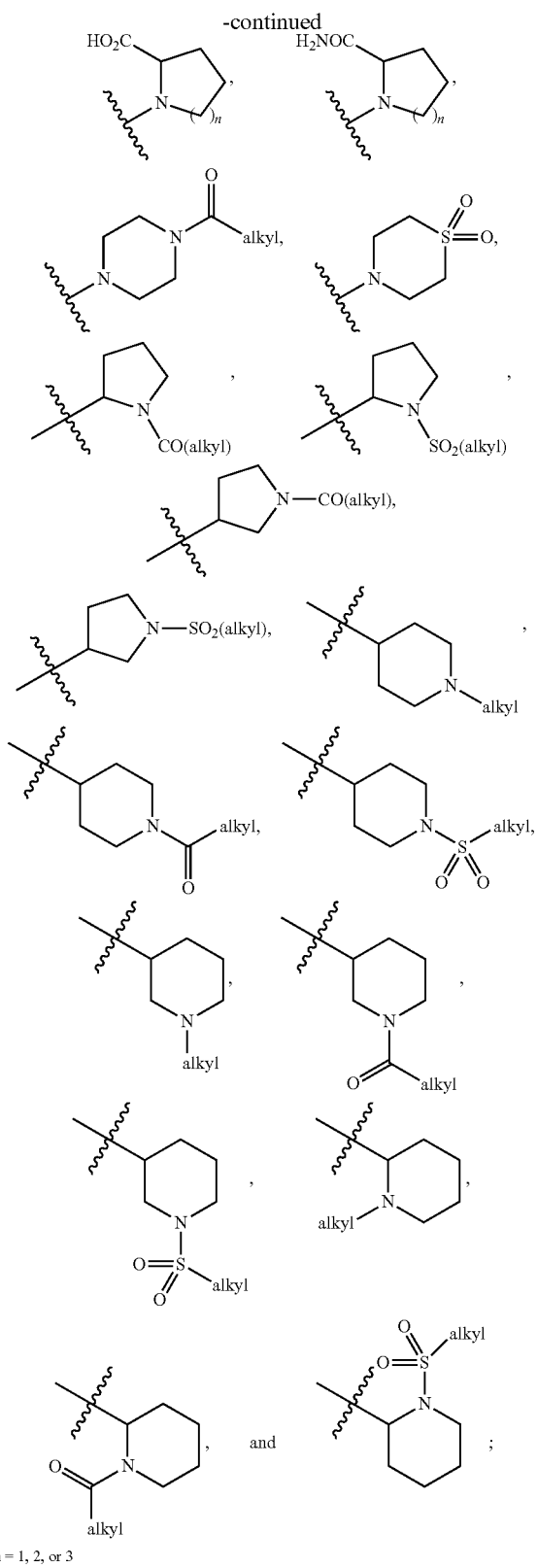

n = 1, 2, or 3 each of $R_4$-$R_7$ are independently selected from the group consisting of: —H, —Br, —Cl, —F, —I, —CH$_3$, —CN, —OH, —OCH$_3$, —NO$_2$, —NH$_2$, —NHCO(alkyl), —NHCO(aryl), or, optionally, $R_4$ and $R_5$, $R_5$ and $R_6$, or $R_6$ and $R_7$ are joined together with a bond to form a 5, 6, or 7-membered ring; or, optionally, $R_4$ and $R_5$, $R_5$ and $R_6$, or $R_6$ and $R_7$ are joined together to form a 1,2-(methylenedioxy)benzene ring system; provided that the compound of Formula II-a is not

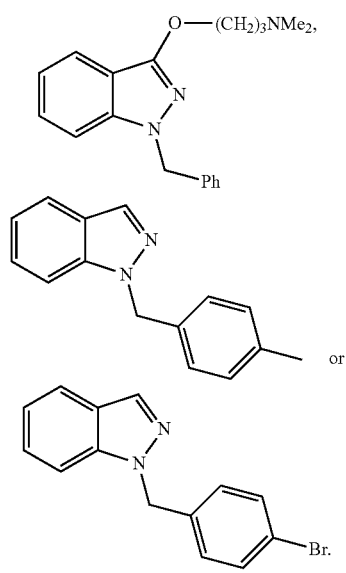

20. The composition of claim 19, further comprising an NS3 protease inhibitor.

21. The composition of claim 19, further comprising an NS5A inhibitor.

22. The composition of claim 19, further comprising an NS3 helicase inhibitor.

23. The composition of claim 19, further comprising a therapeutic agent that is selected from the group consisting of: an HCV NS5B RNA-dependent RNA polymerase inhibitor and a nucleoside analog.

24. The composition of claim 19, further comprising a therapeutic agent that is selected from the group consisting of: a thiazolide and a sustained release thiazolide.

25. The composition of claim 19, further comprising a therapeutic agent that is selected from the group consisting of: an interferon-alpha and a pegylated interferon.

26. The composition of claim 19, further comprising a therapeutic agent that is selected from the group consisting of: ribavirin, levovirin, and viramidine.

27. The composition of claim 19, further comprising a TLR7 agonist.

28. The composition of claim 19, further comprising a TLR9 agonist.

29. The composition of claim 19, further comprising a cyclophilin inhibitor.

30. The composition of claim 19, further comprising an alpha-glucosidase inhibitor.

31. The composition of claim 7, further comprising an NS3 protease inhibitor.

32. The composition of claim 7, further comprising an NS5A inhibitor.

33. The composition of claim 7, further comprising an NS3 helicase inhibitor.

34. The composition of claim 7, further comprising a therapeutic agent that is selected from the group consisting of: an HCV NS5B RNA-dependent RNA polymerase inhibitor and a nucleoside analog.

35. The composition of claim 7, further comprising a therapeutic agent that is selected from the group consisting of: a thiazolide and a sustained release thiazolide.

36. The composition of claim 7, further comprising a therapeutic agent that is selected from the group consisting of: an interferon-alpha and a pegylated interferon.

37. The composition of claim 7, further comprising a therapeutic agent that is selected from the group consisting of: ribavirin, levovirin, and viramidine.

38. The composition of claim 7, further comprising a TLR7 agonist.

39. The composition of claim 7, further comprising a TLR9 agonist.

40. The composition of claim 7, further comprising a cyclophilin inhibitor.

41. The composition of claim 7, further comprising an alpha-glucosidase inhibitor.

42. The composition of claim 17, further comprising an NS3 protease inhibitor.

43. The composition of claim 17, further comprising an NS5A inhibitor.

44. The composition of claim 17, further comprising an NS3 helicase inhibitor.

45. The composition of claim 17, further comprising a therapeutic agent that is selected from the group consisting of: an HCV NS5B RNA-dependent RNA polymerase inhibitor and a nucleoside analog.

46. The composition of claim 17, further comprising a therapeutic agent that is selected from the group consisting of: a thiazolide and a sustained release thiazolide.

47. The composition of claim 17, further comprising a therapeutic agent that is selected from the group consisting of: an interferon-alpha and a pegylated interferon.

48. The composition of claim 17, further comprising a therapeutic agent that is selected from the group consisting of: ribavirin, levovirin, and viramidine.

49. The composition of claim 17, further comprising a TLR7 agonist.

50. The composition of claim 17, further comprising a TLR9 agonist.

51. The composition of claim 17, further comprising a cyclophilin inhibitor.

52. The composition of claim 17, further comprising an alpha-glucosidase inhibitor.

53. A compound having the structure shown below, or a pharmaceutically acceptable salt or a stereoisomer thereof:

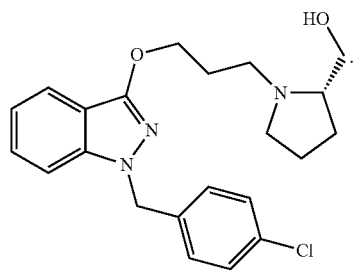 [SMILES: OC[C@@H]1CCCN1CCCOc1nn(Cc2ccc(Cl)cc2)c2ccccc12]

54. A compound having the structure shown below, or a pharmaceutically acceptable salt or a stereoisomer thereof:

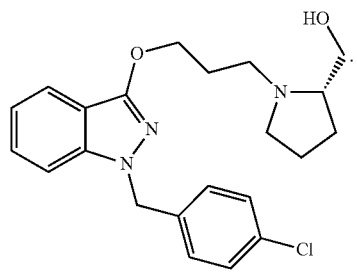 [SMILES: OC[C@@H]1CCCN1CCCOc1nn(Cc2ccc(Cl)cc2)c2ccccc12]

55. A pharmaceutical composition comprising a compound as shown below, or a pharmaceutically acceptable salt, a stereoisomer, a tautomer, or a prodrug thereof:

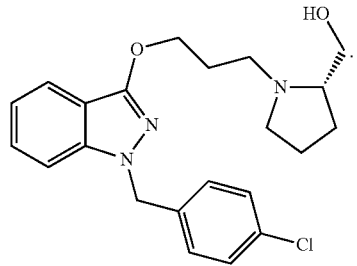 [SMILES: OC[C@@H]1CCCN1CCCOc1nn(Cc2ccc(Cl)cc2)c2ccccc12]

56. A compound having the structure shown below, or a pharmaceutically acceptable salt or a stereoisomer thereof:

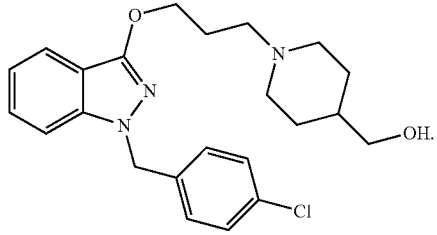 [SMILES: OCC1CCN(CCCOc2nn(Cc3ccc(Cl)cc3)c3ccccc23)CC1]

57. A pharmaceutical composition comprising a compound as shown below, or a pharmaceutically acceptable salt, a stereoisomer, a tautomer, or a prodrug thereof:

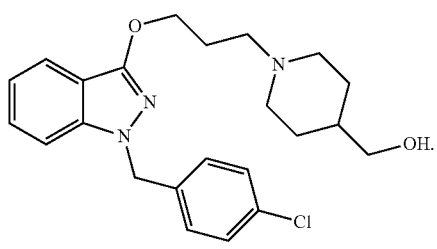 [SMILES: OCC1CCN(CCCOc2nn(Cc3ccc(Cl)cc3)c3ccccc23)CC1]

58. A compound having the structure shown below, or a pharmaceutically acceptable salt or a stereoisomer thereof:
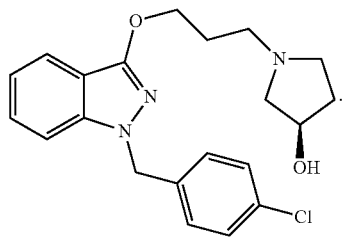 [SMILES: O[C@@H]1CCN(CCCOc2nn(Cc3ccc(Cl)cc3)c3ccccc23)C1]
59. A pharmaceutical composition comprising a compound as shown below, or a pharmaceutically acceptable salt, a stereoisomer, a tautomer, or a prodrug thereof:
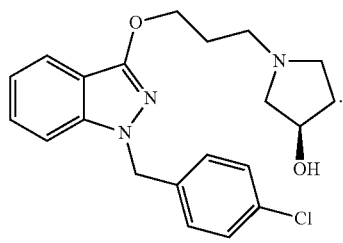 [SMILES: O[C@@H]1CCN(CCCOc2nn(Cc3ccc(Cl)cc3)c3ccccc23)C1]
* * * * *